(12) United States Patent
Khalil et al.

(10) Patent No.: US 11,781,149 B2
(45) Date of Patent: Oct. 10, 2023

(54) SYSTEMS AND METHODS FOR CONTROL OF GENE EXPRESSION

(71) Applicant: TRUSTEES OF BOSTON UNIVERSITY, Boston, MA (US)

(72) Inventors: Ahmad S. Khalil, Lexington, MA (US); Caleb J. Bashor, Boston, MA (US); Nikit Patel, Brookline, MA (US); James J. Collins, Newton, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 16/456,556

(22) Filed: Jun. 28, 2019

(65) Prior Publication Data

US 2020/0002710 A1 Jan. 2, 2020

Related U.S. Application Data

(60) Provisional application No. 62/691,187, filed on Jun. 28, 2018.

(51) Int. Cl.
C12N 15/82 (2006.01)
C07K 14/47 (2006.01)

(52) U.S. Cl.
CPC .......... *C12N 15/8216* (2013.01); *C07K 14/47* (2013.01); *C07K 2319/81* (2013.01)

(58) Field of Classification Search
CPC ................................................ C12N 15/8216
See application file for complete search history.

(56) References Cited

U.S. PATENT DOCUMENTS

| | | | |
|---|---|---|---|
| 6,444,871 B1 | 9/2002 | Yao | |
| 7,153,949 B2 | 12/2006 | Kim et al. | |
| 8,765,403 B2 * | 7/2014 | Dueber | C12N 15/1044 435/41 |
| 10,138,493 B2 | 11/2018 | Khalil et al. | |
| 2012/0003630 A1 | 1/2012 | Collins et al. | |
| 2018/0057838 A1 | 3/2018 | Khalil et al. | |

FOREIGN PATENT DOCUMENTS

| | | |
|---|---|---|
| WO | 2002088346 A2 | 11/2002 |
| WO | 2009/062170 A1 | 5/2009 |
| WO | 2011103049 A2 | 8/2011 |

OTHER PUBLICATIONS

Khalil et. al . A Synthetic Biology Framework for Programming Eukaryotic Transcription Functions, 2012, Cell, 150, 647-658 (Year: 2012).*
Oka et. al. Functional complexes between YAP2 and ZO-2 are PDZ domain-dependent, and regulate YAP2 nuclear localization and signalling, 2010. Biochemical Journal, 432, 461-472 (Year: 2010).*
Williamson. Cooperativity in macromolecular assembly. 2008. Nature Chemical Biology. 4(8) 458-465 (Year: 2008).*
Wiedemann et. al. Quantification of PDZ Domain Specificity, Prediction of Ligand Affinity and Rational Design of Super-binding Peptides 2004. Journal of Molecular Biology. 343(3) 703-718) (Year: 2004).*
Yaghmai et al., "Optimized regulation of gene expression using artificial transcription factors." Molecular therapy 5(6): 385-694 (2002).
Rastinejad et al., "Understanding nuclear receptor form and function using structural biology" Journal of molecular endocrinology 51(3):T1-T21 (2013).
Trapnell et al. "Differential gene and transcript expression analysis of RNA-seq experiments with TopHat and Cufflinks" Nature Protocols. 7(3):562-578 (2012).
Tuch et al. "Evolution of Eukaryotic Transcription Circuits." Science. 319(5871):1797-1799. (2008).
Unger et al. "Monolithic Microfabricated Valves and Pumps by Multilayer Soft Lithography." Science. 288(5463):113-116. (2000).
Vega et al. "Signaling-mediated bacterial persister formation." Nature Chemical Biology. 8: 431-433. (2012).
Veitia "A sigmoidal transcriptional response: cooperativity, synergy and dosage effects" Biological Reviews. 78 (1):149-170. (2003).
Wang "An exact mathematical expression for describing competitive binding of two different ligands to a protein molecule." FEBS Letters. 360(2): 111-114. (1995).
Wang et al. "Natural Variation in Preparation for Nutrient Depletion Reveals a Cost-Benefit Tradeoff" PLOS Biology. 13(1): Article No. e1002041. (2015).
Wang et al."Image segmentation and dynamic lineage analysis in single-cell fluorescence microscopy." Cytometry A. 77(1): 101-110. (2010).
Whitty et al. "Cooperativity and biological complexity", Nat Chem Biol. 4(8): 435-439 (2008).
Wiedemann et al. "Quantification of PDZ Domain Specificity, Prediction of Ligand Affinity and Rational Design of Super-binding Peptides." Journal of Molecular Biology. 343(3): 703-718. (2004).
Williamson "Cooperativity in macromolecular Assembly" Nature Chemical Biology. 4(8):458-465. (2008).
Yosef et al. "Impulse control: Temporal Dynamics in Gene Transcription." Cell. 144(6): 886-896. (2011).
Zalatan et al. "Engineering Complex Synthetic Transcriptional Programs with CRISPR RNA Scaffolds" Cell. 160(1-2): 339-350. (2015).

(Continued)

*Primary Examiner* — Nancy J Leith
(74) *Attorney, Agent, or Firm* — Nixon Peabody LLP; Ronald I. Eisenstein; Susanna C. Benn

(57) ABSTRACT

Embodiments disclosed herein provide artificial expression systems comprising multivalent transcription factor complexes for cooperative transcription factor assembly and modulating gene expression. More specifically, engineered synthetic transcription factors are recruited and structurally organized on synthetic gene circuits using molecular clamps, where the strength of intra-complex interactions can be modulated for fine tuning of gene expression as desired.

18 Claims, 31 Drawing Sheets

Specification includes a Sequence Listing.

(56) References Cited

OTHER PUBLICATIONS

Zhu et al. "Mechanistic basis of MAGUK-organized complexes in synaptic development and signalling." Nature Reviews Neuroscience. 17:209-223. (2016).
Angeli et al. "Detection of multistability, bifurcations, and hyseresis in a large class of biological positive-feedback systems." PNAS. 101(7): 1822-1827. (2004).
Baker et al. "Protein Modularity, Cooperative Binding, and Hybrid Regulatory States Underlie Transcriptional Network Diversification." Cell. 151(1): 80-95. (2012).
Banani et al. "Biomolecular condensates: organizers of cellular biochemistry." Nature Reviews Molecular Cell Biology. 18: 285-298. (2017).
Bashor et al. "Rewiring Cells: Synthetic Biology as a Tool to Interrogate the Organizational Principles of Living Systems." Annual Review of Biophysics. 39:515-537. (2010).
Bennett et al. "Metabolic gene regulation in a dynamically changing environment." Nature. 454: 1119-1122. (2008).
Bhalla et al. "Emergent Properties of Networks of Biological Signaling Pathways." Science. 283 (5400):381-387. (1999).
Bialek et al. "Reading a neural code." Science. 252(5014): 1854-1857. (1991).
Bintu et al. "Transcriptional regulation by the numbers: models." Current Opinion in Genetics& Development. 15(2):116-124.(2005).
Bradford "A rapid and sensitive method for the quantitation of microgram quantities of protein utilizing the principle of protein dye-binding." Analytical Biochemistry. 72 (1-2): 248-254 (1976).
Brophy et al. "Principles of genetic circuit design." Nature Methods. 11(5): 508-520. (2014).
Buchler et al. "On schemes of combinatorial transcription logic." PNAS. 100(9):5136-5141. (2003).
Carey "The Enhanceosome and Transcriptional Synergy." Cell. 92(1): 5-8. (1998).
Cookson et al. "Monitoring dynamics of single-cell gene expression over multiples cell cycles." Molecular Systems Biology. Article No. 2005.024. (2005).
Danino et al. "A synchronized quorum of genetic clocks." Nature. 463: 326-330. (2010).
Duffy et al. "Rapid Prototyping of Microfluidic Systems in Poly(dimethylsiloxane)." Anal. of Chemistry. 70 (23):4974-4984. (1998).
Ferrell Jr. "Self-perpetuating states in signal transduction: positive feedback, double-negative feedback and bistability." Current Opinion in Cell Biology. 14(2) 140-148. (2002).
Ferrell Jr et al. "Ultrasensitvity part III: cascades, bistable switches, and oscillators." Trends in Biochemical Sciences. 39(12): 612-618. (2014).
Garcia et al. "Chapter Two—Thermodynamics of Biological Processes." Methods in Enzymology. 492: 27-59. (2011).
Gertz et al. "Analysis of combinatorial cis-regulation in synthetic and genomic promoters." Nature. 457: 215-218. (2009).
Harris et al. "Energetic Determinants of Internal Motif Recognition by PDZ Domains." Biochemistry. 40(20): 5921-5930. (2001).
Hill "The possible effects of the aggregation of the molecules of haemoglobin on its dissociation curve." J. Physiol. 40, iv-vii(1910).
Hnisz et al. "A Phase Separation Model for Transcriptional Control." Cell. 169(1):13-23. (2017).
Jantz et al. "Probing the DNA-Binding Affinity and Specificity of Designed Zinc Finger Proteins." Biophysical Journal. 98 (5): 852-860. (2010).
Kang. "Correlation between functional and binding activities of designer zinc-finger proteins" Biochemical Journal. 403 (1): 177-182. (2007).
Keung et al. "Using Targeted Chromatin Regulators to Engineer Combinatorial and Spatial Transcriptional Regulation." Cell. 158: 110-120. (2014).
Keymer et al. "Chemosensing in *Escherichia coli*: Two regimes of two-state receptors." PNAS. 103(6): 1786-1791. (2006).
Khalil et al. "A Synthetic Biology Framework for Programming Eukaryotic Transcription Functions" Cell. 150 (3): 647-658. (2012).
Kim et al. "Specific Intermediates in the Folding Reactions of Small Proteins and the Mechanism of Protein Folding." Annual Review of Biochemistry. 51: 459-489. (1982).
Kryazhimskiy et al. "Global epistasis makes adaptation predictable despite sequence-level stochasticity" Science. 344 (6191): 1519-1522. (2014).
Kullback et al. "On Information and Sufficiency." The Annals of Mathematical Statistics. 22(1): 79-86. (1951).
Kussell et al. "Phenotypic Diversity, Population Growth, and Information in Fluctuating Environments." Science. 309 (5743): 2075-2078. (2005).
Levine "Transcriptional Enhancers in Animal Development and Evolution." Current Biology. 20(17): R754-R763. (2010).
Levine et al. "Functional Roles of Pulsing in Genetic Circuits." Science. 342, (6163): 1193-1200. (2013).
Ma et al. "Defining Network Topologies that Can Achieve Biochemical Adaptation." Cell. 138(4):760-773. (2009).
Mangan et al. "Structure and function of the feed-forward loop network motif." PNAS. 100(21): 11980-11985. (2003).
Mangan et al. "The Coherent Feedforward Loop Serves as a Sign-sensitive Delay Element in Transcription Networks." Journal of Molecular Biology. 334(2): 197-204. (2003).
McIsaac et al. "Synthetic gene expression perturbation systems with rapid, tunable, single-gene specificity in yeast." Nucleic Acids Research. 41 (4): e57 (2013).
Mello et al. "An allosteric model for heterogeneous receptor complexes: Understanding bacterial chemotaxis responses to multiple stimuli." PNAS. 102(48): 17354-17359. (2005).
Mitchell et al. "Oscillatory stress stimulation uncovers an Achilles' heel of the yeast MAPK signaling network." Science. 350(6266): 1379-1383. (2015).
Monod et al. "On the Nature of Allosteric Transitions: A Plausible Model." Journal of Molecular Biology. 12: 88-118. (1965).
Nevozhay et al. "Negative autoregulation linearizes the dose-response and suppresses the heterogeneity of gene expression." PNAS.106(13) 5123-5128. (2009).
Novershtern et al. "Densely Interconnected Transcriptional Circuits Control Cell States in Human Hematopoiesis." Cell. 144(2):296-309. (2011).
Ptashne "How eukaryotic transcriptional activators work." Nature. 335: 683-689. (1988).
Purnick et al. "The second wave of synthetic biology: from modules to systems." Nature Reviews Molecular Cell Biology. 10:410-422. (2009).
Purvis et al. "Encoding and Decoding Cellular Information through Signaling Dynamics." Cell. 152(5): 945-956. (2013).
Shea et al. "The OR control system of bacteriophage lambda: A physical chemical model for gene regulation." Journal of Molecular Biology, 181(2): 211-230. (1985).
Sivak et al. "Environmental Statistics and Optimal Regulation." PLOS Computational Biology 10(9): Article No. e1003826 (2014).
Spitz et al. "Transcription factors: from enhancer binding to developmental control." Nature Reviews Genetics. 13: 613-626. (2012).
Struhl. "Mechanisms for diversity in gene expression patterns." Neuron. 7(2): 177-181. (1991).
Thorsen et al. "Microfluidic Large-Scale Integration." Science. 298(5593): 580-584. (2002).

\* cited by examiner

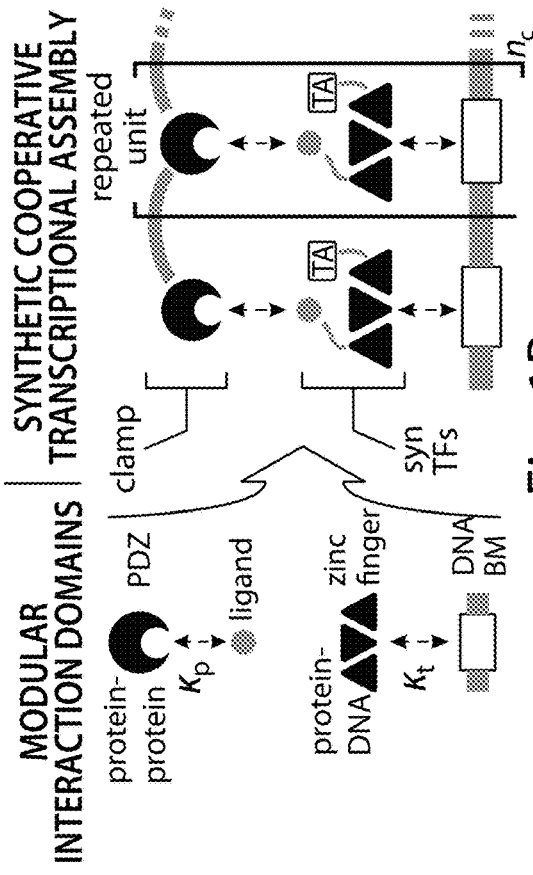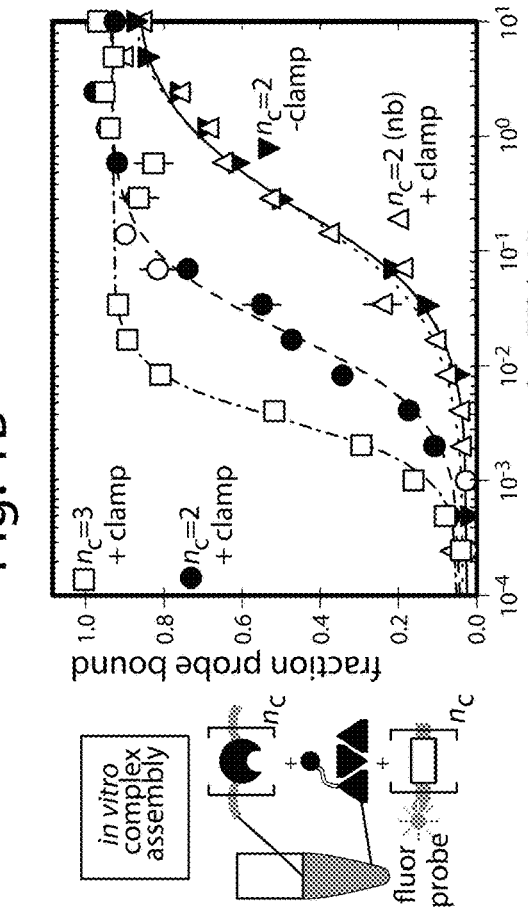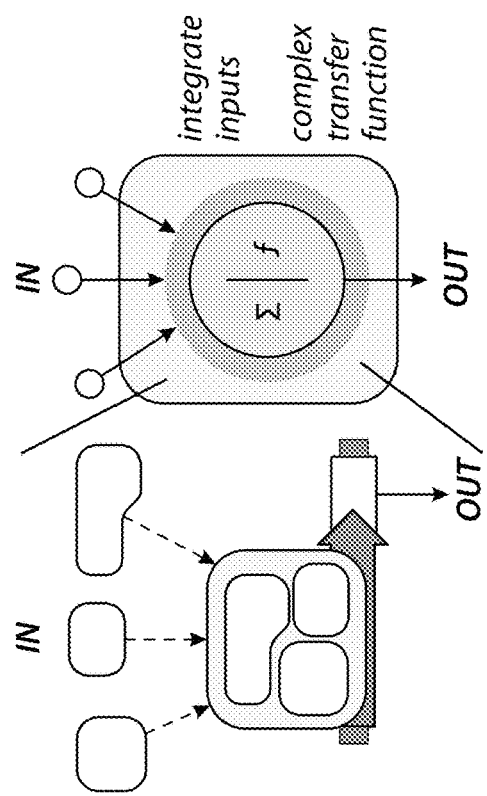
Fig. 1A
Fig. 1B
Fig. 1C

| | competitor ligands | | syn $K_d$ (μM) | erb $K_d$ (μM) |
|---|---|---|---|---|
| syntrophin-specific | s1 | IRETII | 0.062 | nb |
| | s2 | IRETIL | 0.18 | nb |
| | s3 | IRWTIV | 0.49 | 1.73 |
| | s4 | IRETIV | 0.88 | 3.46 |
| | s5 | VKESLV | 1.97 | 5.71 |
| | s6 | VKEALV | 27.3 | nb |
| | s7 | HLETFF | 43.2 | nb |
| no binding | | VKEAAA | nb | nb |
| erbin-specific | E1 | WLVTWV | nb | 0.10 |
| | E2 | WLKTWV | nb | 0.33 |
| | E3 | PVDSWV | 1.57 | 0.42 |

97-4 ZEV ORF 97-4 MPGERPFQCRICMRNFSRQSNLSRHTRTHTGEKPFQCRICMRN
FSRNEHLVLHLRTHTGEKPFQCRICMRNFSQKTGLRVHLKTHLR
GTPA AASTLEDP SAGDMRAANLWPSPLMIKRSKKNSLALSLTAD
QMVSALLDAEPPILYSEYDPTRPFSEASMMGLLTNLADRELVHM
INWAKRVPGFVDLTLHDQVHLLECAWLEILMIGLVWRSMEHPV
EST receptor KLLFAPNLLLDRNQGKCVEGMVEIFDMLLATSSRFRMMNLQGE
EFVCLKSIILLNSGVYTFLSSTLKSLEEKDHIHRVLDKITDTLIHLM
AKAGLTLQQQHQRLAQLLLILSHIRHMSNKGMEHLYSMKCKNV
VPLYDLLLEMLDAHRLHAPTSRGGASVEETDQSHLATAGSTSS
VP16 ELHLDGEDVAMAHADALDDFDLDMLGDGDSPGPGFTPHDSA
PYGALDMADFEFEQMFTDALGIDEYGG

Fig. 8A

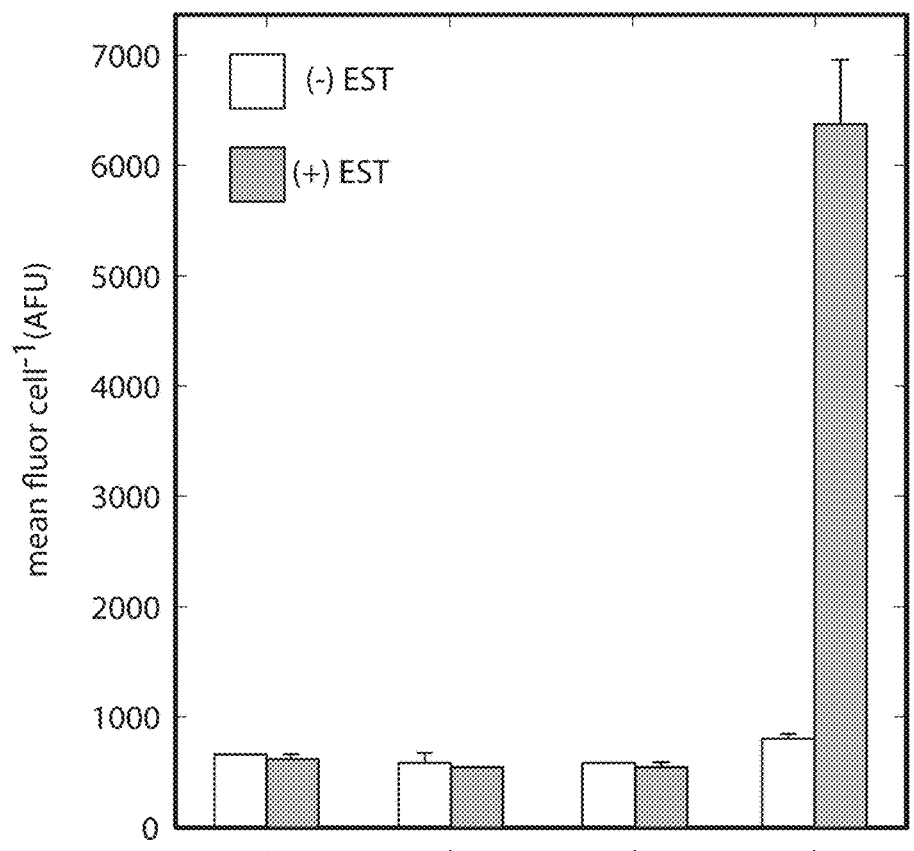

Fig. 8B

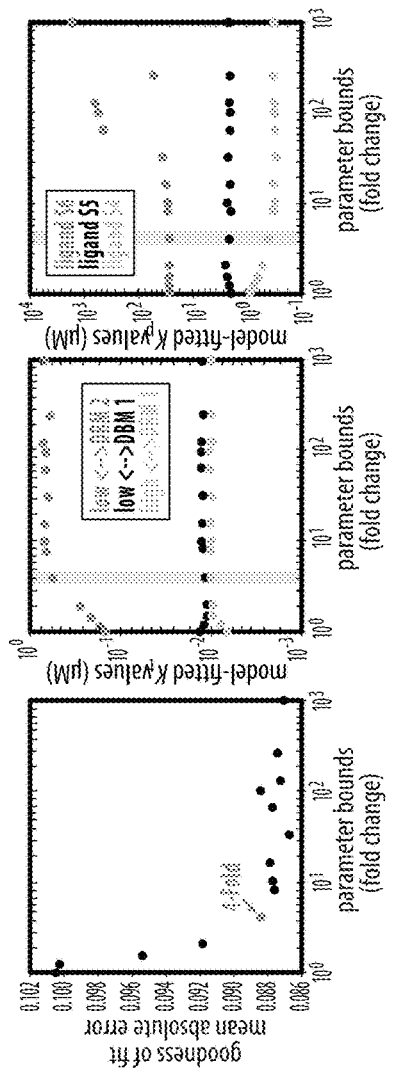
Fig. 12B
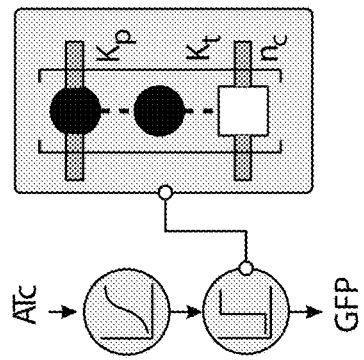
Fig. 13A
thermodynamic model parameter fitting
| | experimentally-measured values | model-fitted values |
|---|---|---|
| $K_t$ values (ZF 43-8-DNA affinities) - from Fig. 6 | | |
| high <--> DBM 1 | 6.5 nM | 9.9 nM |
| low <--> DBM 1 | 13.6 nM | 11.5 nM |
| low <--> DBM2 | 143 nM | 572 nM |
| $K_p$ values (syntrophin-ligand affinities) - from Fig. 7A, Fig. 7B | | |
| ligand S6 | 20.3 µM | 27.5 µM |
| ligand S5 | 1.97 µM | 2.05 µM |
| ligand S4 | 0.88 µM | 0.40 µM |
| **Effective *in vivo* protein concentrations** | | |
| [TF]max | - | 26.7 nM |
| [C]max | - | 129.6 nM |
Fig. 12A

| | assembly configuration | | | Hill coefficient ($n_H$) | |
|---|---|---|---|---|---|
| | $K_t$ (nM) | $K_p$ (µM) | $n_c$ | model | experiment |
| 1 | 13.6 | no clamp | 1 | 1.53 | 1.16 |
| 2 | 13.6 | no clamp | 2 | 1.53 | 1.42 |
| 3 | 13.6 | no clamp | 3 | 1.53 | 1.58 |
| 4 | 13.6 | no clamp | 4 | 1.53 | 1.36 |
| 5 | 13.6 | no clamp | 5 | 1.53 | 1.45 |
| 6 | 13.6 | 1.97 | 2 | 1.84 | 1.84 |
| 7 | 224 | 0.18 | 3 | 2.06 | 2.54 |
| 8 | 224 | 0.18 | 5 | 2.94 | 3.46 |
| 9 | 13.6 | 27.3 | 4 | 1.54 | 1.71 |
| 10 | 224 | 0.88 | 5 | 2.26 | 2.47 |
| 11 | 13.6 | 0.88 | 2 | 2.03 | 1.81 |
| 12 | 143 | 0.18 | 3 | 2.38 | 2.53 |
| 13 | 143 | 1.97 | 4 | 1.91 | 2.89 |
| 14 | 143 | 0.18 | 5 | 3.51 | 2.83 |

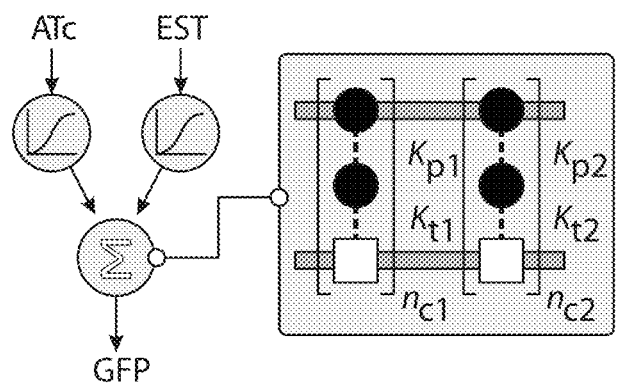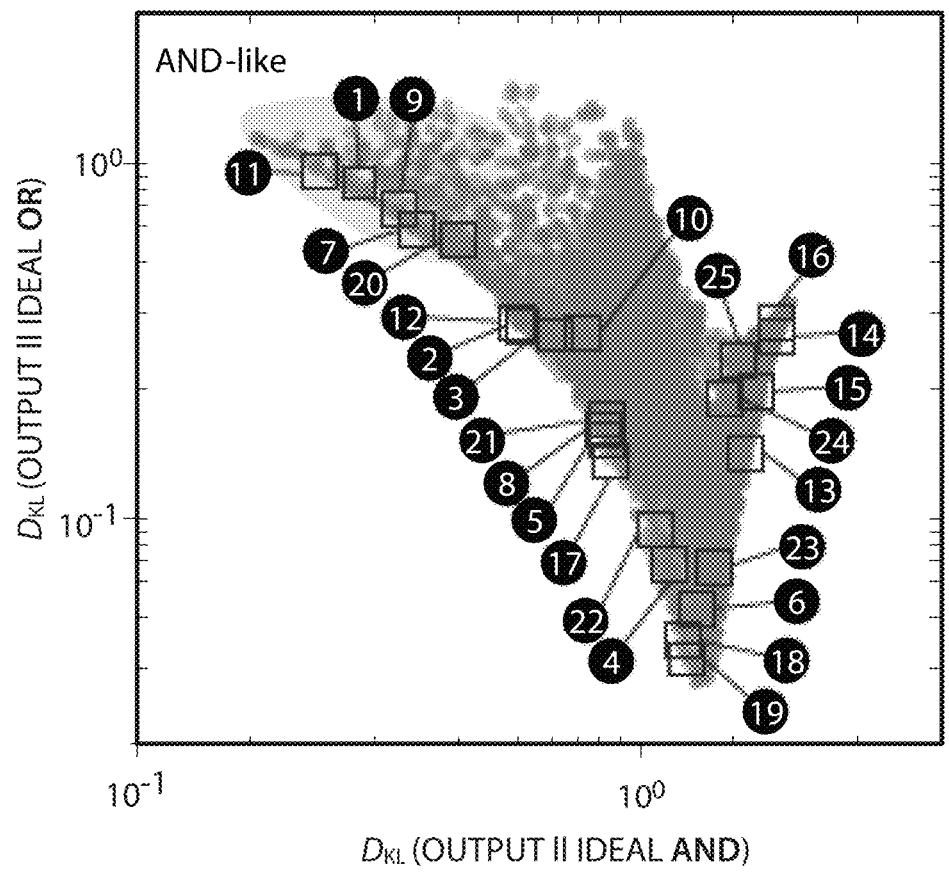
Fig. 14A

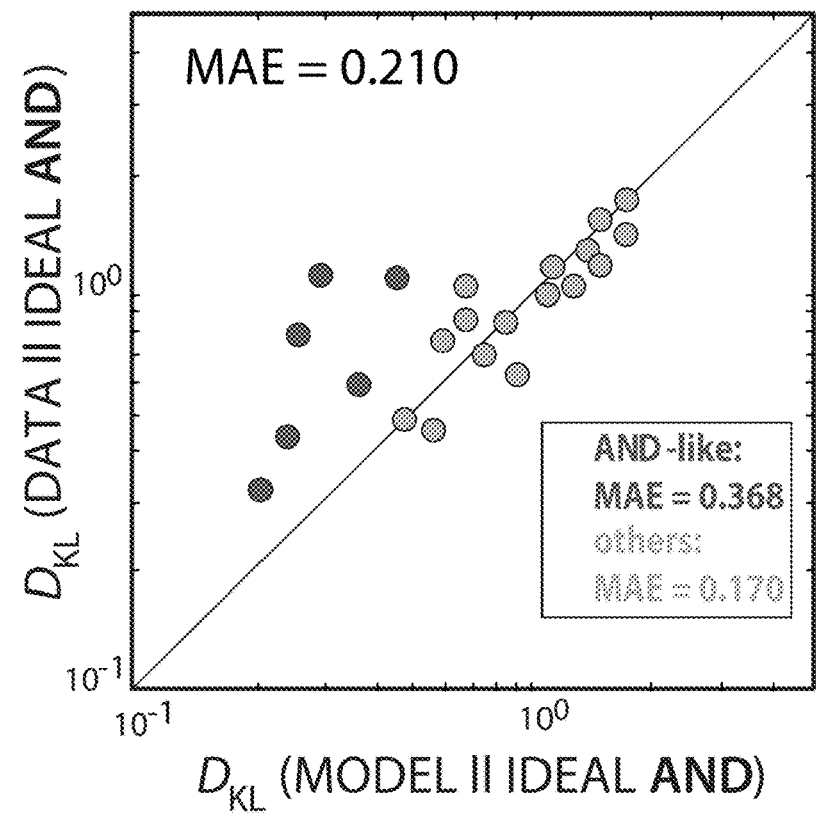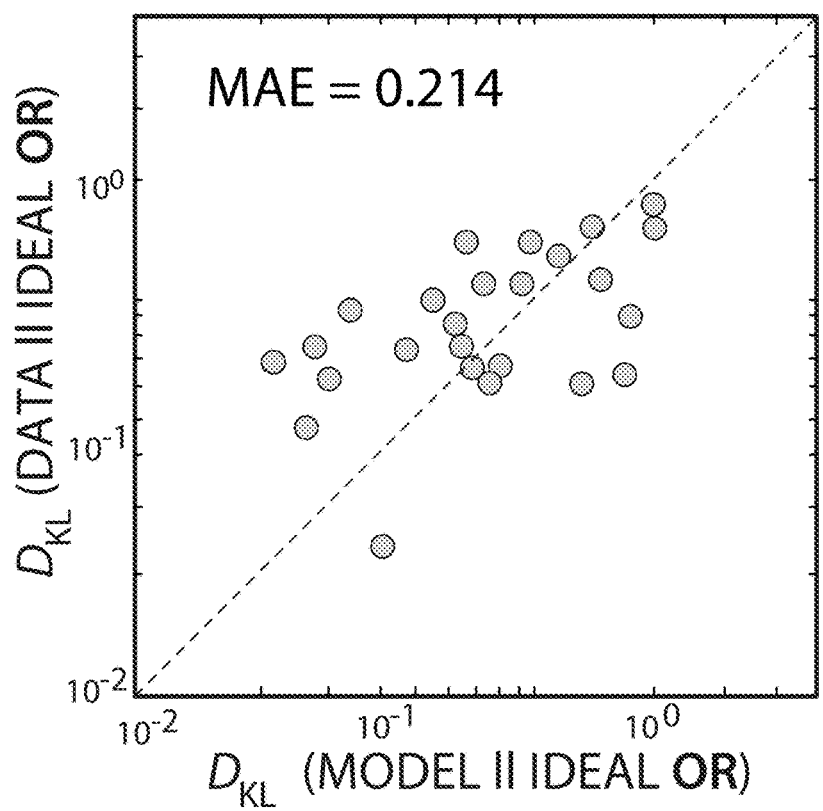
Fig. 14C

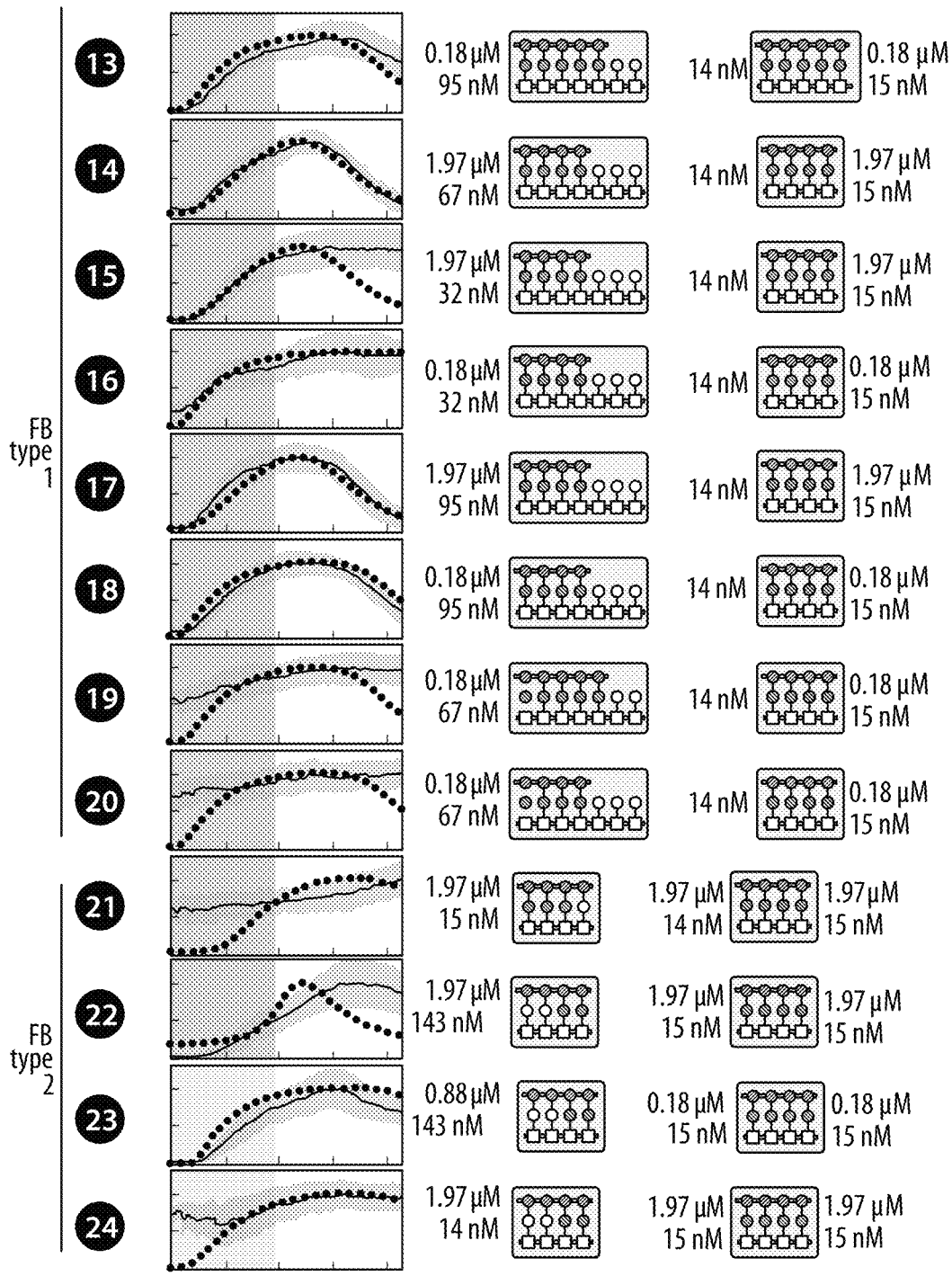
Fig. 15B, CONT.

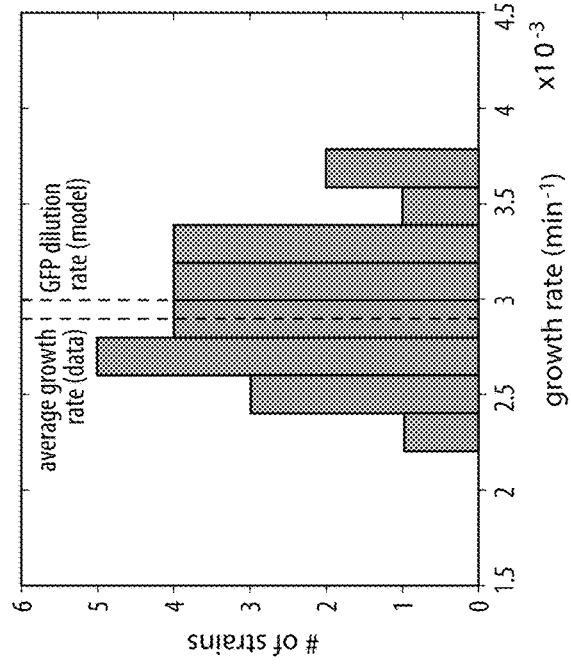
Fig. 16B
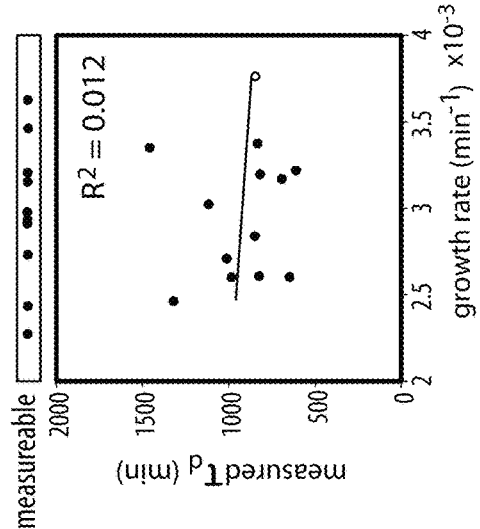
Fig. 16C
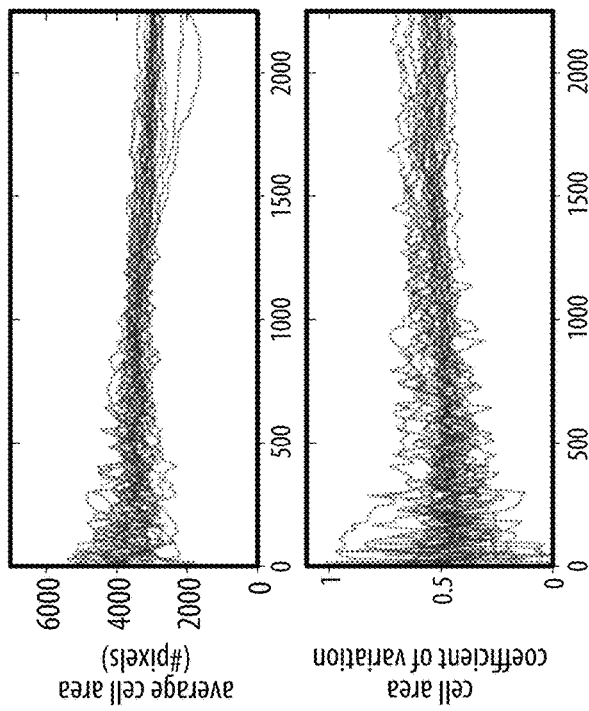
Fig. 16A
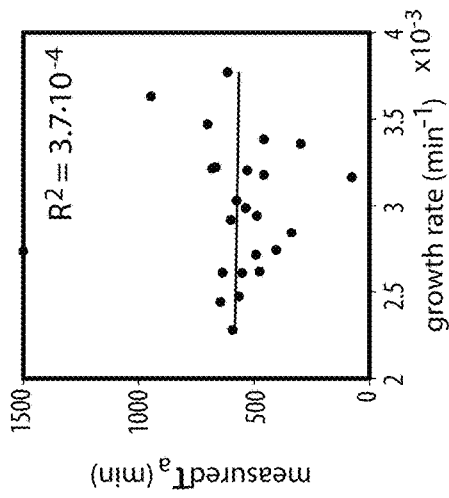

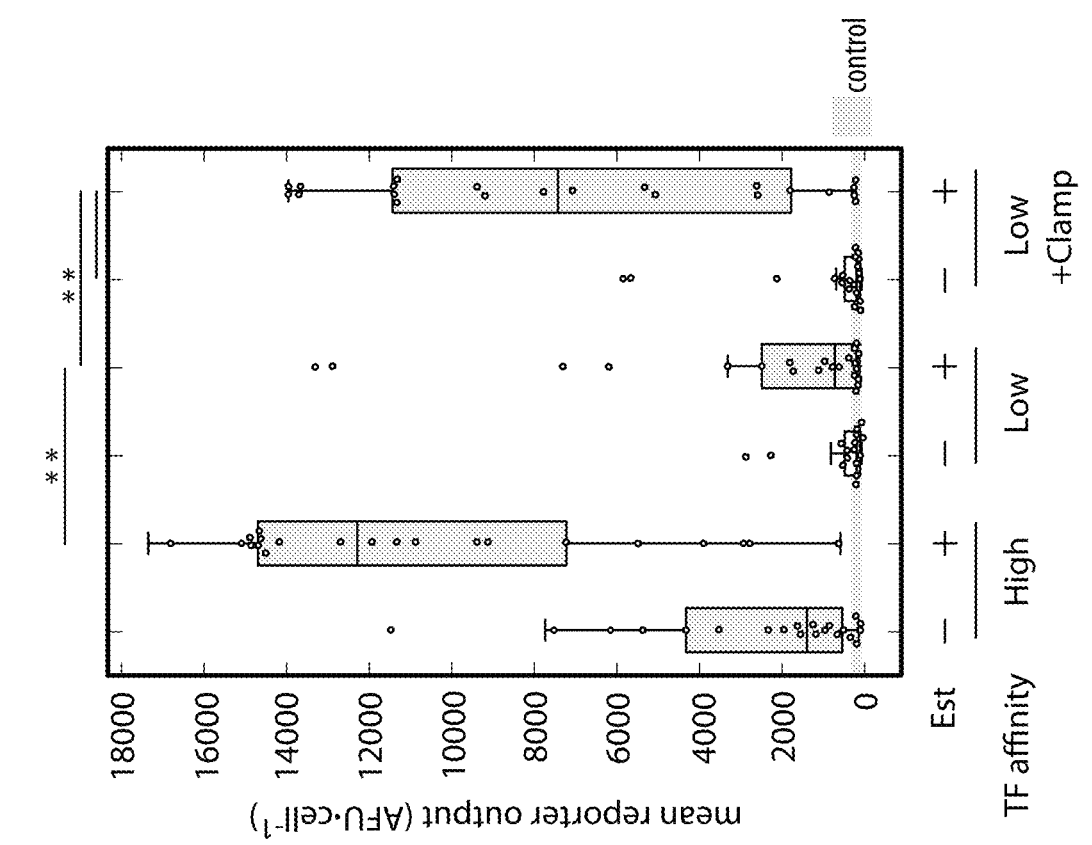
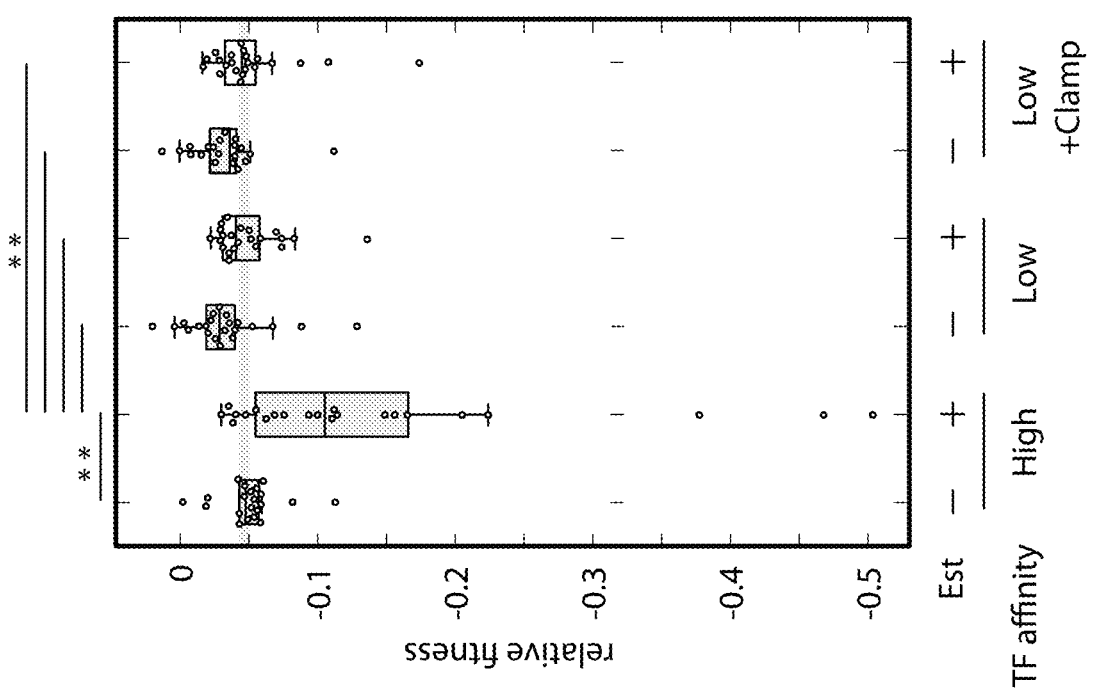
Fig. 18

SYSTEMS AND METHODS FOR CONTROL OF GENE EXPRESSION

CROSS-REFERENCE TO RELATED APPLICATIONS

This application claims benefit under 35 U.S.C. § 119(e) of U.S. Provisional Application No. 62/691,187 filed on Jun. 28, 2018, the contents of which is incorporated herein by reference in its entirety.

GOVERNMENT SUPPORT

This invention was made with government support under the National Science Foundation under Grant No. MCB-1350949 and the Department of Defense Grant No. W911NF-11-2-0056. The government has certain rights in the invention.

SEQUENCE LISTING

The instant application contains a Sequence Listing which has been submitted electronically in ASCII format and is hereby incorporated by reference in its entirety. Said ASCII copy, created on Jun. 27, 2019, is named 701586-086520USPT_SLTXT and is 83,034 bytes in size.

FIELD OF THE INVENTION

The field of the invention relates to the control of gene expression, in particular, controlled gene expression, engineered gene circuits and synthetic transcription factors and multivalent transcription factor complexes.

BACKGROUND

Methods of controlled regulation of gene expression have been increasingly important in a wide range of areas, including but not limited to gene therapy, synthetic biology, plant management, environmental clean-up, bacterial and microbial management and synthetic genetic circuits. Control of gene expression holds vast potential at revolutionizing therapeutics, animal models, and biotechnological processes and are useful to integrate multiple input signals for cell-based therapy and animal model development. Despite rapid advances in recent years, tight control of gene expression remains a challenge due to predictability stemming from unintended interactions between biological components, such as transcription factors etc. A fundamental goal in cellular engineering is to predictably and efficiently express genes at a desired level and under tight control. Such genetically engineered cells hold great promise for advancing therapeutics, diagnostics, animal models, and biotechnological processes.

Cooperativity is a widespread biological phenomenon by which coordinated behavior within a molecular system emerges from energetic coupling between its components. Cooperativity is a well-studied feature of oxygen binding to hemoglobin and protein folding, but is also critical to cellular regulatory networks, where it underpins decision making, allowing network nodes to convert linear, graded inputs into non-linear, "all-or-none" output responses. The molecular basis of cooperativity has been classically understood through the paradigm of protein allostery. Another mechanism for generating cooperativity is through the self-assembly of multimeric complexes, where avidity created by initial binding events render subsequent higher-order assembly steps more energetically favorable. Transcription factor complex assembly underpins decision making in regulatory networks, allowing network nodes to convert linear, graded inputs into non-linear, "all-or-none" output responses. In metazoan systems, gene networks are thought to utilize assembly-based computation to precisely interpret positional and temporal information during cell state decision-making processes like cell type differentiation and developmental tissue patterning.

Most synthetic gene circuits have been constructed using transcription factors that bind to promoters in a one-to-one fashion, however, this constrains the ability to fine tune circuit cooperatively and imposes limits on the engineerable behavior. Therefore, there is a need for synthetic gene circuits that allow for cooperativity of transcription factor and extended signal processing function.

SUMMARY OF THE INVENTION

For gene expression in a modified cell to be effective, gene expression must be both tightly controlled and efficient. In some instances, the gene expression is not tightly controlled and/or inefficient due to a myriad of factors, including but not limited to inefficient or ineffective recruitment of transcription factors, ineffective binding and/or cross reactivity of transcription factors to specific promoters, leaky promoters and the like. While most synthetic gene circuits are constructed using transcription factors that bind to promoters in a one-to-one fashion, herein, the inventors have developed a system for multivalent cooperative transcription factor assembly, which can be tailored by adjusting the number and strength of the intracomplex interactions to finely tune the gene transcription for enhanced signal processing and control.

The technology described herein relates, in part, to a method and compositions for highly-cooperative molecular complexes in cells that can be used to regulate and specifically control or tailor gene expression in a cell. That is, the technology described herein relates to cooperative assembly of multiple transcription factors for controlled regulation of gene expression. Referring to an exemplary embodiment described in the schematic shown in FIG. 1B and FIG. 10, the inventors have developed a system where multiple synthetic transcription factors (sTFs) can bind to tandem DNA binding motifs (DBMs) where the DBMs are located upstream of a core promoter, thereby activating or repressing the transcription of the gene operatively linked to the promoter. A molecular clamp (MC) protein serves to effectively tether or assemble at least two sTF (e.g., so they are assembled in series). The molecular clamp provides a system that allows for cooperative and fine tuning of gene expression using an interconnected assembly of synthetic transcription factors (sTFs).

At a minimum, a synthetic gene circuit for expression of a gene of interest (GOI) will comprise multiple target DNA binding motifs (DBM) located upstream (e.g., 5') of a promoter or other regulatory element, which is operatively linked to a gene or GOI to be expressed or regulated. Gene expression of the GOI from the synthetic gene circuit is controlled by the assembly of multiple synthetic transcription factors ("sTF"), each of which will bind to each DBM upstream of the promoter or regulatory element, and comprise a ligand and transcriptional activator (TA) or transcriptional repressor (TR). The sTFs are essentially tethered together by a molecular clamp protein, which is a repeating unit of PDZ domains, where each PDZ domain are covalently linked by a linker and each PDZ domain comprises a ligand binding domain (LBD) which binds to the ligand on the sTF, therefore creating cooperative sTF assemblies, and allowing fine-tuning of gene expression. Moreover, in addition to modulating the number of DBM upstream of the promoter or regulatory region and the number of sTF, one can further fine-tune the regulation of gene expression by adjusting the binding affinities and/or strength of the binding of sTF to the DBMs, and/or the binding of the LBD of the molecular clamp to the ligand of the sTF. As such, by specifying the strength and/or the number of assembly of sTF subunits, it enables single and multiple-input control of gene expression, as well as predictive and fine-tuning of the expression of the GOI.

In summary, the components of system for cooperative sTF assemblies are described as follows:

(i) Synthetic gene circuit: $[DBM]_n$-promoter (or regulatory element)-GOI (ii) Synthetic transcription factor (sTF): ligand-DNA binding domain (DBD)-Effector domain (e.g., Transcriptional activator (TA) or Transcriptional repressor (TR) or epigenetic effector (EE) domain).

(iii) Molecular clamp (MC): Ligand binding domain (LBD)-[linker-LBD]$_n$

Accordingly, the technology described herein relates to multi-domain molecular clamps (MCs) that comprise multiple ligand binding domains that can selectively bind to a ligand present on an engineered synthetic transcription factor(s) (herein referred to as "sTFs"), resulting in the organization and assembly of components of the sTF such that the sTF can bind to a target DNA binding motif (herein referred to as DBM) function upstream of a promoter, and initiate gene expression. Stated differently, the inventors have described a modular molecular complex whereby synthetic transcription factors are organized and held in position by a molecular clamp, such that the sTFs can efficiently bind to target DNA sequences, thereby allowing efficient transcription of the downstream transgene.

More specifically, the inventors have demonstrated, by using a molecular clamp comprising multiple ligand binding domains (herein referred to as "LBD") each of which bind to a ligand of a sTF, a method for organizing and assembling multiple sTFs to multiple DNA binding motifs (DBMs) that are located upstream of a promoter operatively linked to a gene, thereby resulting in a sophisticated, tightly regulated, control of gene expression. Using such a mechanism, the molecular clamp, with multiple LBDs can bind to multiple sTFs organizing the sTFs to be arranged in series, where they can bind to a series of DBM upstream of a promoter.

In one embodiment, when a molecular clamp recruits and assembles one or more sTFs to one or more DBMs upstream of a promoter, gene expression occurs by bringing a transcription activator (TA) domain of the sTF into proximity of the transcription initiation complex, thereby initiating gene expression. Such an embodiment serves as an "ON" switch. In an alternative embodiment, when a molecular clamp recruits and assembles one or more sTFs to one or more DBMs upstream of a promoter, gene expression can be inhibited by bringing a transcription repressor (TR) domain of the sTF into proximity of the transcription initiation complex, thereby preventing or inhibiting gene expression from the promoter. Such an embodiment serves as an "OFF" switch.

Importantly, the system disclosed herein enables a modular approach to controlling and regulating gene expression, for example, by changing one or more components of the system, such as for example, one or more of: the affinity of the ligand binding domain (LBD) for the ligand, the affinity of the DNA binding Domain (DBD) to the target DNA binding motif (DBM), the number of DBD located upstream of a promoter, the combination of sTFs recruited by the molecular clamp (i.e., whether they comprise transcription activators or repressors), one can tightly control the level of gene expression, which is desirable for numerous applications, including but not limited to therapeutic cell engineering, gene therapy, CRISPR applications and the like.

Additionally, gene expression from the system disclosed herein is also dependent on multi-input signals or control—that is, gene expression is dependent on the expression of both the molecular clamp AND the sTF (referred to herein as "AND input" or "2-input" control of gene expression), providing an additional level of control to gene expression. In some embodiments, a 3-input control can be used, for example, but not limited to, a signal inducing the expression of molecular probe, AND a signal inducing the expression of one sTF, AND/OR a signal inducing the expression of a second transcription factor.

In all aspects, a sTF useful in the systems, compositions and methods disclosed herein comprises a ligand, a DNA binding domain (herein referred to as a "DBD") which binds to the DNA binding motif (DBM), and a transcription activator (TA) domain or transcriptional repressor (TR) domain. In all aspects, a molecular clamp useful in the systems, compositions and methods disclosed herein comprises n, where n is an integer between 1 and 50 ligand binding domains (LBD), where each ligand binding domain is connected to at least one other LBD by a linker, and at least one LBD can bind to the ligand of the at least one sTF; where when the molecular clamp and at least one sTF are both present in a cell, at least one ligand binding domain binds to the ligand of the sTF, wherein if the sTF comprises a TA domain, the TA domain recruits the RNA pol II machinery to the promoter, thereby turning on gene expression ("ON switch"), or alternative embodiments, if the sTF comprises a TR domain, the RNA pol II machinery is prevented or inhibited from binding to the promoter, thereby inhibiting gene expression. ("OFF Switch")

The technology described herein is different and an improvement over that disclosed in Khalil et al., (Cell, 2012; 150(3); 647-658). In Khalil, a cognate pair of transcription factors bind to each other resulting in just one pair of TFs arranged in series upstream of a promoter. That is—Khalil describes a system where a transcription factor comprising a ligand binds directly to a PDZ domain on a cognate transcription factor. Similarly, U.S. Pat. No. 10,138,493 discloses a system of arranging multiple synthetic transcription factors (SynTFs) in series, where the SynTFs are attached to each other using dimerization with attached ligands and ligand-binding domains, where the SynTF in the array or series that is located most 5' to the promoter comprises a terminal effector domain for modulation of gene expression.

In contrast, the technology described herein uses a molecular clamp to bind to and coordinate the arrangement of multiple TFs in series, thereby providing an unlimited number of TFs to be arranged in series upstream of the promoter. Additionally, the presence of the molecular clamp avoids the direct binding or joining of sTF to one another, thus avoiding issues with steric hindrance as well as having to be bound to each other, as well as provide an additional level of control for gene expression. Importantly, the technology described herein also provides an additional level of control, that is, both the interaction of the sTF (i.e., the ligand) with the LBD of the molecular clamp (e.g., Kp) and the interaction between the sTF (i.e., the DBD) and the DBM (e.g., Kt) can be modified, providing an additional magnitude of control, resulting in superior control and fine tuning of gene expression. For example, referring to an exemplary embodiment described in the schematic of FIG. 17, the interaction of the DBD of the sTF can have a high affinity or low affinity for binding to the DNA Binding motifs (DBM). In some embodiments, the molecular clamp serves to stabilize the low affinity sTFs thereby regulating initiation (or repression) of gene expression that would not otherwise occur in the absence of the molecular clamp.

Thus, the technology described herein of cooperative assembly of the sTFs facilitates the creation of signal processing circuitry, enables precision control in applications where non-linear temporal and spatial signal processing are critical, e.g., for circuit-directed cell differentiation or dynamic regulation of homeostasis in engineered tissues.

The technology described herein is discussed in the following paragraphs.

Accordingly, one aspect provided herein is a system for controlling gene expression comprising: (i) at least one synthetic transcription factor (sTF) comprising at least one ligand, a DNA binding domain (DBD) and a transcription activator (TA) domain or transcriptional repressor (TR) domain, wherein the DBD can bind to at least one target DNA binding motif (DBM) located upstream of a promoter operatively linked to a gene, (ii) a molecular clamp comprising n ligand binding domains (LBD), wherein each ligand binding domain is connected to at least one other LBD by a linker, wherein at least one LBD can bind to the ligand of the at least one sTF; wherein n is an integer between 1 and 50; wherein when the molecular clamp and at least one sTF are both present in a cell, at least one ligand binding domain binds to the ligand of the sTF, wherein if a TA domain is present, the TA domain recruits the RNA pol II machinery to the promoter, thereby turning on gene expression ("ON switch"), and wherein if a TR domain is present, the TR domain prevents RNA pol II machinery from binding to the promoter, thereby inhibiting gene expression. ("OFF Switch")

In one embodiment of this aspect and all other aspects provided herein, the linker is a flexible linker.

In another embodiment of this aspect and all other aspects provided herein, the linker comprises a flexible glycine-serine (GS) linker repeat sequence.

In another embodiment of this aspect and all other aspects provided herein, the GS linker repeat sequence is repeated at least 5 times.

In another embodiment of this aspect and all other aspects provided herein, the GS linker repeat sequence is repeated 2-25 times (SEQ ID NO: 56).

In another embodiment of this aspect and all other aspects provided herein, the GS linker repeat sequence is repeated, 5 (SEQ ID NO: 57), 10 (SEQ ID NO: 58) or 20 (SEQ ID NO: 59) times.

In another embodiment of this aspect and all other aspects provided herein, the ligand is a peptide ligand and the ligand binding domain (LBD) is a protein binding domain.

In another embodiment of this aspect and all other aspects provided herein, the protein binding domain is a PDZ domain.

In another embodiment of this aspect and all other aspects provided herein, the PDZ domain is a syntrophin PDZ domain.

In another embodiment of this aspect and all other aspects provided herein, the ligand is selected from any of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), and VKEALV (SEQ ID NO: 8).

In another embodiment of this aspect and all other aspects provided herein, the PDZ domain is a erbin PDZ domain.

In another embodiment of this aspect and all other aspects provided herein, the ligand is selected from any of: WLKTWV (SEQ ID NO: 22), PVDSWV (SEQ ID NO: 23), or VKEALV (SEQ ID NO: 8).

In another embodiment of this aspect and all other aspects provided herein, the molecular clamp comprises a C-terminal nuclear localization signal (NLS).

In another embodiment of this aspect and all other aspects provided herein, the sTF comprises a C-terminal nuclear localization signal (NLS).

In another embodiment of this aspect and all other aspects provided herein, n=2, 3, 4, 5, 6 or between 6-10.

In another embodiment of this aspect and all other aspects provided herein, the DNA binding domain (DBD) is an engineered zinc finger binding domain.

In another embodiment of this aspect and all other aspects provided herein, the DBD is selected from any of: 43-8 (WT), 43-8 (3×), 43-8 (×4), 42-10 (WT), 42-10 (3×) or 42-10 (×4) of VP16.

In another embodiment of this aspect and all other aspects provided herein, the DBD binds to DNA binding motifs (DBM) comprising any of: DBM1 op, DBM2 op, DBM3 op.

In another embodiment of this aspect and all other aspects provided herein, the ligand is located at the N-terminus of the TA or TR domain.

In another embodiment of this aspect and all other aspects provided herein, sTF comprises in the following order; N- to C-terminal: a nuclear localization sequence, a TA domain; a DNA binding domain (DBD); a linker (GSGSG (SEQ ID NO: 60)) and a ligand.

In another embodiment of this aspect and all other aspects provided herein, the TA domain is VP16 minimal activation domain.

In another embodiment of this aspect and all other aspects provided herein, the sTF and molecular clamp are expressed in the cell under the control of different inducible promoters.

In another embodiment of this aspect and all other aspects provided herein, the gene is a fluorescent protein or reporter protein.

In another embodiment of this aspect and all other aspects provided herein, the molecular clamp has the general formula of: [(X)n(Y)]m, where each X is the same or a different ligand binding domain (LBD), wherein n is an integer from one to about 10 (e.g., where n is 1, 2, 3, 4, 5, 6, 7, 8, 9, or 10), where Y, if present, is a linker peptide, and where m is an integer from 2 to about 50 (e.g., from 2 to about 3, from 3 to about 6, from 6 to about 10, from 10 to about 15, from 15 to 20, from 20 to 25, from 25 to 30, from 30 to 35, from 35 to 40, from 40 to 45, or from 45 to 50).

In another embodiment of this aspect and all other aspects provided herein, molecular clamp comprises: NLS[LBD-linker]n-LBD, where n is 1, 2, 3, 4, 5, 6, 7, 8, 9, or 10.

In another embodiment of this aspect and all other aspects provided herein, the LBD is selected from: an SH3 domain, a PDZ domain, a GTPase binding domain (GBD), a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, and a bZIP domain.

Another aspect provided herein relates to a molecular clamp comprising n ligand binding domains (LBD) wherein each LBD is connected to at least one other LBD by a linker, where n is an integer between 1 and 50.

In one embodiment of this aspect and all other aspects provided herein, the ligand binding domain (LBD) is a protein binding domain.

In another embodiment of this aspect and all other aspects provided herein, the protein binding domain is a PDZ domain.

In another embodiment of this aspect and all other aspects provided herein, the molecular clamp comprises at least two PDZ domains.

In another embodiment of this aspect and all other aspects provided herein, the PDZ domain is a syntrophin or erbin PDZ domain.

In another embodiment of this aspect and all other aspects provided herein, the PDZ domain is a syntrophin PDZ domain.

In another embodiment of this aspect and all other aspects provided herein, the PDZ domain binds to a ligand selected from any of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), and VKEALV (SEQ ID NO: 8).

In another embodiment of this aspect and all other aspects provided herein, the PDZ domain is a erbin PDZ domain.

In another embodiment of this aspect and all other aspects provided herein, the PDZ domain binds to a ligand selected from any of: WLKTWV (SEQ ID NO: 22), PVDSWV (SEQ ID NO: 23), or VKEALV (SEQ ID NO: 8).

In another embodiment of this aspect and all other aspects provided herein, n=2, 3, 4, 5, 6 or between 6-10.

In another embodiment of this aspect and all other aspects provided herein, the molecular clamp has the general formula of: [(X)n(Y)]m, where each X is the same or a different ligand binding domain (LBD), wherein n is an integer from one to about 10 (e.g., where n is 1, 2, 3, 4, 5, 6, 7, 8, 9, or 10), where Y, if present, is a linker peptide, and where m is an integer from 2 to about 50 (e.g., from 2 to about 3, from 3 to about 6, from 6 to about 10, from 10 to about 15, from 15 to 20, from 20 to 25, from 25 to 30, from 30 to 35, from 35 to 40, from 40 to 45, or from 45 to 50).

In another embodiment of this aspect and all other aspects provided herein, molecular clamp comprises: NLS[LBD-linker]n-LBD, where n is 1, 2, 3, 4, 5, 6, 7, 8, 9, or 10.

In another embodiment of this aspect and all other aspects provided herein, the LBD is selected from: an SH3 domain, a PDZ domain, a GTPase binding domain (GBD), a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, and a bZIP domain.

In another embodiment of this aspect and all other aspects provided herein, the molecular clamp comprises a nuclear localization signal (NLS).

In another embodiment of this aspect and all other aspects provided herein, at least one ligand binding domain binds to at least one ligand of a synthetic transcription factor.

In another embodiment of this aspect and all other aspects provided herein, the linker is a flexible linker.

In another embodiment of this aspect and all other aspects provided herein, the linker comprises a flexible glycine-serine (GS) linker repeat sequence.

In another embodiment of this aspect and all other aspects provided herein, the GS linker repeat sequence is repeated at least 5 times.

In another embodiment of this aspect and all other aspects provided herein, the GS linker repeat sequence is repeated 2-25 times (SEQ ID NO: 56).

In another embodiment of this aspect and all other aspects provided herein, the GS linker repeat sequence is repeated, 5 (SEQ ID NO: 57), 10 (SEQ ID NO: 58) or 20 (SEQ ID NO: 59) times.

In another embodiment of this aspect and all other aspects provided herein, the nuclear localization sequence is derived from an SV40 nuclear localization sequence.

In another embodiment of this aspect and all other aspects provided herein, the nuclear localization sequence comprises the sequence of: PKKKRKVGIHGVPGG (SEQ ID NO: 1) or PKKKRKVVE (SEQ ID NO: 2).

Also provided herein, in another aspect is vector comprising a nucleic acid encoding a molecular clamp as described herein.

In another embodiment of this aspect and all other aspects provided herein, the vector further comprises an inducible promoter operably linked to the nucleic acid encoding the molecular clamp.

Another aspect provided herein relates to a synthetic transcription factor (sTF) comprising: (i) a ligand, (ii) at least one DNA binding domain (DBD), and (iii) a transcriptional activator (TA) domain or a transcriptional repressor (TR) domain, wherein the DBD can bind to a target DNA binding motif (DBM) located upstream of a promoter operatively linked to a gene, and wherein the ligand can bind a ligand binding domain (LBD).

In one embodiment of this aspect and all other aspects provided herein, the at least one DNA binding domain (DBD) is an engineered zinc finger binding domain.

In another embodiment of this aspect and all other aspects provided herein, the zinc finger binding domain comprises at least one mutation compared to a wild-type zinc finger domain.

In another embodiment of this aspect and all other aspects provided herein, the sTF comprises a triple repeat zinc finger array.

In another embodiment of this aspect and all other aspects provided herein, the DBD binds to tandem DNA binding motifs (DBM) located upstream of a promoter.

In another embodiment of this aspect and all other aspects provided herein, the DBD is selected from any of: 43-8 (WT), 43-8 (3×), 43-8 (×4), 42-10 (WT), 42-10 (3×) or 42-10 (×4) of VP16.

In another embodiment of this aspect and all other aspects provided herein, the DBD binds to DNA binding motifs (DBM) comprising any of: DBM1 op, DBM2 op, and/or DBM3 op.

In another embodiment of this aspect and all other aspects provided herein, the ligand is located at the N-terminus of the TA or TR domain.

In another embodiment of this aspect and all other aspects provided herein, the sTF comprises, in the following order; N- to C-terminal: a nuclear localization sequence, a TA domain; a DNA binding domain (DBD); a linker (GSGSG (SEQ ID NO: 60)) and a ligand.

In another embodiment of this aspect and all other aspects provided herein, the sTF comprises in the following order; N- to C-terminal: a nuclear localization sequence, a ligand, a DNA binding domain (DBD), a TA domain; wherein a linker (GSGSG (SEQ ID NO: 60)) is located between the DNA binding domain and the ligand.

In another embodiment of this aspect and all other aspects provided herein, the TA domain is VP16 minimal activation domain.

In another embodiment of this aspect and all other aspects provided herein, the TA domain is selected from any of: VP16, VP64, p65.

In another embodiment of this aspect and all other aspects provided herein, the ligand is (i) located at the C-terminal end of the sTF, and/or (ii) selected from the group consisting of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), and VKEALV (SEQ ID NO: 8).

In another embodiment of this aspect and all other aspects provided herein, the sTF further comprises an epitope tag.

In another embodiment of this aspect and all other aspects provided herein, the epitope tag comprises a FLAG tag.

In another embodiment of this aspect and all other aspects provided herein, the sTF further comprises a nuclear localization sequence.

In another embodiment of this aspect and all other aspects provided herein, the nuclear localization sequence is derived from an SV40 nuclear localization sequence.

In another embodiment of this aspect and all other aspects provided herein, the nuclear localization sequence comprises the sequence of: PKKKRKVGIHGVPGG (SEQ ID NO: 1) or PKKKRKVVE (SEQ ID NO: 2).

In another embodiment of this aspect and all other aspects provided herein, the transcriptional activator (TA) domain or transcriptional repressor (TR) domain is located between the nuclear localization sequence and the at least one DNA binding domain (DBD).

Also provided herein, in another aspect, is a vector comprising a nucleic acid encoding a sTF as described herein.

In one embodiment of this aspect and all other aspects provided herein, the vector further comprises an inducible promoter operably linked to the nucleic acid encoding the sTF.

Another aspect provided herein relates to a molecular clamp and sTF binding pair comprising: a molecular clamp as described herein, wherein at least one of the ligand binding domains (LBD) of the molecular clamp can bind to the ligand of the sTF, thereby forming a specific binding pair.

Another aspect provided herein, relates to a vector comprising a nucleic acid encoding the molecular clamp as described herein, a nucleic acid encoding the sTF of claim 51, and at least one inducible promoter operably linked to the nucleic acid encoding the molecular clamp and/or the nucleic acid encoding the sTF.

In one embodiment of this aspect and all other aspects provided herein, the vector comprises a first inducible promoter operatively linked to the nucleic acid encoding the molecular clamp, and a second inducible promoter operatively linked to the nucleic acid encoding the sTF, wherein the first and second inducible promoters are different.

Also provided herein, in another aspect, is a system for regulating gene expression, the system comprising: (i) a molecular clamp as described herein, (ii) a synthetic transcription factor (sTF) of as described herein, and (iii) a gene expression unit.

In one embodiment of this aspect and all other aspects provided herein, the molecular clamp and the sTF are expressed from at least one vector.

In another embodiment of this aspect and all other aspects provided herein, the at least one vector further comprises an inducible promoter.

Also provided herein, in another aspect, is a method for regulating gene expression, the method comprising: providing a molecular clamp as described herein to a cell, contacting a synthetic transcription factor (sTF) as described herein with the molecular clamp in the presence of a gene expression unit comprising a DNA binding motif (DBM), whereby the molecular clamp and the sTF form a complex resulting in the sTF binding to the DBM in the gene expression unit and modulates gene expression.

In one embodiment of this aspect and all other aspects provided herein, the molecular clamp and/or the synthetic transcription factor are expressed from a vector.

In one embodiment of this aspect and all other aspects provided herein, the vector further comprises at least one inducible promoter.

In one embodiment of this aspect and all other aspects provided herein, expression of a gene product from the gene expression unit is regulated by providing an agent that modulates the at least one inducible promoter and thus controls expression of the scaffold protein and/or the sTF.

In one embodiment of this aspect and all other aspects provided herein, the vector comprises at least two inducible promoters.

In one embodiment of this aspect and all other aspects provided herein, the at least two inducible promoters are different promoters.

In one embodiment of this aspect and all other aspects provided herein, the agent(s) that modulate(s) the at least one inducible promoter comprise(s) a small molecule.

In one embodiment of this aspect and all other aspects provided herein, expression of the molecular clamp and the sTF are independently regulated by the at least two inducible promoters.

BRIEF DESCRIPTION OF THE FIGURES

FIG. 1A-FIG. 1E is a series of graphs and schematics showing the design scheme for assembly-mediated regulatory control of synthetic gene circuits. (FIG. 1A) Nodes in cellular networks use one-to-one regulatory interactions to execute simple computation-al tasks (top); cooperative interactions within multivalent assemblies enable complex, non-linear signal processing (bottom). (FIG. 1B) Design of synthetic TF regulatory assemblies. Complexes are built from interaction domains (ZF and PDZ) and their respective binding partners (DBM and PDZ ligand). Clamp-mediated synTF complex-formation (TA, transcriptional activator domain drives coding sequence transcription). Interaction affinities (Kt and Kp) and the number of repeated complex units (nc) determine thermodynamics of assembly. (FIG. 1C) In vitro assembly of purified cooperative complex components. Fluorescence anisotropy for synTF titration of DBM oligo probe (FITC labeled) was measured in the presence or absence of clamp (5 µM) and converted to fraction probe bound (Nb, synTFs with binding-deficient PDZ ligand mutants; nc, number of PDZ domains per clamp and DBMs probe). Points represent mean values for three measurements±SE. (FIG. 1D) Testing in vivo complex assembly in yeast using a synthetic gene circuit (GFP output). All genes are chromosomally-integrated (left; see e.g., Table 4). Small molecule-inducible expression systems (ncTET and ncZEV) control intracellular expression levels (see e.g., FIG. 8A, FIG. 8B) of synTF (induced by ATc, 2-500 ng/mL) and clamp (EST, 0.05-12.5 nM), respectively. Adjusting molecular features of assembly (Kt, Kp, nc) tunes overall circuit transfer function (right). (FIG. 1E) Parameterization of thermodynamic complex assembly model. Dose response data for circuit configurations with various Kt, Kp, nc values were fit to a thermodynamic model (see e.g., FIG. 10, FIG. 11); regression plot showing residual from fit are shown at the right. MAE, mean absolute error.

(FIG. 2A) Computational model-driven approach for exploring engineerable circuit behavior. The parts collection (left) defines available configuration space (middle: PDZ-ligand variants, Kp; synTF-DBM variants, Kt; clamp/synTF/DBM units, nc). The model (see e.g., FIG. 24-FIG. 26) computes input-output functions for this space, mapping the potential circuit behavior range (behavior space, right). (FIG. 2B) Programmed complex assembly enables tuning of single-input circuit dose response. For a single-input (2-node) circuit, synTF is induced by ATc addition (input node) and assembles with constitutively-expressed clamp to regulate GFP transcription (reporter node, left). In model-computed circuit behavior space (right), with different complex sizes indicated (nc). Five circuits with different assemblies (parameters: Kt affinity, Kp affinity, nc), were constructed and tested by inducing with ATc and measuring GFP by FACS after 16 h (below). Points represent mean values for three experiments±SE. (FIG. 2C) Programmed complex assembly enables tuning of two-input dose response between linear and non-linear computations. In a two-input circuit, synTF1 and synTF2 are induced by ATc and EST respectively (input nodes), assembling with constitutively-expressed clamp to regulate a downstream reporter node (left). Behavior space for the full set of available circuit configurations (center) are plotted as Kullback-Leibler divergence (DKL): "similarity" between model-computed output surfaces and archetypal Boolean AND and OR surfaces. Grey areas in the plot indicate regions of AND- and OR-like behavior. Selected circuits, with corresponding reporter complex parameters (Kt affinity, blue; Kp affinity, red; nc), were constructed and their 2D output surfaces experimentally measured (right) by inducing with ATc and EST and measuring GFP by FACS after 16 h.

(FIG. 3A) Tuning assembly cooperativity to control phases of circuit activation. synTF complex formation (left) determines circuit activation and deactivation kinetics in response to transient inducer input. Model-generated dose response profiles for two-node cascades regulated by non-cooperative two-TF (light grey) or cooperative four-TF (medium grey) assemblies are shown. Data from time course experiments using time-lapse microscopy in a microfluidic device (lines=mean fluor. cell$^{-1}$, shaded boundaries=±1 SD of population mean; $\tau_a$, activation half-time; $\tau_d$, deactivation half-time) were compared to model-fitted behavior (dots). (FIG. 3B) Cooperative assemblies enable activation and decay phases to be broadly and independently tuned for a three-node cascade motif. Model-predicted dynamic behavior space com-pares $\tau_a$ and $\tau_d$ for two-node and three-node motifs with (light grey) and without (dark grey) feedback ("No decay" indicates that configurations did not return to basal activity upon input removal). Highlighted circuits were tested by time-lapse microscopy/microfluidics (16 h Dox induction, light orange; lines=mean fluor. cell$^{-1}$ normalized to maximum output, shaded boundaries=±1 SD) and compared to model simulations (dots).

(FIG. 4A) Persistence filtering in cooperative assembly circuits. Computationally identified two-node motifs and three-node motifs reveal persistence filtering behavior—activation in response to an in-put of a sufficient duration (left). Circuits predicted to show linear (shallow) and nonlinear (sharp) filtering were tested in microfluidic time course experiments (lines=mean fluor. cell$^{-1}$, shaded region=±1 SD of cell population) by inducing with increasing Dox pulse lengths. "Temporal dose response" curves (line=measured data, dots=model) were generated from normalized time course output maxima. (FIG. 4B) Population-level temporal decoding of frequency input. Computationally identified two-node and three-node network motifs (left) were tested for frequency filtering behavior in microfluidic experiments. Mixed populations of yeast harboring low-pass filtering (LPF) and band-stop filtering (BSF) feed-forward circuits (driving mKate and GFP, respectively) were tested for their ability to decode a frequency-modulated square wave Dox pulses. Model-predicted frequency responses are shown next to each circuit. Experimentally measured frequency response is shown to the right. Maximum reporter output for each input frequency was normalized to maximum output for constitutive Dox. Representative mixed population fluorescence images are shown for highlighted frequencies: constitutive Dox (always ON'), medium frequency treatment (~10-5 Hz, 33%), and high frequency (~10-4 Hz, 33%). Cells without Dox treatment ('OFF') are shown to the right. In images, cells harboring LPF and BSF circuits are false-colored; cell boundaries were determined by segmentation software. Scale bar, 10 µM.

(FIG. 5A) Amino acid sequences common to all synthetic transcription factors (synTFs) and clamps used herein are shown. synTFs feature a FLAG epitope tag, nuclear localization sequence (derived from SV40 NLS), and VP16 transcriptional activation sequence upstream of a triple repeat zinc finger array. For zinc finger affinity alleles, mutated residues are highlighted in bold. Clamps contain the same N-terminal nuclear localization sequence as synTFs. An nc=2 clamp sequence is depicted, and the unit repeated in higher order clamps is highlighted. Flexible GS repeat linker sequences for both synTF (5AAs) and clamp (20 AAs) are depicted at lengths found to be optimal for complex assembly (see e.g., FIG. 9B). Yeast or E. coli optimized coding sequences were cloned into expression plasmids (see e.g., Table 2) at the indicated boundaries. For yeast, N-terminal boundaries directly abut promoter-associated start codons, while E. coli boundaries indicate fusion with expression vector MBP. FIG. 5A discloses SEQ ID NOS 121, 124-127 and 129, respectively, in order of appearance. (FIG. 5B) Promoter/coding sequence pairs used in circuit construction are shown. All combinations of promoter and coding sequence used in Table 2 yeast expression constructs are indicated (left). DNA sequences for pADH1 and (DBM)miniCyc1 promoters, and associated start codons are indicated (right). (DBM)miniCyc1 with 43-8 DNA binding motif (DBM) sites for an nc=2 configuration is depicted. The highlighted unit gets repeated in the 5' direction to create higher order assemblies. Kozak sequence is underlined and translational start (ATG) is indicated. FIG. 5B discloses SEQ ID NO: 130.

FIG. 6 discloses SEQ ID NOS 99-102, 131, 104-108, respectively, in order of appearance.

(FIG. 7A) Competition binding experiments were conducted to measure binding constants for ligand affinity variants. At concentrations of MBP-PDZ and probe at which half-maximal binding was observed (data not shown), 43-8 synTFs were titrated with appended ligands of various affinities. Anisotropy increases accompanying displacement of the probe by the competitor was measured, and competitor ligand Kd values were extracted by fitting data (converted to fraction probe bound) to a cubic equation describing competitive binding. FIG. 7A discloses SEQ ID NO: 8. FIG. 7B shows a table of competitor ligand Kd values collected for both syntrophin and erbin PDZ domains. FIG. 7B discloses SEQ ID NOS 3-5, 7, 6, 8, 132-134, 22 and 23, respectively, in order of appearance. (see e.g., Table 7).

FIG. 8A-FIG. 8B is a series of schematics and graphs showing the characterization of inducible and constitutive expression systems. Experiments were conducted to obtain model input parameters for circuit component expression systems. FIG. 8A shows the amino acid sequence of the ZEV transcription factor involved in the ncZEV activation system. A 97-4 zinc finger was appended with the estrogen receptor harboring a C-terminal VP16 activation domain. Expression of the resulting coding sequence was driven by the pTEF1 promoter (−417 to 0). FIG. 8A discloses SEQ ID NO: 135. (FIG. 8B) ncZEV does not affect transcription of the reporter in the absence of its target synTF1. Strains were constructed with different combinations of: reporter ((p(43-8)4miniCyc1-GFP), ZEV expression cassette, ZEV-inducible clamp, and ZEV-inducible synTF1. All four strains were grown with and without 25 nM EST. Mean GFP fluorescence values were measured by flow cytometry. Error bars represent standard deviation.

FIG. 9A shows the workflow for processing flow cytometry data. In order to determine mean reporter fluorescence intensities, yeast cell populations are gated by forward (FSC) and side scatter (SSC) resulting in ~10,000 events (center). Geometric mean fluorescence intensities are then determined for gated populations (right). Data shown are representative fluorescence distributions for a yeast strain with ncZEV controlling a synTF and corresponding nc=4 reporter (−/+25 nM EST). (FIG. 9B) Flexible interdomain linkers of both synTF and clamp proteins were screened to identify combinations of linker lengths that yield high transcriptional synergy (see FIG. S1 for component sequence details). synTF expression is controlled by ATc-inducible ncTET and clamp is either constitutively expressed or absent (see e.g., FIG. 8A-FIG. 8B); synTF/clamp complex assembles as an nc=2 complex, driving expression of a GFP reporter (top left). GS-repeat linkers interconnect ZF and ligand domains in the synTF, and PDZ domains in the clamp (bottom left). Three different synTF linker lengths (Kt=13.6 nM) were tested against three lengths in the clamp, for three different Kp values (right). Configurations yielding high transcriptional synergy produce high GFP output when synTF is induced and clamp is present (+1+), relative to when components are expressed individually. Grey box highlights the synTF/clamp linker pair exhibiting the highest transcriptional synergy from the screen ((GS)x=glycine-serine linker of length x). FIG. 9B discloses "$(GS)_5$" as SEQ ID NO: 57, "$(GS)_{10}$" as SEQ ID NO: 58, and "$(GS)_{20}$" as SEQ ID NO: 59.

FIG. 12A-FIG. 12B is a series of schematics and graphs showing a summary of thermodynamic model parameters. FIG. 12A shows a comparison of experimentally-measured and model-fitted parameter values. Interaction affinities (ZF-DNA, PDZ-lig) were measured using in vitro binding assays (see e.g., FIG. 6, FIG. 7A, FIG. 7B). Expression parameters were obtained using dose response measurements of the ncTET and ncZEV expression systems (see e.g., FIG. 8A-FIG. 8B). Fitted parameters were obtained by performing a global fit on a set of experimental data of two-input circuits (see e.g., FIG. 1D, FIG. 1E). The two-input circuits consisted of ncTET and ncZEV driving expression of synTF and clamp (for different nc, Kt, and Kp), with complex formation inducing expression of GFP. FIG. 12B shows goodness of fit, evaluated by mean absolute error, between model and data for different choices of parameter fitting bounds on affinity values (left). A 4-fold bound was used in the model fits. Model-fitted affinity values for Kt (middle) and Kp (right) for different choices of parameter fitting bounds (4-fold bound is highlighted in grey).

FIG. 13A-FIG. 13D is a series of schematics and graphs showing use of the model to explore cooperative complex modulation of dose response behavior. The thermodynamic model was used to map circuit dose response behavior onto configuration space for a single-input, two-node circuit where output is regulated by cooperative complex assembly. FIG. 13A is a schematic defining configuration space. ATc induces expression of a synTF (from the ncTET promoter), which forms an assembly with constitutively expressed clamp (pADH1), driving GFP reporter expression (left). Enumeration of available configurations for this assembly (855) and curation (removal of unproductive configurations) resulted in a final set of 603 (right). Using the model, dose responses were simulated for each configuration ([ATc] range=$10^{-1}$-$10^4$ ng/mL). Hill functions were fit to extract $EC_{50}$ ([ATc] at half-maximal response) and $n_H$ (Hill coefficient) values for each dose response. (FIG. 13B) The single-input behavior space of $EC_{50}$ vs. $n_H$. Each point corresponds to a specific circuit configuration (scatter). Above the morphospace is a parameter frequency analysis of values of ($K_p$, $K_t$, $n_c$) for three different regions of the scatter, corresponding to non-cooperative (left box), nonlinear (center box), and highly nonlinear responses (right box). Shown to the right is the range of values for each parameter's frequency analysis distribution. A set of circuit configurations (circles) distributed throughout the behavior space were constructed and used to experimentally test the model predicted dose response behaviors. (FIG. 13C) Table summarizing the 14 circuit configurations highlighted in (FIG. 13B), and their corresponding model-predicted and experimentally-obtained $n_H$ values. (FIG. 13D) Correlation between model predictions and experimental data for the 14 circuit configurations. The top scatter compares $n_H$, while the bottom compares $_{EC50}$. MAE=mean absolute error.

FIG. 14A-FIG. 14C is a series of schematics and graphs showing experimental verification of two-input circuit behavior space. (FIG. 14A) A set of circuits were constructed to test the ability of the model to predict steady state behavior for two-input circuits containing two different synTF species (left). Circuits were selected that were broadly distributed throughout the predicted behavior space (right), including within regions thought to contain Boolean-like behavior (AND- and OR-gates). Circuits were induced with saturating concentrations of ATc and EST, grown for 18 h, and measured by flow cytometry. (FIG. 14B) Model and experimental fluorescence values were normalized to calculated and observed maximum outputs. Circuit configurations highlighted in grey are shown in FIG. 2C. FIG. 14C shows correlation between model predictions vs. experimental data for two-input circuits. The top scatter compares divergence (DKL) of model and data to an ideal AND-gate, while the bottom compares divergence (DKL) of model and data to an ideal OR-gate. DKL is computed as described herein. MAE=mean absolute error. Dark grey points in top graph and corresponding MAE refer to five configurations predicted to have the best AND-like logic. Light grey points in top graph and MAE refer to all other configurations.

FIG. 15A shows the testing of model predictions in strains harboring three-node cascades (with and without feedback), predicted to have a wide range of activation and deactivation times (circles enumerate the 24 circuits on the behavior space). Grey region highlights circuits whose dynamics are outside the microfluidic measurement window. (FIG. 15B) Microfluidic experiments were used to generate GFP trajectories for each circuit in response to a 16 h Dox pulse (10 μg/mL). The measured GFP traces (lines), model predictions (dots), and corresponding assembly configuration parameters for each circuit are shown below the behavior space. No FB, three-node cascade without feedback; FB type 1, feedback architecture in which only synTF2 (dark grey middle dot) is in a clamp complex at the second circuit node; FB type 2, feedback architecture in which synTF1 (medium grey middle dot) and synTF2 (dark grey middle dot) are in clamp complex together at the second circuit node. (FIG. 15C) Comparison of model predicted and experimentally measured activation (Ta, left) and decay times (Td, right). Only circuits with measurable Td were included in the right scatter plot. MAE=mean absolute error. Dark grey dots and light grey dots refer to three-node cascades with and without feedback, respectively. (FIG. 15D) Distributions compare the difference between model and data for six time points across all measurements.

FIG. 16A-FIG. 16C is a series of graphs showing quantification of cell size and growth rate for strains analyzed in microfluidic devices. (FIG. 16A) Mean cell area (top) and cell area coefficient of variation (bottom) quantified over time using segmentation software (CellTracer) for all 24 strains analyzed in FIG. 15A-FIG. 15D. (FIG. 16B) Distribution of growth rates for all strains analyzed in FIG. 15A-FIG. 15D. Growth rates for each strain were calculated using cell counts at each time point. The average growth rate across all strains (0.0029 $min^{-1}$) is indicated (grey dashed line), along with the model dilution rate for GFP (0.003 $min^{-1}$, black dashed line). (FIG. 16C) Comparison of average growth rate and circuit dynamics for all strains analyzed in FIG. 15A-FIG. 15D. Linear regression with associated r-squared values are also shown.

FIG. 18 is a series of graphs showing data from the final time point of a competition experiment. FIG. 18 exposes the poor fitness of strains expressing a high affinity synTF while strains with a low affinity synTF with or without clamp show no fitness cost compared to a no-synTF control. Fluorescent reporter expression of strains with low affinity synTFs+clamp is comparable to those with high affinity synTFs.

DETAILED DESCRIPTION

Figure 1D:
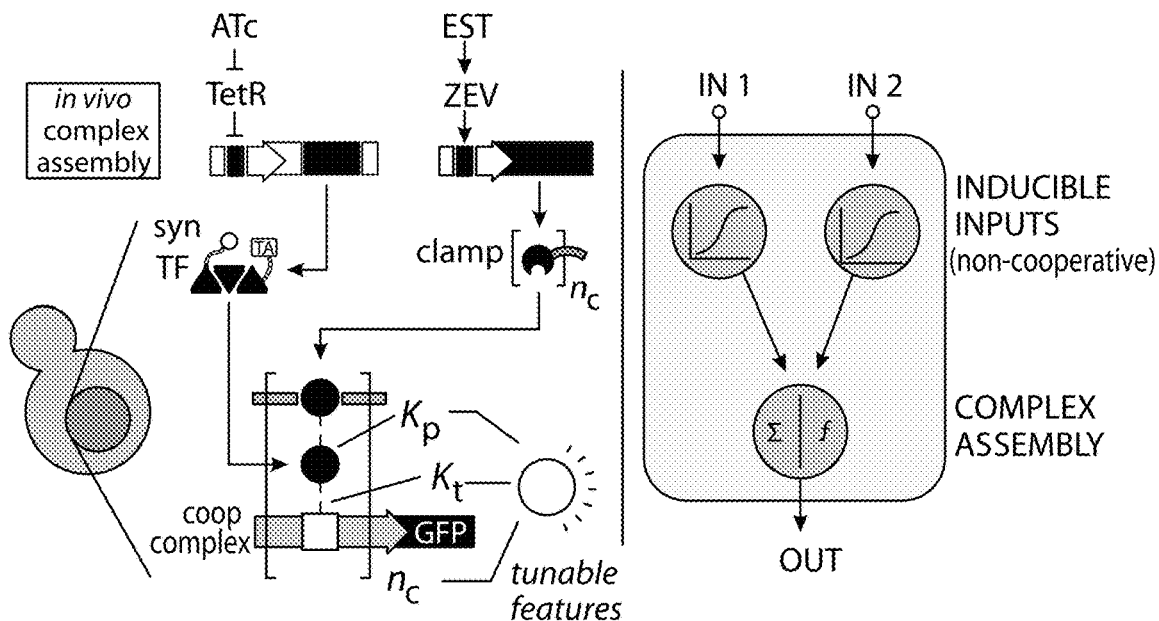

The methods and compositions described herein are based, in part, on the discovery that synthetic molecular clamps can be used to bind and localize transcription factors (e.g., synthetic transcription factors) to the promoter region of DNA, thus regulating expression of a gene product. Stated differently, described herein are compositions and methods related to a modular molecular complex whereby synthetic transcription factors (sTFs) are organized and held in position by a molecular clamp (MC), such that the sTFs can efficiently bind to target DNA sequences at DNA binding motifs (DBMs), thereby allowing efficient transcription of the downstream transgene. Importantly, by specifying the number of assembly units (e.g., number of sTFs), and/or the strength of binding between the complexes (e.g., binding affinity of the ligand binding domain (LBD) of the molecular clamp for the ligand on the sTF and/or binding affinity of the DNA binding domain (DBD) of the sTF for the DNA binding motif (DBM) located upstream (e.g., 5') of the promoter), it enables predictable fine-tuning of gene expression of the GOI, as well as linear and non-linear gene expression from single or multiple inputs.

Provided herein are engineered "multi-domain scaffold proteins" also referred to as "molecular clamps" that can bind to one or more synthetic transcription factors (sTFs) and form the scaffolding basis for the basal transcription machinery. In addition, provided herein are engineered synthetic transcription factors (sTFs) that can be used in conjunction with the engineered scaffold proteins/molecular clamps in a system to regulate gene expression. The regulatory molecules described herein can be used to construct synthetic biomolecular networks and control cellular behavior.

The technology described herein relates to systems, methods and compositions for highly-cooperative molecular complexes in cells that can be used to regulate, and specifically control or tailor gene expression in a cell. In particular, the technology described herein relates to multi-domain molecular clamps that comprise multiple ligand binding domains that can selectively bind to a ligand present on an engineered synthetic transcription factor (herein referred to as "sTF"), resulting in the organization and assembly of components of the sTF such that the sTF can bind to a target DNA binding motif (herein referred to as DBM) function upstream of a promoter, and initiate gene expression.

A molecular clamp described herein comprises n ligand binding domains (herein referred to as "LBD"), where n=1-50, where each LBD binds to a ligand of a sTF, such that the sTFs are recruited and organized and/or assembled at multiple DNA binding motifs (DBMs) located upstream of a promoter operatively linked to a gene. Such a system provides a highly sophisticated, tightly regulated, control of gene expression. A molecular clamp described herein has the advantage over previous systems in that multiple LBDs can bind to multiple sTFs organizing the arrangement of sTFs in series, where they can bind to a series of DBM upstream of a promoter.

In one embodiment, when a molecular clamp recruits and assembles one or more sTFs to one or more DBMs upstream of a promoter, gene expression occurs by bringing a transcription activator (TA) domain of the sTF into proximity of the transcription initiation complex, thereby initiating gene expression. Such an embodiment serves as an "ON" switch. In an alternative embodiment, when a molecular clamp recruits and assembles one or more sTFs to one or more DBMs upstream of a promoter, gene expression can be inhibited by bringing a transcription repressor (TR) domain of the sTF into proximity of the transcription initiation complex, thereby preventing or inhibiting gene expression from the promoter. Such an embodiment serves as an "OFF" switch.

Importantly, the system disclosed herein enables a modular approach to controlling and regulating gene expression, for example, by changing one or more components of the system, such as for example, one or more of: the affinity of the ligand binding domain (LBD) for the ligand, the affinity of the DNA binding Domain (DBD) to the target DNA binding motif (DBM), the number of DBD located upstream of a promoter, the combination of sTFs recruited by the molecular clamp (i.e., whether they comprise transcription activators or repressors), one can tightly control the level of gene expression, which is desirable for numerous applications, including but not limited to therapeutic cell engineering, gene therapy, CRISPR applications and the like.

Additionally, gene expression from the system disclosed herein is also dependent on multi-input signals or control—that is, gene expression is dependent on the expression of both the molecular clamp AND the sTF (referred to herein as "AND input" or "2-input" control of gene expression), providing an additional level of control to gene expression. In some embodiments, a 3-input control can be used, for example, but not limited to, a signal inducing the expression of molecular probe, AND a signal inducing the expression of one sTF, AND/OR a signal inducing the expression of a second transcription factor.

Definitions

As used herein, a "synthetic transcription factor" or "synTF" or "sTF" refers to an engineered DNA binding protein that targets specific DNA sequences and can activate or repress gene expression. In one embodiment, as used herein, a "synthetic transcription factor" or "synTF" or "sTF" refers to an engineered chimeric protein comprising a DNA binding domain (DBD) that binds to a target specific DNA sequences referred to as a DNA binding motif (DBM), a ligand and an effector domain.

As used herein, the term "DNA binding domain" or "DBD" refers to an independently folded protein domain that contains at least one structural motif that recognizes double- or single-stranded DNA. A DBD can recognize a specific DNA sequence (a recognition sequence or DNA binding motif (DBM) or have a general affinity to DNA. Some DNA-binding domains may also include nucleic acids in their folded structure. Examples for DBDs include the helix-turn-helix motif, the zinc finger (ZF) domain, the basic leucine zipper (bZIP) domain, the winged helix (WH) domain, the winged helix-turn-helix (wHTH) domain, the High Mobility Group box (HMG)-box domains, White-Opaque Regulator 3 domains and oligonucleotide/oligosaccharide folding domains. The helix-turn-helix motif is commonly found in repressor proteins and is about 20 amino acids long. The zinc finger domain is generally between 23 and 28 amino acids long and is stabilized by coordinating zinc ions with regularly spaced zinc-coordinating residues (either histidines or cysteines).

The term "zinc finger" or "ZF" refers to a protein having DNA binding domains that are stabilized by zinc. The individual DNA binding domains are typically referred to as "fingers." A zinc finger protein has at least one finger, typically two fingers, three fingers, or six fingers. Each finger binds from two to four base pairs of DNA, typically three or four base pairs of DNA (the "subsite"). A zinc finger protein binds to a nucleic acid sequence called a target site. Each finger typically comprises approximately 30 amino acids as a zinc-chelating, DNA-binding subdomain. An exemplary motif characterizing one class of these proteins (C2H2 class) is -Cys-(X)2-4-Cys-(X)12-His-(X)3-5-His (where X is any amino acid) (SEQ ID NO: 61). Studies have demonstrated that a single zinc finger of this class consists of an alpha helix containing the two invariant histidine residues coordinated with zinc along with the two cysteine residues of a single beta turn (see, e.g., Berg & Shi, Science 271:1081-1085 (1996)).

The "physical separation" between two DNA-binding domains (DBD) refers to the distance between two domains when they are bound to their respective target sites. This distance is used to determine a minimum length of a linker. A minimum length of a linker is the length that would allow the two domains to be connected without providing steric hindrance to the domains or the linker (a minimum linker). A linker that provides more than the minimum length is a "flexible linker."

As used herein, the term "ligand" refers to a substance that forms a complex with a biomolecule to serve a biological purpose. For the purposes of the disclosure herein, the ligand serves as a key and the ligand binding domain as the key hole to which the two entities attach and connect. In protein-ligand binding, the ligand is usually a molecule, e.g., peptide which binds to a site on a target ligand receptor protein. The binding of the ligand typically results in a change of conformational isomerism (conformation) of the target ligand receptor protein. In DNA-ligand binding studies, the ligand can be a small molecule, ion, or protein, which binds to the DNA double helix. The relationship between ligand and binding partner is a function of charge, hydrophobicity, and molecular structure. The instance of binding occurs over an infinitesimal range of time and space, so the rate constant is usually a very small number.

An "effector domain" is also referred to interchangeably as a "regulatory domain" and refers to a protein or a protein domain that has an activity such as transcriptional modulation activity, DNA modifying activity, protein modifying activity and the like when tethered to a DNA binding domain, i.e., a zinc finger protein. Examples of regulatory domains include proteins or effector domains of proteins, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressor, or epigenetic effector proteins.

The term "transcriptional activator domain" or "TA domain" refers to a polypeptide or peptide that binds to promoters and recruits RNA polymerase to directly initiate transcription.

The term "transcriptional repressor domain" or "TR domain" refers to a polypeptide or peptide that sterically hinder transcriptional initiation by RNA polymerase.

The term "epigenetic effector domain" or "EE domain" refers to a polypeptide or peptide that affects the methylation status of the gene or promoter. A EE domain can recruit DNA histone methyltransferase proteins or demethylation proteins, thereby increasing or decreasing methylation of proximally located DNA or RNA, respectively. Examples of EE domains include proteins that (1) catalyze chemical modifications of DNA or histone residues (e.g. DNA methyltransferases, histone methyltransferases, histone acetyltransferases) or (2) remove chemical modifications (e.g. DNA demethylases, DNA di-oxygenases, DNA hydroxylases, histone demethylases, histone deacetylases).

The term "DNA binding motif" or "DBM" or a nucleic acid "target", "target site" or "target sequence" or "DNA target sequence", or "DBM sequence" as used herein, is a nucleic acid sequence to which a DNA binding domain (DBD) (often one or more ZF motifs) of a sTF of the disclosure will bind, provided that conditions of the binding reaction are not prohibitive. A DBM sequence may be a nucleic acid molecule or a portion of a larger polynucleotide. In accordance with the disclosure, a DBM sequence for a DBD of a sTF of the disclosure may comprise a single contiguous nucleic acid sequence. These terms may also be substituted or supplemented with the terms "binding site", "binding sequence", "recognition site" or recognition sequence", which are used interchangeably.

The terms "molecular clamp" or "MC" or "molecular probe" are used interchangeably herein and refer to at least two Ligand binding domains (LBD) connected in series with a linker peptide. The linker can be a flexible or rigid linker peptide. The LBD can be the same or different LBDs. In some embodiments, the LBD is a PDZ domain. The LBD of the molecular clamp binds to a cognate ligand on a synthetic transcription factor (sTF).

As used herein, a "ligand binding domain (LBD)" refers to a domain responsible for the binding of ligands, including peptide ligands, small molecules and hormones. LBDs have been shown to be involved in hormone binding, homo- and/or heterodimerization, formation of heat-shock protein complexes and transcriptional activation and repression.

As used herein, the term "conjugate" or "conjugation" refers to the attachment of two or more entities to form one entity. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are not described in detail herein.

The term "linker" refers to a polymer of amino acids to form a peptide that attaches or facilitates the functional connection of two moieties together. Linkers can have virtually any amino acid sequence, and can be rigid or flexible. As disclosed herein, linkers can be used to join at least two LBD together to form a molecular clamp as disclosed herein. Additionally, as disclosed herein, linkers can be used to join a ligand to a DBD of the sTF, and/or for joining an effector domain (e.g., TA domain, TR domain or EE domain) to a DBD of the sTF. In some embodiments, linkers will have a sequence that results in a generally flexible peptide. Small amino acids, such as glycine and alanine, are of use in creating a flexible peptide. A peptide linker or typically ranges from about 2 to about 50 amino acids in length, which is designed to facilitate the functional connection of two polypeptides into a linked fusion polypeptide. The term "functional connection" denotes a connection that maintains proper folding of the polypeptides in a three dimensional structure that allows the linked fusion polypeptide to mimic some or all of the functional aspects or biological activities of the protein(s) from which its polypeptide constituents are derived. The term functional connection also denotes a connection that confers a degree of stability required for the resulting linked fusion polypeptide to function as desired. The creation of linker sequences is routine to those of skill in the art. A variety of different linkers are commercially available and are considered suitable for use according to the present invention.

As used herein, the term "interaction" when used in the context of a Ligand binding domain (LBD) and its ligand, refers to the binding between the LBD and its ligand as a result of the non-covalent bonds between the ligand-binding site (or fragment) of the LBD and the receptor-binding site (or fragment) of the ligand. In the context of the DNA binding domain (DBD) and the DNA binding motif (DBM) sequence, it refers to the binding between the DBD and its target nucleic acid sequence (DBM) as a result of the non-covalent bonds between the DNA-binding site (or fragment) of the DBD and the protein-binding site of the nucleic acid sequence of the DBM. In the context of two entities, e.g., molecules or proteins, having some binding affinity for each other, the term "interaction" refers to the binding of the two entities as a result of the non-covalent bonds between the two entities. A term "interaction", "complexing" and "bonding" are used interchangeably when used in the context of a LBD or ligand receptor and its ligand and in the context of two binding entities.

As used herein, "binding" refers to a non-covalent interaction between macromolecules (e.g. between DBD of the sTF and a DBM nucleic acid target site or sequence, or between the ligand of the sTF and a LBD of the molecular clamp). In some cases, binding will be sequence-specific, and can be specific for one or more specific nucleotides (or base pairs) (e.g., such as between the binding of the DBD of the sTF and the DBM sequence). In some cases, binding will be specific on one or more specific amino acids (e.g., such as between the binding of the ligand of the sTF and the LBD of the molecular clamp). It will be appreciated, however, that not all components of a binding interaction need to be sequence-specific (e.g. non-covalent interactions with phosphate residues in a DNA backbone). Binding interactions between a DBM nucleic acid sequence and DBD of the sTF of the disclosure may be characterized by binding affinity and/or dissociation constant (Kt). Binding interactions between a ligand binding domain (LBD) and ligand of the sTF of the disclosure may be characterized by binding affinity and/or dissociation constant (Kp). A suitable dissociation constant for a DBD of the disclosure binding to its target DBM sequence may be in the order of 1 µM or lower, 1 nM or lower, or 1 pM or lower.

The term "affinity" refers to the strength of binding of two binding partners, such as a sTF to a given DNA binding motif (Kt) or a molecular clamp to a given ligand on the sTF (Kp). Typically, as the binding affinity increases, the Kt or Kp will reduce in value. Affinity can refer to the strength of binding of a sTF as described herein to DNA, RNA, and/or even proteins. In some embodiments, a sTF of the disclosure is designed or selected to have sequence-specific dsDNA-binding activity. For example, the DBM site for a particular DBD is a sequence to which the DBD concerned is capable of nucleotide-specific binding. It will be appreciated, however, that depending on the amino acid sequence of a DBM, the DBD of the sTF may bind to or recognize more than one target DBM sequence, although typically one sequence will be bound in preference to any other recognized sequences, depending on the relative specificity of the individual non-covalent interactions. Thus, in some embodiments, the sTF will bind the preferred sequence with high affinity and non-target sites with low affinity (or will not bind at all: "lack of affinity"). In some embodiments, the sTFs as described herein can be designed or selected to have a desirable affinity for a given target (e.g., high affinity vs. low affinity sequence specific dsDNA-binding). It will be appreciated that high affinity binding of a sTF to a DNA binding site will deter other endogenous or synthetic transcription factors with lower affinity from displacing the high affinity binding partner to the site. Thus, selecting for high affinity binding vs. low affinity binding between two binding partners can be used to fine-tune the desired modulation of gene expression and/or the reversibility of the gene expression by modulating the strength of interaction between the two binding partners. Generally, high affinity binding comprises a dissociation constant (Kt or Kp) of 1 nM or lower, 100 pM or lower; or 10 pM or lower. In some embodiments, a DBD of a sTF of the disclosure binds to a specific DBM target sequence with a dissociation constant (Kt) of 500 nM or lower, or 100 nM or lower, or 1 nM or lower, or 1 pM or lower, or 0.1 pM or lower, or even 10 fM or lower. In some embodiments, a ligand binding domain (LBD) of the molecular clamp of the disclosure binds to a specific ligand of a sTF with a dissociation constant (Kp) of 100 µM or lower, or 1 µM or lower, or 1 nM or lower, or 1 pM or lower, or 0.1 pM or lower, or even 10 fM or lower.

By "non-target" it is meant that the nucleic acid sequence concerned is not appreciably bound by the relevant DBD of the sTF. In some embodiments it may be considered that, where a DBD of the sTF as described herein has a known sequence-specific target sequence, all other nucleic acid sequences may be considered to be non-target sequences. From a practical perspective it can be convenient to define an interaction between a non-target sequence and a particular DBD of the sTF as being sub-physiological (i.e. not capable of creating a physiological response under physiological target sequence/DBD concentrations). For example, if any binding can be measured between the DBD of the sTF and the non-target sequence, the dissociation constant (Kd) is typically weaker than 1 µM, such as 10 µM or weaker, 100 µM or weaker, or at least 1 mM.

The term "high affinity" refers to a binding affinity correlating with a lower value range Kd (e.g., Kt or Kp) value, e.g., a lower Kd value than that for a low-affinity binding agent. In some embodiments, a high-affinity DBD of a sTF of the disclosure binds to a specific DBM target sequence with a dissociation constant (Kt) of 50 nM or lower, or 40 nM or lower, or 30 nM or lower, or 20 nM or lower, or 10 nM or lower, or 5 nM or lower, or 4 nM or lower, or 3 nM or lower, or 2 nM or lower, or 1 nM or lower, or 0.5 nM or lower, or 0.1 nM or lower, or 0.01 nM or lower (see e.g., Example 8, Table 6). In one embodiment, a sTF that binds to a DBD with high affinity comprises a Kt in the range of 0.5-50 nM (e.g., 0.5-40 nM, 0.5-30 nM, 0.5-20 nM, 0.5-10 nM, 0.5-5 nM, 0.5-4 nM, 0.5-3 nM, 0.5-2 nM, 1-50 nM, 1-40 nM, 1-30 nM, 1-20 nM, 1-10 nM, 1-5 nM, 1-4 nM, 1-3 nM, 1-2 nM, 5-50 nM, 5-40 nM, 5-30 nM, 5-20 nM, 5-10 nM, 10-50 nM, 10-40 nM, 10-30 nM, 10-20 nM, 25-50 nM, 25-40 nM, 25-30 nM, 30-50 nM, 30-40 nM, 40-50 nM or any range therebetween. In some embodiments, a high-affinity ligand binding domain (LBD) of the molecular clamp of the disclosure binds to a specific ligand of a sTF with a dissociation constant (Kp) of 1 µM or lower, or 0.9 µM or lower, or 0.8 µM or lower, or 0.7 µM or lower, or 0.6 µM or lower, or 0.5 µM or lower, or 0.4 µM or lower, or 0.3 µM or lower, or 0.2 µM or lower, or 0.1 µM or lower, or 0.05 µM or lower, or 0.01 µM or lower (see e.g., Example 8, Table 7). In one embodiment, a sTF that binds to a molecular clamp with high affinity comprises a Kp in the range of 0.01-1 µM, 0.01-0.5 µM, 0.01-0.1 µM, 0.01-0.05 µM, 0.05-1 µM, 0.05-0.5 µM, 0.1-1 µM, 0.1-0.5 µM, 0.2-1 µM, 0.2-0.5

µM, 0.3-1 µM, 0.3-0.5 µM, 0.4-1 µM, 0.4-0.5 µM, 0.5-1 µM, 0.5-0.75 µM or any range therebetween. In some embodiments, a high-affinity sTF as described herein comprises 3 arginine-to alanine (R2A) mutations in the arginine backbone of the sTF.

The term "low affinity" refers to a binding affinity correlating with a higher Kd value or range of values (e.g., Kt or Kp) value, e.g., a higher Kd value than a that of a sTF that binds with high-affinity to its binding partner. In some embodiments, a low-affinity DBD of a sTF of the disclosure binds to a specific DBM target sequence with a dissociation constant (Kt) of 5 nM or higher, or 10 nM or higher, or 50 nM or higher, or 100 nM or higher, or 200 nM or higher, or 300 nM or higher, or 400 nM or higher, or 500 nM or higher (see e.g., Example 8, Table 6). In one embodiment, a sTF that binds a DBD with low affinity comprises a Kt in the range of 5-500 nM (e.g., between 10-500 nM, 10-400 nM, 10-300 nM, 10-200 nM, 10-100 nM, 10-50 nM, 10-25 nM, 25-500 nM, 25-400 nM, 25-300 nM, 25-200 nM, 25-100 nM, 25-50 nM, 50-500 nM, 50-400 nM, 50-300 nM, 50-200 nM, 50-100 nM, 100-500 nM, 100-400 nM, 100-300 nM, 100-200 nM, 200-500 nM, 200-400 nM, 200-300 nM, 300-500 nM, 300-400 nM, 400-500 nM or any range therebetween. In some embodiments, a low-affinity ligand binding domain (LBD) of the molecular clamp of the disclosure binds to a specific ligand of a sTF with a dissociation constant (Kp) of 100 µM or higher, or 90 µM or higher, or 80 µM or higher, or 70 µM or higher, or 60 µM or higher, or 50 µM or higher, or 40 µM or higher, or 30 µM or higher, or 20 µM or higher, or 10 µM or higher, or 9 µM or higher, or 8 µM or higher, or 7 µM or higher, or 6 µM or higher, or 5 µM or higher, or 4 µM or higher, or 3 µM or higher, or 2 µM or higher, or 1 µM or higher (see e.g., Example 8, Table 7). In one embodiment, a ligand of a sTF that binds to a molecular clamp with low affinity comprises a Kp in the range of 1 µm-100 µm (e.g., between 1-75 µm, 1-50 µm, 1-40 µm, 1-30 µm, 1-20 µm, 1-10 µm, 1-5 µm, 1-2 µm, 5-100 µm, 5-75 µm, 5-50 µm, 5-40 µm, 5-30 µm, 5-20 µm, 5-10 µm, 10-100 µm, 10-75 µm, 10-50 µm, 10-25 µm, 10-20 µm, 10-15 µm, 25-100 µm, 25-75 µm, 25-50 µm, 50-75 µm, 50-100 µm or any range therebetween. In one embodiment, a low-affinity sTF comprises four arginine to alanine (R2A) mutations in the arginine backbone of the sTF.

The term "amino acid" in the context of the present disclosure is used in its broadest sense and is meant to include naturally occurring L α-amino acids or residues. The commonly used one and three letter abbreviations for naturally occurring amino acids are used herein: A=Ala: C=Cys; D=Asp; E=Glu; F=Phe; G=Gly; H=His; I=Ile; K=Lys; L=Leu; M=Met; N=Asn; P=Pro; Q=Gln; R=Arg; S=Ser; T=Thr; V=Val; W=Trp; and Y=Tyr (Lehninger, A. L., (1975) Biochemistry, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesized compounds having properties known in the art to be characteristic of an amino acid, such as β-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

The term "peptide" as used herein (e.g., in the context of a sTF or ligand) refers to a plurality of amino acids joined together in a linear or circular chain. The term oligopeptide is typically used to describe peptides having between 2 and about 50 or more amino acids. Peptides larger than about 50 amino acids are often referred to as polypeptides or proteins. For purposes of the present disclosure, however, the term "peptide" is not limited to any particular number of amino acids, and is used interchangeably with the terms "polypeptide" and "protein".

The terms "nucleic acids" and "nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., inosine and xanthine, non-natural sugars, e.g., 2'-methoxy ribose, or non-natural phosphodiester linkages, e.g., methylphosphonates, phosphorothioates and peptides.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene", "cDNA", and "mRNA". As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C—C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the latter being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the latter being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence that is "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e g enhancers, silencers, promoters, terminators etc.), which may be adjacent to or distant to the relevant coding sequence, as well as the coding and/or transcribed regions encoding the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors of utility in the methods and engineered genetic counters described herein are often in the form of "plasmids," which refer to circular double stranded DNA loops which, in their vector form are not bound to the chromosome.

The terms "synthetic gene circuit" or "response promoter element" are used interchangeably herein and refer to a nucleic acid construct containing a promoter sequence that has at least one target DNA binding motif (DBM) sequence operably linked upstream of the promoter sequence such that the target DBM sequence confer a responsive property to the promoter when the DBM sequence is bound by its respective DNA binding domain (DBD) of the synthetic transcription factor, the responsive property being whether gene transcription initiation from that promoter is enhanced or repressed when the upstream nearby DBM target sequences are bound by a DBD of the synthetic transcription factor. There may be more than one DBM target sequence operably linked upstream of the promoter sequence. When there is one DBM target sequence, the promoter is referred to a "1×" promoter, where the "1×" refers to the number of DBM target sequence present in the promoter construct. For example, a 4× responsive promoter would be identified as having four DBM target sequences in the engineered response promoter construct, and the four DBM target sequences are upstream of the promoter sequence.

As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. In some embodiments, the promoter is constitutive. In some embodiments, the promoter is inducible. In some embodiments, the promoter is a mammalian promoter. As discussed herein, a promoter can be applied in any type of cassettes. Promoters are located near the transcription start sites of genes, on the same strand and upstream on the DNA.

As used herein, an "inducible promoter" is one that is characterized by initiating or enhancing transcriptional activity when in the presence of, influenced by or contacted by an inducer or inducing agent. An "inducer" or "inducing agent" may be endogenous or a normally exogenous compound or protein that is administered in such a way as to be active in inducing transcriptional activity from the inducible promoter.

The term "operatively linked" or "operable linkage" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences may also be positioned between the two sequences. The insertion of sequences may also lead to the expression of fusion proteins, or serve as ribosome binding sites. In some embodiments, the expression construct, consisting of a linkage of promoter and nucleic acid sequence to be expressed, can exist in a vector integrated form and be inserted into a plant genome, for example by transformation.

As used herein, the term "operably linked" when used in context of the DBM target sequences described herein or the promoter sequence (RNA polymerase binding site) in a nucleic acid construct or synthetic gene circuit, a responsive reporter, and in an engineered transcription unit means that the DBM target sequences and the promoters are in-frame and in proper spatial and distance away from a nucleic acid coding for a protein or peptide or an RNA to permit the effects of the respective binding by transcription factors or RNA polymerase on transcription.

As used herein, the term "responsive" in the context of a promoter of a synthetic gene circuit, the term refers to whether gene transcription initiation from the promoter is enhanced or repressed when upstream nearby DBM target sequences are bound by their DBD of the synthetic transcription factors.

The terms "promoter," "promoter element," or "promoter sequence" are equivalents and as used herein, refer to a DNA sequence which when operatively linked to a nucleotide sequence of interest is capable of controlling the transcription of the nucleotide sequence of interest into mRNA.

A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulatable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter may be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term "minimal promoter" as used herein refers to the minimal nucleic acid sequence comprising a promoter element while also maintaining a functional promoter. A minimal promoter may comprise an inducible, constitutive or tissue-specific promoter.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of an RNAi molecule, which refers to expression and transcription of an RNAi agent such as siRNA, shRNA, and antisense DNA but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a non-translated RNA, in the sense or antisense direction. The nucleic acid construct as disclosed herein can be chimeric, meaning that at least one of its components is heterologous with respect to at least one of its other components.

The term "leakiness" or "leaky" as used in reference to "promoter leakiness" refers to some level of expression of the nucleic acid sequence which is operatively linked to the promoter, even when the promoter is not intended to result in expression of the nucleic acid sequence (i.e., when the promoter is in the "off" state, a background level of expression of the nucleic acid sequence which is operatively linked to such promoter exists). In one illustrative example using inducible promoters, for example a Tet-on promoter, a leaky promoter is where some level of the nucleic acid sequence expression (which is operatively linked to the Tet-on promoter) still occurs in the absence of the inducer agent, tetracycline. Typically, most inducible promoters and tissue-specific promoters have approximately 10%-30% or 10-20% unintended or background nucleic acid sequence expression when the promoter is not active, for example, the background of leakiness of nucleic acid sequence expression is about 10%-20% or about 10-30%. As an illustrative example using a tissue-specific promoter, a "leaky promoter" is one in which expression of the nucleic acid sequence occurs in tissue where a tissue-specific promoter is not active, i.e. expression occurs in a non-specific tissue. Stated in another way using a kidney-specific promoter as an example; if at least some level of the nucleic acid sequence expression occurs in at least one tissue other than the kidney, where the nucleic acid sequence is operably linked to a kidney specific promoter, the kidney specific promoter would be considered a leaky promoter The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

The terms "nucleic acid construct" or "engineered construct" or "synthetic gene circuit" as used herein refer to a nucleic acid at least partly created by recombinant methods. The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are described, for example, in Maniatis T, Fritsch EF and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

The term "in vivo" refers to assays or processes that occur in or within an organism, such as a multicellular animal. In some of the aspects described herein, a method or use can be said to occur "in vivo" when a unicellular organism, such as bacteria, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing an engineered genetic counter in a non-cellular system, such as a media not comprising cells or cellular systems, such as cellular extracts.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

A. System for Cooperative sTF Assemblies

The technology described herein relates to systems, methods and compositions for highly-cooperative molecular complexes in cells that can be used to regulate and specifically control or tailor gene expression in a cell. That is, the technology described herein relates to a system for cooperative assembly of multiple transcription factors for controlled regulation of gene expression. Referring to an exemplary embodiment described in the schematic shown in FIG. 1B and FIG. 10, the inventors have developed a system where multiple synthetic transcription factors (sTFs) can bind to tandem DNA binding motifs (DBMs) where the DBMs are located upstream of a core promoter or regulatory element, thereby activating or repressing the transcription of the gene operatively linked to the promoter. A molecular clamp protein serves to effectively tether or assemble at least two sTF (e.g., so they are assembled in series). The molecular clamp provides a system that allows for cooperative and fine tuning of gene expression using an interconnected assembly of synthetic transcription factors (sTFs).

Figure 17:
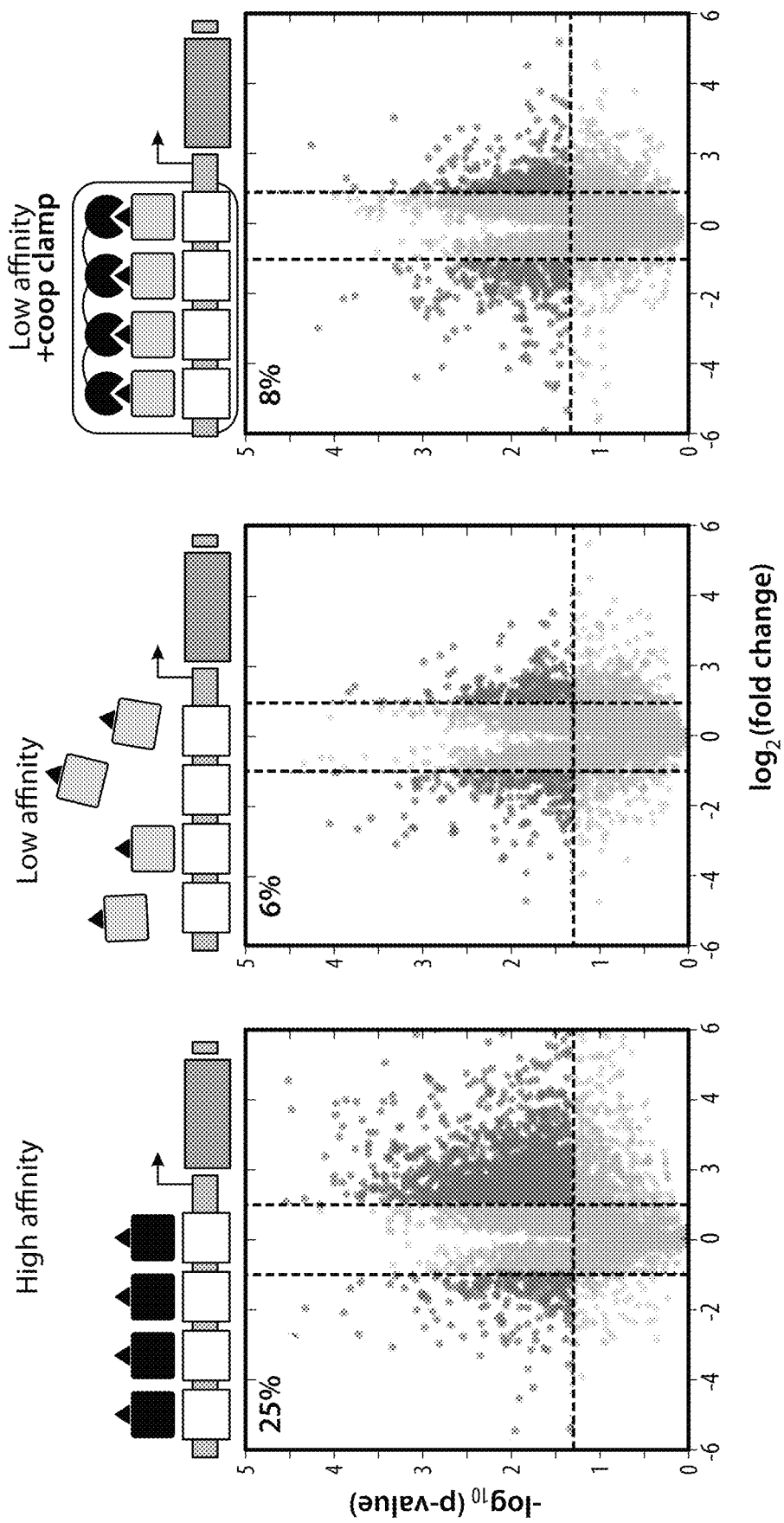
FIG. 17 is a series of schematics and graphs. RNA-seq highlights consistent low misregulation of the endogenous transcriptome from a low affinity synTF with or without the addition of clamp. Expression of a high affinity synTF imparts increased misregulation. X-axis is fold change relative to a no-synTF control.

Moreover, in addition to modulating the number of DBMs upstream of the promoter or regulatory region and the number of sTF, one can further fine-tune the regulation of gene expression by adjusting the binding affinities and/or strength of the binding of sTF to the DBMs, and/or the binding of the LBD of the molecular clamp to the ligand of the sTF. As such, by specifying the strength and/or the number of assembly of sTF subunits, it enables single and multiple-input control of gene expression, as well as predictive and fine-tuning of the expression of the GOI. Stated differently, adjusting either the number of clamp/sTF/DBM repeats ($n_c$), and/or the affinity of the sTF-DBM interactions (Kt) and/or sTF-molecular clamp interactions ($K_p$) (see e.g., FIG. 10), one can modulate and fine-tune the cooperative assembly and resulting gene expression. Moreover, as shown in the schematic of FIG. 17, in some embodiments, the interaction of the DBD of the sTF can have a high affinity or low affinity for binding to the DNA Binding motifs (DBM) (e.g., low or high Kt). As shown in FIG. 17, in some embodiments, the molecular clamp serves to stabilize the low affinity sTFs thereby regulating initiation (or repression) of gene expression that would not otherwise occur in the absence of the molecular clamp. As shown in FIG. 18, the assembly of the molecular clamp and low affinity sTF results in significantly increased gene expression as compared to the low affinity sTFs alone, and overlaps with the level of gene expression achieved with high affinity sTFs in the absence of the molecular clamp.

In summary, the components of system for cooperative sTF assemblies comprise:

(i) Synthetic gene circuit: A synthetic gene circuit comprises at least two DNA binding motifs (DBM) upstream (e.g., 5') to a promoter or other regulatory element, where the promoter or regulatory element is operatively linked to a gene of interest (GOI). The nucleotide sequence of one or more of nucleotides of one or more DBMs can be modified to change (e.g., increase or decrease) the binding affinity for binding of the DBD of the sTF (see e.g., FIG. 6). The synthetic gene circuit can be represented as comprising: [DBM]$_n$-promoter/regulatory element-GOI.

Figure 5A:
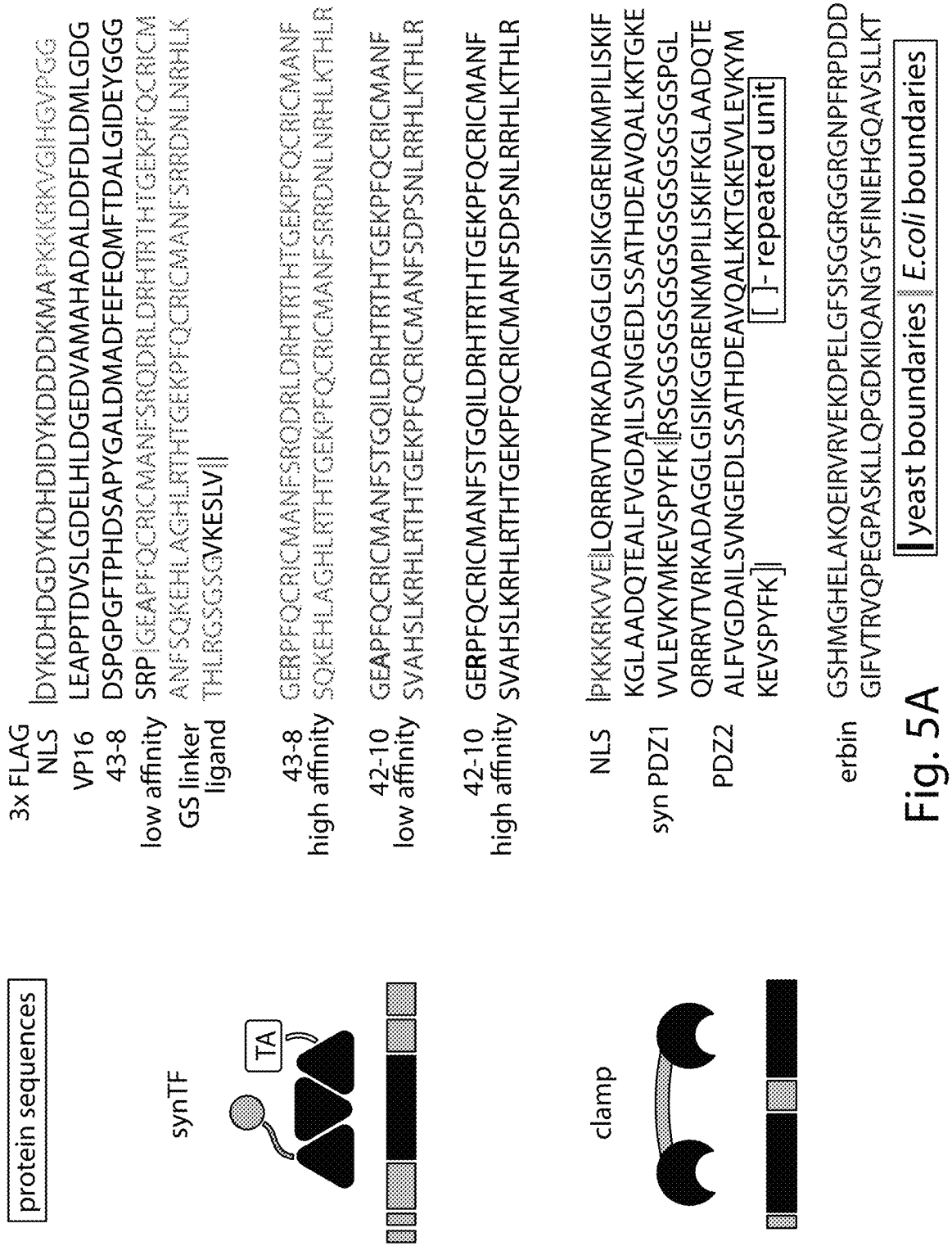
FIG. 5A-FIG. 5B is a series of schematics showing the sequence details of synthetic promoter and protein components. Plasmid constructs listed in Table 2 are composed entirely of molecular components described in FIG. 5A-FIG. 5B.

(ii) Synthetic transcription factor (sTF): A sTF comprises a ligand, a DNA binding domain (DBD), which binds to the DBM on the synthetic gene circuit, and a Transcriptional activator (TA) or Transcriptional repressor (TR). The ligand binds to the Ligand Binding domain (LBD) on the molecular clamp, and the Transcriptional activator (TA) or Transcriptional repressor (TR) turn on ("ON switch") or turn OFF ("OFF switch") gene expression at the promoter or regulatory element operatively linked to the GOI. Importantly, the sTF can be modified to alter binding to the DBM and/or the LBD. For example, as shown in FIG. 5A, the DBD can have low or high affinity for the DBM. Similarly, in some embodiments, the ligand is a peptide ligand, and the peptide ligand can be modified or have one or more amino acids changed to alter affinity of binding to the LBD of the molecular clamp (see, e.g., FIG. 7A-FIG. 7B). In some embodiments, the ligands of the sTF can be selected for high affinity, or low affinity for the LBD, such that competive binding with a competitor ligand can be used to detach the sTF from the molecular clamp and thereby turn off gene expression (see, e.g., FIG. 7B). The sTF can be represented as a complex comprising: a ligand, a DBD and a TA or TR, but does not necessarily need to be in a specified order. That is, the DBD may have the ligand linked and a TA or TR attached, or the ligand may be attached to the TA or TR, which in turn is attached to the DBD.

(iii) Molecular clamp (MC): A molecular clamp (MC) comprises multiple linked ligand binding domains (LBD). Each LBD binds to a ligand of sTF. The LBD can be modified to alter the binding affinity for the ligand of the sTF. Additionally, the clamp linker between each LBD domain can be modified in length to modify the strength of the sTF-molecular clamp interaction ($K_p$) (e.g., see FIG. 9A). In some embodiments, the clamp linker between LBD domains is a repeating unit of $(GS)_n$ amino acids, where n=1-5 (SEQ ID NO: 62), or 6-10 (SEQ ID NO: 63), or 11-20 (SEQ ID NO: 64), or 21-30 (SEQ ID NO: 65). In some embodiments, the clamp linker is a repeating unit of $(GS)_{1-5}$ (SEQ ID NO: 62), or $(GS)_{6-10}$ (SEQ ID NO: 63), or $(GS)_{11-20}$ (SEQ ID NO: 64), or $(GS)_{21-30}$ (SEQ ID NO: 65), or any integer between 1-30. The molecular clamp can be represented as comprising: [LBD]-[linker-LBD]$_n$, where n=1, 2, 3, 4, 5, 6, 7, 8, 9, 10, 11, 12, 13, 14, 15, 16, 17, 18, 19, 20, 21, 22, 23, 24, 25, 26, 26, 28, 29, 30, 31, 32, 33, 34, 35, 36, 37, 38, 39, 40, 41, 42, 43, 44, 45, 46, 47, 48, 49, or 50 or any integer between 1-50.

Accordingly, the technology described herein relates to multi-domain molecular clamps (MCs) that comprise multiple ligand binding domains (LBDs) that can selectively bind to a ligand present on an engineered synthetic transcription factors (sTFs), resulting in the organization and assembly of components of the sTF such that the sTF can bind to a target DNA binding motif (herein referred to as DBM) function upstream of a promoter, and initiate gene expression.

More specifically, the inventors have demonstrated, by using a molecular clamp comprising multiple ligand binding domains (herein referred to as "LBD") each of which bind to a ligand of a sTF, a method for organizing and assembling multiple sTFs to multiple DNA binding motifs (DBMs) that are located upstream of a promoter operatively linked to a gene, thereby resulting in a sophisticated, tightly regulated, control of gene expression. Using such a mechanism, the molecular clamp, with multiple LBDs can bind to multiple sTFs organizing the sTFs to be arranged in series, where they can bind to a series of DBM upstream of a promoter.

In one embodiment, when a molecular clamp recruits and assembles one or more sTFs to one or more DBMs upstream of a promoter, gene expression occurs by bringing a transcription activator (TA) domain of the sTF into proximity of the transcription initiation complex, thereby initiating gene expression. Such an embodiment serves as an "ON" switch. In an alternative embodiment, when a molecular clamp recruits and assembles one or more sTFs to one or more DBMs upstream of a promoter, gene expression can be inhibited by bringing a transcription repressor (TR) domain of the sTF into proximity of the transcription initiation complex, thereby preventing or inhibiting gene expression from the promoter. Such an embodiment serves as an "OFF" switch.

Importantly, the system disclosed herein enables a modular approach to controlling and regulating gene expression, for example, by changing one or more components of the system, such as for example, one or more of: the affinity of the ligand binding domain (LBD) for the ligand (e.g., $K_p$), the affinity of the DNA binding Domain (DBD) to the target DNA binding motif (DBM) (e.g., $K_t$), the number of DBD located upstream of a promoter, the combination of sTFs recruited by the molecular clamp (i.e., whether they comprise transcription activators or repressors), one can tightly control the level of gene expression, which is desirable for numerous applications, including but not limited to therapeutic cell engineering, gene therapy, CRISPR applications and the like.

Additionally, gene expression from the system disclosed herein is also dependent on multi-input signals or control— that is, gene expression is dependent on the expression of both the molecular clamp AND the sTF (referred to herein as "AND input" or "2-input" control of gene expression), providing an additional level of control to gene expression. In some embodiments, a 3-input control can be used, for example, but not limited to, a signal inducing the expression of molecular probe, AND a signal inducing the expression of one sTF, AND/OR a signal inducing the expression of a second transcription factor.

In all aspects, a molecular clamp useful in the systems, compositions and methods disclosed herein comprises n, where n is an integer between 1 and 50 ligand binding domains (LBD), where each ligand binding domain is connected to at least one other LBD by a linker, and at least one LBD can bind to the ligand of the at least one sTF; where when the molecular clamp and at least one sTF are both present in a cell, at least one ligand binding domain binds to the ligand of the sTF, wherein if the sTF comprises a TA domain, the TA domain recruits the RNA pol II machinery to the promoter, thereby turning on gene expression ("ON switch"), or alternative embodiments, if the sTF comprises a TR domain, the RNA pol II machinery is prevented or inhibited from binding to the promoter, thereby inhibiting gene expression. ("OFF Switch")

In all aspects, a sTF useful in the systems, compositions and methods disclosed herein comprises a ligand, a DNA binding domain (herein referred to as a "DBD") which binds to the DNA binding motif (DBM), and a transcription activator (TA) domain or transcriptional repressor (TR) domain. In all aspects, a molecular clamp useful in the systems, compositions and methods disclosed herein comprises n, where n is an integer between 1 and 50 ligand binding domains (LBD), where each ligand binding domain is connected to at least one other LBD by a linker, and at least one LBD can bind to the ligand of the at least one sTF; where when the molecular clamp and at least one sTF are both present in a cell, at least one ligand binding domain binds to the ligand of the sTF, wherein if the sTF comprises a TA domain, the TA domain recruits the RNA pol II machinery to the promoter, thereby turning on gene expression ("ON switch"), or alternative embodiments, if the sTF comprises a TR domain, the RNA pol II machinery is prevented or inhibited from binding to the promoter, thereby inhibiting gene expression. ("OFF Switch").

Such systems can be designed for use with specific synthetic transcription factors and cognate molecular clamps, where the molecular clamp comprises a ligand binding domain and the synthetic transcription factor comprises a ligand binding domain (or vice versa).

In some embodiments, such systems or molecular clamp/sTF cognate pairs are provided in a kit.

B. Synthetic Transcription Factors (sTFs)

Provided herein are synthetic transcription factors (sTF) that mimic the function of endogenous eukaryotic transcription factors in regulating gene expression. Such synthetic transcription factors can be engineered and arrayed with a given DNA specificity to form the basis for synthetic and customizable transcriptional modules, which can be used to control eukaryotic transcription. In some embodiments, the sTFs as described herein comprise orthogonally-functioning synthetic TFs that activate cognate synthetic promoters, using engineered zinc-finger arrays that direct protein-DNA recognition.

In general, the synthetic transcription factors provided herein comprise at least three different domains: (i) at least one DNA binding domain (DBD), (ii) a transcriptional activator (TA) domain or transcriptional repressor (TA) domain, and (iii) a ligand. These domains can be designed in any desired configuration e.g., for controlling expression of a particular gene. In one embodiment, the synthetic transcription factors described herein comprise, in the following order from N- to C-terminal: a nuclear localization sequence, a ligand, a DNA binding domain (DBD) a transcriptional activator domain, wherein a linker (GSGSG) (SEQ ID NO: 60) is located between the DNA binding domain and the ligand. In alternative embodiments, the synthetic transcription factors described herein comprise, in the following order from N- to C-terminal: a nuclear localization sequence, a ligand, a DNA binding domain, a transcriptional activator domain, wherein a linker (GSGSG) (SEQ ID NO: 60) is located between the DNA binding domain (DBD) and the ligand.

In some embodiments, the sTF comprise a DNA binding domain (DBD) which is a synthetic zinc finger (ZF) proteins fused to a transcriptional activator (TA) or transcriptional repressor (TR) domain.

(i) DNA Binding Domain (DBD)

In some embodiments, the sTF comprises a DNA binding domain which is a zinc finger protein. A zinc finger (ZF) protein is a finger-shaped fold in a protein that permits it to interact with nucleic acid sequences such as DNA and RNA. Such a fold is well known in the art. The fold is created by the binding of specific amino acids in the protein to a zinc atom. Zinc-finger containing proteins (also known as ZF proteins) can regulate the expression of genes as well as nucleic acid recognition, reverse transcription and virus assembly.

A ZF is a relatively small polypeptide domain comprising approximately 30 amino acids, which folds to form an α-helix adjacent an antiparallel β-sheet (known as a ββα-fold). The fold is stabilized by the co-ordination of a zinc ion between four largely invariant (depending on zinc finger framework type) Cys and/or His residues, as described further below. Natural zinc finger domains have been well studied and described in the literature, see for example, Miller et al., (1985) EMBO J. 4: 1609-1614; Berg (1988) Proc. Natl. Acad. Sci. USA 85: 99-102; and Lee et al., (1989) Science 245: 635-637. A ZF domain recognizes and binds to a nucleic acid triplet, or an overlapping quadruplet (as explained below), in a double-stranded DNA target sequence. However, ZFs are also known to bind RNA and proteins (Clemens, K. R. et al. (1993) Science 260: 530-533; Bogenhagen, D. F. (1993) Mol. Cell. Biol. 13: 5149-5158; Searles, M. A. et al. (2000) J. Mol. Biol. 301: 47-60; Mackay, J. P. & Crossley, M. (1998) Trends Biochem. Sci. 23: 1-4).

In one embodiment, as used herein, the term "zinc finger" (ZF) or "zinc finger motif" (ZF motif) or "zinc finger domain" (ZF domain) refers to an individual "finger", which comprises a beta-beta-alpha (ββα)-protein fold stabilized by a zinc ion as described elsewhere herein. The Zn-coordinated ββα protein fold produces a finger-like protrusion, a "finger." Each ZF motif typically includes approximately 30 amino acids. The term "motif" as used herein refers to a structural motif. The ZF motif is a supersecondary structure having the ββα-fold that stabilized by a zinc ion.

In one embodiment, the term "ZF motif" according to its ordinary usage in the art, refers to a discrete continuous part of the amino acid sequence of a polypeptide that can be equated with a particular function. ZF motifs are largely structurally independent and may retain their structure and function in different environments. Because the ZF motifs are structurally and functionally independent, the motifs also qualify as domains, thus are often referred as ZF domains. Therefore, ZF domains are protein motifs that contain multiple finger-like protrusions that make tandem contacts with their target molecule. Typically, a ZF domain binds a triplet or (overlapping) quadruplet nucleotide sequence. Adjacent ZF domains arranged in tandem are joined together by linker sequences to form an array. A ZF peptide typically contains a ZF array and is composed of a plurality of "ZF domains", which in combination do not exist in nature. Therefore, they are considered to be artificial or synthetic ZF peptides or proteins.

$C_2H_2$ zinc fingers ($C_2H_2$-ZFs) are the most prevalent type of vertebrate DNA-binding domain, and typically appear in tandem arrays (ZFAs), with sequential $C_2H_2$-ZFs each contacting three (or more) sequential bases. $C_2H_2$-ZFs can be assembled in a modular fashion. Given a set of modules with defined three-base specificities, modular assembly also presents a way to construct artificial proteins with specific DNA-binding preferences.

ZF-containing proteins generally contain strings or chains of ZF motifs, forming an array of ZF (ZFA). Thus, a natural ZF protein may include 2 or more ZF, i.e. a ZFA consisting of 2 or more ZF motifs, which may be directly adjacent one another (i.e. separated by a short (canonical) linker sequence), or may be separated by longer, flexible or structured polypeptide sequences. Directly adjacent ZF domains are expected to bind to contiguous nucleic acid sequences, i.e. to adjacent trinucleotides/triplets. In some cases cross-binding may also occur between adjacent ZF and their respective target triplets, which helps to strengthen or enhance the recognition of the target sequence, and leads to the binding of overlapping quadruplet sequences (Isalan et al., (1997) Proc. Natl. Acad. Sci. USA, 94: 5617-5621) By comparison, distant ZF domains within the same protein may recognize (or bind to) non-contiguous nucleic acid sequences or even to different molecules (e.g. protein rather than nucleic acid).

Engineered ZF-containing sTF proteins are chimeric proteins composed of a DNA-binding zinc finger protein domain (ZF protein domain) and another domain through which the protein exerts its effect (effector domain). The effector domain may be a transcriptional activator or repressor, a methylation domain or a nuclease. DNA-binding ZF protein domain would contain engineered zinc finger arrays (ZFAs).

In some embodiments, the DBD of the sTF as disclosed herein comprises non-natural and suitably contain 3 or more, for example, 4, 5, 6, 8, 9, 10, 11, 12, 13, 14, 15, 16, 17, 18 or more (e.g. up to approximately 30 or 32) ZF motifs arranged adjacent one another in tandem, forming arrays of ZF motifs or ZFA. Particularly ZF-containing sTF proteins of the disclosure include at least 3 ZF, at least 4 ZF motifs, at least 5 ZF motifs, or at least 6 ZF motifs, at least 7 ZF motifs, at least 8 ZF motifs, at least 9 ZF motifs, at least 10 ZF motifs, at least 11 or at least 12 ZF motifs; and in some cases at least 18 ZF motifs. In other embodiments, the DBD of the sTF contains up to 6, 7, 8, 10, 11, 12, 16, 17, 18, 22, 23, 24, 28, 29, 30, 34, 35, 36, 40, 41, 42, 46, 47, 48, 54, 55, 56, 58, 59, or 60 ZF motifs. The ZF-containing sTF of the disclosure bind to contiguous orthogonal target nucleic acid binding sites. That is, the DBD of the sTF comprise a ZF domain that binds orthogonal target nucleic acid sequences or DBMs.

In some embodiments, the DBD comprises a Cys2-His2 zing-finger domain. The Cys2-His2 zinc-finger domain is the most common DNA-binding motif in the human proteome and a single zinc finger contains approximately 30 amino acids. Zinc finger domains typically function by binding three consecutive base pairs of DNA via interactions of a single amino acid side chain per base pair. The modular structure of zinc-finger motifs permits the generation of several domains in series (e.g., zinc finger arrays), allowing for the recognition and targeting of extended sequences in multiples of three nucleotides. As a result, a zinc-finger protein can be designed to bind with high affinity and specificity to essentially any target site in a cellular genome.

Transcription factors (TFs) of virtually all taxa utilize Cys2-His2 zinc finger (ZF) domains to solve the combinatorial problem of DNA recognition and binding. ZF engineering can be used to purposefully re-engineer ZF DNA binding specificities to recognize a wide variety of different sequences and to covalently link them together into multi-finger arrays capable of recognizing longer DNA sequences. Notably, with Oligomerized Pool Engineering (OPEN)[17,18] and other "context-dependent" engineering methods, customized multi-finger arrays have been successfully generated to create ZF nucleases (ZFNs) for highly-targeted genome modification" and artificial TFs for modulating endogenous gene targets.

ZFs represent conserved functional domains underlying the design and function of many TFs as well as versatile scaffolds for rational engineering. These properties make ZF domains attractive candidates as the basis for synthetic elements that can not only direct transcriptional connections, but also program higher-order transcriptional and cellular outputs.

In some embodiments, the at least one DNA binding domain comprises a zinc finger domain. In some embodiments, the synthetic transcription factors described herein comprise 1, 2, 3, 4, or even 5 zinc finger domains. In one embodiment, the at least one DNA binding domain comprises a zinc finger array (e.g., a triple zinc finger array). Zinc finger arrays that recognize a unique or specific site can be designed based on the specificity of each one of the e.g., three zinc fingers in the array. Thus, in certain embodiments, the at least one DNA binding domain comprises an engineered zinc finger binding domain or engineered zinc finger array. Engineered zinc finger domains or arrays can comprise one or more mutations compared to a wild-type zinc finger. In some embodiments, the synthetic transcription factors described herein comprise a triple repeat zinc finger array.

In some embodiments, each DBD of a synTF as disclosed herein can comprise six to eight ZF motifs. The ZF motif is a small protein structural motif consisting of an α helix and an antiparallel β sheet (αββ) and is characterized by the coordination of one zinc ion by two histidine residues and two cysteine residues in the motif in order to stabilize the finger-like protrusion fold, the "finger". In some embodiments, the ZF motif in the DBD of a sTF disclosed herein is a Cys2His2 zinc finger motif. In one embodiment, the ZF motif comprises, consists essentially of, or consists of a peptide of formula II: [X0-3CX1-5CX2-7-(helix)-HX3-6H] (SEQ ID NO: 66) wherein X is any amino acid, the subscript numbers indicate the possible number of amino acid residues, C is cysteine, H is histidine, and (helix) is a-six contiguous amino acid residue peptide that forms a short alpha helix. The helix is variable. This short alpha helix forms one facet of the finger formed by the coordination of the zinc ion by two histidine residues and two cysteine residues in the ZF motif. For each DBD, the six to eight ZF motifs therein are linked to each other, $NH_2$— to COOH— terminus by a peptide linker having about four to six amino acid residues to form an array of ZF motifs or ZFs. The finger-like protrusion fold of each ZF motif interacts with and binds nucleic acid sequence. Approximately a peptide sequence for two ZF motif interacts with and binds a ~six-base pair (bp) nucleic acid sequence. The multiple ZF motifs in a DBD form finger-like protrusions that would make contact with an orthogonal target DNA sequence. Hence, for example, a DBD with six ZF motifs or finger-like protrusions (a six-finger ZFs) interacts and binds a ~18-20 bp nucleic acid sequence, and an eight-finger ZFA would bind a ~24-26 bp nucleic acid sequence.

In another embodiment of any aspect described herein, the ZF motif of the DBD comprises a peptide of formula III: [X3CX2CX5-(helix)-HX3H] (SEQ ID NO: 67) wherein X is any amino acid, the subscript numbers indicate the possible number of amino acid residues, C is cysteine, H is histidine, and (helix) is a-six contiguous amino acid residue peptide that forms a short alpha helix.

In one embodiment of any aspect described herein, for a DBD of a sTF disclosed herein comprises a single ZF motif, the ZF protein domain comprises, consists essentially of, or consists of a sequence: N'-PGERPFQCRICMRNFS-(Helix 1)-HTRTHTGEKPFQCRICMRNFS-(Helix 2)-HLRTH-TGSQK PFQCRICMRNFS-(Helix 3)-HTRTHTGEK PFQCRICMRNFS-(Helix 4)-HLRTH-TGSQKPFQCRICMRNFS-(Helix 5)-HTRTHTGEK PFQCRICMRNFS-(Helix 6)-HLRTHLR-C' (SEQ ID NO: 149), wherein the (Helix) is a-six contiguous amino acid residue peptide that forms a short alpha helix. In one embodiment, all six of the helix 1, 2, 3, 4, 5 and 6 are distinct and different from each other. In another embodiment, all six of the helix 1, 2, 3, 4, 5 and 6 are identical to each other. Alternatively, at least two of the six helices are identical and the same with each other. In other embodiments, at least three of the six helices in a DBD are identical and the same with each other, at least four of the six helices in a DBD are identical and the same with each other, or at least five of the six helices in a DBD of the sTF are identical and the same with each other.

In some embodiments of any aspect described herein, the helices of the six to eight ZF motifs of an individual DBD disclosed herein are selected from the six-amino acid residue peptide sequences disclosed in one of the Groups 1-11 of U.S. Pat. No. 10,138,493, which is incorporated herein in its entirety by reference. Combinations of arrangements of ZF motifs for DBD for sTF are also disclosed in U.S. Pat. No. 10,138,493, which is incorporated herein in its entirety by reference.

The DNA binding domains (DBD) of the synthetic transcription factors described herein bind and recognize targeted tandem DNA binding motifs, which are typically upstream of a promoter where the control of gene expression is desired. In some embodiments, the DNA binding domain binds to DNA binding motifs comprising any of: DBM1 op, DBM2 op, or DBM3 op. In some embodiments of any aspect described herein, in the DBD of the synTF as described herein are specifically designed to bind orthogonal target DNA sequences of SEQ ID NOS: 81-91 of U.S. Pat. No. 10,138,493, which is incorporated herein in its entirety by reference.

In some embodiments of any aspect described herein, the ZF backbone or ZF framework can be mutated to modulate affinity. In some embodiments, the mutations can be in regions of the ZF framework that mediate non-specific interactions with the phosphate backbone of the nucleic acid target. As a non-limiting example, a ZF framework can comprise at least 1 mutation to at least 10 mutations. As a non-limiting example, a mutation can comprise an arginine to alanine mutation, also referred to herein as a Z-to-A mutation or a Z2A mutation. As a non-limiting example, a ZF framework can comprise 1 Z2A mutation, 2 Z2A mutations, 3 Z2A mutations, 4 Z2A mutations, 5 Z2A mutations, 6 Z2A mutations, 7 Z2A mutations, 8 Z2A mutations, 9 Z2A mutations, or at least 10 Z2A mutations. In some embodiments, high affinity ZF frameworks have 3 Arginine-to-Alanine (R2A) mutations. In some embodiments, low affinity ZF frameworks have 4 R2A mutations. (see e.g., Khalil et al., Cell. 150, 647-658 2012, which is incorporated by reference in its entirety). Any such mutation(s) can be introduced into any of the ZF compositions as described herein (e.g., sTFs).

(ii) Transcription Activator Domain or Transcription Repressor Domains

Synthetic transcription factors as described herein, can essentially comprise a transcriptional regulator domain, (herein sometimes referred to as an "effector domain") that regulates transcription of a gene. Such transcriptional regulator domains include transcriptional activator (TA) domains and transcriptional repressor (TR) domains. In some embodiments, the effector domain, or transcriptional regulator domain is an epigenetic effector (EE) domain. In some embodiments, the effector domain, (e.g., TA domain, TR domain or epigenetic effector (EE) domain) is fused or covalently attached (e.g., cross-linked) to a DBD of the sTF.

In one embodiment, the synthetic transcription factor is a transcription activator and comprises a transcription activator element (TAE).

In one embodiment of any aspect described herein, in the sTF as described herein, the effector domain is a transcription activating domain or a transcription repressor domain. For example, the effector domain is selected from the group consisting of a Herpes Simplex Virus Protein 16 (VP16) activation domain; an activation domain consisting of four tandem copies of VP16, a VP64 activation domain; a p65 activation domain of NFκB; an Epstein-Barr virus R transactivator (Rta) activation domain; a tripartite activator consisting of the VP64, the p65, and the Rta activation domains, the tripartite activator is known as a VPR activation domain; a histone acetyltransferase (HAT) core domain of the human E1A-associated protein p300, known as a p300 HAT core activation domain; a Krüppel associated box (KRAB) repression domain; a Repressor Element Silencing Transcription Factor (REST) repression domain; a WRPW motif (SEQ ID NO: 68) of the hairy-related basic helix-loop-helix repressor proteins, the motif is known as a WRPW (SEQ ID NO: 68) repression domain; a DNA (cytosine-5)-methyltransferase 3B (DNMT3B) repression domain; and an HP1 alpha chromoshadow repression domain.

In another embodiment of any aspect described herein, the effector domain of the synTF as described herein, is an epigenetic effector domain. For example, an epigenetic effector (EE) domain is selected from one or more chromatin regulating enzymes that (1) catalyze chemical modifications of DNA or histone residues (e.g. DNA methyltransferases, histone methyltransferases, histone acetyltransferases) or (2) remove chemical modifications (e.g. DNA demethylases, DNA di-oxygenases, DNA hydroxylases, histone demethylases, histone deacetylases). For example, a DNA methyltransferase DNMT (DNMT1, DNMT3) catalyzes the transfer of methyl group to cytosine, which typically results in transcriptional repression through the recruitment of repressive regulatory proteins. Another example of a EE domain is CBP/p300 histone acetyltransferase, which is typically associated with transcriptional activation through the interactions with multiple transcription factors. Related epigenetic effector domains associated with the deposition of biochemical marks on DNA or histone residue(s) include HAT1, GCN5, PCAF, MLL, SET, DOT1, SUV39H, G9a, KAT2A/B and EZH1/2. Related epigenetic effector domains associated with the removal of biochemical marks from DNA or histone residue(s) include TET1/2, SIRT family, LSD1, and KDM family.

In one embodiment, the HSV VP16 activation domain is used as a transcriptional activator (see, e.g., Hagmann et al., J. Virol. 71:5952-5962 (1997)). Exemplary DNA binding domains of VP16 include, but are not limited to, 43-8 (WT), 43-8 (3×), 43-8 (×4), 42-10 (WT), 42-10 (3×) or 42-10 (×4) of VP16. Other preferred transcription activator elements include, but are not limited to, the VP64 activation domain (Seipel et al., EMBO J. 11:4961-4968 (1996)); nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); and EGR-1 (early growth response gene product-1; Yan et al., Proc. Natl. Acad. Sci. U.S.A. 95:8298-8303 (1998); and Liu et al., Cancer Gene Ther. 5:3-28 (1998)).

Where the synthetic transcription factor is desired to repress gene expression, such a sTF can be made without a transcription activator element or with a repressor element such that the sTF binds to the multi-domain scaffold and directly represses expression or sterically hinders the binding of the basal transcription machinery. In one embodiment, a sTF comprises a repressor regulatory element, such as the KRAB repressor form the human KOX-1 gene (Thiesen et al., New Biologist 2:363-374 (1990); Margolin et al., Proc. Natl. Acad. Sci. U.S.A. 91:4509-4513 (1994); Pengue et al., Nucl. Acids Res. 22:2908-2914 (1994); Witzgall et al., Proc. Natl. Acad. Sci. U.S.A. 91:4514-4518 (1994)). In another embodiment, KAP-1, a KRAB co-repressor, is used with KRAB (Friedman et al., Genes Dev. 10:2067-2078 (1996)). Alternatively, KAP-1 can be used alone with a zinc finger protein. Other preferred transcription factor domains that act as transcriptional repressors include MAD (see, e.g., Sommer et al., J. Biol. Chem. 273:6632-6642 (1998); Gupta et al., Oncogene 16:1149-1159 (1998); Queva et al., Oncogene 16:967-977 (1998); Larsson et al., Oncogene 15:737-748 (1997); Laherty et al., Cell 89:349-356 (1997); and Cultraro et al., Mol Cell. Biol. 17:2353-2359 (19977)); FKHR (forkhead in rhabdosarcoma gene; Ginsberg et al., Cancer Res. 15:3542-3546 (1998); Epstein et al., Mol. Cell. Biol. 18:4118-4130 (1998)); EGR-1 (early growth response gene product-1; Yan et al., Proc. Natl. Acad Sci. U.S.A. 95:8298-8303 (1998); and Liu et al., Cancer Gene Ther. 5:3-28 (1998)); the ets2 repressor factor repressor domain (ERD; Sgouras et al., EMBO J. 14:4781-4793 ((19095)); p65; and the MAD smSIN3 interaction domain (SID; Ayer et al., Mol. Cell. Biol. 16:5772-5781 (1996)).

Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Transcriptional regulators for use in accordance with the invention include any transcriptional regulator described herein or known to one of ordinary skill in the art. Examples of genes encoding transcriptional regulators that may be used in accordance with the invention include, without limitation, those regulators provided in Table 63 of U.S. Patent Application No. 2012/0003630, which is incorporated herein in its entirety by reference.

In one embodiment, the effector domain of the sTF as disclosed herein is the VP64 activation domain comprising the sequence:

```
                                        (SEQ. ID. NO: 69)
GRADALDDFDLDMLGSDALDDFDLDMLGSDALDDFDLDMLGSDALDDFDL

DML.
```

In one embodiment, the effector domain of the sTF as disclosed herein is the p65 activation domain of NFκB comprising the sequence:

```
                                        (SEQ ID NO: 96)
DEFPTMVFPSGQISQASALAPAPPQVLPQAPAPAPAPAMVSALAQAPAPV

PVLAPGPPQAVAPPAPKPTQAGEGTLSEALLQLQFDDEDLGALLGNSTDP

AVFTDLASVDNSEFQQLLNQGIPVAPHTTEPMLMEYPEAITRLVTGAQRP

PDPAPAPLGAPGLPNGLLSGDEDFSSIADMDFSALLSQISS.
```

In one embodiment, the effector domain of the sTF as disclosed herein is the p300 HAT Core activation domain comprising the sequence:

```
                                        (SEQ. ID. NO: 70)
IFKPEELRQALMPTLEALYRQDPESLPFRQPVDPQLLGIPDYFDIVKSPM

DLSTIKRKLDTGQYQEPWQYVDDIWLMFNNAWLYNRKTSRVYKYCSKLSE

VFEQEIDPVMQSLGYCCGRKLEFSPQTLCCYGKQLCTIPRDATYYSYQNR
```

-continued

YHFCEKCFNEIQGESVSLGDDPSQPQTTINKEQFSKRKNDTLDPELFVEC

TECGRKMHQICVLHHEIIWPAGFVCDGCLKKSARTRKENKFSAKRLPSTR

LGTFLENRVNDFLRRQNHPESGEVTVRVVHASDKTVEVKPGMKARFVDSG

EMAESFPYRTKALFAFEEIDGVDLCFFGMHVQEYGSDCPPPNQRRVYISY

LDSVHFFRPKCLRTAVYHEILIGYLEYVKKLGYTTGHIWACPPSEGDDYI

FHCHPPDQKIPKPKRLQEWYKKMLDKAVSERIVHDYKDIFKQATEDRLTS

AKELPYFEGDFWPNVLEESIKELEQEEEERKREENTSNESTDVTKGDSKN

AKKKNNKKTSKNKSSLSRGNKKKPGMPNVSNDLSQKLYATMEKHKEVFFV

IRLIAGPAANSLPPIVDPDPLIPCDLMDGRDAFLTLARDKHLEFSSLRRA

QWSTMCMLVELHTQSQD.

In one embodiment, the effector domain of the sTF as disclosed herein is the KRAB repressive domain comprising the sequence:

(SEQ ID NO: 71)
MDAKSLTAWSRTLVTFKDVFVDFTREEWKLLDTAQQILYRNVMLENYKNL

VSLGYQLTKPDVILRLEKGEEPWLVEREIHQETHPDSETAFEIKSSV.

In one embodiment, the effector domain of the sTF as disclosed herein is the HP1 alpha chromoshadow repressive domain comprising the sequence:

(SEQ. ID. NO: 72)
MKKREQSNDIARGFERGLEPEKIIGATDSCGDLMFLMKWKDTDEADLVLA

KEANVKCPQIVIAFYEERLTWHAYPEDAENKEK.

In one embodiment, the effector domain of the sTF as disclosed herein is the DNMT3B repression domain comprising the sequence:

(SEQ. ID. NO: 73)
MKGDTRHLNGEEDAGGREDSILVNGACSDQSSDSPPILEAIRTPEIRGRR

SSSRLSKREVSSLLSYTQDLTGDGDGEDGDGSDTPVMPKLFRETRTRSES

PAVRTRNNNSVSSRERHRPSPRSTRGRQGRNHVDESPVEFPATRSLRRRA

TASAGTPWPSPPSSYLTIDLTDDTEDTHGTPQSSSTPYARLAQDSQQGGM

ESPQVEADSGDGDSSEYQDGKEFGIGDLVWGKIKGFSWWPAMVVSWKATS

KRQAMSGMRWVQWFGDGKFSEVSADKLVALGLFSQHFNLATFNKLVSYRK

AMYHALEKARVRAGKTFPSSPGDSLEDQLKPMLEWAHGGFKPTGIEGLKP

NNTQPENKTRRRTADDSATSDYCPAPKRLKTNCYNNGKDRGDEDQSREQM

ASDVANNKSSLEDGCLSCGRKNPVSFHPLFEGGLCQTCRDRFLELFYMYD

DDGYQSYCTVCCEGRELLLCSNTSCCRCFCVECLEVLVGTGTAAEAKLQE

PWSCYMCLPQRCHGVLRRRKDWNVRLQAFFTSDTGLEYEAPKLYPAIPAA

RRRPIRVLSLFDGIATGYLVLKELGIKVGKYVASEVCEESIAVGTVKHEG

NIKYVNDVRNITKKNIEEWGPFDLVIGGSPCNDLSNVNPARKGLYEGTGR

LFFEFYHLLNYSRPKEGDDRPFFWMFENVVAMKVGDKRDISRFLECNPVM

IDAIKVSAAHRARYFWGNLPGMNRPVIASKNDKLELQDCLEYNRIAKDLW

LSCALHRRVQHGPWCPPEAAGKVLERACHPTPLRPSEGLLCM.

Accordingly, the sTF as disclosed herein can comprise a covalently linked effector domain selected from any of: a VP64 activation domain, a KRAB repressive domain, a HP1 repressive domain, and a p65 activation domain.

In some embodiments of the sTFs described herein, effector domain, (e.g., TA domain and/or TR domain or EE domain) is attached to the DBD and are joined together using chemical cross-linking agents. Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, Bioconjugate Chem., 1: 2-12 (1990)).

Homobifunctional cross-linker molecules have two reactive sites which are chemically the same. Non-limiting examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., disuccinimidyl suberate, dithiobis (succinimidyl propionate), and soluble bis-sulfonic acid and salt thereof (see, e.g., Pierce Chemicals, Rockford, Ill.; Sigma-Aldrich Corp., St. Louis, Mo.).

A bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the disclosure include, without limitation, m-maleimidobenzoyl-N-hydroxysuccinimide ester (see, Green et al., Cell, 28: 477-487 (1982); Palker et al., Proc. Natl. Acad. Sci (USA), 84: 2479-2483 (1987)): m-maleimido-benzoylsulfosuccinimide ester; maleimidobutyric acid N-hydroxysuccinimide ester; and N-succinimidyl 3-(2-pyridyl-dithio)propionate (see, e.g., Carlos et al., Biochem. J., 173: 723-737 (1978); Sigma-Aldrich Corp., St. Louis, Mo.).

In alternative embodiments of the sTFs described herein, effector domain, (e.g., TA domain and/or TR domain or EE domain) is attached to the DBD with a linker peptide, e.g., a flexible or rigid peptide linker, as disclosed herein.

(iii) Ligands

The systems, methods and compositions provided herein have the distinct advantage of being able to tightly control gene expression in a predictable manner. In the systems described herein for gene expressional control, synthetic transcription factors are used together with a molecular clamp. The synthetic transcription factor and the molecular clamp interact by way of a ligand binding domain and a cognate ligand. In one embodiment, the synthetic transcription factors described herein comprise a ligand while the molecular clamp as described herein comprises a corresponding ligand binding domain (LBD). While any ligand/LBD pair can be used, one of skill in the art will recognize that the size of the ligand should be small enough such that it does not interfere with formation of a complex (e.g., highly ordered complex) on the molecular clamp.

Thus, in some embodiments, the ligand comprises a short amino acid sequence of 4-8 amino acids (e.g., 6 amino acids). Exemplary ligands can be selected from the group consisting of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), OR VKEALV (SEQ ID NO: 8). In some embodiments, the ligand is present at the C-terminus of the synthetic transcription factor.

In certain embodiments, the ligand comprises a PDZ domain ligand. A PDZ domain binds to the C-terminal 4-5 residues of target proteins. In some embodiments, a consensus PDZ domain ligand comprises a hydrophobic residue, e.g., Val or Ile, at the carboxyl terminus. Exemplary, non-limiting examples of amino acid sequences of peptides comprising PDZ domain ligands include: IESDV (SEQ ID NO: 9); VKESLV (SEQ ID NO: 10); GVKESLV (SEQ ID NO: 11); GVKQSLL (SEQ ID NO: 12); GVKESGA (SEQ ID NO: 13); YVKESLV (SEQ ID NO: 14); and VETDV (SEQ ID NO: 15).

In other embodiments, the ligand comprises a GBD ligand. In some embodiments, an HP is a GBD ligand. An exemplary, non-limiting GBD ligand comprises the amino acid sequence LVGALMHVMQKRSRAIHSSDEGEDQAGDEDED (SEQ ID NO: 16).

In some embodiments, the ligand comprises leucine zipper peptides, which interact via a coiled-coil domain. Amino acid sequences of leucine zipper domains are known in the art. Leucine zipper peptides include an EE12RR345L leucine zipper peptide; an RR12EE354L leucine zipper peptide; and the like.

An example of an amino acid sequence of a leucine zipper peptide is an EE12RR345L leucine zipper of the amino acid sequence: LEIEAAFLERENTALETRVAELRQRVQRLR NRVSQYRTRYGPLGGGK (SEQ ID NO: 17). Another non-limiting example of an amino acid sequence of a leucine zipper peptide is an RR12EE345L leucine zipper peptide of the amino acid sequence: LEIRAAFLRQRNTALRT EVAELEQEVQRLENEVSQYETRYGPLGGGK (SEQ ID NO: 18).

An EE12RR345L leucine zipper peptide as described above and an RR12EE345L leucine zipper peptide as described above bind to one another. In some embodiments, the EE12RR345L leucine zipper peptide is the LBD and the RR12EE345L leucine zipper peptide is the ligand. In other embodiments, the RR12EE345L leucine zipper peptide is the LBD and the EE12RR345L leucine zipper peptide is the ligand.

In some embodiments, the synthetic transcription factors described herein comprise an SH3 domain ligand. An SH3 domain binds proline-rich peptides that form a left-handed poly-proline type II helix, where such peptides comprise the minimal consensus sequence Pro-X-X-Pro. In some embodiments, each Pro is preceded by an aliphatic residue. Exemplary, non-limiting examples of amino acid sequences of peptides comprising SH3 domain ligands include: RPLPVAP (SEQ ID NO: 19; bound by a Class I SH3 domain); PPPALPPKRRRPG (SEQ ID NO:20); and PPPALPPKKR (SEQ ID NO: 21; bound by a Class II SH3 domain).

Numerous receptor ligand binding-ligand pairs are known in the art, for examples, (1) the receptor-ligand pair is a WVF A1 domain and a GP1b α subunit, the template mRNAs for PCR cloning of a DNA encoding an A1 domain and a GP1b α can be the *Homo sapiens* glycoprotein Ib (platelet), alpha polypeptide (GP1BA) mRNA GENBANK™ Accession No. NM_000173.4; the von Willebrand factor A1 domain isoform 1 precursor mRNA GENBANK™ Accession No. NM_022834.4; and the von Willebrand factor A 1 domain isoform 2 precursor mRNA GENBANK™ Accession No. NM_199121.2; (2) the receptor-ligand pair is an α4b7 integrin and a madcam-1, the template mRNAs for PCR cloning of a DNA encoding an α4b7 integrin and a madcam-1 can be the *Homo sapiens* integrin alpha L isoform b precursor GENBANK™ Accession No. NM_001114380.1; the integrin alpha L isoform a precursor GENBANK™ Accession No. NM_002209.2; and the intercellular adhesion molecule 1 (ICAM-1) precursor GENBANK™ Accession No. NM_000201.2; (3) the receptor-ligand pair is an aL integrin I domain and an ICAM-1(D1+D2), the template mRNAs for PCR cloning of the DNAs encoding an aL integrin I domain and an ICAM-1(D1+D2) can be the mRNA of the integrin alpha L isoform a precursor GENBANK™ Accession No. NM_002209.2 and the mRNA of the *Homo sapiens* intercellular adhesion molecule 1 precursor (ICAM-1) GENBANK™ Accession No. NM_000201.2; (4) the receptor-ligand pair is the aL integrin I domain and ICAM-3(D1), the template mRNAs for PCR cloning of the DNAs encoding an aL integrin I domain and an ICAM-3(D1) can be the mRNA of the integrin alpha L isoform a precursor GENBANK™ Accession No. NM_002209.2 and the mRNA of the *Homo sapiens* intercellular adhesion molecule 3 precursor (ICAM-3) GENBANK™ Accession No. NM_002162.3. The I domain encompasses amino acid residues 145-324 of the 1145 amino acid long mature aL integrin subunit protein (amino acid residues 26-1170 of GenBank Accession No. NP_002200); and (5) the receptor-ligand pair is a fimH pilin+lectin domain and a N-linked carbohydrates, the template mRNA for PCR cloning the DNA encoding a fimH pilin+lectin domain can be the *Escherichia coli* strain J96 type 1 fimbrial adhesin precursor (fimH) gene, GENBANK™ Accession No. AY914173, described in PCT publication WO2011/103049, the contents of which are incorporated herein by reference in its entirety.

In some embodiments, the ligand is attached to the DBD of the sTF by a linker. In some embodiments, the linker is a rigid peptide linker and in some embodiments, the linker is a flexible peptide linker. In some embodiments of any aspect described herein, in ligand of the sTF as described is attached to the DBD by peptide linkers having four to six amino acid residues.

In some embodiments of any aspect described herein, a ligand of the sTF as described is attached to the DBD by a rigid peptide linker, such as, e.g., TGEKP (SEQ ID NO: 74), TGGKP (SEQ ID NO: 75), TGSKP (SEQ ID NO: 76), TGQKP (SEQ ID NO: 77), SGEKP (SEQ ID NO: 78), SGSKP (SEQ ID NO: 79), SGQKP (SEQ ID NO: 80), and SGGKP (SEQ ID NO: 81). The rigid linker aids in conferring synergistic binding of the ligand with the LBD of the molecular clamp.

In some embodiments of any aspect described herein, a ligand of the sTF as described is attached to the DBD by a flexible linker peptide, e.g., a flexible linker between 1-20 amino acids long. An exemplary flexible peptide linker is TGSQKP (SEQ ID NO: 147). In another embodiment, the ligand is attached to the DBD of the sTF by chemical crosslinkers. Chemical crosslinkers are known in the art.

In some embodiments of any aspect described herein, in the sTF as described herein, all the helices within an individual ZFA are linked by a combination of rigid peptide linkers and flexible peptide linkers.

As will be readily recognized by one of skill in the art, synthetic transcription factors can further comprise domains or components that permit isolation, intracellular tracking, and visualization such as e.g., epitope tags (e.g., FLAG tags, 6×HIS tags (SEQ ID NO: 82), c-myc tags etc.). One of skill in the art can readily incorporate such domains into the synthetic transcription factor as described herein and will recognize that such tags should not interfere with the binding of the ligand to LBD, or the functioning of the molecular clamp/formation of higher ordered complexes to control gene expression.

A synthetic transcription factor with a desired specificity can be designed and generated using any method known in the art including, but not limited to e.g., site-directed mutagenesis and rational design or through the use of large combinatorial libraries by phage display. In one embodiment, the synthetic transcription factors are generated by the methods described in e.g., Khalil et al. *Cell* 150:647-658 (2012), U.S. Pat. No. 7,153,949 or US 2018/0057838, the contents of each of which are incorporated herein by reference in their entirety. Synthetic transcription factors for use with the multi-domain scaffold protein(s) described herein can be those described in US 2018/0057838, the contents of which is incorporated herein by reference in its entirety.

C. Molecular Clamps

Natural TFs often operate as multimeric complexes, in which their monomeric components must cooperate to achieve full or more sophisticated functionality for tasks, such as tuning switch-like input-output responses and increasing substrate specificity. The engineered molecular clamps, (also referred to as multi-domain scaffold proteins) as described herein can permit the formation of multimeric complexes of the same transcription factor or heterodimers with other transcription factors by bringing the one or more transcription factors together in space, such that the one or more transcription factors are localized to the promoter region of a desired gene.

Such molecular clamps are designed to organize transcription factors and transcriptional machinery in a functional complex. Molecular clamps (MCs) as described herein, comprise one, two or more protein binding elements (PBEs), such as ligand binding domains (LBD). Binding of the LBD to a synthetic transcription factor comprising a cognate ligand as described herein provides for immobilization of the sTF on the scaffold polypeptide/molecular clamp.

Accordingly, in general, a molecular clamp (MC) comprises multiple linked ligand binding domains (LBD), where the LBD binds to a ligand of sTF. The LBD can be modified to alter the binding affinity for the ligand of the sTF, such that the LBD-ligand interaction ($K_p$) are strengthened or weakened. Where two or more ligand binding domains are used to generate a multi-domain scaffold protein, a given LBD can be immediately adjacent to another LBD, or can be separated from an adjacent LBD through a linker (e.g., a flexible linker) In some embodiments, the flexible linker is (GS)n. The molecular clamp can be introduced to a variety of different types of host cells, e.g., by introducing into a host cell a nucleic acid comprising a nucleotide sequence encoding the molecular clamp.

Provided herein are molecular clamps comprising at least one ligand binding domain. For example, the molecular clamps described herein can have any number of desired ligand binding domains (e.g., n domains), wherein the ligand binding domains are connected by a linker. Where there is more than one ligand binding domain, the ligand binding domains can be the same (i.e., multiple copies of a given LBD) or different (e.g., at least two different ligand binding domains). In some embodiments, a molecular clamp as described herein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 ligand binding domains. The ligand binding domains can comprise different binding domains, identical binding domains, or any mixture of the two. Each LBD can independently be present in one or more copies. The copies can be in tandem, or separated by a linker. For example, a clamp may comprise one copy of a first LBD (LBD-1), two copies of LBD-2, and three copies of LBD-3, where the copies are in tandem, or are separated by a linker.

In some embodiments, a multi-domain molecular clamp comprises at least two different LBDs, thus, for example, the clamp can bind two or more synthetic transcription factors. A molecular clamp can provide binding of 2 to 3 sTF, 2-4 sTF, 2-5 sTF, 2-6 sTF, 2-7 sTF, 2-8 sTF, 2-9 sTF, 2-10 sTF, 3-4 sTF, 3-5 sTF, 3-6 sTF, 4-6 sTF, 4-8 sTF, 5-7 sTF, 5-10 sTF, or any range there between.

In some embodiments, a molecular clamp has a general formula of [(X)n(Y)]m, where each X is a different LBD, wherein n is an integer from one to about 10 (e.g., where n is 1, 2, 3, 4, 5, 6, 7, 8, 9, or 10), where Y, if present, is a linker peptide, and where m is an integer from 2 to about 50 (e.g., from 2 to about 3, from 3 to about 6, from 6 to about 10, from 10 to about 15, from 15 to 20, from 20 to 25, from 25 to 30, from 30 to 35, from 35 to 40, from 40 to 45, or from 45 to 50).

For example, in some embodiments, a molecular clamp has the formula (X1)n1(Y1)(X2)n2(Y2)(X3)n3, where X1 is a first LBD that provides for binding of a first chimeric biosynthetic pathway enzyme; where X2 is a second LBD that provides for binding of a second chimeric biosynthetic pathway enzyme; where X3 is a third LBD that provides for binding of a third chimeric biosynthetic pathway enzyme; where each of n1, n2, and n3 is independently an integer from one to about 10; and where each Y, if present, is a linker peptide. As another example, in some embodiments, a molecular clamp has the formula (X1)n1(Y1)(X2)n2(Y2)(X3)n3(X4)n4(Y4)(X5)n5(Y5)(X6)n6, where X1 is a first LBD that binds a first ligand on a first sTF; where X2 is a second LBD that binds a second ligand on a second sTF; where X3 is a third LBD that binds a third ligand on a third sTF; X4 is a fourth LBD that binds a fourth ligand on a fourth sTF; where X5 is a fifth LBD that binds a fifth ligand on a fifth sTF; where X6 is a sixth LBD that binds a sixth ligand on a sixth sTF; where each of n1, n2, n3, n4, n5, and n6 is independently an integer from one to about 10; and where each Y, if present, is a linker peptide.

Figure 9A:
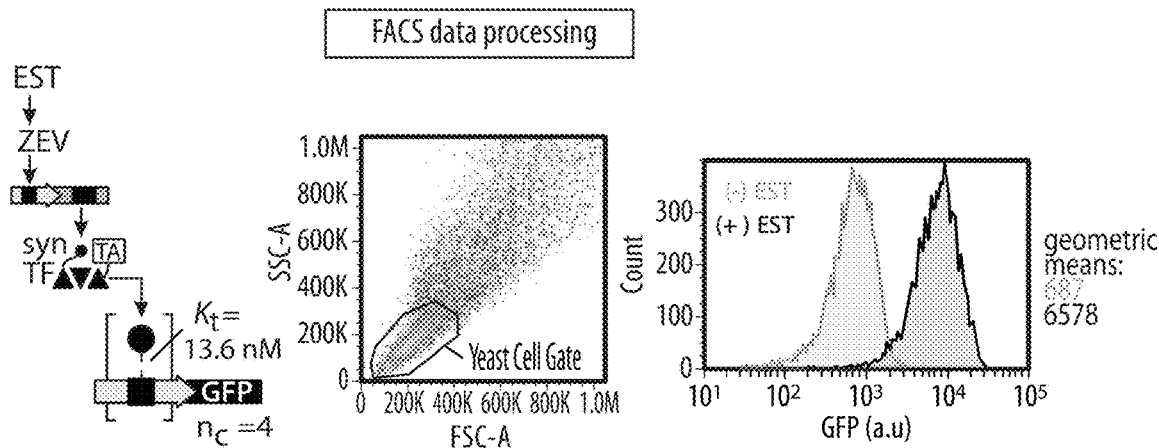
FIG. 9A-FIG. 9B is a series of schematics and graphs showing the screening of linker length combinations to optimize complex-mediated transcriptional output.
Figure 9B:
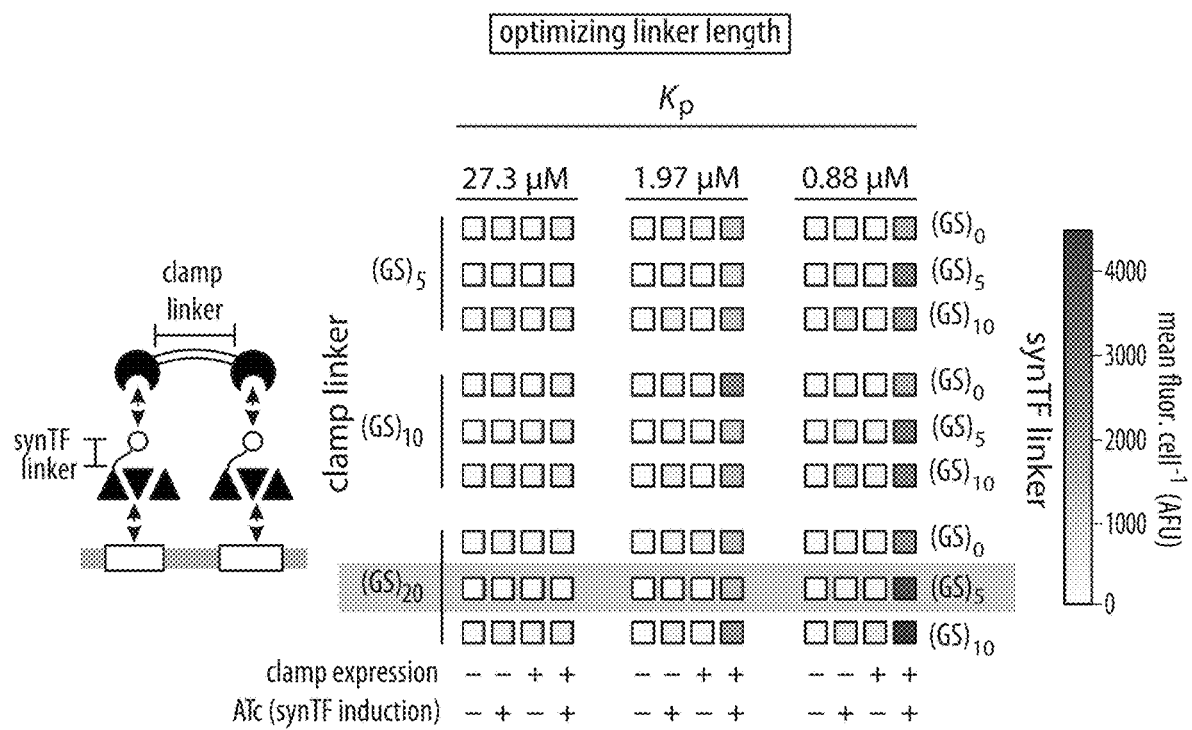

Additionally, the clamp linker between each LBD domain can be modified in length to modify the strength of the sTF-molecular clamp interaction ($K_p$) (e.g., see FIG. 9B). In some embodiments, the clamp linker between LBD domains is a repeating unit of $(GS)_n$ amino acids, where n=1-5 (SEQ ID NO: 62), or 6-10 (SEQ ID NO: 63), or 11-20 (SEQ ID NO: 64), or 21-30 (SEQ ID NO: 65). In some embodiments, the clamp linker is a repeating unit of $(GS)_{1-5}$ (SEQ ID NO: 62), or $(GS)_{6-10}$ (SEQ ID NO: 63), or $(GS)_{11-20}$ (SEQ ID NO: 64), or $(GS)_{21-30}$ (SEQ ID NO: 65), or any integer between 1-30. The molecular clamp can be represented as comprising: LBD-[linker-LBD]$_n$ In some embodiment, the molecular clamps comprise a nuclear localization sequence. In some embodiments, the molecular clamp comprises: nuclear localization sequence NLS-[LBD-linker]n-LBD, wherein n is 1, 2, 3, 4, 5, 6, 7, 8, 9 or 10.

Exemplary nuclear localization sequences are provided in the following Table.

TABLE 1

Nuclear Localization Signals

| SOURCE | SEQUENCE | SEQ ID NO. |
|---|---|---|
| SV40 virus large T-antigen | PKKKRKV | 36 |
| nucleoplasmin | KRPAATKKAGQAKKKK | 37 |
| c-myc | PAAKRVKLD | 38 |
|  | RQRRNELKRSP | 39 |
| hRNPA1 M9 | NQSSNFGPMKGGNFGGRSSGPYGGGGQYFAKPRNQGGY | 40 |
| IBB domain from importin-alpha | RMRIZFKNKGKDTAELRRRRVEVSVELRKAKKDEQILKRRNV | 41 |
| myoma T protein | VSRKRPRP | 42 |
|  | PPKKARED | 43 |
| human p53 | PQPKKKPL | 44 |
| mouse c-abl IV | SALIKKKKKMAP | 45 |
| influenza virus NS1 | DRLRR | 46 |
|  | PKQKKRK | 47 |
| Hepatitis virus delta antigen | RKLKKKIKKL | 48 |
| mouse Mx1 protein | REKKKFLKRR | 49 |
| human poly(ADP-ribose) polymerase | KRKGDEVDGVDEVAKKKSKK | 50 |
| steroid hormone receptors (human) glucocorticoid | RKCLQAGMNLEARKTKK | 51 |
| derived from SV40 NLS | PKKKRKVGIHGVPGG | 1 |
| derived from SV40 NLS | PKKKRKVVE | 2 |

A ligand binding domain can have a length of from about 25 amino acids to about 200 amino acids—e.g., from about 25 amino acids to about 50 amino acids, from about 50 amino acids to about 60 amino acids, from about 60 amino acids about 75 amino acids, from about 75 amino acids to about 80 amino acids, from about 80 amino acids to about 90 amino acids, from about 90 amino acids to about 100 amino acids, from about 100 amino acids to about 125 amino acids, from about 125 amino acids to about 150 amino acids, from about 150 amino acids to about 175 amino acids, or from about 175 amino acids to about 200 amino acids.

In some embodiments, the LBD does not naturally occur in the host cell so that only the engineered protein-protein interactions occur.

Exemplary LBDs include, but are not limited to, an SH3 domain, a PDZ domain, a GTPase binding domain (GBD), a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a BCL-2 homology domain, a coiled-coil domain or a bZIP domain.

In some embodiments, a ligand binding domain as described herein can be a protein binding domain, such as a PDZ domain. PDZ domains can be derived from any source including, but not limited to, syntrophin and erbin PDZ domains. In one embodiment, the PDZ domain is a syntrophin PDZ domain and the PDZ domain binds to a ligand selected from IRETII (SEQ ID NO: 3), IRETIL (SEQ ID NO: 4), IRWTIV (SEQ ID NO: 5) VKESLV (SEQ ID NO: 6), IRETIV (SEQ ID NO: 7), or VKEALV (SEQ ID NO: 8). In an alternative embodiment, the PDZ domain is an erbin domain and the PDZ domain binds to a ligand selected from WLKTWV (SEQ ID NO: 22), PVDSWV (SEQ ID NO: 23), and VKEALV (SEQ ID NO: 8).

In certain embodiments, the LBD is a PDZ domain. Amino acid sequences of PDZ domains are known in the art. See, for example, amino acids 108-191, amino acids 201-287, and amino acids 354-434 of the amino acid sequence provided in Gen Bank Accession No. AAC52113 (*Homo sapiens* post-synaptic density protein 95); and amino acids 80-161 of the amino acid sequence provided in GenBank Accession No. NP-033254 (*Mus musculus* syntrophin).

In some embodiments, a synthetic transcription factor as described herein comprises a leucine zipper peptide that binds to a coiled-coil ligand binding domain. Leucine zipper peptides are unusual in that they can act as either a ligand or ligand-binding domain. Thus, in some embodiments, the molecular clamps described herein comprise such coiled-coil domains or leucine zipper proteins. The EE12RR345L leucine zipper peptide and an RR12EE345L leucine zipper peptide as described above bind to one another (e.g., as a ligand/LBD pair). In some embodiments, the EE12RR345L leucine zipper peptide is the LBD and the RR12EE345L leucine zipper peptide is the ligand. In other embodiments, the RR12EE345L leucine zipper peptide is the LBD and the EE12RR345L leucine zipper peptide is the ligand.

In some embodiments, a LBD is/are SH3 domains. SH3 domains include, but are not limited to, Class I SH3 domains; Class II SH3 domains; and unconventional SH3 domains. Amino acid sequences of SH3 domains are known in the art. See, for example, amino acids 136-189 of the amino acid sequence provided in GenBank Accession No. NP-058431 (*Homo sapiens* Crk protein); amino acids 136-189 of the amino acid sequence provided in GenBank Accession No. AAH31149 (*Mus musculus* Crk protein); and amino acids 4-77 of the amino acid sequence provided in GenBank Accession No. P27986 (*Homo sapiens* p85 subunit of phosphatidylinositol 3-kinase).

In some embodiments, an SH3 domain is a Class I SH3 domain and comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, from about 50 amino acids to about 60 amino acids, from about 60 amino acids to about 70 amino acids, or from about 70 amino acids to about 74 amino acids of the amino acid sequence: EGYQYRA LYDYKKEREE DIDLHLGDIL TVNKGSLVAL GFSDGQEARP EEIGWLNGYN ETTGERGDFP GTYVEYI (SEQ ID NO: 24).

In some embodiments, an SH3 domain is a Class II SH3 domain and comprises an amino acid sequence having at least about 75%, at least about 80%, at least about 85%, at least about 90%, at least about 95%, at least about 98%, at least about 99%, or 100%, amino acid sequence identity over a contiguous stretch of from about 40 amino acids to about 45 amino acids, from about 45 amino acids to about 50 amino acids, or from about 50 amino acids to about 54 amino acids of the amino acid sequence: YVRALFDFNG-NDEEDLPFKKGDILRIRDKPEEQWWNAEDSEGKRG-MIPVPYVEK (SEQ ID NO: 25). As one non-limiting example, an SH3 domain comprises the amino acid sequence: MAEYVRALFDFNGNDEEDLPFKKGDIL-RIRDKPEEQWWNAEDSEGKRGMIPVPYVEKY (SEQ ID NO: 26).

An SH3 domain binds proline-rich peptides that form a left-handed poly-proline type II helix, where such peptides comprise the minimal consensus sequence Pro-X-X-Pro. In some embodiments, each Pro is preceded by an aliphatic residue. Exemplary, non-limiting examples of amino acid sequences of peptides comprising SH3 domain ligands include: RPLPVAP (SEQ ID NO: 19; bound by a Class I SH3 domain); and PPPALPPKKR (SEQ ID NO: 21; bound by a Class II SH3 domain).

In other embodiments, the ligand binding domain comprises one or more GTP-ase binding domains (GBD). GBDs are also referred to as Cdc42/Rac-interactive binding (CRIB) motifs. In some embodiments, a GBD binds Cdc42p-like and/or a Rho-like small GTPase. Amino acid sequences of GBD are known in the art. See, e.g., amino acids 198-240 of the amino acid sequence provided in GenBank Accession No. NP-001103835 (*Rattus norvegicus* Wiskott-Aldrich syndrome-like protein (WASP)); amino acids 69-112 of the amino acid sequence provided in GenBank Accession No. Q13177 (*Homo sapiens* PAK-2); and amino acids 70-105 of the amino acid sequence provided in GenBank Accession No. P35465 (*Rattus norvegicus* PAK-1). See also the amino acid sequences PAK (75-111), ACK (504-549), and WASP (232-274), presented in FIG. 3A of Garrard et al. (2003) EMBO J. 22:1125. See also the amino acid sequences ACK (505-531), WASP (236-258), PAK1 (70-94), PAK2 (71-91), PAK-4 (6-30), presented in FIG. 1A of Bishop and Hall (2000) Biochem. J. 348:241.

In some embodiments, a suitable GBD comprises an amino acid sequence having at least about 75%, at least about 80%, at least about 85%, at least about 90%, at least about 95%, at least about 98%, at least about 99%, or 100%, amino acid sequence identity over a contiguous stretch of from about 20 amino acids to about 25 amino acids, from about 25 amino acids to about 30 amino acids, from about 30 amino acids to about 35 amino acids, from about 35 amino acids to about 40 amino acids, or from about 40 amino acids to about 43 amino acids, of the amino acid sequence: ADI GTPSNFQHIG HVGWDPNTGF DLNNLDPELK NLFDMCGISE (SEQ ID NO: 150).

In some embodiments, a suitable GBD comprises an amino acid sequence having at least about 75%, at least about 80%, at least about 85%, at least about 90%, at least about 95%, at least about 98%, at least about 99%, or 100%, amino acid sequence identity over a contiguous stretch of from about 20 amino acids to about 25 amino acids, from about 25 amino acids to about 30 amino acids, from about 30 amino acids to about 35 amino acids, from about 35 amino acids to about 40 amino acids, or from about 40 amino acids to about 42 amino acids, of the amino acid sequence:

```
                                       (SEQ ID NO: 27)
KERPEISLPSDFEHTIHVGFDAVTGEFTGMPEQWAR.
```

In some embodiments, a suitable GBD comprises an amino acid sequence having at least about 75%, at least about 80%, at least about 85%, at least about 90%, at least about 95%, at least about 98%, at least about 99%, or 100%, amino acid sequence identity over a contiguous stretch of from about 45 amino acids to about 50 amino acids, from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, or from about 75 amino acids to about 80 amino acids, of the amino acid sequence:

```
                                       (SEQ ID NO: 28)
MTKADIGTPSNFQHIGHVGWDPNTGFDLNNLDPELKNLFDMCGISEAQLK

DRETSKVIYDFIEKTGGVEAVKNELRRQAP.
```

In some embodiments, the LBD of the molecular clamp can be any receptor selected from ligand receptors as discussed infra in the section B(iii) entitled "ligands".

As described above, in one embodiment, the ligand binding domain is a steroid receptor ligand binding domain such as estrogen receptor. In one embodiment, the ligand is tamoxifen or other estrogen analogs. In one embodiment, the ligand binding domain is VWF A1 domain and the corresponding ligand on the sTF is the GP1bα subunit. The VWF A1 domain/GP1bα subunit forms a receptor ligand binding domain-ligand pair.

In other embodiments, the LBD-ligand pair, e.g., the LBD of the molecular clamp and the cognate ligand on the sTF, is selected from the group consisting of α4b7 integrin-madcam-1, αL integrin I domain-ICAM-1(D1+D2), αL integrin I domain-ICAM-3 (D1); and fimH pilin+lectin domain-N-linked carbohydrate.

In one embodiment, the LBD of the molecular clamp and the cognate ligand on the sTF, is protein interaction/dimerization domains, e.g., PYL1 (Abscisic Acid Receptor) or ABI1 (Abscisic Acid Insensitive 1). In another embodiment, the LBD of the molecular clamp and the cognate ligand on the sTF, is FKBP (FK506 Binding Protein) or Frb, each is another example of a protein interaction/dimerization domain.

In some embodiments, two adjacent LBDs are separated by a linker. Suitable linkers include peptides of between about 6 and about 40 amino acids in length, e.g., from about 6 amino acids to about 8 amino acids, from about 8 amino acids to about 10 amino acids, from about 10 amino acids to about 12 amino acids, from about 12 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, or from about 35 amino acids to about 40 amino acids in length. In some embodiments, a peptide linker has a degree of flexibility. The linking peptides can have virtually any amino acid sequence, bearing in mind that linkers will have a sequence that results in a generally flexible peptide. Small amino acids, such as glycine and alanine, are of use in creating a flexible peptide. The creation of such sequences is routine to those of skill in the art. A variety of different linkers are commercially available and are considered suitable for use according to the present invention.

Amino acid sequences rich in alanine and proline residues are known to impart flexibility to multi-domain protein structures. For example, alanine-proline rich regions are found in myosin light chains. Suitable linkers include peptides having multiple serine residues. Suitable linkers include peptides having multiple glycine residues. In some embodiments, a suitable linker includes peptides having multiple glycine and multiple serine residues, where exemplary linkers include glycine-serine repeats (e.g. [GS]$_x$ where x is any integer between 2 and 30 (SEQ ID NO: 83), e.g., 2, 4, 5, 6, 7, 8, 9, 10, 11, 12, 13, 14, 15, 16, 17, 18, 19, 20, 21, 22, 23, 24, 25, 26, 27, 28, 29, or 30). Other linkers contemplated for use with the multi-domain scaffold proteins described herein comprise a combination of glycine, alanine, proline and methionine residues, such as AAAGGM (SEQ ID NO: 29); AAAGGMPPAAAGGM (SEQ ID NO: 30); and PPAAAGGMM (SEQ ID NO: 31). However, any flexible linker generally between about 6 and about 40 amino acids in length may be used. Linkers may have virtually any sequence that results in a generally flexible peptide, including alanine-proline rich sequences of the type exemplified above.

In some embodiments, the flexible linker comprises a glycine-serine (GS) repeat sequence, for example, [GS]n wherein n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more.

Additional examples of linker peptide include, but are not limited to: PGER (SEQ ID NO: 84), TGSQK (SEQ ID NO: 85), TGEKP (SEQ ID NO: 74), THLR (SEQ ID NO: 86), TGGGEKP (SEQ ID NO: 87), FHYDRNNIA-VGADESVVKEAH-REVINSSTEGLLLNIDKDIRKILSGYIVEIEDTE (SEQ ID NO: 88); VEIEDTE (SEQ ID NO: 89), KDIRKILSGYIVEIEDTE (SEQ ID NO: 90); STEGLLLNIDKDIRKILSGYIVEIEDTE (SEQ ID NO: 91), EVKQENRLLNESES (SEQ ID NO: 92); and VGADESVVKEAH-REVINSSTEGLLLNIDKDIRKILSGYIVEIEDTE (SEQ ID NO: 93). For examples, TGSQK (SEQ ID NO: 85) or TGEKP (SEQ ID NO: 74) or TGGGEKP (SEQ ID NO: 87) is used as linker between the LBD of the molecular clamp; VEIEDTE (SEQ ID NO: 89) or GGSGGS (SEQ ID NO: 94) are used to link LBD domains together.

Flexible linkers are generally composed of small, non-polar or polar residues such as Gly, Ser and Thr. In one embodiment of any fusion protein described herein that includes a linker, the linker peptide comprises at least one amino acid that is Gly or Ser. In one embodiment of a fusion protein described herein that includes a linker, the linker is a flexible polypeptide between 1 and 25 residues in length. Common examples of flexible peptide linkers include (GGS)n, where n==1 to 8 (SEQ ID NO: 148), or (Gly4Ser)n repeat where n=1-8 (SEQ ID NO: 95), preferably, n=3, 4, 5, or 6, that is (Gly-Gly-Gly-Gly-Ser)n (SEQ ID NO: 97), where n indicates the number of repeats of the motif. For example, the flexible linker is (GGS)2 (SEQ ID NO: 94), GGSGGS (SEQ ID NO: 94). Alternatively, flexible peptide linkers include Gly-Ser repeats (Gly-Ser)p where p indicates the number of Gly-Ser repeats of the motif, p=1-8 (SEQ ID NOS: 98), preferably, n=3, 4, 5, or 6. Another example of a flexible linker is TGSQK (SEQ ID NO: 85) or TGSQKP (SEQ ID NO: 147)

In one embodiment of the LBD of the molecular clamp are joined together with a linker peptide, the linker peptide is about 1-20 amino acids long. In one embodiment, the linker peptide does not comprise Lys, or does not comprise Arg, or does not comprise both Lys and Arg.

In some embodiments, the LBD of the molecular clamp are linked by a combination of rigid peptide linkers and flexible peptide linkers.

D. Synthetic Gene Circuit Components

As disclosed herein, the molecular clamp is used to organize sTF for binding to DNA binding motifs in a synthetic gene circuit. In some embodiments, a synthetic gene circuit comprises at least two DNA binding motifs (DBM) upstream (e.g., 5') to a promoter or other regulatory element, where the promoter or regulatory element is operatively linked to a gene of interest (GOI). The nucleotide sequence of one or more of nucleotides of one or more DBMs can be modified to change (e.g., increase or decrease) the binding affinity for binding of the DBD of the sTF (see e.g., FIG. 6). The synthetic gene circuit can be represented as comprising: [DBM]$_n$-promoter/regulatory element-GOI.

The DBMs of the synthetic gene circuit are DNA sequence elements are specially designed to be "target" DNA, "target," "target" DNA sequence or "target" DNA sequence elements in the context of the DNA binding domain (DBD) of the synthetic transcription factor, and are used interchangeably. Moreover, these DNA sequence elements are specially designed to be recognized and bound specially by engineered synthetic transcription factors. When used together in vivo, these DNA sequence elements (e.g., DBM) and their specially engineered synthetic transcription factors form the basic components of a regulatable, programmable gene expression system that allows the modulation of gene expression in vivo.

In one embodiment, this DBM nucleic acid sequence is part of an engineered responsive promoter or transcriptional unit, where the sequence is located upstream of the promoter sequence. Upstream as is conventionally used in the art means 5' of the promoter sequence.

In one embodiment, this DBM nucleic acid sequence is operably linked to the promoter sequence to influence the transcription initiation when the DBM nucleic acid sequence is occupied by the DBD of the sTF having an effector domain (e.g., TA domain, TR domain or EE domain, as disclosed herein).

In some embodiments, the synthetic gene circuit comprises repeat DBM sequences, for example, [DBM]n wherein n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more.

The nucleotide sequence of the DBM for the synthetic gene circuit is dependent on the DNA binding domain (DBD) of the sTF, and in some embodiments, the cognate DNA binding sequence of the zinc finger domain of the DBD. In some embodiments, the DBM is at least 8-15 nucleotides in length. In some embodiments, the DBD is 8, 9, 10, 11, 12, 13, 14, 15, 16, 17, 18, 19, 20, 21 nucleotides in length. In some embodiments, the DBM comprises synthetic nucleotides.

Exemplary DBMs can for 43-8 (ZF1) be selected from: aGAGTGAGGAC (SEQ ID NO: 99), aCAGTGAGGAC (SEQ ID NO: 100) (DBM2); aTAGTGAGGAC (SEQ ID NO: 101) (DBM3); Exemplary DBMs can for 42-10 (ZF2) be selected from: aGACGCTGCTc (SEQ ID NO: 102); tGACGCTGCTc (SEQ ID NO: 103); aGACGGTGCTc (SEQ ID NO: 104); aCACGCTGCTc (SEQ ID NO: 105); aGACGCTACTc (SEQ ID NO: 106); aGACGCTGCTa (SEQ ID NO: 107); aGACTCTGCTc (SEQ ID NO: 108).

In some embodiments of any aspect described herein, in the synTF described or any ZF-containing fusion protein described herein, the individual ZFA therein described are specifically designed to bind orthogonal target DNA sequences such as the following SEQ ID NO: 81-90 of U.S. Pat. No. 10,138,493, which is incorporated herein in its entirety by reference.

In some embodiments of any aspect described herein, in the nucleotide sequence of the DBM DBD of the synthetic circuit is an orthogonal target DNA sequences of SEQ ID NOS: 81-91 disclosed in U.S. Pat. No. 10,138,493, which is incorporated herein in its entirety by reference.

In some embodiments, the synthetic gene circuit comprises multiple DBM's that are the same, i.e., bind the same DBD on the sTF. In alternative embodiments, the DBM's in a synthetic gene circuit are not the same (e.g., the DBM's bind to different DBDs, or alternatively, have different binding affinities for the same DBD on the sTF). For exemplary purposes, where a synthetic gene circuit comprises multiple DBMs, the synthetic gene circuit can comprise (DBM1)n-promoter-GOI; (DBD1-DBM2-DBM3-DBM4)n-promoter-GOI, [DBM1]n-[DBM2]n-promoter-GOI; [DBM1]n-[DBM2]n-[DBM3]n-promoter-GOI; [DBM1]n-[DBM2]n-[DBM3]n-[DBM4]n-promoter-GOI; where DBM1, DBM2, DBM3, DBM4 bind to different DBDs, or alternatively, have different binding affinities for the same DBD on the sTF.

In some embodiments, the synthetic gene circuit as disclosed herein comprises a promoter operatively linked to the gene to be expressed (e.g., gene of interest, GOD. In some embodiments, the synthetic gene circuit as disclosed herein comprises a promoter sequence. Provided herein are promoter sequences ("promoters") for use in the recombinase-based synthetic logic and memory systems of the invention. As used herein, a "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. In some embodiments, the promoter is constitutive. In some embodiments, the promoter is inducible. In some embodiments, the promoter is a mammalian promoter. As discussed herein, a promoter can be applied in any type of cassettes.

A promoter drives expression or drives transcription of the nucleic acid sequence that it regulates. An "inverted promoter," as described above, is a promoter in which the nucleic acid sequence is in the reverse orientation, such that what was the coding strand is now the non-coding strand, and vice versa. Inverted promoter sequences can be used in various embodiments of the invention to regulate the state of a logic gate (e.g., high output, "ON," or low/no output, "OFF"). Thus, in some embodiments, the promoter is an inverted promoter, flanked by complementary recombinase recognition sites that, upon recombination of the sites, inverts to the correct orientation and drives expression of an operatively linked nucleic acid sequence. In some embodiments of the invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter and/or the encoded nucleic acid.

A promoter is classified as strong or weak according to its affinity for RNA polymerase (and/or sigma factor); this is related to how closely the promoter sequence resembles the ideal consensus sequence for the polymerase. The strength of a promoter may depend on whether initiation of transcription occurs at that promoter with high or low frequency. Different promoters with different strengths may be used to construct logic gates with different digitally settable levels of gene output expression (e.g., the level of gene expression initiated from a weak promoter is lower than the level of gene expression initiated from a strong promoter).

A promoter may be one naturally associated with a gene or sequence, as may be obtained by isolating the 5' non-coding sequences located upstream of the coding segment and/or exon of a given gene or sequence. Such a promoter can be referred to as "endogenous." Similarly, an enhancer may be one naturally associated with a nucleic acid sequence, located either downstream or upstream of that sequence.

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic, viral or eukaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including PCR, in connection with the logic gates disclosed herein (see U.S. Pat. Nos. 4,683,202 and 5,928,906). Furthermore, control sequences that direct transcription and/or expression of sequences within non-nuclear organelles such as mitochondria, chloroplasts and the like, may be used in accordance with the invention.

In some embodiments, the promoter in the cassette or switch is a constitutive or tissue-specific promoter. Tissue-specific promoters are active in a specific type of cells or tissues such as B cells, monocytic cells, leukocytes, macrophages, muscle, pancreatic acinar cells, endothelial cells, astrocytes, and lung. Tissue-specific promoters are available as native or composite promoter. Native promoters, also called minimal promoters, consist of a single fragment from the 5' region of a given gene. Each of them comprises a core promoter and its natural 5'UTR. In some cases, the 5'UTR contains an intron. Composite promoters combine promoter elements of different origins or were generated by assembling a distal enhancer with a minimal promoter of the same origin. Tissue-specific promoters are commercially available through vendors such as InvivoGen.

Non-limiting constitutive promoters include EF1alpha, SFFV, CMV, RSV, SV40, PGK, CAGGS, pTK, Ubc, Ubi, hU6, and H1.

In some embodiments, the promoter in the cassette is an inducible promoter.

Inducible Promoters

Inducible promoters for use in accordance with the invention may function in both prokaryotic and eukaryotic host organisms. In some embodiments, mammalian inducible promoters are used. Examples of mammalian inducible promoters for use herein include, without limitation, promoter type $P_{ACT}$:$P_{AIR}$, $P_{ART}$, $P_{BIT}$, $P_{CR5}$, $P_{CTA}$, $P_{ETR}$, $P_{NIC}$, $P_{PIP}$, $P_{ROP}$, $P_{SPA}$/$P_{SCA}$, $P_{TET}$, $P_{TtgR}$, promoter type $P_{Rep}$: $P_{CuO}$, $P_{ETR}$, ON8, $P_{NIC}$, $P_{PIR}$ ON, $P_{SCA}$ ON8, $P_{TetO}$, $P_{UREXS}$, promoter type $P_{Hyb}$:teto$_7$-ETR$_8$-$P_{hCMVmin}$, tet0$_7$-PIR3-ETR$_8$-$P_{hCMVmin}$, and scbR$_8$-PIR$_3$-$P_{hCMVmin}$. In some embodiments, inducible promoters from other organisms, as well as synthetic promoters designed to function in a prokaryotic or eukaryotic host may be used. Examples of non-mammalian inducible promoters for use herein include, without limitation, Lentivirus promoters (e.g., EFa, CMV, Human Synapsin1 (hSyn1), CaMKIIa, hGFAP and TPH-2) and Adeno-Associated Virus promoters (e.g., CaMKIIa (AAV5), hSyn1 (AAV2), hThy1 (AAV5), fSST (AAV1), hGFAP (AAV5, AAV8), MBP (AAV8), SST (AAV2)). One important functional characteristic of the inducible promoters of the present invention is their inducibility by exposure to an externally applied inducer. Other examples of inducible promoters include tetracycline inducible (pTRE), streptogramin inducible (pPIR), macrolide inducible (pETR), allolactose or isopropyl ß-D-thiogalactopyranoside inducible (pLacO), ponasterone A inducible, coumermycin/novobiocin-regulated gene expression system, hypoxia inducible (hypoxia response elements), TGFbeta inducible (SMAD response elements), amino acid deprivation inducible (ATF3/ATF3/ATF2).

The administration or removal of an inducer results in a switch between the "ON" or "OFF" states of the transcription of the operatively linked nucleic acid sequence (e.g., nucleic acid encoding a recombinase). Thus, as used herein, the "ON" state of a promoter operatively linked to a nucleic acid sequence refers to the state when the promoter is actively driving transcription of the nucleic acid sequence (i.e., the linked nucleic acid sequence is expressed). Conversely, the "OFF" state of a promoter operatively linked, or conditionally operatively linked, to a nucleic acid sequence refers to the state when the promoter is not actively driving transcription of the nucleic acid sequence (i.e., the linked nucleic acid sequence is not expressed). In some embodiments, the inducer can be doxycycline, tamoxifen, rapamycin, or abscisic acid for the promoter operative linked to a nucleic acid sequence encoding a recombinase.

An inducible promoter for use in accordance with the invention may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof. The condition(s) and/or agent(s) that induce or repress an inducible promoter can be input(s) of the logic gates described herein.

Promoters that are inducible by ionizing radiation can be used in certain embodiments, where gene expression is induced locally in a cell by exposure to ionizing radiation such as UV or x-rays. Radiation inducible promoters include the non-limiting examples of fos promoter, c-jun promoter or at least one CArG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems as described herein can be Zn2+ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

In some embodiments, the inducer or inducing agent, i.e., a chemical, a compound or a protein, can itself be the result of transcription or expression of a nucleic acid sequence (i.e., an inducer can be a transcriptional repressor protein, such as LacI), which itself can be under the control of an inducible promoter. In some embodiments, an inducible promoter is induced in the absence of certain agents, such as a repressor. In other words, in such embodiments, the inducible promoter drives transcription of an operably linked sequence except when the repressor is present. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

The promoters for use in the molecular/biological circuits described herein encompass the inducibility of a prokaryotic or eukaryotic promoter by, in part, either of two mechanisms. In some embodiments, the molecular/biological circuits comprise suitable inducible promoters that can be dependent upon transcriptional activators that, in turn, are reliant upon an environmental inducer. In other embodiments, the inducible promoters can be repressed by a transcriptional repressor which itself is rendered inactive by an environmental inducer, such as the product of a sequence driven by another promoter. Thus, unless specified otherwise, an inducible promoter can be either one that is induced by an inducing agent that positively activates a transcriptional activator, or one which is repressed by an inducing agent that negatively regulates a transcriptional repressor. In such embodiments of the various aspects described herein, where it is required to distinguish between an activating and a repressing inducing agent, explicit distinction will be made.

Inducible promoters that are useful in the molecular/biological circuits and methods of use described herein also include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and Drosophila cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the cassettes, switches, and methods of use described herein.

Inducible promoters useful in some embodiments of the cassettes, switches, and methods of use disclosed herein also include those that are repressed by "transcriptional repressors" that are subject to inactivation by the action of environmental, external agents, or the product of another gene. Such inducible promoters can also be termed "repressible promoters" where it is required to distinguish between other types of promoters in a given module or component of a cassette or switch described herein. Examples include prokaryotic repressors that can transcriptionally repress eukaryotic promoters that have been engineered to incorporate appropriate repressor-binding operator sequences.

In some embodiments, repressors for use in the cassettes or switches described herein are sensitive to inactivation by a physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline or doxycycline will cause the dissociation of the tet repressor from the engineered promoter and allow transcription of the sequence downstream of the engineered promoter to occur.

Inducible promoters for use in accordance with the invention include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, the inducer used in accordance with the invention is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters. In some embodiments, the inducer used in accordance with the invention is anhydrotetracycline (aTc), which is a derivative of tetracycline that exhibits no antibiotic activity and is designed for use with tetracycline-controlled gene expression systems, for example, in bacteria. Other inducible promoter systems may be used in accordance with the invention.

Inducible promoters useful in the functional modules, cassettes, and switches as described herein for in vivo uses can include those responsive to biologically compatible agents, such as those that are usually encountered in defined animal tissues or cells. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

The administration or removal of an inducer or repressor as disclosed herein results in a switch between the "on" or "off" states of the transcription of the operably linked heterologous target gene. Thus, as defined herein the "on" state, as it refers to a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the cassettes and switches described herein is the Lac repressor (lacR)/operator/inducer system of $E.$ $coli$ that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra).

Thus, in some embodiments described herein, components of the Lac system are utilized. For example, a lac operator (LacO) can be operably linked to a tissue specific promoter, and control the transcription and expression of the heterologous target gene and another protein, such as a repressor protein for another inducible promoter. Accordingly, the expression of the heterologous target gene is inversely regulated as compared to the expression or presence of Lac repressor in the system.

Components of the tetracycline (Tc) resistance system of $E.$ $coli$ have also been found to function in eukaryotic cells and have been used to regulate gene expression. For example, the Tet repressor (TetR), which binds to tet operator (tetO) sequences in the absence of tetracycline or doxycycline and represses gene transcription, has been expressed in plant cells at sufficiently high concentrations to repress transcription from a promoter containing tet operator sequences (Gatz, C. et al. (1992) Plant J. 2:397-404). In some embodiments described herein, the Tet repressor system is similarly utilized in the molecular/biological circuits described herein.

A temperature- or heat-inducible gene regulatory system can also be used in the cassettes and switches described herein, such as the exemplary TIGR system comprising a cold-inducible transactivator in the form of a fusion protein having a heat shock responsive regulator, rheA, fused to the VP16 transactivator (Weber et al. 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivates the exemplary rheO-CMVmin promoter, permitting expression of the target gene. At 41° C., the cold-inducible transactivator no longer transactivates the rheO promoter. Any such heat-inducible or heat-regulated promoter can be used in accordance with the circuits and methods described herein, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-168; Ohtsuka & Hata (2000) lnt J Hyperthermia 16(3):231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-190; Kiang et al. (1998) FASEB J 12(14):1571-16-579), calreticulin (Szewczenko-Pawlikowski et al. (1997) Mol Cell Biochem 177(1-2): 145-152); clusterin (Viard et al. (1999) J Invest Dermatol 112(3):290-296; Michel et al. (1997) Biochem J 328(Ptl): 45-50; Clark & Griswold (1997) J Androl 18(3):257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):317-325) are upregulated in response to heat. In the case of clusterin, a 14 base pair element that is sufficient for heat-inducibility has been delineated (Michel et al. (1997) Biochem J 328(Ptl):45-50). Similarly, a two sequence unit comprising a 10- and a 14-base pair element in the calreticulin promoter region has been shown to confer heat-inducibility (Szewczenko-Pawlikowski et al. (1997) Mol Cell Biochem 177(1-2): 145-152).

Other inducible promoters useful in the cassettes and switches described herein include the erythromycin-resistance regulon from $E.$ $coli$, having repressible (Eoff) and inducible (Eon) systems responsive to macrolide antibiotics, such as erythromycin, clarithromycin, and roxithromycin (Weber et al., 2002). The Eoff system utilizes an erythromycin-dependent transactivator, wherein providing a macrolide antibiotic represses transgene expression. In the Eon system, the binding of the repressor to the operator results in repression of transgene expression. Thus, in the presence of macrolides, gene expression is induced.

Fussenegger et al. (2000) describe repressible and inducible systems using a Pip (pristinamycin-induced protein) repressor encoded by the streptogramin resistance operon of

*Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the PipON and PipOFF systems in their respective manners, as described therein.

Another example of a promoter expression system useful for the cassettes and switches described herein utilizes a quorum-sensing (referring to particular prokaryotic molecule communication systems having diffusible signal molecules that prevent binding of a repressor to an operator site, resulting in repression of a target regulon) system. For example, Weber et al. (2003b) employ a fusion protein comprising the *Streptomyces coelicolor* quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another are utilized in the modules, cassettes, and switches described herein (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) lnt J Radiat Biol 72(6):653-660), the hsp27 promoter is activated by 17-β-estradiol and estrogen receptor agonists (Porter et al. (2001) J Mol Endocrinol 26(1):31-42), the HLA-G promoter is induced by arsenite, hsp promoters can be activated by photodynamic therapy (Luna et al. (2000) Cancer Res 60(6): 1637-1644). A suitable promoter can incorporate factors such as tissue-specific activation. For example, hsp70 is transcriptionally impaired in stressed neuroblastoma cells (Drujan & De Maio (1999) 12(6):443-448) and the mortalin promoter is upregulated in human brain tumors (Takano et al. (1997) Exp Cell Res 237(1):38-45). A promoter employed in methods described herein can show selective up-regulation in tumor cells as described, for example, for mortalin (Takano et al. (1997) Exp Cell Res 237(1):38-45), hsp27 and calreticulin (Szewczenko-Pawlikowski et al. (1997) Mol Cell Biochem 177(1-2): 145-152; Yu et al. (2000) Electrophoresis 21(14):3058-3068)), grp94 and grp78 (Gazit et al. (1999) Breast Cancer Res Treat 54(2): 135-146), and hsp27, hsp70, hsp73, and hsp90 (Cardillo et al. (2000) Anticancer Res 20(6B):4579-4583; Strik et al. (2000) Anticancer Res 20(6B):4457-4552).

In some exemplary embodiments, an inducible promoter is an arabinose-inducible promoter PBAD comprising the sequence:

```
                                       (SEQ ID NO: 109)
AAGAAACCAATTGTCCATATTGCATCAGACATTGCCGTCACTGCGTCTTT

TACTGGCTCTTCTCGCTAACCAAACCGGTAACCCCGCTTATTAAAAGCAT

TCTGTAACAAAGCGGGACCAAAGCCATGACAAAAACGCGTAACAAAAGTG

TCTATAATCACGGCAGAAAAGTCCACATTGATTATTTGCACGGCGTCACA

CTTTGCTATGCCAATAGCATTTTTATCCATAAGATTAGCGGATCCTACCT

GACGCTTTTTATCGCAACTCTCTACTGTTTCTCCATA.
```

In some exemplary embodiments, an inducible promoter is a LuxR-inducible promoter PLuxR comprising the sequence:

```
                                       (SEQ ID NO: 110)
ACCTGTAGGATCGTACAGGTTTACGCAAGAAAATGGTTTGTTATAGTCGA

ATAAA.
```

In some exemplary embodiments, an inducible promoter is a mutated LuxR-targeted promoter with modulated binding efficiency for LuxR, such as, for example, pluxR3:

```
                                       (SEQ ID NO: 111)
AATTTGGGGATCGTACAGGTTTACGCAAGAAAATGGTTTGTTATAGTCG

AATAAA;

pluxR28:
                                       (SEQ ID NO: 112)
CTGGCGGGGATCGTACAGGTTTACGCAAGAAAATGGTTTGTTATAGTCG

AATAAA;

pluxR56:
                                       (SEQ ID NO: 113)
TGGGGTAGGATCGTACAGGTTTACGCAAGAAAATGGTTTGTTATAGTCG

AATAAA.
```

In some exemplary embodiments, the inducible promoter comprises an Anhydrotetracycline (aTc)-inducible promoter as provided in PLtetO-1 (Pubmed Nucleotide #U66309) with the sequence comprising:

```
                                       (SEQ ID NO: 114)
GCATGCTCCCTATCAGTGATAGAGATTGACATCCCTATCAGTGATAGAGA

TACTGAGCACATCAGCAGGACGCACTGACCAGGA.
```

In some exemplary embodiments, the inducible promoter is an isopropyl β-D-1-thiogalactopyranoside (IPTG) inducible promoter. In one embodiment, the IPTG-inducible promoter comprises the $P_{TAC}$ sequence found in the vector encoded by PubMed Accession ID #EU546824. In one embodiment, the IPTG-inducible promoter sequence comprises the $P_{Trc-2}$ sequence:

```
                                       (SEQ ID NO: 115)
CCATCGAATGGCTGAAATGAGCTGTTGACAATTAATCATCCGGCTCGTAT

AATGTGTGGAATTGTGAGCGGATAACAATTTCACACAGGA.
```

In some exemplary embodiments, the IPTG-inducible promoter comprises the $P_{LlacO-1}$ sequence:

```
                                       (SEQ ID NO: 116)
ATAAATGTGAGCGGATAACATTGACATTGTGAGCGGATAACAAGATACTG

AGCACTCAGCAGGACGCACTGACC.
```

In some exemplary embodiments, the IPTG-inducible promoter comprises the P$_{A1lacO\text{-}1}$ sequence:

```
                                     (SEQ ID NO: 117)
AAAATTTATCAAAAAGAGTGTTGACTTGTGAGCGGATAACAATGATACTT

AGATTCAATTGTGAGCGGATAACAATTTCACACA.
```

In some exemplary embodiments, the IPTG-inducible promoter comprises the P$_{lac/ara\text{-}1}$ sequence

```
                                     (SEQ ID NO: 118)
CATAGCATTTTTATCCATAAGATTAGCGGATCCTAAGCTTTACAATTGTG

AGCGCTCACAATTATGATAGATTCAATTGTGAGCGGATAACAATTTCACA

CA.
```

In some exemplary embodiments, the inducible promoter sequence comprises the P$_{Ls1con}$ sequence:

```
                                     (SEQ ID NO: 119)
GCATGCACAGATAACCATCTGCGGTGATAAATTATCTCTGGCGGTGTTGA

CATAAATACCACTGGCGGTtATAaTGAGCACATCAGCAGGGTATGCAAAG

GA.
```

Other non-limiting examples of promoters are provided in Tables 1-36 of US Patent Application US2017/0183654, which is incorporated herein in its entirety by reference.

E. Vector components

Essentially any expression vector including, but not limited to, plasmids and viral vectors can be used to express the components of the system for regulating gene expression as described herein, for example, the molecular clamp proteins and/or sTF proteins. The vectors described herein can include any number of sequences known to those of skill in the art, such as promoters (e.g., constitutive or inducible), enhancers, long-terminal repeats (LTRs), multiple cloning sites, restriction sequences, and the like. It will be appreciated by those of ordinary skill in the art that a vector can be designed to include any number of optional sequences e.g., to enhance expression of a given molecular clamp and/or sTF. Some non-limiting examples of these sequences, referred to herein as "viral components" are described herein.

The vectors described herein can contain zero, one or more of the following components: promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, or epitope tags.

Promoters used with the vector compositions described herein can be constitutive, or inducible.

As used herein, the term "constitutive promoter" refers to a promoter that continually or continuously allows for transcription of an operably linked sequence. Constitutive promoters may be a "ubiquitous promoter" that allows expression in a wide variety of cell and tissue types or a "tissue-specific promoter" that allows expression in a restricted variety of cell and tissue types. Illustrative ubiquitous promoters include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

As used herein, "conditional expression" may refer to any type of conditional expression including, but not limited to, inducible expression; repressible expression; expression in cells or tissues having a particular physiological, biological, or disease state, etc. Certain embodiments of the methods and compositions herein provide conditional expression of a molecular clamp or sTF e.g., expression is controlled by subjecting a host cell, to a treatment or condition that causes the polynucleotide to be expressed or that causes an increase or decrease in expression of the molecular clamp polynucleotide or sTF encoded by the nucleic acid. The concept of inducible expression of a polypeptide is well known in the art and/or could be envisioned by one of skill in the art. As such, the mechanisms of inducible gene expression are not described at length herein.

An inducible promoter/system useful in the methods and systems as disclosed herein can be induced by one or more physiological conditions, such as changes in pH, temperature, cell surface binding, and the concentration of one or more extrinsic or intrinsic inducing agents. The extrinsic inducer or inducing agent can comprise amino acids and amino acid analogs, nucleic acids, protein transcriptional activators and repressors, cytokines, hormones, and combinations thereof.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

In some embodiments, the administration or removal of an inducer or repressor as described herein results in a switch between the "on" or "off" states of the transcription of one or more components of the gene expression system described herein. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative embodiment can fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

An exemplary repressible promoter useful in the synthetic transcription factors as disclosed herein is the Lac repressor (lacR)/operator/inducer system of $E.\ coli$ that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments of the aspects described herein, components of the Lac system are utilized. For example, a lac operator (LacO) can be operably linked to tissue specific promoter, and control the transcription and expression of a desired protein and another repressor protein, such as the TetR. Accordingly, the expression of the heterologous target gene is inversely regulated as compared to the expression or presence of Lac repressor in the system.

In one embodiment, the vectors described herein can include an "internal ribosome entry site" or "IRES," which refers to an element that promotes direct internal ribosome entry to the initiation codon, such as ATG, of a cistron (a protein encoding region), thereby leading to the cap-independent translation of the gene. In particular embodiments, the vectors contemplated herein may include one or more nucleic acid sequences encoding e.g., a multi-domain scaffold protein and/or a synthetic transcription factor. To achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (SEQ ID NO: 32; Kozak, 1986. Cell. 44(2):283-92, and Kozak, 1987. Nucleic Acids Res. 15(20):8125-48).

In particular embodiments, vectors comprise a polyadenylation sequence 3' of a polynucleotide encoding a polypeptide to be expressed. Polyadenylation sequences can promote mRNA stability by addition of a polyA tail to the 3' end of the coding sequence and thus, contribute to increased translational efficiency. Recognized polyadenylation sites include an ideal polyA sequence (e.g., ATTAAA (SEQ ID NO: 33), ATTAAA (SEQ ID NO: 34), AGTAAA (SEQ ID NO: 35)), a bovine growth hormone polyA sequence (BGHpA), a rabbit β-globin polyA sequence (rβgpA), or another suitable heterologous or endogenous polyA sequence known in the art.

If desired, the vectors described herein can comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977. Cell 11:223-232) and adenine phosphoribosyltransferase (Lowy et al., 1990. Cell 22:817-823) genes which can be employed in tk- or aprt-cells, respectively.

The term 'nucleic acid cassette" as used herein refers to genetic sequences within the vector which can express an RNA, and subsequently a protein of interest (e.g., a molecular clamp or sTF). The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In one embodiment, the nucleic acid cassette contains the sequence of a nucleic acid encoding a molecular clamp or sTF as described herein. The cassette can be removed and inserted into a plasmid or viral vector as a single unit.

When a nuclear localization signal peptide is desired on one or more of the components of the gene expression system described herein, a vector can include a nucleic acid sequence encoding such a nuclear localization sequence on the sTF or scaffold protein. Exemplary nuclear localization sequences are provided in Table 1 disclosed herein.

F. Uses of Engineered Genetic Counters

The system for cooperative sTF assemblies as described herein is useful for engineering complex behavioral phenotypes in cellular systems, such as prokaryotic, eukaryotic, or synthetic cells, or in non-cellular systems, including test tubes, viruses and phages. The novel system for cooperative sTF assemblies as described herein combine the power of nucleic acid-based engineering methods with systems biology approaches to elicit specific levels of gene expression in cellular and non-cellular systems, such as the ability for fine-tuning single and multiple inputs for controlled gene expression.

In some of the aspects described herein, the system for cooperative sTF assemblies as described herein can be used in cellular systems, such as bacteria. In some aspects, the system for cooperative sTF assemblies as described herein can be used in non-cellular systems, such as viruses or phages, for controlled gene expression in non-cellular system.

The system for cooperative sTF assemblies as described herein can be used for a variety of applications and in many different types of methods, including, but not limited to, bioremediation, biosensing, and biomedical therapeutics.

The methods and uses of system for cooperative sTF assemblies as described herein can be used for in vivo, ex vivo, or in vitro systems.

A cell to be engineered for use with the system for cooperative sTF assemblies as described herein and can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Host cells of use in the aspects of the invention upon transformation or transfection with vectors for expression of the components for cooperative sTF assemblies as described herein include any host cell that is capable of supporting the activation and expression of the engineered genetic counters. In some embodiments of the aspects described herein, the cells are bacterial cells. The term "bacteria" as used herein is intended to encompass all variants of bacteria, for example, prokaryotic organisms and cyanobacteria. Bacteria are small (typical linear dimensions of around 1 m), non-compartmentalized, with circular DNA and ribosomes of 70S. The term bacteria also includes bacterial subdivisions of Eubacteria and Archaebacteria. Eubacteria can be further subdivided on the basis of their staining using Gram stain, and both gram-positive and gram-negative eubacteria, which depends upon a difference in cell wall structure are also included, as well as classified based on gross morphology alone (into cocci, bacilli, etc.).

In some embodiments, the bacterial cells are gram-negative cells and in alternative embodiments, the bacterial cells are gram-positive cells. Non-limiting examples of species of bacterial cells useful for engineering with the engineered genetic counters of the invention include, without limitation, cells from *Escherichia coli, Bacillus subtilis, Salmonella typhimurium* and various species of *Pseudomonas, Streptomyces,* and *Staphylococcus*. Other examples of bacterial cells that can be genetically engineered for use with the biological circuit chemotactic converters of the invention include, but are not limited to, cells from *Yersinia* spp., *Escherichia* spp., *Klebsiella* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., and *Erysipelothrix* spp. In some embodiments, the bacterial cells are *E. coli* cells. Other examples of organisms from which cells may be transformed or transfected with the engineered genetic counters of the present invention include, but are not limited to the following: *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helicobacter pylori, Selenomonas ruminatium, Shigella sonnei, Zymomonas mobilis, Mycoplasma mycoides,* or *Treponema denticola, Bacillus thuringiensis, Staphylococcus lugdunensis, Leuconostoc oenos, Corynebacterium xerosis, Lactobacillus planta* rum, *Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Streptomyces ghanaenis, Halobacterium* strain GRB, and *Halobaferax* sp. strain Aa2.2.

In alternative embodiments, the cells can be any cell, for example mammalian cells, plant cells and chimeric cells. In some embodiments, the cells can be from any organism or multi-cell organism. Examples of eukaryotic cells that can be useful in aspects of the invention include eukaryotic cells selected from, e.g., mammalian, insect, yeast, or plant cells. In some embodiments, the eukaryotic cells are from a vertebrate animal. The present invention contemplates the use of any such vertebrate cells for the engineered genetic counters, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells.

In other embodiments of the aspects described herein, the system for cooperative sTF assemblies as described herein can be introduced into a non-cellular system such as a virus or phage, by direct integration of the engineered genetic counter nucleic acid, for example, into the viral genome. A virus for use with the engineered genetic counters described herein can be a dsDNA virus (e.g. Adenoviruses, Herpesviruses, Poxviruses), a ssDNA viruses ((+)sense DNA) (e.g. Parvoviruses); a dsRNA virus (e.g. Reoviruses); a (+)ssRNA viruses ((+)sense RNA) (e.g. Picornaviruses, Togaviruses); (−)ssRNA virus ((−)sense RNA) (e.g. Orthomyxoviruses, Rhabdoviruses); a ssRNA-Reverse Transcriptase viruses ((+)sense RNA with DNA intermediate in life-cycle) (e.g. Retroviruses); or a dsDNA-Reverse Transcriptase virus (e.g. Hepadnaviruses).

Viruses can also include plant viruses and bacteriophages or phages. Examples of phage families that can be used with the engineered genetic counters described herein include, but are not limited to, Myoviridae (T4-like viruses; P1-like viruses; P2-like viruses; Mu-like viruses; SPO1-like viruses; φH-like viruses); Siphoviridaeλ-like viruses (T1-like viruses; T5-like viruses; c2-like viruses; L5-like viruses; ψM1-like viruses; φC3 Hike viruses; N15-like viruses); Podoviridae (T7-like viruses; φ29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudivirus); Fuselloviridae (Fusellovirus); Inoviridae (Inovirus, Plectrovirus); Microviridae (Microvirus, Spiromicrovirus, Bdellomicrovirus, Chlamydiamicrovirus); Leviviridae (Levivirus, Allolevivirus) and Cystoviridae (Cystovirus). Such phages can be naturally occurring or engineered phages.

In some embodiments, components of the system for cooperative sTF assemblies as described herein are introduced into a cellular or non-cellular system using a vector or plasmid for use in counting events in the system.

Other expression vectors can be used in different embodiments of the invention, for example, but not limited to, plasmids, episomes, bacteriophages or viral vectors, and such vectors can integrate into the host's genome or replicate autonomously in the particular cellular system used. Other forms of expression vectors known by those skilled in the art which serve the equivalent functions can also be used. Expression vectors comprise expression vectors for stable or transient expression encoding the DNA. A vector can be either a self-replicating extrachromosomal vector or a vector which integrates into a host genome. One type of vector is a genomic integrated vector, or "integrated vector", which can become integrated into the chromosomal DNA or RNA of a host cell, cellular system, or non-cellular system. In some embodiments, the nucleic acid sequence or sequences encoding the engineered genetic counter integrates into the chromosomal DNA or RNA of a host cell, cellular system, or non-cellular system along with components of the vector sequence. In other embodiments, the nucleic acid sequence encoding the engineered genetic counter directly integrates into chromosomal DNA or RNA of a host cell, cellular system, or non-cellular system, in the absence of any components of the vector by which it was introduced. In such embodiments, the nucleic acid sequence encoding the engineered genetic counter can be integrated using targeted insertions, such as knock-in technologies or homologous recombination techniques, or by non-targeted insertions, such as gene trapping techniques or non-homologous recombination. The number of copies of an engineered genetic counter that integrate into the chromosomal DNA or RNA of a cellular or non-cellular system can impact the fidelity of counting, and thus it is preferred that only one copy is integrated per cellular system. Accordingly, in some embodiments of the aspects described herein, only one copy of an engineered genetic counter is integrated in the chromosomal DNA or RNA of a cellular or non-cellular system. In some embodiments, the number of copies is less than 10, less than 9, less than 8, less than 7, less than 6, less than 6, less than 4, less than 3, or less than 2.

Another type of vector is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the engineered genetic counters are introduced into a cellular system using a BAC vector.

The vectors comprising components of the system for cooperative sTF assemblies as described herein may be "introduced" into cells as polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid:nucleic acid complexes, viral vector transduction, injection, contacting with naked DNA, gene gun, and the like. The vectors, in the case of phage and viral vectors may also be introduced into cells as packaged or encapsidated virus by well-known techniques for infection and transduction. Viral vectors may be replication competent or replication defective. In the latter case, viral propagation generally occurs only in complementing host cells. In some embodiments, the engineered genetic counters are introduced into a cell using other mechanisms known to one of skill in the art, such as a liposome, microspheres, gene gun, fusion proteins, such as a fusion of an antibody moiety with a nucleic acid binding moiety, or other such delivery vehicle.

The system for cooperative sTF assemblies as described herein or the vectors comprising the components of the system for cooperative sTF assemblies as described herein can be introduced into a cell using any method known to one of skill in the art. The term "transformation" as used herein refers to the introduction of genetic material (e.g., a vector comprising an engineered genetic counter) comprising one or more modules or engineered genetic counters described herein into a cell, tissue or organism. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme linked immunosorbent assay (ELISA), which detects the presence of a polypeptide encoded by one or more of the transgenes. Alternatively, transient transformation may be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

The present invention can be defined in any of the following numbered paragraphs:

1. A system for controlling gene expression comprising:
   (a) at least one a synthetic transcription factor (sTF) comprising at least one ligand, a DNA binding domain (DBD) and a transcription activator (TA) domain or transcriptional repressor (TR) domain, wherein the DBD can bind to at least one target DNA binding motif (DBM) located upstream of a promoter operatively linked to a gene,
   (b) a molecular clamp comprising n ligand binding domains (LBD), wherein each ligand binding domain is connected to at least one other LBD by a linker, wherein at least one LBD can bind to the ligand of the at least one sTF;
   wherein n is an integer between 1 and 50;
   wherein when the molecular clamp and at least one sTF are both present in a cell, at least one ligand binding domain binds to the ligand of the sTF,
      wherein if a TA domain is present, the TA domain recruits the RNA pol II machinery to the promoter, thereby turning on gene expression ("ON switch"), and wherein if a TR domain is present, the TR domain prevents RNA pol II machinery from binding to the promoter, thereby inhibiting gene expression. ("OFF Switch")
2. The system of paragraph 1, wherein the linker is a flexible linker.
3. The system of paragraph 2, wherein the linker comprises a flexible glycine-serine (GS) linker repeat sequence.
4. The system of paragraph 3, wherein the GS linker repeat sequence is repeated at least 5 times.
5. The system of paragraph 4, wherein the GS linker repeat sequence is repeated 2-25 times (SEQ ID NO: 56).
6. The system of paragraph 5, wherein the GS linker repeat sequence is repeated, 5 (SEQ ID NO: 57), 10 (SEQ ID NO: 58) or 20 (SEQ ID NO: 59) times.
7. The system of paragraph 1, wherein the ligand is a peptide ligand and the ligand binding domain (LBD) is a protein binding domain.
8. The system of paragraph 3, wherein the protein binding domain is a PDZ domain.
9. The system of paragraph 3, wherein the PDZ domain is a syntrophin PDZ domain.
10. The system of paragraph 9, wherein the ligand is selected from any of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), and VKEALV (SEQ ID NO: 8).
11. The system of paragraph 3, wherein the PDZ domain is a erbin PDZ domain.
12. The system of paragraph 11, wherein the ligand is selected from any of: WLKTWV (SEQ ID NO: 22), PVDSWV (SEQ ID NO: 23), or VKEALV (SEQ ID NO: 8).
13. The system of paragraph 1, wherein the molecular clamp comprises a C-terminal nuclear localization signal (NLS).
14. The system of paragraph 1, wherein the sTF comprises a C-terminal nuclear localization signal (NLS).
15. The system of paragraph 1, wherein n=2, 3, 4, 5, 6 or between 6-10.
16. The system of paragraph 1, wherein the DNA binding domain (DBD) is an engineered zinc finger binding domain.
17. The system of paragraph 16, wherein the DBD is selected from any of: 43-8 (WT), 43-8 (3×), 43-8 (×4), 42-10 (WT), 42-10 (3×) or 42-10 (×4) of VP16.
18. The system of paragraph 17, wherein the DBD binds to DNA binding motifs (DBM) comprising any of: DBM1 op, DMB2 op, DBM3 op.
19. The system of paragraph 1, wherein the ligand is located at the N-terminus of the TA or TR domain.
20. The system of paragraph 1, wherein the sTF comprises in the following order; N- to C-terminal: a nuclear localization sequence, a TA domain; a DNA binding domain (DBD); a linker (GSGSG (SEQ ID NO: 60)) and a ligand.
21. The system of paragraph 1, wherein the TA domain is VP16 minimal activation domain.
22. The system of paragraph 1, wherein the sTF and molecular clamp are expressed in the cell under the control of different inducible promoters.
23. The system of paragraph 1, wherein the gene is a fluorescent protein or reporter protein.
24. The system of any of the above paragraphs, wherein molecular clamp has the general formula of: $[(X)_n(Y)]_m$, where each X is the same or a different ligand binding domain (LBD), wherein n is an integer from one to about 10 (e.g., where n is 1, 2, 3, 4, 5, 6, 7, 8, 9, or 10), where Y, if present, is a linker peptide, and where m is an integer from 2 to about 50 (e.g., from 2 to about 3, from 3 to about 6, from 6 to about 10, from 10 to about 15, from 15 to 20, from 20 to 25, from 25 to 30, from 30 to 35, from 35 to 40, from 40 to 45, or from 45 to 50).
25. The system of any of the above paragraphs, wherein molecular clamp comprises: NLS-[LBD-linker]n-LBD, where n is 1, 2, 3, 4, 5, 6, 7, 8, 9, or 10.
26. The system of any of the above paragraphs, wherein the LBD is selected from: an SH3 domain, a PDZ domain, a GTPase binding domain (GBD), a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, and a bZIP domain.
27. A molecular clamp comprising n ligand binding domains (LBD) wherein each LBD is connected to at least one other LBD by a linker, where n is an integer between 1 and 50.
28. The molecular clamp of paragraph 27, wherein the ligand binding domain (LBD) is a protein binding domain.
29. The molecular clamp of paragraph 28, wherein the protein binding domain is a PDZ domain.
30. The molecular clamp of paragraph 29, comprising at least two PDZ domains.
31. The molecular clamp of paragraphs 29 or 30, wherein the PDZ domain is a syntrophin or erbin PDZ domain.
32. The molecular clamp of paragraph 29, wherein the PDZ domain is a syntrophin PDZ domain.

33. The molecular clamp of paragraph 32, wherein the PDZ domain binds to a ligand selected from any of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), and VKEALV (SEQ ID NO: 8).

34. The molecular clamp of paragraph 29, wherein the PDZ domain is a erbin PDZ domain.

35. The molecular clamp of paragraph 34, wherein the PDZ domain binds to a ligand selected from any of: WLKTWV (SEQ ID NO: 22), PVDSWV (SEQ ID NO: 23), or VKEALV (SEQ ID NO: 8).

36. The molecular clamp of paragraph 27, wherein n=2, 3, 4, 5, 6 or between 6-10.

37. The molecular clamp of any of paragraphs 27-36, wherein molecular clamp has the general formula of: $[(X)_n(Y)]_m$, where each X is the same or a different ligand binding domain (LBD), wherein n is an integer from one to about 10 (e.g., where n is 1, 2, 3, 4, 5, 6, 7, 8, 9, or 10), where Y, if present, is a linker peptide, and where m is an integer from 2 to about 50 (e.g., from 2 to about 3, from 3 to about 6, from 6 to about 10, from 10 to about 15, from 15 to 20, from 20 to 25, from 25 to 30, from 30 to 35, from 35 to 40, from 40 to 45, or from 45 to 50).

38. The molecular clamp of any of paragraphs 27-36, wherein molecular clamp comprises: NLS-[LBD-linker]n-LBD, where n is 1, 2, 3, 4, 5, 6, 7, 8, 9, or 10.

39. The molecular clamp of any of paragraphs 27-37, wherein the LBD is selected from: an SH3 domain, a PDZ domain, a GTPase binding domain (GBD), a leucine zipper domain, an SH2 domain, a PTB domain, an FHA domain, a WW domain, a 14-3-3 domain, a death domain, a caspase recruitment domain, a bromodomain, a chromatin organization modifier, a shadow chromo domain, an F-box domain, a HECT domain, a RING finger domain, a sterile alpha motif domain, a glycine-tyrosine-phenylalanine domain, a SNAP domain, a VHS domain, an ANK repeat, an armadillo repeat, a WD40 repeat, an MH2 domain, a calponin homology domain, a Dbl homology domain, a gelsolin homology domain, a PB1 domain, a SOCS box, an RGS domain, a Toll/IL-1 receptor domain, a tetratricopeptide repeat, a TRAF domain, a Bcl-2 homology domain, a coiled-coil domain, and a bZIP domain.

40. The molecular paragraph of paragraph 27 comprising a nuclear localization signal (NLS).

41. The molecular clamp of paragraph 27, wherein at least one ligand binding domain binds to at least one ligand of a synthetic transcription factor.

42. The molecular clamp of paragraph 27, wherein the linker is a flexible linker.

43. The molecular clamp of paragraph 42, wherein the linker comprises a flexible glycine-serine (GS) linker repeat sequence.

44. The molecular clamp of paragraph 43, wherein the GS linker repeat sequence is repeated at least 5 times.

45. The molecular clamp of paragraph 44, wherein the GS linker repeat sequence is repeated 2-25 (SEQ ID NO: 56) times.

46. The molecular clamp of paragraph 45, wherein the GS linker repeat sequence is repeated, 5 (SEQ ID NO: 57), 10 (SEQ ID NO: 58) or 20 (SEQ ID NO: 59) times.

47. The molecular clamp of paragraph 40, wherein the nuclear localization sequence is derived from an SV40 nuclear localization sequence.

48. The molecular clamp of paragraph 47, wherein the nuclear localization sequence comprises the sequence of: PKKKRKVGIHGVPGG (SEQ ID NO: 1) or PKKKRKVVE (SEQ ID NO: 2).

49. A vector comprising a nucleic acid encoding the molecular clamp of paragraph 27.

50. The vector of paragraph 49, further comprising an inducible promoter operably linked to the nucleic acid encoding the molecular clamp.

51. A synthetic transcription factor (sTF) comprising:
  a. a ligand,
  b. at least one DNA binding domain (DBD), and
  c. a transcriptional activator (TA) domain or a transcriptional repressor (TR) domain, and
    wherein the DBD can bind to a target DNA binding motif (DBM) located upstream of a promoter operatively linked to a gene, and wherein the ligand can bind a ligand binding domain (LBD).

52. The sTF of paragraph 51, wherein the at least one DNA binding domain (DBD) is an engineered zinc finger binding domain.

53. The sTF of paragraph 52, wherein the zinc finger binding domain comprises at least one mutation compared to a wild-type zinc finger domain.

54. The sTF of paragraph 51, wherein the sTF comprises a triple repeat zinc finger array.

55. The sTF of paragraph 51, wherein the DBD binds to tandem DNA binding motifs (DBM) located upstream of a promoter.

56. The sTF of paragraph 51, wherein the DBD is selected from any of: 43-8 (WT), 43-8 (3×), 43-8 (×4), 42-10 (WT), 42-10 (3×) or 42-10 (×4) of VP16.

57. The sTF of paragraph 51, wherein the DBD binds to DNA binding motifs (DBM) comprising any of: DBM1 op, DBM2 op, and/or DBM3 op.

58. The sTF of paragraph 48, wherein the ligand is located at the N-terminus of the TA or TR domain.

59. The sTF of paragraph 51, wherein the sTF comprises, in the following order; N- to C-terminal: a nuclear localization sequence, a TA domain; a DNA binding domain (DBD); a linker (GSGSG (SEQ ID NO: 60)) and a ligand.

60. The sTF of paragraph 51, wherein the sTF comprises in the following order; N- to C-terminal: a nuclear localization sequence, a ligand, a DNA binding domain (DBD), a TA domain; wherein a linker (GSGSG (SEQ ID NO: 60)) is located between the DNA binding domain and the ligand.

61. The sTF of paragraph 51, wherein the TA domain is VP16 minimal activation domain.

62. The sTF of paragraph 51, wherein the TA domain is selected from any of: VP16, VP64, p65.

63. The sTF of paragraph 51, wherein the ligand is
  a. located at the C-terminal end of the sTF,
  b. selected from the group consisting of: IRETII (SEQ ID NO: 3), IRETIL (SEQ ID NO: 4), IRWTIV (SEQ ID NO: 5), VKESLV (SEQ ID NO: 6), IRETIV (SEQ ID NO: 7), and VKEALV (SEQ ID NO: 8).

64. The sTF of paragraph 51, wherein the sTF further comprises an epitope tag.

65. The sTF of paragraph 64, wherein the epitope tag comprises a FLAG tag.

66. The sTF of paragraph 51, wherein the sTF further comprises a nuclear localization sequence.

67. The sTF of paragraph 66, wherein the nuclear localization sequence is derived from an SV40 nuclear localization sequence.

68. The sTF of paragraph 67, wherein the nuclear localization sequence comprises the sequence of: PKKKRKVGIHGVPGG (SEQ ID NO: 1) or PKKKRKVVE (SEQ ID NO: 2).
69. The sTF of paragraph 51, wherein the transcriptional activator (TA) domain or transcriptional repressor (TR) domain is located between the nuclear localization sequence and the at least one DNA binding domain (DBD).
70. A vector comprising a nucleic acid encoding the sTF of paragraph 51.
71. The vector of paragraph 70, further comprising an inducible promoter operably linked to the nucleic acid encoding the sTF.
72. A molecular clamp and sTF binding pair comprising: a molecular clamp of paragraph 27, and a sTF of paragraph 51, wherein at least one of the ligand binding domains (LBD) of the molecular clamp can bind to the ligand of the sTF, thereby forming a specific binding pair.
73. A vector comprising a nucleic acid encoding the molecular clamp of paragraph 27, a nucleic acid encoding the sTF of paragraph 51, and at least one inducible promoter operably linked to the nucleic acid encoding the molecular clamp and/or the nucleic acid encoding the sTF.
74. The vector of paragraph 73, comprising a first inducible promoter operatively linked to the nucleic acid encoding the molecular clamp, and a second inducible promoter operatively linked to the nucleic acid encoding the sTF, wherein the first and second inducible promoters are different.
75. A system for regulating gene expression, the system comprising:
    a. a molecular clamp of paragraph 27,
    b. a synthetic transcription factor (sTF) of paragraph 51, and
    c. a gene expression unit.
76. The system of paragraph 74, wherein the molecular clamp and the sTF are expressed from at least one vector.
77. The system of paragraph 74, wherein the at least one vector further comprises an inducible promoter.
78. A method for regulating gene expression, the method comprising: providing a molecular clamp of paragraph 27 to a cell, contacting a synthetic transcription factor (sTF) of paragraph 51 with the molecular clamp in the presence of a gene expression unit comprising a DNA binding motif (DBM), whereby the molecular clamp and the sTF form a complex resulting in the sTF binding to the DBM in the gene expression unit and modulates gene expression.
79. The method of paragraph 77, wherein the molecular clamp and/or the synthetic transcription factor are expressed from a vector.
80. The method of paragraph 77, wherein the vector further comprises at least one inducible promoter.
81. The method of paragraph 77, wherein expression of a gene product from the gene expression unit is regulated by providing an agent that modulates the at least one inducible promoter and thus controls expression of the scaffold protein and/or the sTF.
82. The method of paragraph 77, wherein the vector comprises at least two inducible promoters.
83. The method of paragraph 81, wherein the at least two inducible promoters are different promoters.
84. The method of paragraph 79 or 80, wherein the agent(s) that modulate(s) the at least one inducible promoter comprise(s) a small molecule.
85. The method of paragraph 82, wherein expression of the molecular clamp and the sTF are independently regulated by the at least two inducible promoters.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and "consisting essentially of shall be closed or semi-closed transitional phrases, respectively, as set forth in the United States Patent Office Manual of Patent Examining Procedures, Section 2111.03.

EXAMPLES

The following provides non-limiting Examples demonstrating and supporting the technology as described herein.

The cooperative assembly of transcriptional regulatory complexes plays a critical signal processing role in eukaryotic gene networks. For many genes, transcriptional activation occurs when core initiation machinery is recruited to basal promoter regions by assemblies of enhancer-bound transcription factors (TFs) and associated co-factors. Here, cooperativity is driven by TF multivalency, which supports formation of mutually-reinforcing protein-protein and protein-DNA interactions. The resulting nucleoprotein complexes are thought to function as computational devices. For example, complex assembly can convert an analog TF input gradient into a switch-like transcriptional output. By incorporating more than one TF, complexes can carry out Boolean decision functions, activating transcription only when the correct combination of TFs is present. In metazoan systems, gene networks are thought to utilize assembly-based computation to precisely interpret positional and temporal information during cell state decision making processes like cell type differentiation and developmental tissue patterning. To date, most synthetic gene circuits have been constructed using TFs that bind to promoters in one-to-one fashion. While binary interactions offer a facile means for making circuit connections, their use precludes any ability to tune circuit cooperativity, potentially imposing limits on engineerable behavior.

The methods and compositions described herein quantitatively program cooperative TF assembly based on the configuration and strength of synthetic intra-complex interactions, and construct circuits composed of interconnected regulatory assemblies. The method provided herein systematically tests the behavioral capacity of transcriptional networks in which nonlinearity associated with each node's transfer function can be freely programmed. The method described herein involves engineering multivalent TF assemblies and scaling well-defined binary interactions predicted by a mathematical model.

Transcription is activated when synthetic zinc-finger (ZF) proteins fused to transcriptional activator domains (synTFs) bind to tandem DNA binding motifs (DBMs) located upstream of a core promoter. Cooperative interactions between synTFs are implemented through a multi-domain PDZ "clamp" protein, which binds to peptide ligands on C-termini of tandemly bound synTFs. The free energy of the assembled complex can be adjusted by varying either the number of tandem clamp/synTF/DBM units ($n_c$), or the affinity of synTF-DBM and PDZ-ligand interactions ($K_f$ and $K_p$, respectively) Tuning of complex stability is enabled by part selection, as affinity variants are available for both ZF and PDZ domains (15 ZF-DNA and 14 PDZ-ligand interactions). Additionally, using orthogonal ZF and PDZ species makes it possible to either program mutually exclusive interactions within a single complex, or create networks comprised of multiple, discrete assemblies.

Example 1: Complex Signal Processing in Synthetic Gene Circuits Using Cooperative Regulatory Assemblies Eukaryotic genes are regulated by multivalent transcription factor complexes. Through cooperative self-assembly, these complexes perform non-linear regulatory operations involved in cellular decision-making and signal processing. Herein, this design principle is applied to synthetic networks, testing whether engineered cooperative assemblies can program non-linear gene circuit behavior in yeast. Using a model-guided approach it is shown that specifying strength and number of assembly subunits enables predictive tuning between linear and non-linear regulatory response for single- and multi-input circuits. Assemblies can be adjusted to control circuit dynamics. This capability is harnessed to engineer circuits that perform dynamic filtering, enabling frequency-dependent decoding in cell populations. Programmable cooperative assembly provides a versatile way to tune nonlinearity of network connections, dramatically expanding the engineerable behaviors available to synthetic circuits.

To date, most synthetic gene circuits have been constructed using TFs that bind to promoters in one-to-one fashion, constraining the ability to tune circuit cooperativity and potentially imposing limits on engineerable behavior (see e.g., FIG. 1A, top). Herein, it is determined whether circuits with expanded signal processing function can be implemented using engineered multivalent assembly (see e.g., FIG. 1A, bottom). Theoretical and design frameworks are established for programming cooperative TF assembly based on the configuration and strength of intra-complex interactions, and construct synthetic gene circuits composed of interconnected regulatory assemblies.

In the scheme for engineering cooperative TF assemblies (see e.g., FIG. 1B), transcription is activated when synthetic zinc-finger (ZF) proteins fused to transcriptional activator domains (synTFs) bind tandem DNA binding motifs (DBMs) located upstream of a core promoter. Assembly is mediated by a "clamp" protein: multiple covalently-linked PDZ domains that bind peptide ligands located on the C-termini of adjacent DBM-bound synTFs. Complex free energy can be adjusted by varying either the number of clamp/synTF/DBM repeats (nc), or the affinity of synTF-DBM and PDZ-ligand interactions (Kt and Kp, respectively), which is enabled by affinity variants for both domains (15 ZF-DNA and 13 PDZ-ligand interactions) (see e.g., FIG. 6, FIG. 7A, FIG. 7B).

In order to directly test whether the synTF/clamp/DBM module can support cooperative assembly, in vitro fluorescence anisotropy binding experiments were conducted on purified complex components (see e.g., FIG. 6, FIG. 7A, FIG. 7B, Examples 2 and 3). synTF binding to a nc=2 probe showed a non-cooperative dose response profile, while presence of a two-PDZ clamp lowered the synTF binding threshold and steepened the dose response, an effect not observed for a non-binding synTF or for an nc=1 probe (see e.g., FIG. 1C). Complex formation using an nc=3 probe (and three-PDZ clamp) demonstrated a still sharper, lower-threshold response. Thus, synTF binding cooperativity is enhanced by the clamp and scales in magnitude with complex size.

In vivo complex assembly was next demonstrated in yeast cells by constructing a transcriptional circuit in which a nc=2 synTF assembly drives a GFP reporter, with synTF and clamp levels controlled via non-cooperative, small-molecule inducible expression systems (see e.g., FIG. 1D, FIG. 8A, FIG. 8B): ncTET (for synTF expression), induced with anhydrotetracycline (ATc), and ncZEV (for clamp expression), induced by estradiol (EST). A dose response surface was obtained by titrating ATc against EST and recording GFP fluorescence output using flow cytometry (see e.g., FIG. 1E, upper left). Consistent with clamp-enhanced synTF binding, ATc dose response threshold was reduced in the presence of increasing EST (see e.g., FIG. 1E).

To quantitatively describe complex formation, a simple statistical thermodynamic model was formulated relating intracellular synTF and clamp expression to promoter occupancy and resulting GFP output (see e.g., FIG. 10, FIG. 11, FIG. 12A-FIG. 12B; see e.g., Example 3 for full model description). The model was fit to experimental two-input dose response data for seven complex configurations, where Kt, Kp, and nc were experimentally adjusted (see e.g., FIG. 1E). Parameter fitting was constrained by in vitro-measured PDZ and ZF interaction affinities (see e.g., FIG. 6, FIG. 7A, FIG. 7B) and inducible component expression data (see e.g., FIG. 8A, FIG. 8B). The fitted model can be used to guide circuit engineering, enumerating potential circuit behaviors (behavior space) based on input-output functions calculated for available configurations of parts (configuration space) (see e.g., FIG. 2A, FIG. 6, FIG. 7A, FIG. 7B, FIG. 8A, FIG. 8B).

Figure 2A:
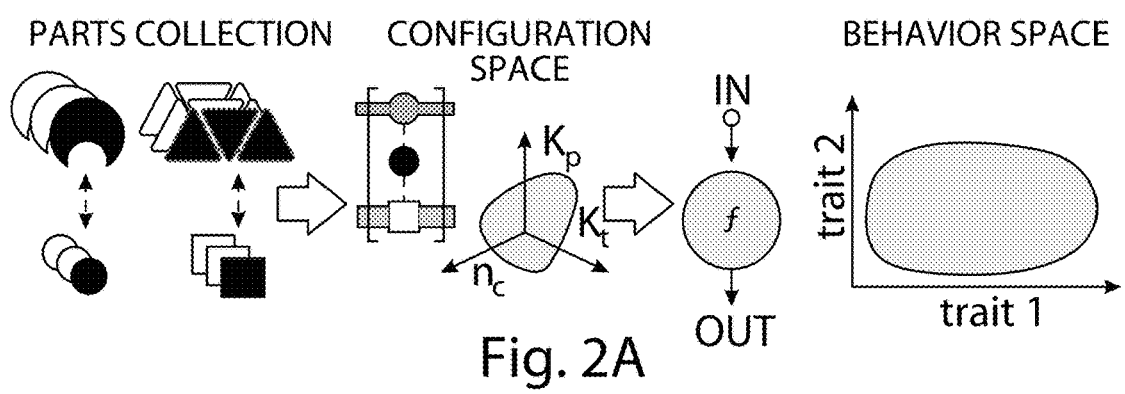
FIG. 2A-FIG. 2C is a series of schematics and graphs showing that constructing gene circuits using cooperative TF assemblies enables expanded steady-state signal processing behavior.
Figure 2B:
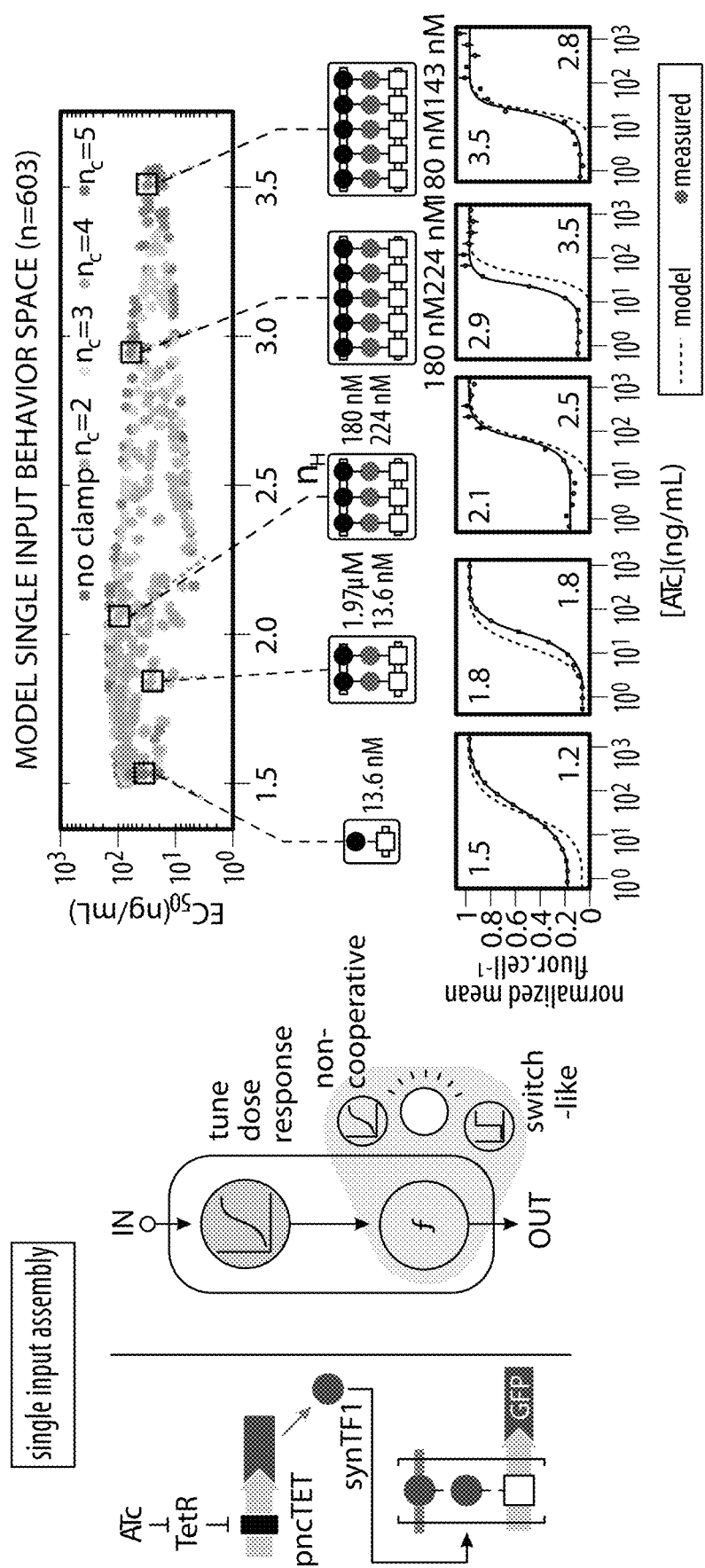

Dose response behavior was examined for a single-input (2-node) circuit motif consisting of an inducible upstream input node (driving synTF production) and a downstream reporter node where the synTF assembles with constitutively expressed clamp (see e.g., FIG. 2B). It was determined whether features of the circuit dose response—half-maximal dose response (EC50) and Hill coefficient (nH) —could be systematically tuned by adjusting complex Kt, Kp and nc (see e.g., FIG. 2B). Dose responses for all part-allotted configurations (603) were computed, and EC50 and nH values plotted as a two-dimensional behavior space (see e.g., FIG. 2B, FIG. 13A-FIG. 13D). Low valency configurations conferred linear (lower nH) dose responses, while those with higher nc were broadly distributed, including configurations exhibiting the most switch-like (nH>3.0) behavior (see e.g., FIG. 13A-FIG. 13D). Circuit configurations with different predicted nH values were tested experimentally (see e.g., FIG. 13A-FIG. 13D), and showed good correspondence with the model (see e.g., FIG. 2B, FIG. 13C).

Figure 2C:
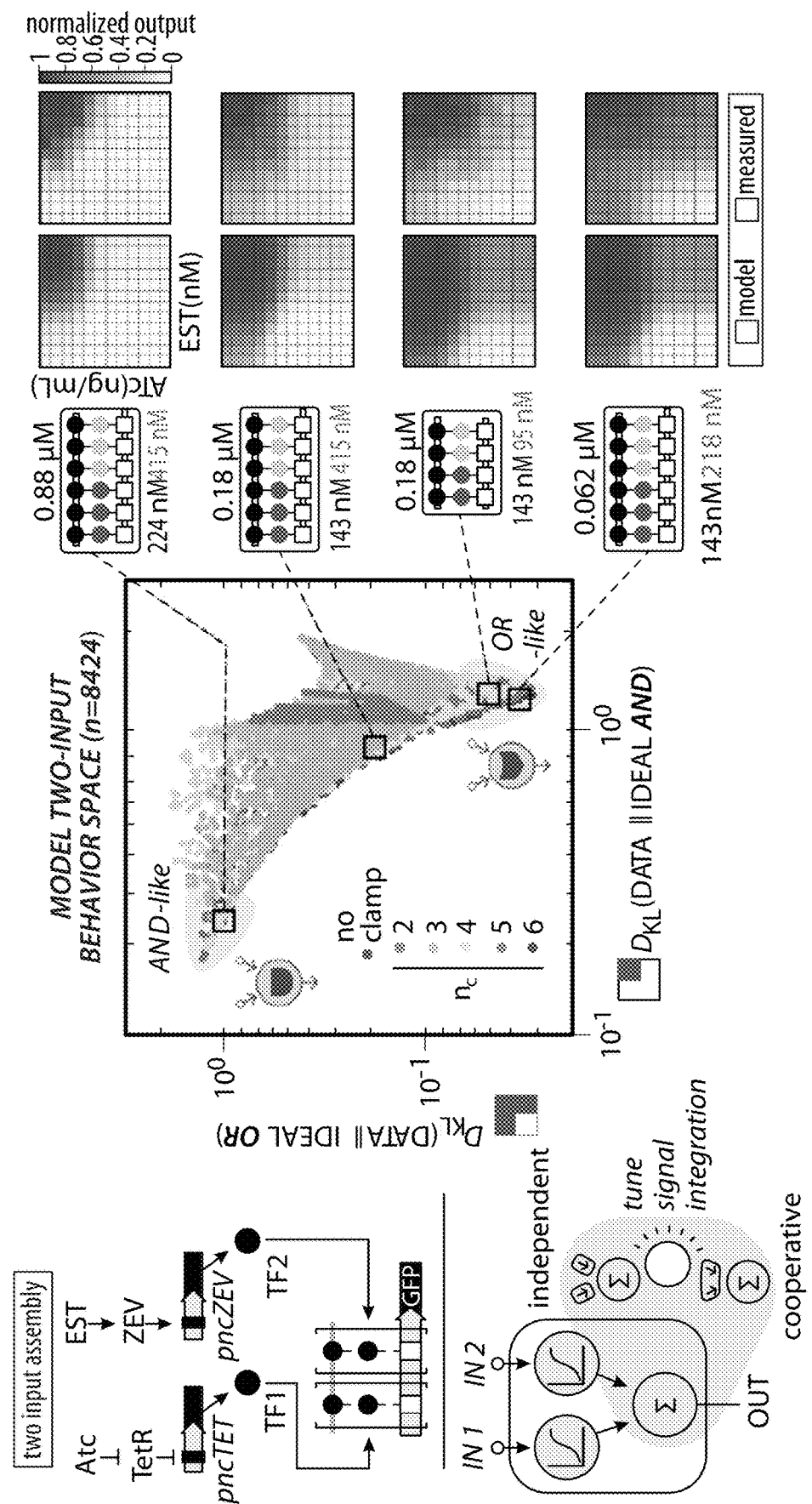

The relationship between assembly and Boolean computation was next assessed for complexes integrating multiple synTF inputs (TF1 and TF2 respectively controlled by ncTET and ncZEV) (see e.g., FIG. 2C). Dose response surfaces were calculated for two-input circuits containing complexes ranging from nc=2 to 6, for all possible combinations of TF1 and TF2 occupancy and interaction affinity (8,424 in total) (data not shown). Kullback-Leibler (K-L) divergence was used to compare idealized digital AND- and OR-like logic functions and simulated circuit behavior (data not shown). Plotting K-L divergences as a scatter revealed that regions of behavior space containing the most non-linear, Boolean-like circuits generally contained higher-order (nc>3) assemblies (see e.g., FIG. 2C). Circuits were constructed and experimentally tested for configurations representing different regions of configuration space, with most performing in model-predicted fashion (see e.g., FIG. 14A-FIG. 14C), including those from AND- and OR-like regions (see e.g., FIG. 2C).

The timing of complex assembly is dependent on the rate of synTF accumulation. Without wishing to be bound by theory, it was hypothesized that assembly configuration could be adjusted to control circuit dynamics (see e.g., FIG. 3A). Using time-lapse fluorescence microscopy of microfluidic device-cultured yeast (see e.g., Example 2), circuit GFP expression was measured in response to transient doxycycline (Dox) inducer pulses (data not shown). The model was extended to account for temporal circuit behavior by fitting the model to time course experiments (see e.g., Example 3). Two fitted circuits are highlighted: a nc=2 complex that exhibits a non-cooperative steady-state dose response, and one with a more cooperative nc=4 complex (see e.g., FIG. 3A). The later exhibits a delayed activation onset and rapid decay upon Dox removal, demonstrating that the timing of circuit activation and deactivation phases can be tuned by adjusting complex cooperativity.

Circuit dynamics behavior space was analyzed for three-node cascades in two distinct synTF assemblies connected in series (see e.g., FIG. 3B), examining the basis of apparent half-time for circuit activation ($\tau_a$) and decay ($\tau_d$). Circuits were considered with two middle node configurations: one with a single-synTF assembly and the other where the promoter is also under positive autoregulation by its own output synTF. Plotting of simulated dynamics for part-permitted three-node behavior space (12,774) revealed a broad distribution of temporal behaviors (see e.g., FIG. 3B), with circuits composed of cooperative, higher nc assemblies demonstrating the broadest τa and τd tuning (data not shown). Only positive feedback configurations can access both slow activation/slow decay behavior and stable memory (no decay), indicating circuit sensitivity to TF integration at the middle node of the cascade (see e.g., FIG. 3B). Circuit configurations were selected located throughout the behavior space to test experimentally; performance of these circuits confirmed the model's ability to describe the range of temporal behaviors that can be achieved (see e.g., FIG. 3B, FIG. 15A-FIG. 15D).

Cellular networks are capable of responding to information encoded in the dynamics of an input signal, responding to inputs of a specific duration, or decoding features of an input time series (e.g., frequency). To demonstrate that cooperative assemblies could facilitate engineering of dynamic filtering behavior, two- and three-node motifs (data not shown) were computationally identified that were capable of persistence filtering—activation only in the presence of a sufficiently long duration input (see e.g., FIG. 4A). Filtering behavior with steep duration-dependent threshold was exhibited by three-node cascades with cooperative, high nc complexes (data not shown). Results of Dox pulse titration experiments were consistent with these predictions: a two-node circuit with a low valency assembly demonstrated linear filtering, while a three-node circuit with highly cooperative assemblies showed sharp filtering (see e.g., FIG. 4A).

Figure 4A:
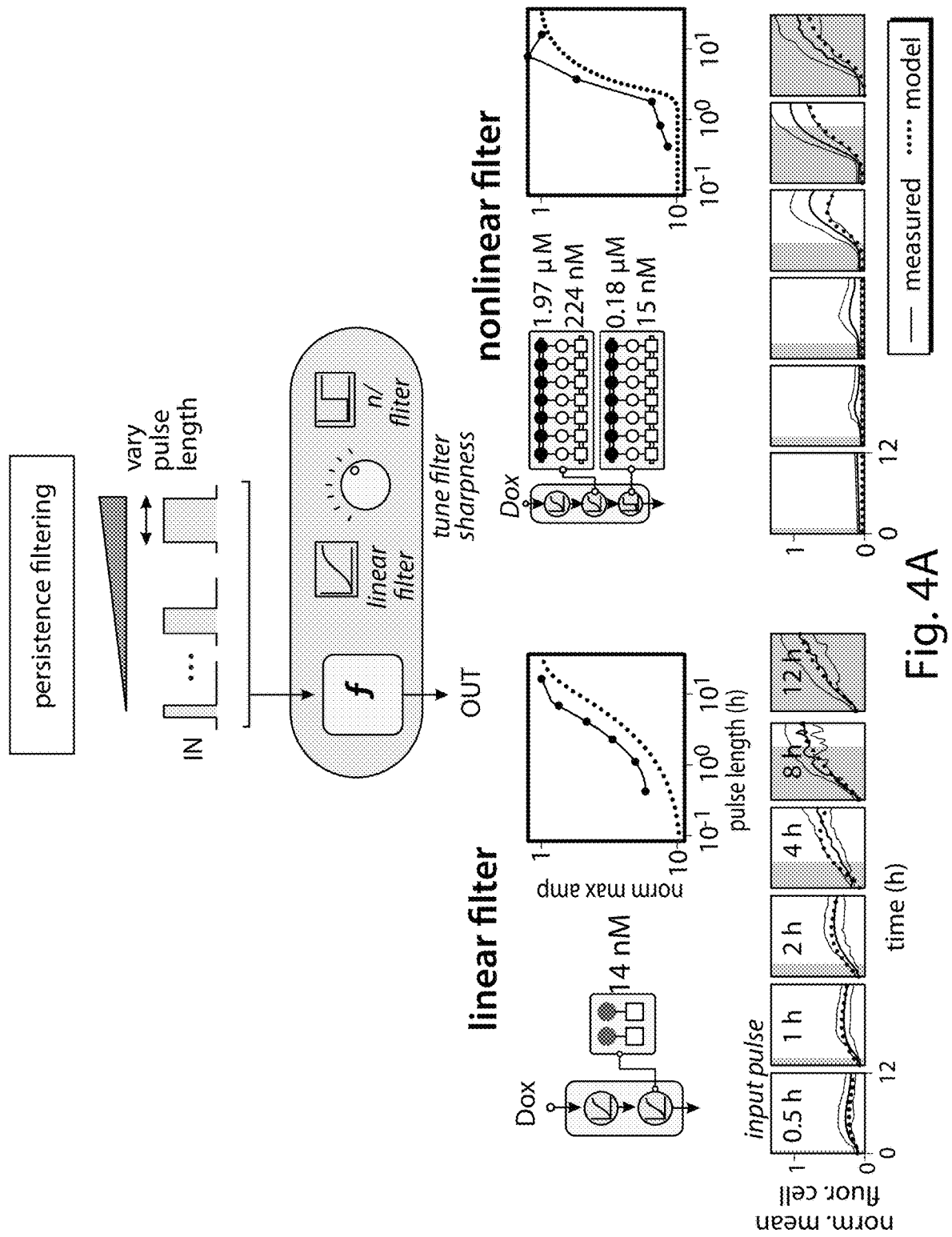
FIG. 4A-FIG. 4B is a series of schematics and graphs showing that circuits engineered with cooperative assemblies perform temporal signal processing behavior.
Figure 4B:
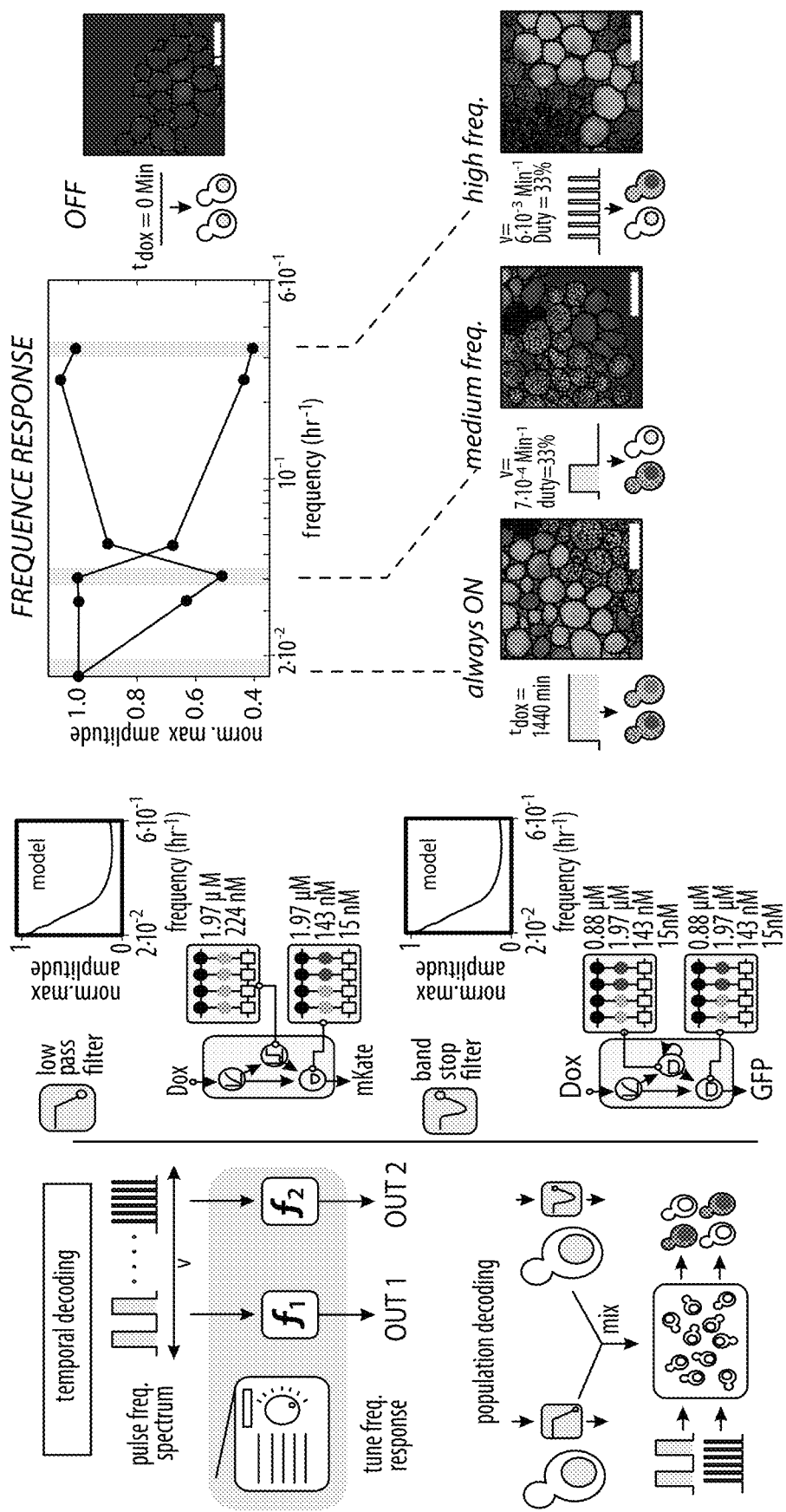

Sets of circuits were next identified that were capable of differentially responding to distinct input frequencies (see e.g., FIG. 4B). A pair of circuits were computationally identified, both coherent feed-forward loops (CFFL), activated by distinct square-wave frequencies (data not shown). This included low-pass filters (LPF), which only respond to low frequency input, and band-stop filters (BSF), which filter medium frequency while activating at high frequency (both with 33% duty cycle). For both circuits, cooperative, high nc assemblies were critical for sharp filtering (data not shown). To test filtering function, we created two strains: a BSF circuit driving a GFP reporter, and an LPF with mKate reporter. As predicted, at different input frequencies, strains differentially activated within a mixed population (BSF at ~10-4; LPF at ~10-5 Hz) (see e.g., FIG. 4B).

This work demonstrates that cooperative assembly is a powerful, highly flexible design strategy for engineering non-linear circuit behavior, and offers insights as to why TF assemblies evolved as a dominant mode of transcriptional regulatory control. Adjusting promoter assemblies have provided networks with a simple way to interpolate between diverse regions of functional space. Use of engineering approaches that incorporate cooperative assembly can facilitate creation of signal processing circuitry, enabling precision control in applications where non-linear temporal and spatial signal processing are critical, such as circuit-directed cell differentiation or dynamic regulation of homeostasis in engineered tissues.

Example 2: Materials and Methods

All plasmid constructs used herein are listed in Table 2. Construct architecture and open reading frame sequences are described in FIG. 5A-FIG. 5B. For constructs used in yeast experiments, codon optimized versions of all ORFs were synthesized (IDT) and cloned into pRS-derived integrating plasmids (Stratagene). Strains were constructed by sequential plasmid transformations using standard lithium acetate-based transformation techniques and growth on selective auxotrophic minimal media (Sunrise). The background strain for all experiments was *S. cerevisiae* YPH500 (α, ura3-52, lys2-801, ade2-101, trp1, his3, leu21) (Stratagene). Genotypes for experimentally tested strains are listed in Table 3. Experimental replicates, unless otherwise noted, comprised distinct colonies picked from a transformation plate following construct integration and selection.

Recombinant Protein Expression and Purification

Figure 5B:
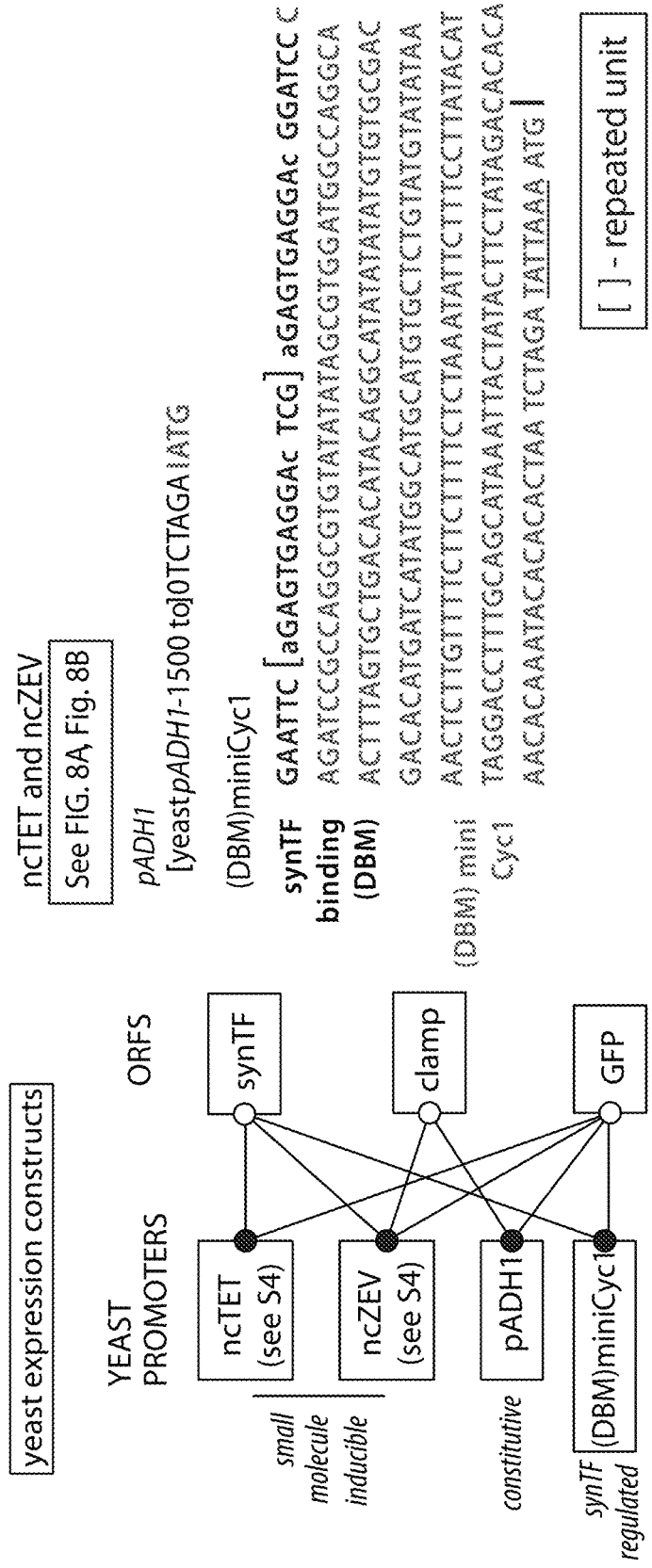

For recombinant protein expression and purification, plasmids were designed as described in FIG. 5 and Table 2. Amino acid sequences were identical to those used in yeast, except where indicated in FIG. 5A-FIG. 5B. Synthetic sequences, codon optimized for *E. coli* expression, were synthesized (IDT) and cloned into the pMAL-c5X vector (NEB), and the vectors transformed into BL-21 Rosetta (DE3)pLysS (Novagen) for recombinant expression.

Cultures (500 mL, Luria broth supplemented with 1 μM ZnCl2) were grown under constant shaking at 37° C. to 0.4 OD600 and induced with 1 mM IPTG, whereupon cultures were transferred to 25° C. and grown overnight. Cells were pelleted, harvested by sonication into extraction buffer (20 mM Tris, pH 8.0, 100 mM NaCl, 20 mM MgCl2, 1 mM ZnCl2, 0.02% NP-40, 20% glycerol), and cleared lysates were incubated with a 0.5 mL bed volume of amylose resin (NEB) at 4° C. for 3 h to bind fusion proteins.

Resin was washed with 20 column volumes of wash buffer (20 mM Tris, pH 8.0, 100 mM NaCl, 20 mM MgCl2, 1 μM ZnCL2, 10% glycerol), and for species harboring MBP (see e.g., FIG. 5A-FIG. 5B, FIG. 6, FIG. 7A-FIG. 7B), proteins were eluted with wash buffer supplemented with 10 mM maltose.

For proteins requiring MBP cleavage (see e.g., FIG. 5A-FIG. 5B, FIG. 6, FIG. 7A-FIG. 7B), resin was mixed with 2.5 mL of wash buffer supplemented with 2 mM CaCl2 and 2 μg Factor Xa (NEB) and incubated overnight at 4° C. Protease was purified away from cleaved protein using a HiTrap benzamidine FF column (GE Healthcare). Proteins were dialyzed into buffer containing 20 mM Tris, pH 8.0, 100 mM NaCl2, 50 μM ZnCl2, 5% glycerol and then concentrated to ~10 mg/ml prior to freezing at −80° C. Concentrations of all protein species were measured by Bradford assay.

In Vitro Binding Assay

In vitro binding assays were performed according to the methods of Jantz and Berg, with modifications (see e.g., Jantz, D. and J. M. Berg, Probing the DNA-binding affinity and specificity of designed zinc finger proteins. Biophys J. 98, 852-60 (2010)). The probe sequences (IDT DNA) listed below were used for ZF-DNA binding experiments and represent the upper oligo of a temperature annealed duplex:

```
43-8 n_c = 1 (SEQ ID NO: 52):
5'-GAA_fluor TTCGTCCTCACTCTGGATCC-3'

42-10 n_c = 1 (SEQ ID NO: 53):
5'-GAATTCA_fluor GACGCTGCTCGGATCC-3'

43-8 n_c = 2 (SEQ ID NO: 54):
5'-GAA_fluor TTCGTCCTCACTCTTCGGTCCTCACTCTGGATCC-3'

43-8 n_c = 3 (SEQ ID NO: 55):
5'-GAA_fluor TTCGTCCTCACTCTTCGGTCCTCACTCTTCGGTCCTCAC
TCTGGATCC-3'
```

$A_{fluor}$ indicates the presence of fluorescein label on the thymidine in the bottom (reverse) oligo in the duplex, and underlined sequence indicates DNA binding motif (DBM) for single zinc finger arrays (ZF).

Probes were generated by annealing an unlabeled top oligo to a labeled bottom oligo in a 2:1 ratio, while binding competitor oligos were generated using unlabeled top and bottom oligos mixed at equimolar ratios. For PDZ binding experiments, fluorescein-labeled peptide probe (ordered from Selleckhem) used for PDZ binding measurements contained the sequence VKESLV* (SEQ ID NO: 6), where the N-terminus was labeled with a FITC conjugate. Probe concentration was assessed by measuring Abs490. Competitor peptides were purified as MBP-ZF43-8 fusions (see e.g., FIG. 5A-FIG. 5B, FIG. 7A-FIG. 7B).

All assays were conducted in 20 mM Tris, pH 7.5, 100 mM NaCl$_2$, 50 µM ZnCl$_2$ buffer at 25° C. Proteins, probes, and competitor oligos were added to a final volume of 300 µL. Probes were used at 10 nM in all experiments. For complex assembly experiments (FIG. 1C), indicated concentrations of MBP-ZF$_{43-8}$ harboring a VSKESLV* ligand (SEQ ID NO: 120) (see e.g., FIG. 5A-FIG. 5B, FIG. 7A-FIG. 7B) were titrated against 5 µM concentrations of clamp. Mixtures were allowed to equilibrate at 25° C. for 10 min in Costar black 96-well plates prior to reading. Fluorescence anisotropy (FA) measurements were made at 494 nm using a SpectraMax M5 (Molecular Devices) fluorescence plate reader. For all measurements, anisotropy (r) was calculated using the following equation, wherein $I_{\parallel}$ and $I_{\perp}$ are parallel and perpendicular fluorescence, respectively:

$$r = \frac{I_{\parallel} - I_{\perp}}{I_{\parallel} - 2I_{\perp}}$$

Fraction of bound probe was calculated using the following equation, wherein $r_{bound}$ and $r_{free}$ are the anisotropy values for fully bound and fully unbound probe, respectively:

$$f_b = \frac{r - r_{free}}{(r_{bound} - r) \cdot Q + (r - r_{free})}$$

Each of these values was measured independently of binding curves with either a 100× excess or absence of ZF (in the case of ZF-oligo binding) or PDZ (in the case of PDZ-ligand binding). Q is the ratio of total fluorescence (measured at 454 nm) under $r_{bound}$ and $r_{free}$ conditions. To obtain binding constants for ZF-probe and PDZ-probe interactions, binding data were fit to the following quadratic equation, wherein [P] is the total concentration of either ZF or PDZ, [probe] is the total concentration of the oligo or peptide probe, and $K_d$ is the dissociation constant of the interaction:

$$f_b = \frac{[P] + [\text{probe}] + K_d - \sqrt{([P] + [\text{probe}] + K_d)^2 - 4[P] \cdot [\text{probe}]}}{2[\text{probe}]}$$

Competition binding curves were calculated by fitting competition binding curves to the following cubic equation, wherein $f_b$ is fraction probe bound, [L*T] is the total probe concentration, [RT] and [R] are total and free concentrations of the ZF, respectively, while [LT] and [L] are total and free concentrations of competitor. $K_{d1}$ is the affinity for TF and probe, while $K_{d2}$ is the affinity between TF and competitor:

$$f_b = \frac{[RL^*]}{[L_T^*]} = \frac{[R]}{K_{d1} + [R]} = \frac{2 \cdot \sqrt{(a^2 - 3b)} \cdot \cos\frac{\theta}{3} - a}{3 \cdot K_{d1} + 2 \cdot \sqrt{(a^2 - 3b)} \cdot \cos\frac{\theta}{3} - a}$$

wherein $a = K_{d1} + K_{d2} + [L_T] + [L_T^*] - [R_T]$ $b = K_{d2} \cdot ([L_T^*] - [R_T]) + K_{d1} \cdot ([L_T] - [R_T]) + K_{d1} \cdot K_{d2}$ $c = -K_{d1} \cdot K_{d2} \cdot [R_T]$ $$\theta = \cos^{-1}\left[\frac{-2a^3 + 9ab - 27c}{2 \cdot \sqrt{(a^2 - 3b)^3}}\right]$$

All binding curve fitting was done using MATLAB (Mathworks, Natick, Mass.) with function Anistropy.Fit.m (code description in Table 4).

Western Blot

Four mL yeast cultures were grown in triplicate to mid log phase in YPGal (YEP+2% galactose) media in the presence or absence of inducers. Cultures were pelleted and total protein extracted by direct lysis in 200 µL boiling SDS-PAGE sample buffer (Biorad) containing 5 mM dithiothreitol. SynTFs were detected using mouse anti-FLAG (Sigma, #F3165) as primary and Alexa Fluor 488 anti-mouse as the secondary antibody (Cell Signaling, #4408). For hexokinase loading controls, rabbit anti-hexokinase (US Biological Life Sciences, #H2035-02) and anti-rabbit Alexa Fluor 647 (Cell Signaling, #4414) antibodies were used for primary and secondary probes, respectively. Western blot fluorescence was visualized using a Typhoon FLA 9000 (GE Healthcare). Image J (NIH) software was used to quantitate the background-subtracted, integrated intensities of FLAG bands and then normalize to that of the corresponding hexokinase bands.

TABLE 2

Plasmid Table

Figure 1E:
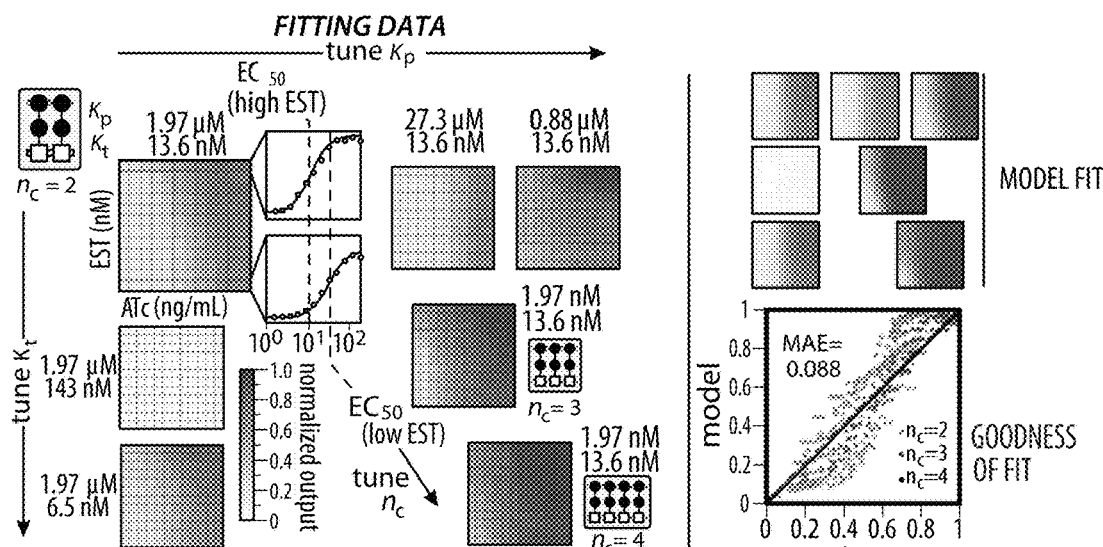

| FIG. | PLASMID # | PARENT | PROMOTER | ORF |
| --- | --- | --- | --- | --- |
| FIG. 1C | pCB342 | pMAL-c5 | Ptac | MBP-43-8(low)-syn. lig.(S5) |
| | pCB348 | pMAL-c5 | Ptac | MBP-43-8(low)-syn. lig.(no bind) |
| | pCB376 | pMAL-c5 | Ptac | MBP-2x syn. clamp |
| | pCB428 | pMAL-c5 | Ptac | MBP-3x syn. clamp |
| FIG. 1E | pN8 | pRS406 | p($n_c$ = 2, 43-8 DBM1)minCyc1 | GFP |
| | CB269 | pRS406 | p($n_c$ = 2, 43-8 DBM2)minCyc1 | GFP |
| | pCB277 | pRS406 | p($n_c$ = 3, 43-8 DBM1)minCyc1 | GFP |
| | pCB228 | pRS406 | p($n_c$ = 4, 43-8 DBM1)minCyc1 | GFP |

TABLE 2-continued

Plasmid Table

Figure 3A:
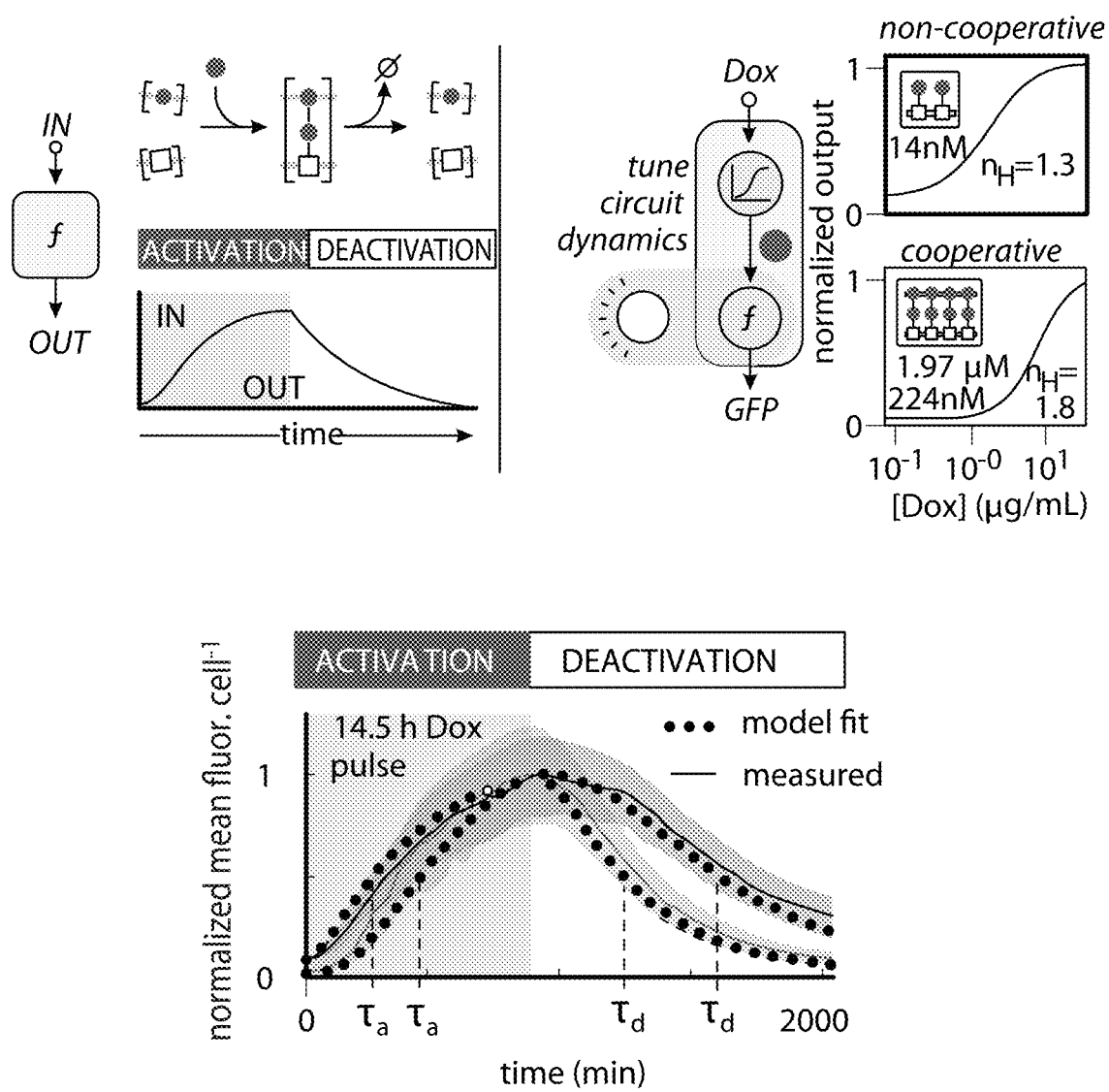
FIG. 3A-FIG. 3B is a series of schematics and graphs showing the control of gene circuit dynamics using programmed complex assembly.
Figure 3B:
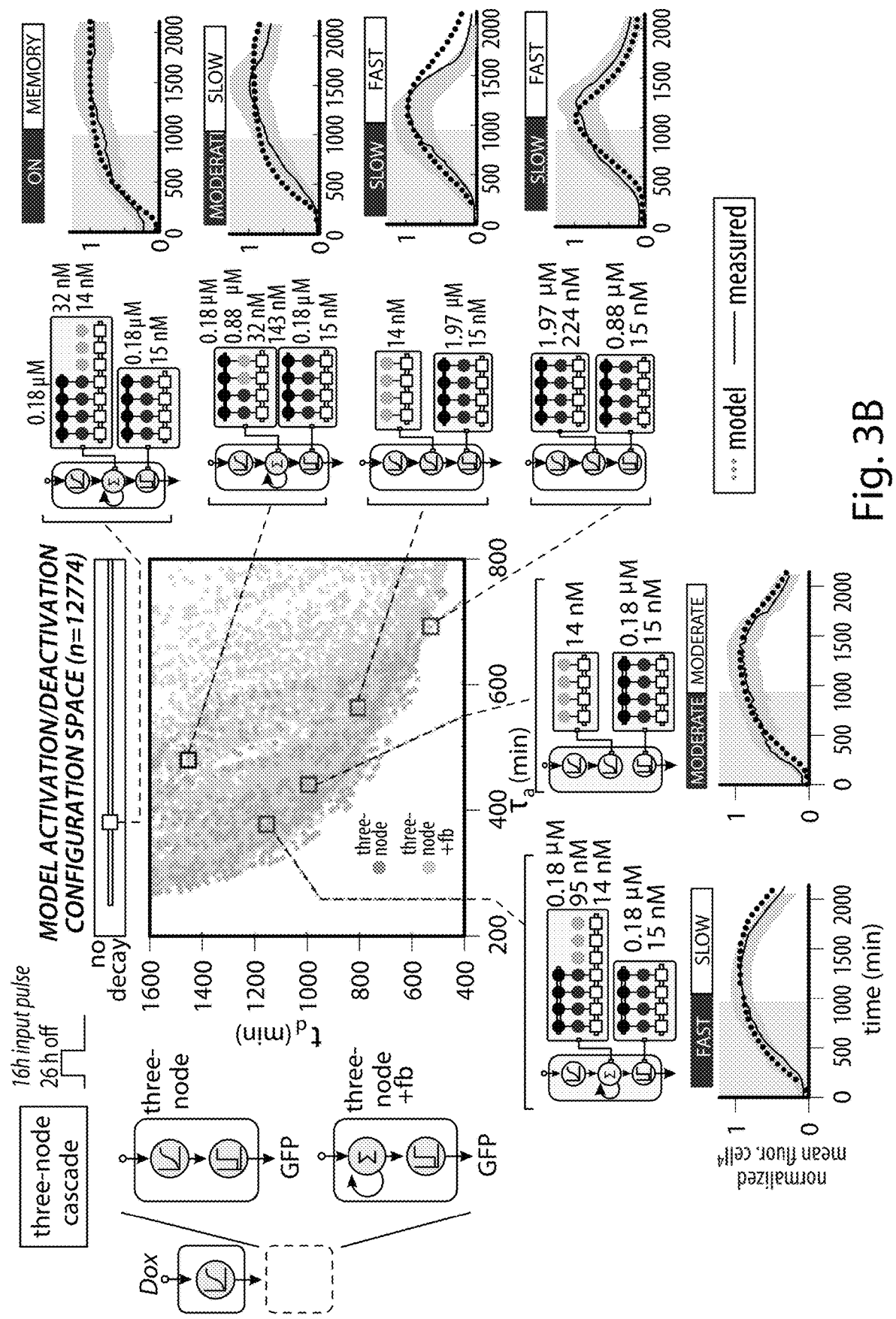
Figure 6:
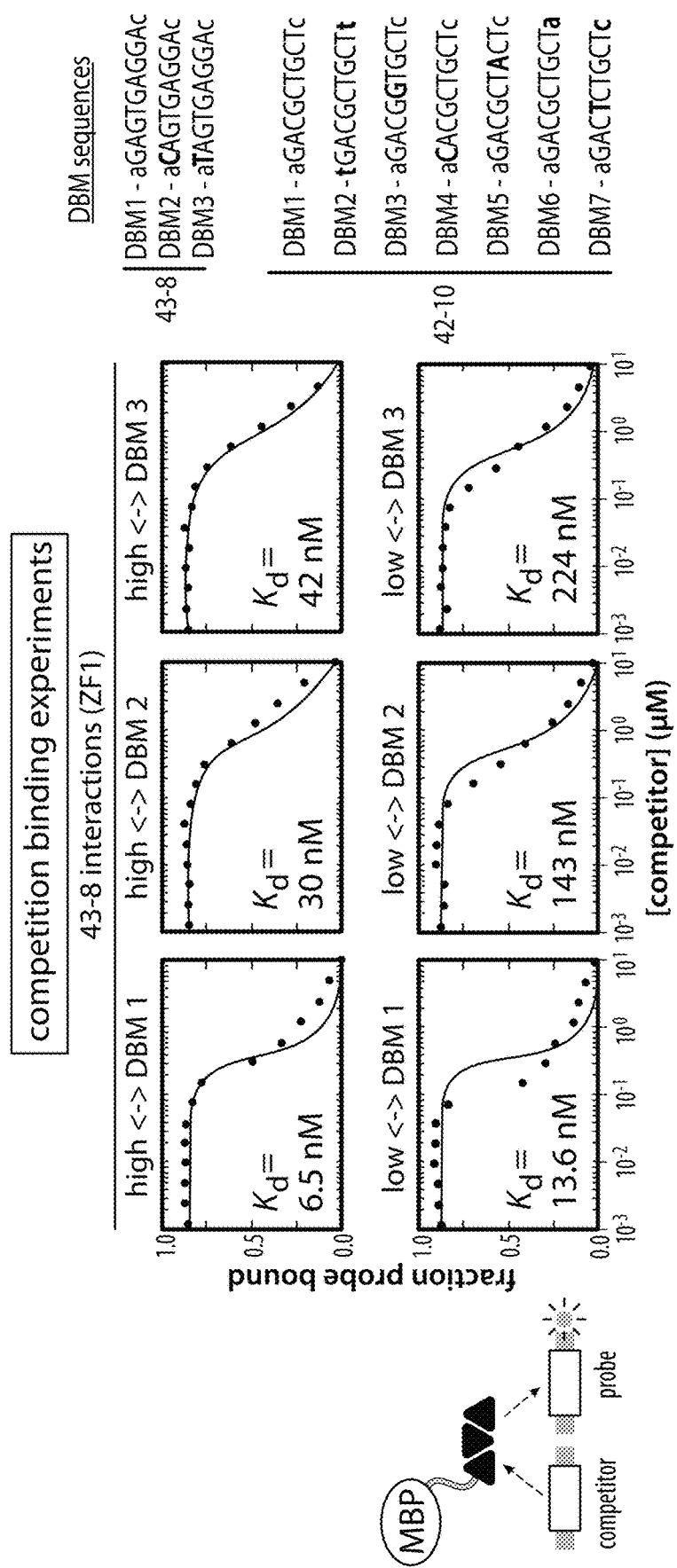
FIG. 6 is a series of graphs and schematics showing in vitro measurement of TF-DBM binding constants by fluorescence anisotropy (FA), using competition binding experiments to measure binding constants for DBM affinity variants. At concentrations of MBP-ZF and probe at which half-maximal binding was observed (data not shown), unlabeled oligo competitors containing DBM affinity variants were titrated, and anisotropy increases were measured, accompanying displacement of the probe by the competitor. Competitor oligo Kd values were extracted by fitting data (converted to fraction probe bound) to a cubic equation describing competitive binding (see e.g., Table 6). Sequences for both sets of DBM affinity variants are listed on the right. Residues mutated from the WT sequence are indicated by bold type.
Figure 6:
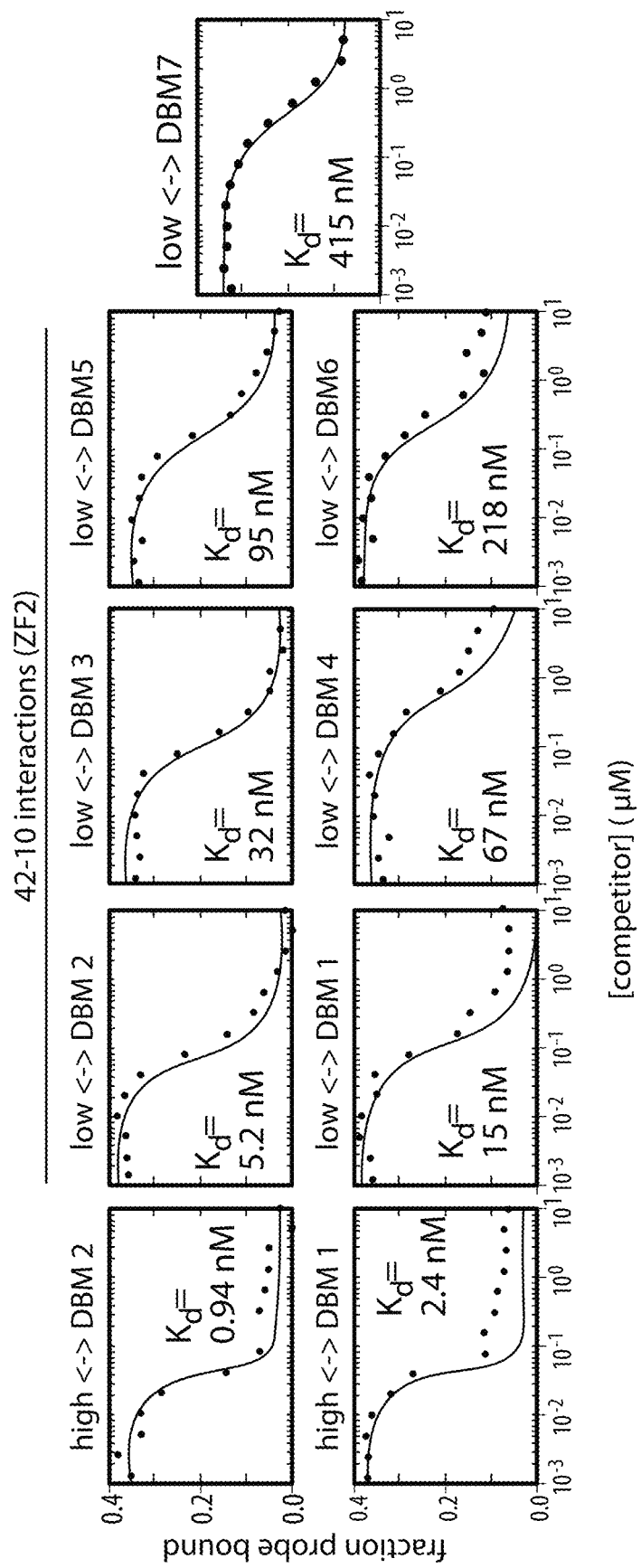

| FIG. | PLASMID # | PARENT | PROMOTER | ORF |
|---|---|---|---|---|
| | pCB298 | pRS304 | pNcTET | 43-8(low)-syn. lig(S5) |
| | pCB300 | pRS304 | pNcTET | 43-8(low)-syn. lig(S6) |
| | pCB302 | pRS304 | pNcTET | 43-8(low)-syn. lig(S4) |
| | pCB706 | pRS304 | pNcTET | 43-8(high)-syn. lig(S5) |
| | pN187 | pRS605 | pNcZEV | 2x syn. clamp |
| | pCB397 | pRS605 | pNcZEV | 3x syn. clamp |
| | pCB398 | pRS605 | pNcZEV | 4x syn. clamp |
| FIG. 2B | pCB707 | pRS406 | p($n_c$ = 1, 43-8 DBM1)minCyc1 | GFP |
| | pN8 | pRS406 | p($n_c$ = 2, 43-8 DBM1)minCyc1 | GFP |
| | pN18 | pRS406 | p($n_c$ = 3, 43-8 DBM3)minCyc1 | GFP |
| | pCB280 | pRS406 | p($n_c$ = 5, 43-8 DBM3)minCyc1 | GFP |
| | pCB281 | pRS406 | p($n_c$ = 5, 43-8 DBM2)minCyc1 | GFP |
| | pCB298 | pRS304 | pNcTET | 43-8(low)-syn. lig(S5) |
| | pCB393 | pRS304 | pNcTET | 43-8(low)-syn. lig(S2) |
| | pCB245 | pRS605 | pADH1 | 2x syn. clamp |
| | pCB247 | pRS605 | pADH1 | 3x syn. clamp |
| | pCB266 | pRS605 | pADH1 | 5x syn. clamp |
| FIG. 2C | pCB726 | pRS406 | p($n_c$ = 3, 43-8 DBM3, $n_c$ = 3, 42-10 DMB7)minCyc1 | GFP |
| | pCB730 | pRS406 | p($n_c$ = 3, 43-8 DBM2, $n_c$ = 3, 42-10 DMB7)minCyc1 | GFP |
| | pCB723 | pRS406 | p($n_c$ = 2, 43-8 DBM2, $n_c$ = 2, 42-10 DMB5)minCyc1 | GFP |
| | pCB729 | pRS406 | p($n_c$ = 3, 43-8 DBM2, $n_c$ = 3, 42-10 DMB6)minCyc1 | GFP |
| | pCB302 | pRS304 | pNcTET | 43-8(low)-syn. lig(S4) |
| | pCB393 | pRS304 | pncTET | 43-8(low)-syn. lig(S2) |
| | pCB395 | pRS304 | pncTET | 43-8(low)-syn. lig(S1) |
| | pN288 | pRS304 | pNcZEV | 42-10(low)-syn. lig.(S4) |
| | pCB515 | pRS304 | pNcZEV | 42-10(low)-syn. lig.(S2) |
| | pCB516 | pRS304 | pNcZEV | 42-10(low)-syn. lig.(S1) |
| | pCB263 | pRS605 | pADH1 | 4x syn. clamp |
| | pCB266 | pRS605 | pADH1 | 5x syn. clamp |
| | pCB564 | pRS605 | pADH1 | 6x syn. clamp |
| FIG. 3A | pN8 | pRS406 | p($n_c$ = 2, 43-8 DBM1)minCyc1 | GFP |
| | pCB278 | pRS406 | p($n_c$ = 4, 43-8 DBM3)minCyc1 | GFP |
| | pCB298 | pRS304 | pNcTET | 43-8(low)-syn. lig(S5) |
| | pCB263 | pRS605 | pADH1 | 4x syn. clamp |
| FIG. 3B | pN367 | pRS306 | p($n_c$ = 4, 42-10 DBM2, $n_c$ = 3, 43-8 DBM1)minCyc1 | 42-10(low)-syn. lig.(S2) |
| | pN410 | pRS306 | p($n_c$ = 2, 42-10 DBM1, $n_c$ = 2, 43-8 DBM2)minCyc1 | 42-10(low)-syn. lig.(S2) |
| | pN488 | pRS406 | p($n_c$ = 4, 43-8 DBM1)minCyc1 | 42-10(low)-syn. lig.(S5) |
| | pN489 | pRS406 | p($n_c$ = 4, 43-8 DBM1)minCyc1 | 42-10(low)-syn. lig.(S4) |
| | pN464 | pRS306 | p($n_c$ = 4, 43-8 DBM3)minCyc1 | 42-10(low)-syn. lig.(S4) |
| | pN369 | pRS306 | p($n_c$ = 4, 42-10 DBM4, $n_c$ = 3, 43-8 DBM1)minCyc1 | 42-10(low)-syn. lig.(S2) |
| | pN281 | pRS304 | pNcTET | 43-8(low)-no lig. |
| | pCB298 | pRS304 | pNcTET | 43-8(low)-syn. lig(S5) |
| | pCB301 | pRS304 | pNcTET | 43-8(low)-syn. lig(S4) |
| | pCB263 | pRS605 | pADH1 | 4x syn. clamp |
| | pN286 | pRS603 | p($n_c$ = 4, 42-10 DBM1)minCyc1 | GFP |
| FIG. 4A | pN8 | pRS406 | p($n_c$ = 2, 43-8 DBM1)minCyc1 | GFP |
| | pN468 | pRS306 | p($n_c$ = 5, 43-8 DBM3)minCyc2 | 42-10(low)-syn. lig.(S2) |
| | pCB298 | pRS304 | pNcTET | 43-8(low)-syn. lig(S5) |
| | pCB266 | pRS605 | pADH1 | 5x syn. clamp |
| | pN287 | pRS603 | p($n_c$ = 5, 42-10 DBM1)minCyc1 | GFP |
| FIG. 4B, FIG. 16A, FIG. 16B, FIG. 16C | pN463 | pRS306 | p($n_c$ = 4, 43-8 DBM3)minCyc1 | 42-10(low)-syn. lig.(S5) |
| | pN409 | pRS306 | p($n_c$ = 2, 42-10 DBM1, $n_c$ = 2, 43-8 DBM2)minCyc1 | 42-10(low)-syn. lig.(S5) |
| | pCB298 | pRS304 | pNcTET | 43-8(low)-syn. lig(S5) |
| | pCB301 | pRS304 | pNcTET | 43-8(low)-syn. lig(S4) |
| | pCB263 | pRS605 | pADH1 | 4x syn. clamp |
| | pN451 | pRS603 | p($n_c$ = 2, 43-8 DBM2, $n_c$ = 2, 42-10 DBM1)minCyc1 | mKate |
| | pN400 | pRS603 | p($n_c$ = 2, 43-8 DBM2, $n_c$ = 2, 42-10 DBM1)minCyc1 | GFP |
| FIG. 6 | pCB342 | pMAL-c5 | Ptac | MBP-43-8(low)-syn. lig.(S5) |
| | pCB347 | pMAL-c5 | Ptac | MBP-43-8(high)-syn. lig.(S5) |
| | pN93 | pMAL-c5 | Ptac | MBP-42-10(low)-syn. lig.(S5) |
| | pN313 | pMAL-c5 | Ptac | MBP-42-10(high)-syn. lig.(S5) |

TABLE 2-continued

Plasmid Table

Figures 7A, 7B:
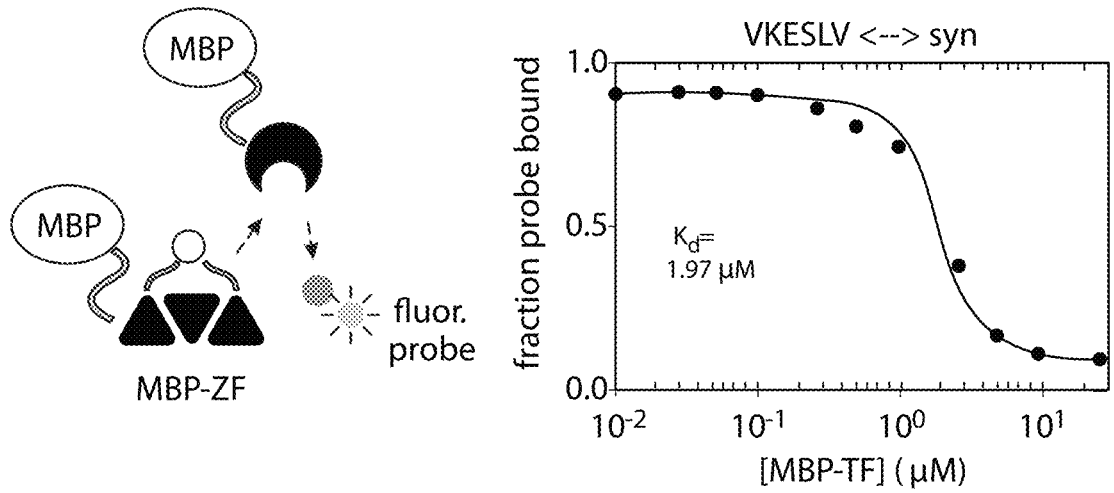
FIG. 7A-FIG. 7B is a series of schematics and graphs showing in vitro measurement of PDZ-ligand binding constants by fluorescence anisotropy.

| FIG. | PLASMID # | PARENT | PROMOTER | ORF |
|---|---|---|---|---|
| FIG. 7A, FIG. 7B | pCB378 | pMAL-c5 | Ptac | MBP-syn. |
| | pCB425 | pMAL-c5 | Ptac | MBP-erb. |
| | pCB380 | pMAL-c5 | Ptac | MBP-43-8(low)-syn. lig. (S1) |
| | pCB381 | pMAL-c5 | Ptac | MBP-43-8(low)-syn. lig. (S2) |
| | pCB382 | pMAL-c5 | Ptac | MBP-43-8(low)-syn. lig. (S3) |
| | pCB384 | pMAL-c5 | Ptac | MBP-43-8(low)-syn. lig. (S4) |
| | pCB385 | pMAL-c5 | Ptac | MBP-43-8(low)-syn. lig. (S5) |
| | pCB386 | pMAL-c5 | Ptac | MBP-43-8(low)-syn. lig. (S6) |
| | pCB387 | pMAL-c5 | Ptac | MBP-43-8(low)-syn. lig. (S7) |
| | pCB379 | pMAL-c5 | Ptac | MBP-43-8(low)-syn. lig. (S5) |
| Not shown | pRS406 | pRS406 | n/a | n/a |
| | pL329 | pRS304 | pNcTET | GFP |
| | pL330 | pRS304 | NL-TET | GFP |
| | pCB702 | pRS603 | pNcZEV | GFP |
| | pCB703 | pRS603 | pADH1 | GFP |
| | pCB704 | pRS605 | pNcTET | GFP |
| | pCB705 | pRS605 | pADH1 | GFP |
| Not shown | pCB298 | pRS304 | pNcTET | 43-8(low)-syn. lig.(S5) |
| FIG. 8A | pN20 | pRS406 | p(n = 2, 43-8 DBM1)minCyc1 | GFP |
| | pN187 | pRS605 | pNcZEV | 2x syn. clamp |
| | pN496 | pRS605 | pLEF1 | 97-4 ZEV |
| | pN498 | pRS605 | pNcZEV | 43-8_4x, lig S5 (5GS) |
| Not shown | pCB342 | pMAL-c5 | Ptac | MBP-43-8(low)-syn. lig.(S5) |
| | pCB429 | pMAL-c5 | Ptac | 1x syn. |
| FIG. 9A, FIG. 9B | pN8 | pRS406 | p($n_c$ = 2, 43-8 DBM1)minCyc1 | GFP |
| | pCB230 | pRS605 | pADH1 | 2x syn. clamp (5GS) |
| | pCB244 | pRS605 | pADH1 | 2x syn. clamp (10GS) |
| | pCB245 | pRS605 | pADH1 | 2x syn. clamp (20GS) |
| | pCB303 | pRS304 | pNcTET | 43-8(low)-syn. lig. (S6) (0GS) |
| | pCB300 | pRS304 | pNcTET | 43-8(low)-syn. hg (S6) (5GS) |
| | pCB299 | pRS304 | pNcTET | 43-8(low)-syn. lig. (S6) (10GS) |
| | pL372 | pRS304 | pNcTET | 43-8(low)-syn. lig. (S5) (0GS) |
| | pCB298 | pRS304 | pNcTET | 43-8(low)-syn. lig. (S5) (5GS) |
| | pCB304 | pRS304 | pNcTET | 43-8(low)-syn. lig. (S5) (10GS) |
| | pCB303 | pRS304 | pNcTET | 43-8(low)-syn. lig. (S4) (0GS) |
| | pCB301 | pRS304 | pNcTET | 43-8(low)-syn. lig. (S4) (5GS) |
| | pCB267 | pRS304 | pNcTET | 43-8(low)-syn. lig. (S4) (10GS) |
| FIG. 13C | pCB707 | pRS406 | p(nc = 1, 43-8 DBM1)minCyc1 | GFP |
| | pN8 | pRS406 | p(n = 2, 43-8 DBM1)minCyc1 | GFP |
| | pN27 | pRS406 | p(n = 3, 43-8 DBM1)minCyc1 | GFP |
| | pN20 | pRS406 | p(n = 4, 43-8 DBM1)minCyc1 | GFP |
| | pCB282 | pRS406 | p(n = 5, 43-8 DBM1)minCyc1 | GFP |
| | pN18 | pRS406 | p(n = 3, 43-8 DBM3)minCyc1 | GFP |
| | pCB280 | pRS406 | p(n = 5, 43-8 DBM3)minCyc1 | GFP |
| | pCB276 | pRS406 | p(n = 3, 43-8 DBM2)minCyc1 | GFP |
| | pCB279 | pRS406 | p(n = 4, 43-8 DBM2)minCyc1 | GFP |
| | pCB281 | pRS406 | p(n = 5, 43-8 DBM2)minCyc1 | GFP |
| | pCB298 | pRS304 | pNcTET | 43-8(low)-syn. lig(S5) |
| | pCB300 | pRS304 | pNcTET | 43-8(low)-syn. lig(S6) |
| | pCB393 | pRS304 | pNcTET | 43-8(low)-syn. lig(S2) |
| | pCB301 | pRS304 | pNcTET | 43-8(low)-syn. lig(S4) |
| | pCB245 | pRS605 | pADH1 | 2x syn. clamp |
| | pCB247 | pRS605 | pADH1 | 3x syn. clamp |
| | pCB263 | pRS605 | pADH1 | 4x syn. clamp |
| | pCB266 | pRS605 | pADH1 | 5x syn. clamp |

TABLE 2-continued

Plasmid Table

Figure 14B:
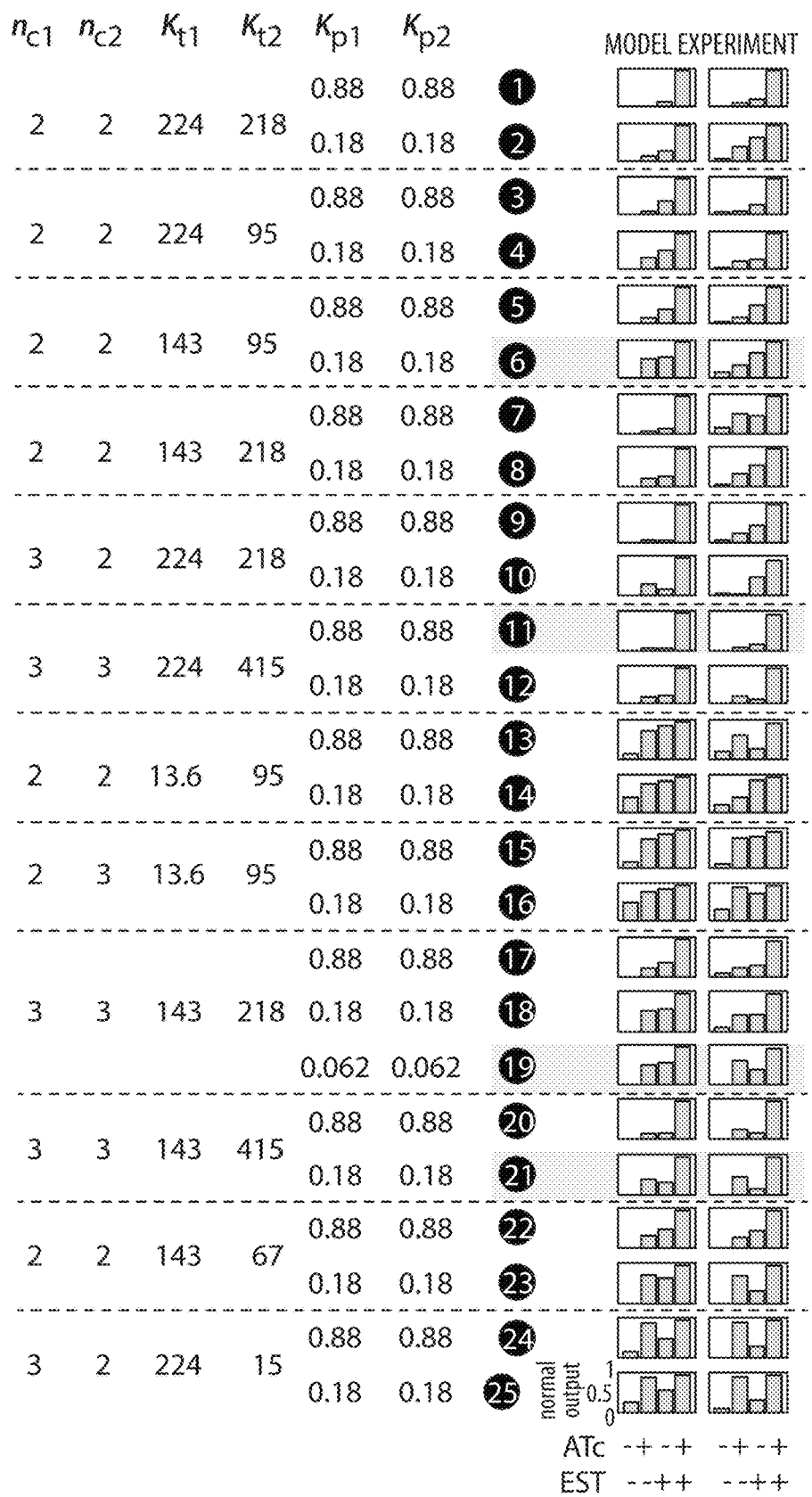
Figure 15A:
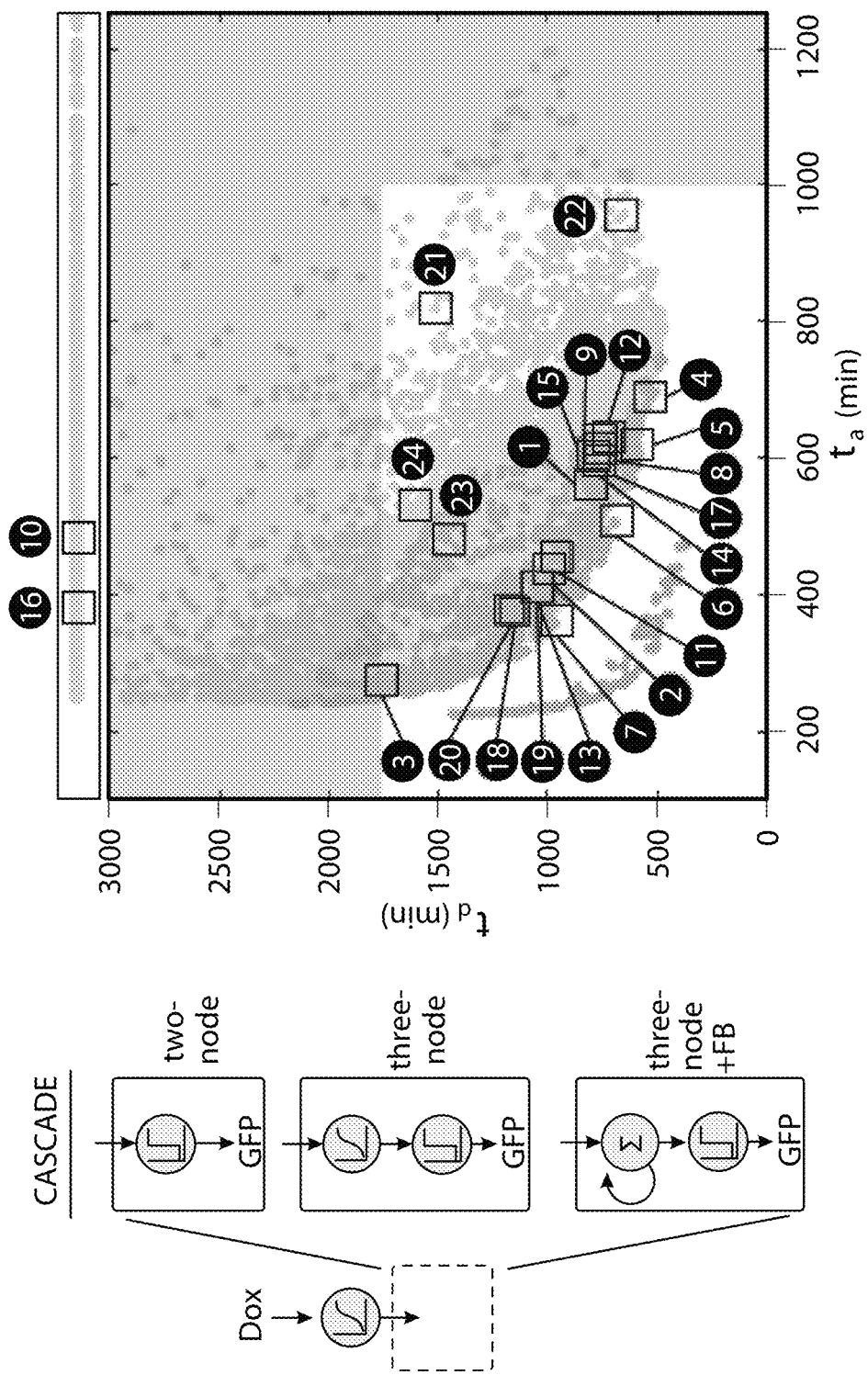
FIG. 15A-FIG. 15D is a series of schematics and graphs showing experimental verification of activation/deactivation behavior space.
Figure 15B:
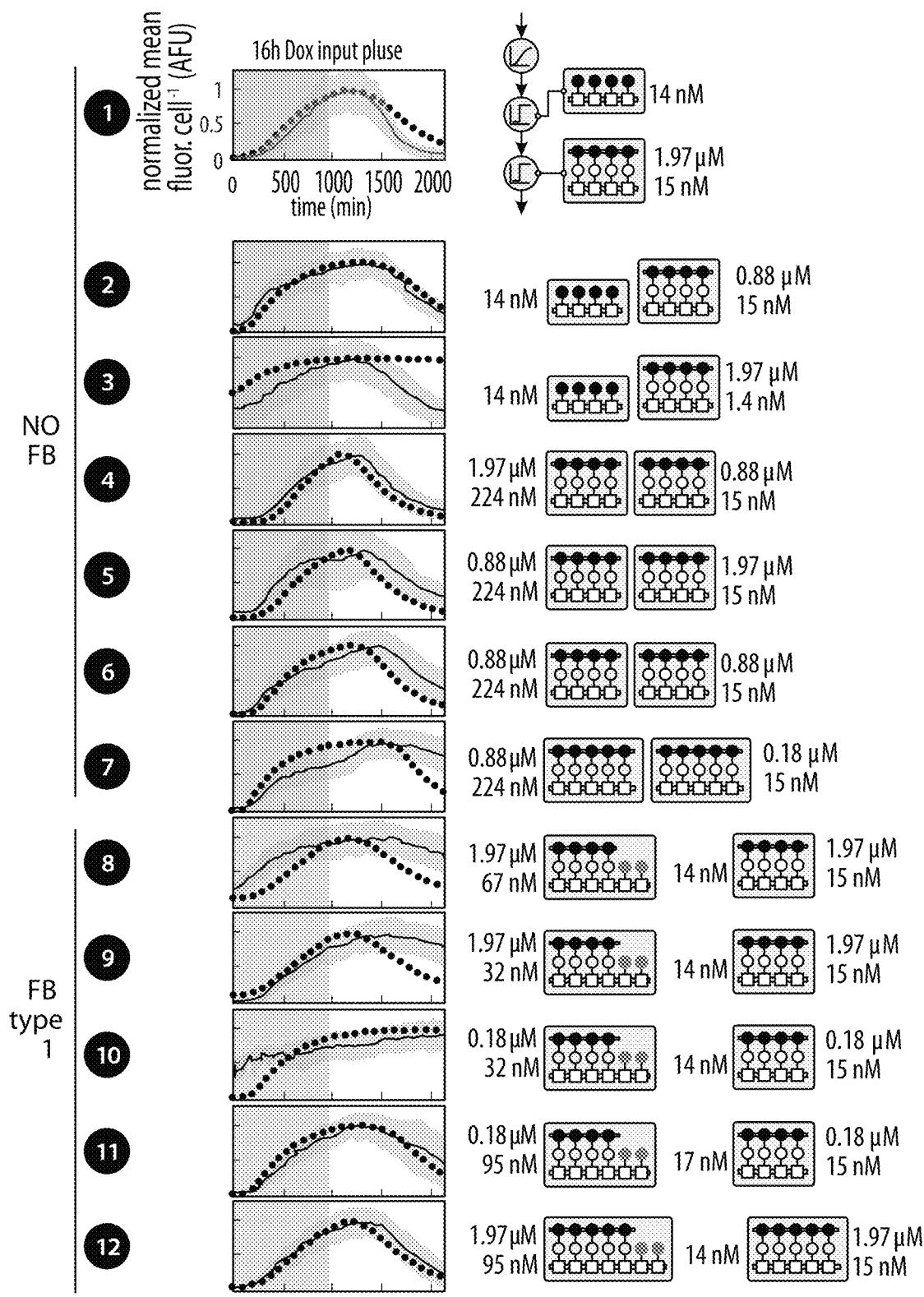
Figure 15C:
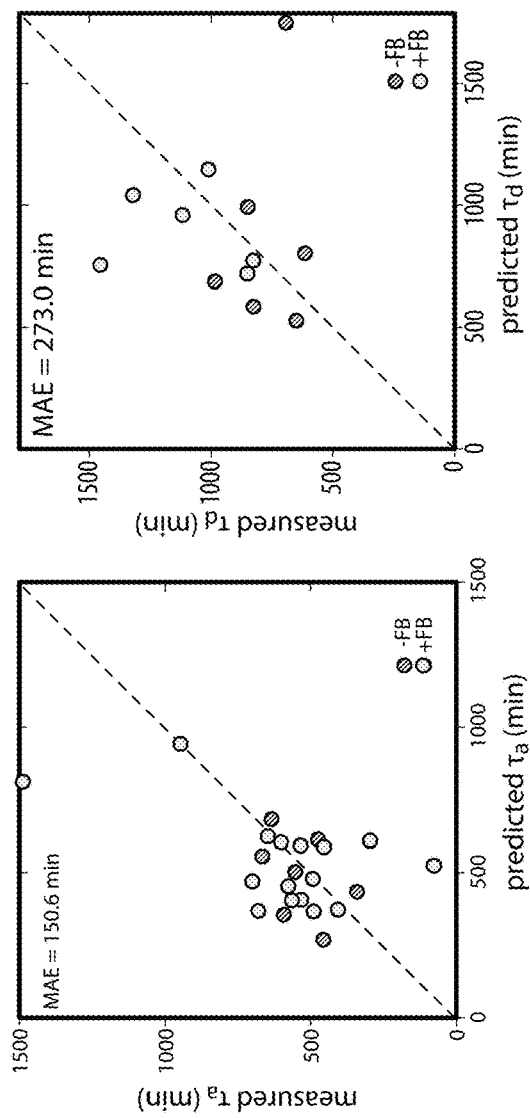
Figure 15D:
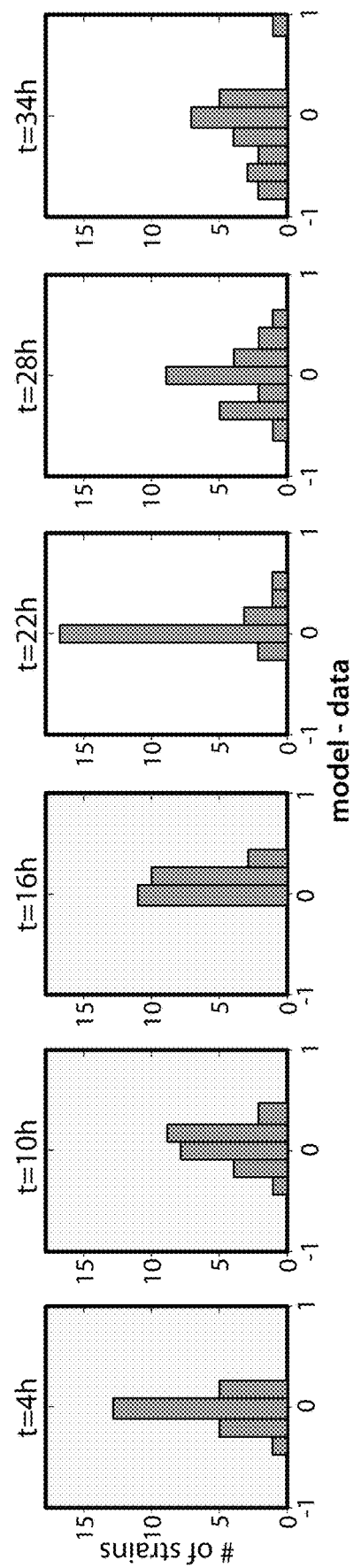

| FIG. | PLASMID # | PARENT | PROMOTER | ORF |
|---|---|---|---|---|
| FIG. 14A, | pCB721 | pRS406 | p($n_c$ = 2, 43-8 DBM3, $n_c$ = 2, 42-10 DMB6)minCyc1 | GFP |
| FIG. 14B, | pCB722 | pRS406 | p($n_c$ = 2, 43-8 DBM3, $n_c$ = 2, 42-10 DMB5)minCyc1 | GFP |
| FIG. 14C | pCB723 | pRS406 | p($n_c$ = 2, 43-8 DBM2, $n_c$ = 2, 42-10 DMB5)minCyc1 | GFP |
| | pCB724 | pRS406 | p($n_c$ = 2, 43-8 DBM2, $n_c$ = 2, 42-10 DMB6)minCyc1 | GFP |
| | pCB725 | pRS406 | p($n_c$ = 3, 43-8 DBM3, $n_c$ = 2, 42-10 DMB6)minCyc1 | GFP |
| | pCB726 | pRS406 | p($n_c$ = 3, 43-8 DBM3, $n_c$ = 3, 42-10 DMB7)minCyc1 | GFP |
| | pCB727 | pRS406 | p($n_c$ = 2, 43-8 DBM1, $n_c$ = 2, 42-10 DMB5)minCyc1 | GFP |
| | pCB728 | pRS406 | p($n_c$ = 2, 43-8 DBM1, $n_c$ = 3, 42-10 DMB5)minCyc1 | GFP |
| | pCB729 | pRS406 | p($n_c$ = 3, 43-8 DBM2, $n_c$ = 3, 42-10 DMB6)minCyc1 | GFP |
| | pCB730 | pRS406 | p($n_c$ = 3, 43-8 DBM2, $n_c$ = 3, 42-10 DMB7)minCyc1 | GFP |
| | pCB731 | pRS406 | p($n_c$ = 2, 43-8 DBM2, $n_c$ = 2, 42-10 DMB4)minCyc1 | GFP |
| | pCB732 | pRS406 | p($n_c$ = 3, 43-8 DBM3, $n_c$ = 2, 42-10 DBM1)minCyc1 | GFP |
| | pCB302 | pRS304 | pNcTET | 43-8(low)-syn. lig.(S4) |
| | pCB393 | pRS304 | pncTET | 43-8(low)-syn. lig.(S2) |
| | pCB395 | pRS304 | pncTET | 43-8(low)-syn. lig.(S1) |
| | pN288 | pRS603 | pNcZEV | 42-10(low)-syn. lig.(S4) |
| | pCB515 | pRS603 | pNcZEV | 42-10(low)-syn. lig.(S2) |
| | pCB516 | pRS603 | pNcZEV | 42-10(low)-syn. lig.(S1) |
| | pCB263 | pRS605 | pADH1 | 4x syn. clamp |
| | pCB266 | pRS605 | pADH1 | 5x syn. clamp |
| | pCB564 | pRS605 | pADH1 | 6x syn. clamp |
| Not shown | pRS406 | pRS406 | empty | empty |
| | pL329 | pRS304 | multiple (see FIG. S4) | multiple (see FIG. S4) |
| Not shown | pRS406 | pRS406 | empty | GFP |
| | pN8 | pRS406 | p($n_c$ = 2, 43-8 DBM1)minCyc1 | GFP |
| | pN491 | pRS406 | p($n_c$ = 4, 43-8 DBM1)minCyc1 | 42-10(low)-no lig. |
| | pN488 | pRS406 | p($n_c$ = 4, 43-8 DBM1)minCyc1 | 42-10(low)-syn. lig.(S5) |
| | pL329 | pRS304 | pNcTET | GFP |
| | pCB298 | pRS304 | pNcTET | 43-8(low)-syn. lig.(S5) |
| | pN281 | pRS304 | pNcTET | 43-8(low)-no lig. |
| | pN286 | pRS603 | p($n_c$ = 4, 42-10 DBM1)minCyc1 | GFP |
| Not shown | pN8 | pRS406 | p($n_c$ = 2, 43-8 DBM1)minCyc1 | GFP |
| | pCB277 | pRS406 | p($n_c$ = 3, 43-8 DBM1)minCyc1 | GFP |
| | pN20 | pRS406 | p($n_c$ = 4, 43-8 DBM1)minCyc1 | GFP |
| | pCB282 | pRS406 | p($n_c$ = 5, 43-8 DBM1)minCyc1 | GFP |
| | pCB301 | pRS304 | pNcTET | 43-8(low)-syn. lig.(S4) |
| | pCB245 | pRS605 | pADH1 | 2x syn. clamp |
| | pCB247 | pRS605 | pADH1 | 3x syn. clamp |
| | pCB263 | pRS605 | pADH1 | 4x syn. clamp |
| | pCB266 | pRS605 | pADH1 | 5x syn. clamp |
| FIG. 15A, | pN490 | pRS406 | p($n_c$ = 4, 43-8 DBM1)minCyc1 | 42-10(high)-syn. lig.(S5) |
| FIG. 15B, | pN488 | pRS406 | p($n_c$ = 4, 43-8 DBM1)minCyc1 | 42-10(low)-syn. lig.(S5) |
| FIG. 15C, | pN489 | pRS406 | p($n_c$ = 4, 43-8 DBM1)minCyc1 | 42-10(low)-syn. lig.(S4) |
| FIG. 15D | pN350 | pRS306 | p($n_c$ = 4, 42-10 DBM3, $n_c$ = 2, 43-8 DBM1)minCyc1 | 42-10(low)-syn. lig.(S5) |
| | pN354 | pRS306 | p($n_c$ = 4, 42-10 DBM2, $n_c$ = 2, 43-8 DBM1)minCyc1 | 42-10(low)-syn. lig.(S5) |
| | pN355 | pRS306 | p($n_c$ = 4, 42-10 DBM2, $n_c$ = 2, 43-8 DBM1)minCyc1 | 42-10(low)-syn. lig.(S2) |
| | pN359 | pRS306 | p($n_c$ = 4, 42-10 DBM4, $n_c$ = 2, 43-8 DBM1)minCyc1 | 42-10(low)-syn. lig.(S2) |
| | pN360 | pRS306 | p($n_c$ = 5, 42-10 DBM4, $n_c$ = 2, 43-8 DBM1)minCyc1 | 42-10(low)-syn. lig.(S5) |
| | pN361 | pRS306 | p($n_c$ = 5, 42-10 DBM4, $n_c$ = 2, 43-8 DBM1)minCyc1 | 42-10(low)-syn. lig.(S2) |
| | pN364 | pRS306 | p($n_c$ = 4, 42-10 DBM3, $n_c$ = 3, 43-8 DBM1)minCyc1 | 42-10(low)-syn. lig.(S5) |
| | pN366 | pRS306 | p($n_c$ = 4, 42-10 DBM2, $n_c$ = 3, 43-8 DBM1)minCyc1 | 42-10(low)-syn. lig.(S5) |
| | pN367 | pRS306 | p($n_c$ = 4, 42-10 DBM2, $n_c$ = 3, 43-8 DBM1)minCyc1 | 42-10(low)-syn. lig.(S2) |
| | pN368 | pRS306 | p($n_c$ = 4, 42-10 DBM4, $n_c$ = 3, 43-8 DBM1)minCyc1 | 42-10(low)-syn. lig.(S5) |

TABLE 2-continued

Plasmid Table

| FIG. | PLASMID # | PARENT | PROMOTER | ORF |
|---|---|---|---|---|
| | pN369 | pRS306 | p($n_c$ = 4, 42-10 DBM4, $n_c$ = 3, 43-8 DBM1)minCyc1 | 42-10(low)-syn. lig.(S2) |
| | pN353 | pRS306 | p($n_c$ = 5, 42-10 DBM3, $n_c$ = 2, 43-8 DBM1)minCyc1 | 42-10(low)-syn. lig.(S2) |
| | pN365 | pRS306 | p($n_c$ = 4, 42-10 DBM3, $n_c$ = 3, 43-8 DBM1)minCyc1 | 42-10(low)-syn. lig.(S2) |
| | pN409 | pRS306 | p($n_c$ = 2, 42-10 DBM1, $n_c$ = 2, 43-8 DBM2)minCyc1 | 42-10(low)-syn. lig.(S5) |
| | pN410 | pRS306 | p($n_c$ = 2, 42-10 DBM1, $n_c$ = 2, 43-8 DBM2)minCyc1 | 42-10(low)-syn. lig.(S2) |
| | pN348 | pRS306 | p($n_c$ = 2, 42-10 DBM1, $n_c$ = 2, 43-8 DBM1)minCyc1 | 42-10(low)-syn. lig.(S5) |
| | pN344 | pRS306 | p($n_c$ = 3, 42-10 DBM1, $n_c$ = 1, 43-8 DBM1)minCyc1 | 42-10(low)-syn. lig.(S5) |
| | pN464 | pRS306 | p($n_c$ = 4, 43-8 DBM3)minCyc1 | 42-10(low)-syn. lig.(S4) |
| | pN463 | pRS306 | p($n_c$ = 4, 43-8 DBM3)minCyc1 | 42-10(low)-syn. lig.(S5) |
| | pN464 | pRS306 | p($n_c$ = 4, 43-8 DBM3)minCyc1 | 42-10(low)-syn. lig.(S4) |
| | pN468 | pRS306 | p($n_c$ = 5, 43-8 DBM3)minCyc1 | 42-10(low)-syn. lig.(S2) |
| | pN281 | pRS304 | pNcTET | 43-8(low)-no lig. |
| | pCB298 | pRS304 | pNcTET | 43-8(low)-syn. lig.(S5) |
| | pCB301 | pRS304 | pNcTET | 43-8(low)-syn. lig.(S4) |
| | pCB263 | pRS605 | pADH1 | 4x syn. clamp |
| | pCB266 | pRS605 | pADH1 | 5x syn. clamp |
| | pN286 | pRS603 | p($n_c$ = 4, 42-10 DBM1)minCyc1 | GFP |
| | pN287 | pRS603 | p($n_c$ = 5, 42-10 DBM1)minCyc1 | GFP |

TABLE 3

Yeast Strains. URA3, TRP4, LEU2, and/or HIS3 indicate different plasmid loci or markers.

| FIG. | STRAIN ID | URA3 | TRP4 | LEU2 | HIS3 |
|---|---|---|---|---|---|
| FIG. 1E | sCB01 | pN8 | pCB298 | pN187 | |
| | sCB02 | pN8 | pCB300 | pN187 | |
| | sCB03 | pN8 | pCB302 | pN187 | |
| | sCB04 | pCB277 | pCB298 | pCB397 | |
| | sCB05 | pCB228 | pCB298 | pCB398 | |
| | sCB06 | CB269 | pCB298 | pN187 | |
| | sCB07 | pN8 | pCB706 | pN187 | |
| FIG. 2A | sCB08 | pCB707 | pCB298 | | |
| | sCB09 | pN8 | pCB298 | pCB245 | |
| | sCB10 | pN18 | pCB393 | pCB247 | |
| | sCB11 | pCB280 | pCB393 | pCB266 | |
| | sCB56 | pCB281 | pCB393 | pCB266 | |
| FIG. 2B | sCB12 | pCB726 | pCB302 | pCB564 | pN288 |
| | sCB13 | pCB730 | pCB393 | pCB564 | pCB515 |
| | sCB14 | pCB723 | pCB393 | pCB263 | pCB515 |
| | sCB15 | pCB729 | pCB395 | pCB564 | pCB516 |
| FIG. 3A | sCB16 | pN8 | pCB298 | | |
| | sCB17 | pCB278 | pCB298 | pCB263 | |
| FIG. 3B | yN483 | pN367 | pN281 | pCB263 | pN286 |
| | yN143 | pN410 | pCB301 | pCB263 | pN286 |
| | yN005 | pN488 | pN281 | pCB263 | pN286 |
| | yN006 | pN489 | pN281 | pCB263 | pN286 |
| | yN233 | pN464 | pCB298 | pCB263 | pN286 |
| | yN485 | pN369 | pN281 | pCB263 | pN286 |
| FIG. 4A | sCB18 | pN8 | pCB298 | | |
| | yN267 | pN468 | pCB298 | pCB266 | pN287 |
| FIG. 4B, FIG. 16A-FIG. 16C Not shown | yN473 | pN463 | pCB298 | pCB263 | pN451 |
| | yN140 | pN409 | pCB301 | pCB263 | pN400 |
| | sCB19 | pRS406 | pL329 | | |
| | sCB20 | pRS406 | pL330 | | |
| | sCB21 | | | pCB704 | |
| | sCB22 | | | | pCB702 |
| | sCB23 | | | pCB705 | |
| | sCB24 | | | | pCB703 |
| | sCB25 | pRS406 | pCB298 | | |
| FIG. 8B | yN701 | pN20 | | | |
| | yN711 | pN20 | | pN187 | |
| | yN712 | pN20 | | pN496 | |
| | yN757 | pN20 | | pN498 | |

TABLE 3-continued

Yeast Strains. URA3, TRP4, LEU2, and/or HIS3 indicate different plasmid loci or markers.

Figure 13B:
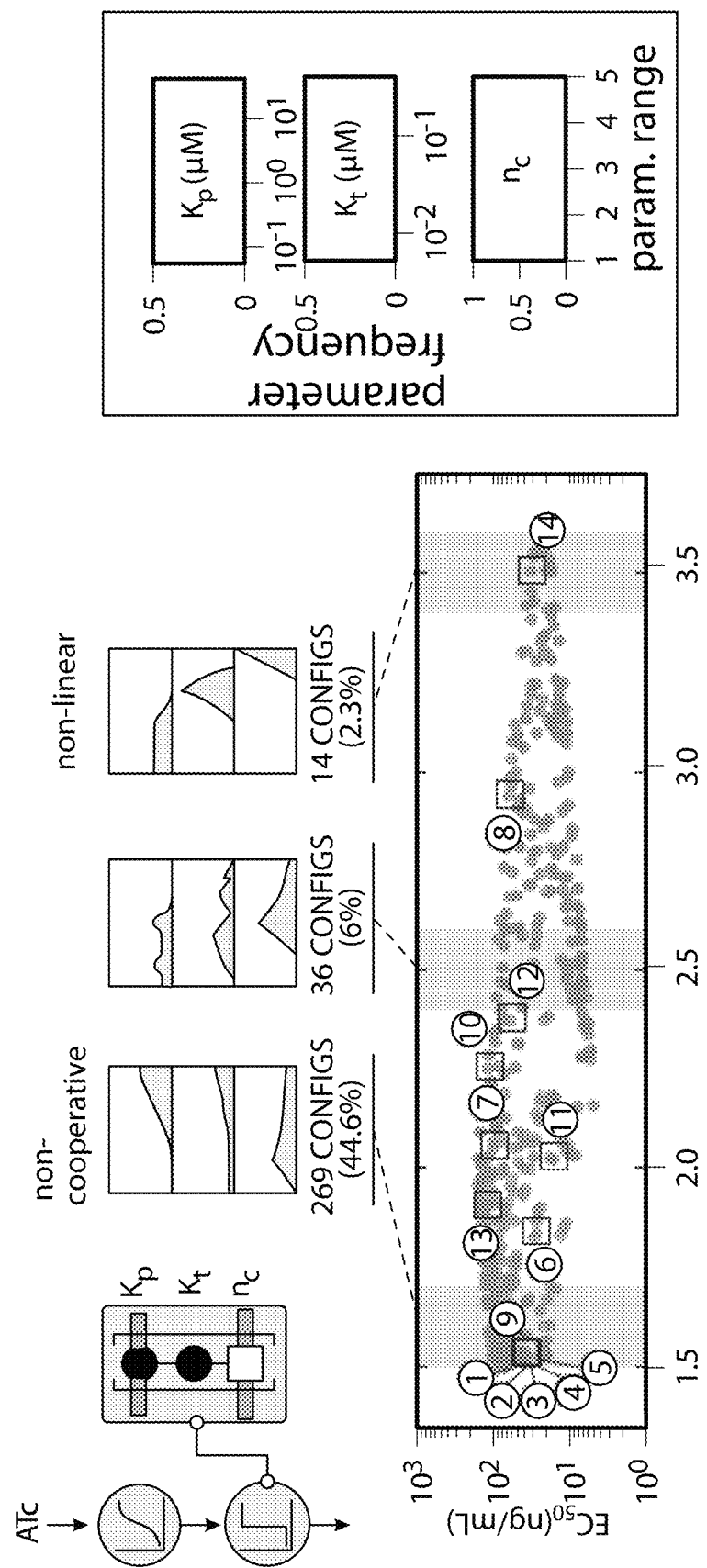
Figures 13C, 13D:
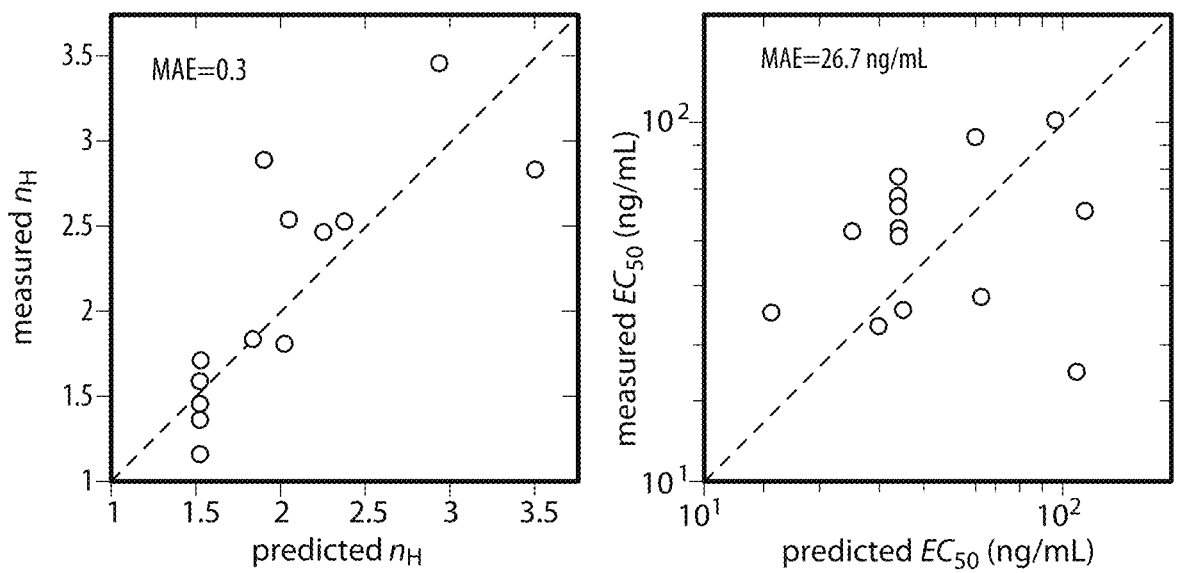

| FIG. | STRAIN ID | URA3 | TRP4 | LEU2 | HIS3 |
|---|---|---|---|---|---|
| FIG. 9A, FIG. 9B | yN490 | pN8 | pCB303 | pCB230 | |
| | yN491 | pN8 | pCB300 | pCB230 | |
| | yN492 | pN8 | pCB299 | pCB230 | |
| | yN493 | pN8 | pL372 | pCB230 | |
| | yN494 | pN8 | pCB298 | pCB230 | |
| | yN495 | pN8 | pCB304 | pCB230 | |
| | yN496 | pN8 | pCB303 | pCB230 | |
| | yN497 | pN8 | pCB301 | pCB230 | |
| | yN498 | pN8 | pCB267 | pCB230 | |
| | yN499 | pN8 | pCB303 | pCB244 | |
| | yN500 | pN8 | pCB300 | pCB244 | |
| | yN501 | pN8 | pCB299 | pCB244 | |
| | yN502 | pN8 | pL372 | pCB244 | |
| | yN503 | pN8 | pCB298 | pCB244 | |
| | yN504 | pN8 | pCB304 | pCB244 | |
| | yN505 | pN8 | pCB303 | pCB244 | |
| | yN506 | pN8 | pCB301 | pCB244 | |
| | yN507 | pN8 | pCB267 | pCB244 | |
| | yN508 | pN8 | pCB303 | pCB245 | |
| | yN509 | pN8 | pCB300 | pCB245 | |
| | yN510 | pN8 | pCB299 | pCB245 | |
| | yN511 | pN8 | pL372 | pCB245 | |
| | yN512 | pN8 | pCB298 | pCB245 | |
| | yN513 | pN8 | pCB304 | pCB245 | |
| | yN514 | pN8 | pCB303 | pCB245 | |
| | yN515 | pN8 | pCB301 | pCB245 | |
| | yN516 | pN8 | pCB267 | pCB245 | |
| FIG. 13C | sCB08 | pCB707 | pCB298 | | |
| | yN715 | pN8 | pCB298 | | |
| | yN716 | pN27 | pCB298 | | |
| | yN717 | pN20 | pCB298 | | |
| | yN718 | pCB282 | pCB298 | | |
| | sCB09 | pN8 | pCB298 | pCB245 | |
| | sCB10 | pN18 | pCB393 | pCB247 | |
| | sCB11 | pCB280 | pCB393 | pCB266 | |
| | sCB51 | pN20 | pCB300 | pCB263 | |
| | sCB52 | pCB280 | pCB301 | pCB266 | |
| | sCB53 | pN8 | pCB301 | pCB245 | |

TABLE 3-continued

Yeast Strains. URA3, TRP4, LEU2,
and/or HIS3 indicate different plasmid loci or markers.

| FIG. | STRAIN ID | URA3 | TRP4 | LEU2 | HIS3 |
|---|---|---|---|---|---|
|  | sCB54 | pCB276 | pCB393 | pCB247 |  |
|  | sCB55 | pCB279 | pCB298 | pCB263 |  |
|  | sCB56 | pCB281 | pCB393 | pCB266 |  |
| FIG. 14A-FIG. 14C | sCB26 | pCB721 | pCB302 | pCB263 | pN288 |
|  | sCB27 | pCB721 | pCB393 | pCB263 | pCB515 |
|  | sCB28 | pCB722 | pCB302 | pCB263 | pN288 |
|  | sCB29 | pCB722 | pCB393 | pCB263 | pCB515 |
|  | sCB30 | pCB723 | pCB302 | pCB263 | pN288 |
|  | sCB14 | pCB723 | pCB393 | pCB263 | pCB515 |
|  | sCB31 | pCB724 | pCB302 | pCB263 | pN288 |
|  | sCB32 | pCB724 | pCB393 | pCB263 | pCB515 |
|  | sCB33 | pCB725 | pCB302 | pCB266 | pN288 |
|  | sCB34 | pCB725 | pCB393 | pCB266 | pCB515 |
|  | sCB12 | pCB726 | pCB302 | pCB564 | pN288 |
|  | sCB35 | pCB726 | pCB393 | pCB564 | pCB515 |
|  | sCB36 | pCB727 | pCB302 | pCB263 | pN288 |
|  | sCB37 | pCB727 | pCB393 | pCB263 | pCB515 |
|  | sCB38 | pCB728 | pCB302 | pCB266 | pN288 |
|  | sCB39 | pCB728 | pCB393 | pCB266 | pCB515 |
|  | sCB40 | pCB729 | pCB302 | pCB564 | pN288 |
|  | sCB41 | pCB729 | pCB393 | pCB564 | pCB515 |
|  | sCB15 | pCB729 | pCB395 | pCB564 | pCB516 |
|  | sCB42 | pCB730 | pCB302 | pCB564 | pN288 |
|  | sCB13 | pCB730 | pCB393 | pCB564 | pCB515 |
|  | sCB43 | pCB731 | pCB302 | pCB263 | pN288 |
|  | sCB44 | pCB731 | pCB393 | pCB263 | pCB515 |
|  | sCB45 | pCB732 | pCB302 | pCB266 | pN288 |
|  | sCB46 | pCB732 | pCB393 | pCB266 | pCB515 |
| Not shown | sCB30 | pRS406 | pL329 |  |  |
| Not shown | sCB31 | pRS406 | pL329 |  |  |
|  | sCB32 | pN8 | pCB298 |  |  |
|  | yN474 | pN491 | pN281 |  | pN286 |
|  | yN005 | pN488 | pN281 | pCB263 | pN286 |
| Not shown | sCB47 | pN8 | pCB301 | pCB245 |  |
|  | sCB48 | pCB277 | pCB301 | pCB247 |  |
|  | sCB49 | pN20 | pCB301 | pCB263 |  |
|  | sCB50 | pCB282 | pCB301 | pCB266 |  |
| FIG. 15A-FIG. 15D | yN004 | pN488 | pN281 | pCB263 | pN286 |
|  | yN005 | pN489 | pN281 | pCB263 | pN286 |
|  | yN006 | pN490 | pN281 | pCB263 | pN286 |
|  | yN475 | pN350 | pN281 | pCB263 | pN286 |
|  | yN476 | pN354 | pN281 | pCB263 | pN286 |
|  | yN477 | pN355 | pN281 | pCB263 | pN286 |
|  | yN478 | pN359 | pN281 | pCB263 | pN286 |
|  | yN479 | pN360 | pN281 | pCB266 | pN287 |
|  | yN480 | pN361 | pN281 | pCB266 | pN287 |
|  | yN481 | pN364 | pN281 | pCB263 | pN286 |
|  | yN482 | pN366 | pN281 | pCB263 | pN286 |
|  | yN483 | pN367 | pN281 | pCB263 | pN286 |
|  | yN484 | pN368 | pN281 | pCB263 | pN286 |
|  | yN485 | pN369 | pN281 | pCB263 | pN286 |
|  | yN486 | pN353 | pN281 | pCB266 | pN287 |
|  | yN487 | pN365 | pN281 | pCB263 | pN286 |
|  | yN137 | pN409 | pCB298 | pCB263 | pN286 |
|  | yN143 | pN410 | pCB301 | pCB263 | pN286 |
|  | yN488 | pN348 | pCB298 | pCB263 | pN286 |
|  | yN489 | pN344 | pCB298 | pCB263 | pN286 |
|  | yN233 | pN464 | pCB298 | pCB263 | pN286 |
|  | yN241 | pN463 | pCB301 | pCB263 | pN286 |
|  | yN245 | pN464 | pCB301 | pCB263 | pN286 |
|  | yN288 | pN468 | pCB301 | pCB266 | pN287 |

Flow Cytometry

Yeast colonies were picked from plates and cultured overnight in 2 mL liquid SD media with appropriate auxotrophic dropouts. Cultures were diluted 1:50 into 500 μL of YPGal and grown for 16 h in the presence or absence of inducers. Prior to flow cytometry reading, cells were diluted 1:10 into 200 μL of PBS supplemented with 20 μg/ml cyclohexamide and incubated at 25° C., in the dark, for 3 h to allow for complete GFP fluorophore maturation. Typically, 10,000 events were acquired using a BD LSRFortessa equipped with a high throughput sampler (BD Biosciences). Events were gated by forward and side scatter, and geometric means of the fluorescence distributions were calculated in FlowJo (Treestar Software) (see e.g., FIG. 9A).

Microfluidic Device Construction

Single-cell microfluidic experiments were performed using custom microfluidic devices designed to support monolayer growth of S. cerevisiae cells and enable rapid, automated on-chip switching of liquid inputs. To enforce monolayer growth, a previously reported cell trapping design was used in which chambers were constructed with heights matching the cylindrical diameters of yeast cells (see e.g., Cookson et al., Mol Syst1, 2005 0024 (2005); Vega et al. Nature chemical biology. 8, 431-33 (2012)). To this "flow layer", a "control layer" of integrated elastomeric valves was overlaid to facilitate rapid on-chip switching of liquid inputs and outputs. Two variations of this common design were developed. The first, termed '12S2T', was designed to screen a maximum of 12 different strains with up to two distinct environmental time series (six strains per time series). The second, termed '12S6T', also accommodates a maximum of 12 strains with the possibility for six distinct time series (two strains per time series).

Devices were fabricated using soft lithographic techniques, as described previously (see e.g., Duffy, et al., Anal Chem. 70, 4974-84 (1998); Unger et al. Science. 288, 113-6 (2000)). Two photoresist-based molds, corresponding to flow and control layers, were patterned with respective microchannel structures. The flow layer mold was constructed by first patterning SU-8 2 negative photoresist (MicroChem Corp.) at the appropriate feature height onto a silicon wafer then transferring the cell trapping chamber pattern from a high-resolution transparency photomask (CAD/Art Services, Inc.). Next, AZ4620 positive photoresist (Capitol Scientific, Inc.) was patterned at the greater flow channel feature height and aligned to the trapping chamber pattern before transferring. The completed flow layer mold was placed on a hotplate at 145° C. for 1 min to reflow the photoresist and round the channel profiles for complete valve closure in assembled devices. The control layer mold was constructed by patterning SU-8 10 negative photoresist (MicroChem Corp.) onto a second silicon wafer and similarly transferring the control layer pattern from a photomask.

Devices were created by replica molding from the master molds. PDMS/Sylgard 184 was mixed in a 10:1 ratio of elastomer base:curing agent, poured onto the control layer mold to a thickness of ~5 mm, and baked at 80° C. for 3 h. Elastomer was prepared in a similar fashion and spun onto the flow layer master (3500 rpm for 60 s), and baked at 80° C. for ~10 min. The cured control layer was peeled from the master and aligned over the flow mold under a microscope. The multilayer devices were then baked for an additional 3 h, peeled from the master, cleaned, and finally sealed to pre-cleaned No. 1.5 glass coverslips (Fisher Scientific). Devices were operated using a previously-described microfluidic platform that integrates plumbing, hardware, and the software that controls valve and liquid delivery (see e.g., Vega et al. Nature chemical biology. 8, 431-33 (2012)).

Time-Lapse Microscopy and Image Analysis

Imaging of microfluidic experiments was conducted using an Eclipse Ti-E inverted microscope (Nikon Instruments, Inc.) equipped with a Controlled Environment Microscope Incubator, a XYZ-motorized "Perfect Focus System", and a Clara-E charge-coupled device (CCD) camera (Andor Technology). Images were acquired at 100× magnification (Plan Apo Lambda 100×, NA 1.45). Filters, light sources (Nikon LED and Lumencor SPECTRA X Light Engine), and stage movement were automatically controlled by the supplier's software (NIS-Elements Advanced Research).

Colonies were picked from plates and cultured overnight under auxotrophic selection in 2 mL liquid SD, and then diluted 1:20 into 0.4 mL YPGal and allowed to grow for ~20 h (OD~0.8) before seeding devices. Flow channels were loaded individually by flowing suspended culture through the 'inlet' ports until 2-10 cells of a particular strain were trapped in at least four growth chambers. Loaded devices were placed on the microscope stage and incubated at 30° C. under constant YPGal flow for 5-6 h prior to experimental time course initiation. Cells were then subjected to a specific environmental time series by toggling on-chip valves to control the different media inputs. Phase contrast and GFP images were collected every 15 min at programmed XY positions in three chambers per loaded flow channel. The duration of time-lapse imaging (following a short pre-growth in chambers) in all the experiments was limited to 50 h, after which accumulation of cells at efflux ports can affect the consistent delivery of media and growth of cells across all chambers. Following each experiment, images were analyzed by first using CellTracer 11 to segment single cells within each image. Single cell GFP fluorescence values, normalized by cell area, were extracted from segmented images using custom MATLAB software. Background fluorescence in the device was subtracted from each segmented cell's fluorescence values. Fluorescence trajectories shown throughout this study represent the mean and standard deviation of all cells across multiple chambers from a single channel (except for device precision experiments).

Fluorescence images shown in FIG. 4B were generated by segmenting cells and normalizing the background-subtracted fluorescence intensities for each cell to maximum circuit output under constitutive Dox. Strains producing mKate and GFP were false colored. Cells boundaries determined by the segmentation software are overlaid on each image.

Example 3: Model-Driven Programming of Circuit Input-Output Behavior Using Cooperative Assemblies The objective herein was to explore how sophisticated non-linear signal processing behavior can emerge from synthetic gene circuitry regulated by cooperative TF complex assembly. It was sought to capture essential features of multivalent, cooperative TF binding observed in natural promoter regulation using a simple, modular assembly scheme (see e.g., FIG. 1A). In this design, cooperativity arises when synthetic transcription factors (synTFs) bound in tandem to a multisite promoter are coordinated by a multivalent co-factor (the "clamp") (see e.g., FIG. 1B). The configuration of a synTF complex is defined by three tunable molecular features that determine the free energy of complex formation: the number of synTFs in the complex ($n_c$), the affinities of the synTFs for the promoter ($K_t$), and the affinity of the clamp for the synTF ($K_p$). Understanding how complex configuration gives rise to regulatory behavior requires modeling the functional relationship between $K_t$, $K_p$, $n_c$, and the free energy of complex assembly. Such a model provides a powerful tool for circuit engineering by enabling the systematic computational exploration of the behavioral space accessible to circuits regulated by cooperative assemblies. This allows for identification of sets of circuit designs that fulfill a particular target behavior prior to physical construction. Motivated by these possibilities, a modeling framework was created consisting of the following modules: (1) A thermodynamic module that relates cooperative assembly to transcriptional output for a given complex configuration ($n_c$, $K_p$, $K_t$), and (2) A differential equation module that describes temporal dynamics for circuits composed of interacting synTF assemblies.

Provided herein is a detailed description of how molecular parts used for synTF complex construction were selected, how their relevant properties were experimentally measured, model parameterization based on these measurements was performed, and then the model was used to simulate circuit input/output behavior and guide circuit construction.

Molecular Parts Library: Selection and Parameter Measurement

As a first step toward construction of a molecular assembly scheme amenable to modeling, a set of part variants was identified comprising a range of $K_t$ and $K_p$ values, and then in vitro binding experiments were conducted to directly measure their binding affinities (see e.g., FIG. 6, FIG. 7A, FIG. 7B). Fluorescence anisotropy (FA) was used to measure affinities for two types of purified ZFs (e.g., 43-8 'ZF1' and 42-10 'ZF2'), and their respective oligo DBMs. For each ZF, previously described R-to-A ZF backbone mutations were used as affinity variants (see e.g., Khalil et al., Cell. 150, 647-658 2012). DBM affinity series (DBM1, DBM2, etc.) for both ZFs by were also generated by systematically mutating nucleotides both in the core and directly flanking the core 9-bp recognition sequence (ZF 1: aGAGTGAGGAc (SEQ ID NO: 99); ZF2: aGACGCTGCTc (SEQ ID NO: 102)). Similarly, PDZ-ligand affinities were measured for two domains (syntrophin 'syn' and erbin 'erb') and their respective partner ligands. For each pair, ligands of various affinities were obtained from published reports (S1, S2, . . . ; E1, E2, . . . )12, 13 (see e.g., FIG. 7A, FIG. 7B). Altogether, this yielded a set of component interactions consisting of 15 ZF-DNA and 13 PDZ-ligand pairs with in vitro-measured values ranging from mid µM to low nM, permitting broad, tunable control of $K_t$ and $K_p$.

For in vivo experiments, cellular concentrations of synTF and clamp species ([TF]tot and [C]tot) were controlled by one of two small molecule-inducible expression systems. Both were selected for their non-cooperative dose response profiles. The first is a TetR-regulated pGAL1 expression system modified to have a linearized, non-cooperative dose-response (ncTET). The second is a non-cooperative system that utilizes a chimeric estrogen receptor transactivator (ncZEV). ncTET and ncZEV are induced by anhydrotetracycline (ATc) and estradiol (EST), respectively. To quantitatively characterize dose responses for these expression systems, yeast strains were constructed, which harbor either GFP or FLAG-tagged synTF1 (derived from ZF1) placed under expression system control. Dose response curves were obtained for both systems by flow cytometry analysis of inducer-dependent GFP expression (see e.g., Example 2). After subtracting background/intrinsic fluorescence, each dose response was fit to the following Hill model (see e.g., FIG. 8A, FIG. 8B, code description in Table 4):

$$F_{obs} = F_{min} + F_{max} \cdot [I]^{nH} / (EC_{50}^{nH} + [I]^{nH})$$

[I] is the concentration of chemical inducer, nH the Hill coefficient, EC50 the chemical inducer concentration at half-maximal response, and Fmin and Fmax the minimum and maximum fluorescence values measured in the dose response curves. nH, EC50, and the fold change of GFP fluorescence ($F_{max}/F_{min}$) were extracted from this fit and used during model parameterization (see below) as a proxy for the fold change of protein concentration resulting from promoter induction. In order to validate GFP as an accurate surrogate for expression, ncTET induction was assessed by Western blot (data not shown). Fitted values were found to be similar for both systems: EC50 (60.7 ng/ml by flow cytometry compared to 107 ng/ml by western) and nH (1.53 by flow cytometry compared to 1.14 by western). Additionally, constitutive fluorescence was measured from a pADH1 promoter driving GFP expression for different integration loci.

TABLE 4

Data Fitting

| Name of Fitting Function | Data Type | Output Parameters | MATLAB solver | Associated FIGS. |
|---|---|---|---|---|
| Hillfun.m (hill function) | fluor. anisotropy dose response | Hill parameters | least squares | FIG. 1C, FIG. 2A, FIG. 3A, FIG. 13A-FIG. 13D |
| Anisotropy_Fit.m (Wang fit) | fluor. anisotropy competition | protein-competitor affinity | least squares | FIG. 6, FIG. 7A, FIG. 7B |
| MeanTxn_OneTF.m | thermodynamic model for a one TF assembly | [TF], [Clamp] binding affinities | least squares | FIG. 1E |
| polyfitB.m (polynomial degree of 1) | thermodynamic model parameter extrapolation | slope and intercept of linear fit | polynomial fit | Data not shown |
| fit_logistic.m (logistic function) | promoter rate extrapolation | logistic function variables | least squares | Data not shown |
| OneNode.m, TwoNode.m, ThreeNode.m | microfluidic time courses | kinetic rates | Pattern Search | Data not shown |

Demonstrating Complex Formation In Vitro

In order to provide a direct demonstration that the molecular components (DNA, synTF, and clamp) are capable of cooperative assembly, a FA binding assay was used to test the effect of both clamp and complex size ($n_c$) on the cooperativity ($n_H$) and midpoint ($EC_{50}$) of a synTF titration (see e.g., FIG. 1C). Species used in the binding assay are described in FIG. 5A and FIG. 5B, and descriptions for protein purification and the binding assay are described elsewhere herein. For the nc=2 binding curves depicted in FIG. 1C, an oligo probe with two tandem DBMs and a clamp with two tandem PDZ domains was used. Probe and clamp species with three repeats were used for the nc=3 binding curve. Adding clamp to the system (2 μM) increased the affinity of synTFs for the probe ($EC_{50}$ of 210 nM to 18 nM) and cooperativity ($n_H$=1.07 to 1.81). This effect was PDZ-binding dependent, as indicated by the absence of corresponding affinity and cooperativity increases with titration of synTFs containing non-binding ligands (nb). Increasing nc to 3 further enhanced both affinity and cooperativity ($EC_{50}$=5.1 nM, $n_H$=2.55), verifying that greater stability is conferred by higher complex valency.

To confirm that nearly all of the change in anisotropy measured during complex formation results from binding of MBP-ZF (and not clamp) to the DNA probe, a control experiment was conducted (data not shown) where a single PDZ domain was titrated into a mixture containing probe with fully-saturated MBP-ZF binding. Addition of the PDZ made a minimal contribution (<5%) to the overall anisotropy signal, confirming that binding of species composed of low molecular weight PDZ domains have little effect on the anisotropy of synTF-probe complexes.

Optimizing Cooperative Complex Molecular Configuration

Individual domains comprising both synTF and clamp species are interconnected by flexible GS-repeat linkers (see e.g., FIG. 5A, FIG. 5B). These occur between ligand and ZF in the synTF, and between PDZ domains in the clamp. Without wishing to be bound by theory, it was postulated that free energy of complex assembly would depend heavily on domain interdistance, and thus it was attempted to identify a set of linker lengths that would best facilitate complex formation and transcriptional activation (see e.g., FIG. 9A, FIG. 9B). Circuits were constructed in which synTF expression is driven by ncTET, clamp is constitutive expressed with pAHD1, and nc=2 complex assembly takes place at a GFP reporter locus. Within this context, three GS linker lengths were tested for synTF1 (0, 5, 10 AAs) against three clamp linker lengths (5, 10, 20 AAs) at three different Kp values. Complex assembly at a GFP reporter locus was assessed by flow cytometry. Induced (ATc) and uninduced circuits were compared in strains in which clamp was either present or absent. The ability of the synTF and clamp to induce higher GFP expression when co-expressed was assessed, and the best performing set of linkers (5 GS for synTF and 20 GS for clamp) was selected for circuit construction (see e.g., FIG. 9B).

Thermodynamic Model: Model Description

Constructing a thermodynamic model for synTF complex assembly involves first identifying all possible promoter-bound synTF/clamp configurations for a given nc, and then assigning to each a characteristic transcriptional rate (r). A weight (w) describing the change in free energy for all interactions within each state is computed based on intracellular component concentrations and dissociation constants. Relative transcriptional contributions from each state are given by w*r. Because states within the system are assumed to be in thermal equilibrium with one another (which holds true as long as transcription initiation is much slower than rates of synTF binding), the following equation can be used to compute promoter output by averaging relative transcriptional contributions from each state, where i are transcriptionally active states and j are all promoter states:

$$txn = \Sigma_i r_i \cdot w_i / \Sigma_j w_j$$

Figure 10:
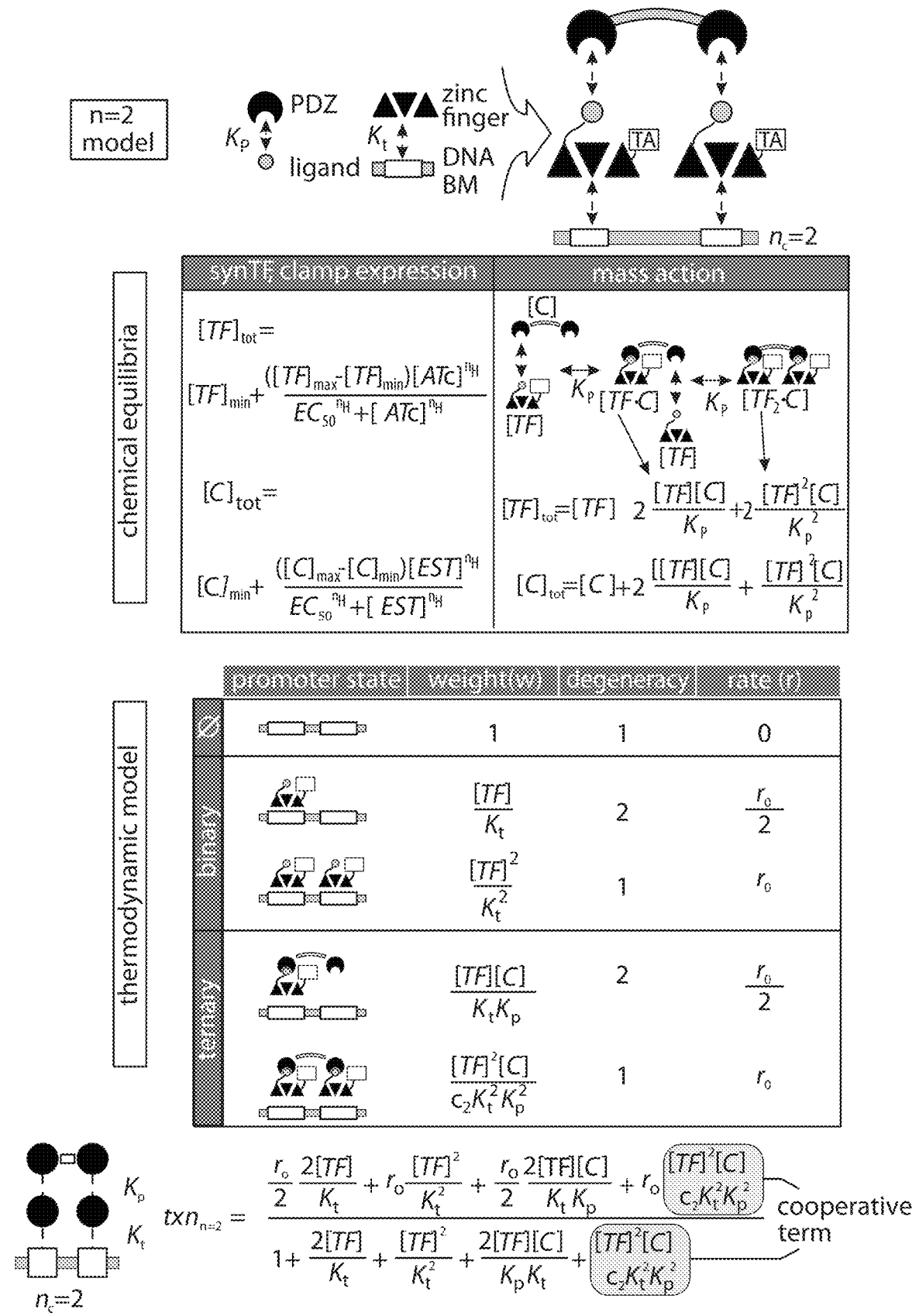
FIG. 10 is a schematic showing the thermodynamic model for nc=2 complex assembly. The mathematical model describing assembly of an nc=2 promoter complex has three components: (1) Top boxes: Chemical equilibria dictate concentrations of freely-diffusing species available for promoter binding. In the experimental system, synTF and clamp expression is controlled by ATc-inducible ncTET and EST-inducible ncZEV, respectively. Thus, Hill equations are used to describe the relationship between inducer and the in vivo concentrations of expressed components (left box; see e.g., FIG. 8A-FIG. 8B). Mass-action equations are used to account for concentrations of all available species, including free monomeric components ([TF] and [C]) and non-promoter multimeric complexes (right box). (2) Bottom boxes: Enumeration of possible promoter states. Each of the five states is assigned a corresponding thermodynamic weight (w) that describes the change in free energy for interactions within that state. (Kt=synTF-promoter binding affinity; Kp=PDZ-ligand binding affinity; nc=size of the complex) Each state is assigned a degeneracy that accounts for thermodynamically equivalent sub-states, and a transcription rate (r) proportional to the number of bound synTFs. (r0=maximum transcriptional output of the promoter.) The weight for the ternary complex (synTF+clamp) features a cooperativity constant (c) that represents additional stability afforded by the multivalent interaction. (3) Transcriptional activity (bottom): A function describing transcriptional output (NO is obtained by averaging the relative transcriptional contributions (w*r) of all promoter states.
Figure 11:
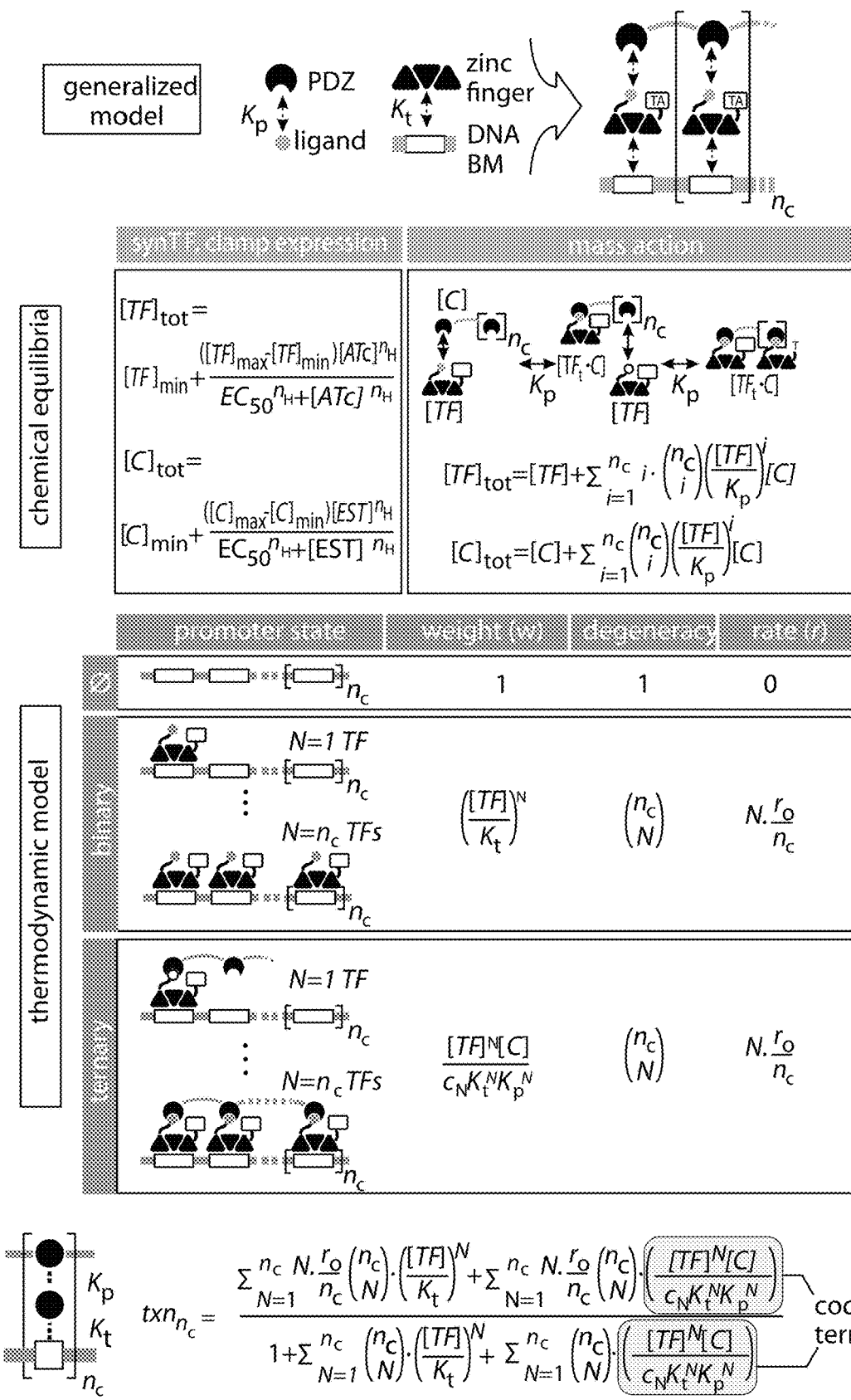
FIG. 11 is a schematic showing the generalized thermodynamic model for synTF/clamp complex assembly. The nc=2 model of FIG. 10 is generalized for synTF/clamp complexes of arbitrary size. (N=the number of promoter-bound synTFs; nc=total number of DNA binding sites; cN=cooperativity constant that defines the additional stability the clamp gives to a complex of N-bound synTFs.)

In FIG. 10, this framework is applied to the assembly of an nc=2 promoter complex. To model complex formation under different synTF and clamp expression levels, promoter-bound complex assembly was first distinguished from interactions between promoter-dissociated species in the nucleus. Hill equations relate inducer concentration to component expression, while mass-action equations describing formation of non-promoter complexes (synTF•Clamp and 2*synTF•Clamp) as a function of total synTF and clamp expression levels ([TF]tot, [C]tot) dictate the concentrations of species available to bind to the promoter. It is assumed that these equilibria are unaffected by promoter complex formation. Next, the thermodynamic promoter states are enumerated. Under conditions with both synTF and clamp present, the promoter can assume one of five possible states: unoccupied, one synTF bound, two synTFs bound, one synTF bound to clamp, and the full assembly containing two synTFs plus clamp. States containing a single bound synTF are degenerate—they can exist in one of two configurations assumed to be energetically and transcriptionally equivalent. Of the five states, four contain at least one bound synTF and are therefore transcriptionally active. Binding energies for each state are calculated based on the following parameters: (1) concentrations of free synTF and clamp ([TF] and [C]), which are related by chemical equilibria to [TF]tot and [C]tot, (2) dissociation constants for ZF-DNA ($K_t$) and PDZ-ligand ($K_p$) interactions, and (3) a constant (c2) that accounts for assembly cooperativity by acting as an interaction constant multiplier for the state in which two synTFs are bound to clamp. The values of w are then multiplied by the degeneracy of each state. Finally, each state is assigned an r proportional to the number of bound synTFs. It is assumed that neither synTF position within the DBM array, nor the presence of the clamp itself, influence r. For clarity, the expression describing the nc=2 system is written explicitly in FIG. 10. To model nc>2 complexes, the nc=2 case was generalized such that the number of states and their corresponding r and degeneracy are functions of nc and the number (N) of bound synTFs, and cn is a function of N (see e.g., FIG. 11, MATLAB function MeanTxn_OneTF.m in Table 5).

Thermodynamic Model: Fitting and Model Parameterization

In order to turn this model into a generalizable tool that can be used to accurately predict regulatory functions for arbitrary complex configurations, parametric fitting was conducted on a set of circuit induction training data (see e.g., FIG. 1D, FIG. 1E). Experimentally measured values for both in vitro component binding affinity (see e.g., FIG. 6, FIG. 7A, FIG. 7B) were used as initial parameter guesses to constrain the fit (see e.g., FIG. 10-FIG. 12). These values account for affinities between interacting complex components ($K_t$, $K_p$). Fitting allows one to infer parameter values for which there are not a priori estimates: the complex cooperativity factor ($c_n$) and effective maximum in vivo concentrations of complex components ([$TF_{tot}$] and [$C_{tot}$]). By fitting data from configurations featuring different $n_c$, $K_t$, and $K_p$ under various promoter induction levels (see e.g., FIG. 1D, FIG. 1E), generalizable functional relationships between not only complex size ($n_c$) and $c_n$, but also between promoter induction ([ATc], [EST]) and [$TF_{tot}$] and [$C_{tot}$] were obtained.

The seven circuits comprising the model fitting dataset are shown in FIG. 1E. Component expression is driven by ncTET (synTF) and ncZEV (clamp). Each circuit has a slightly different complex configuration (see e.g., FIG. 1E): for nc=2 complexes $K_t$ (6.5 nM, 13.6 nM, 143 nM) and $K_p$ (0.88 µM, 1.97 µM, 27.3 µM) affinities were varied, while nc was varied from 2-4 with fixed $K_t$ and $K_p$ values of 13.6 nM and 1.97 µM, respectively. For each of the strains in this set, input-output dose response surfaces (12 ATc by 12 EST doses; 144 total data points) were generated by measuring GFP expression as a function of inducer concentration. A global fit on all surfaces was performed using the trust-region-reflective algorithm implementation of Matlab's nonlinear least-squares solver (see e.g., FIG. 1E, code description in Table 4). Parameters describing the expression of synTF and clamp by the induction systems (e.g., $n_H$, $EC_{50}$, and species fold change) were fixed to experimentally measured values. Unmeasured values [TF]$_{max}$, [C]$_{max}$, and $c_n$ were unconstrained during the fit. Measured affinity values (see e.g., FIG. 6, FIG. 7A, FIG. 7B) were constrained to a 4-fold bound, chosen initially based on reported comparisons of binding affinities in vitro vs. in vivo for well-characterized TFs. To test the fitting methods, multiple parameter fits were performed across a broad range of fitting bounds and found that the goodness of fit of the model, evaluated by mean absolute error (MAE), as well as the fitted affinity values do not change for bounds larger than 4-fold (see e.g., FIG. 12B). As show in FIG. 1E, the fitted solution revealed good correspondence between model and data across the entire fitted data set (MAE=0.088).

The resulting set of fitted parameters represent a transformation of experimental measurements into values that describe effective component behavior in model space. For example, $K_t$ and $K_p$ values fit-adjusted to optimize [TF]$_{max}$, [C]$_{max}$, which serve as de facto proportionality constants relating component affinity to expression system induction. To obtain model space-transformed values for the full set of values measured (see e.g., FIG. 6, FIG. 7A, FIG. 7B, FIG. 8A, FIG. 8B), linear extrapolation was used. First, expression strength of pADH1 was calculated based on GFP expression data (see e.g., FIG. 8A, FIG. 8B). In order to obtain a full set of affinity values ($K_t$ and $K_p$) (see e.g., FIG. 6, FIG. 7A, FIG. 7B), a log-log relationship was chosen to extrapolate model affinities from the measured values. Though absolute affinities can differ in vitro and in vivo, relative differences between biochemically measured affinities correlate well with relative differences in in vivo activity (see e.g., Kang, Biochem J. 403, 177-82 (2007)), thus making this relationship a reasonable approximation. Additionally, $c_n$ values for configurations with nc>4 were extrapolated following a log linear fit of the three fitted clamp constants using the following equation (see e.g., code description in Table 4), where k is a scaling term which was determined from the fit to be 1.88:

$$c_n = 10^{-k \cdot n}$$

This relationship was chosen because it represents the simplest approximation for the role the clamp plays in affecting the free energy of the complex. It was assumed that each clamped synTF contributes the same amount of free energy to the complex, in which case the $K_d$ of binding, being proportional to the exponential of the free energy of the complex, depends exponentially with the number of binding sites (n).

Relating Cooperative Complex Configuration to Circuit Behavior

The fully parameterized thermodynamic model was used to quantitatively map the relationship between complex configuration and circuit behavior for a number of different circuit motifs (see e.g., FIG. 2A-FIG. 2C, FIG. 4A-FIG. 4B, FIG. 13A-FIG. 15D). In each case, a database of all possible complex configurations ("configuration space") was generated based on the combinatorics furnished by the available part space. Transcriptional input/output functions were simulated for each configuration, and then used to compute circuit behavior variables ("behavior space"). 2D behavior space plots for relevant variables were generated and used to identify relationships between regions of circuit behavior space and characteristics of corresponding complex configuration space.

Mapping Circuit Behavior Space for Single-Input Circuits

One fundamental signal processing function that cellular regulatory networks perform is the conversion of a non-cooperative regulatory input (dose) into a nonlinear, switch-like output (response). Nonlinear dose response can emerge from cooperative assembly when the titration of a molecular species into a system dominated by weak, low valency interactions leads to the formation of stable, high valency complexes. The greater the energetic difference between low and high valency regimes, the greater the nonlinearity in the relationship between concentration of the titrated species (input) and complex formation (output). The parameterized model is used to demonstrate how nonlinearity can arise from titration and complex formation for a single synTF. It was evaluated how the free energy state distribution for a synTF-clamp complex changes by altering configuration features. Total Gibbs free energy change ($\Delta G$) for each state was calculated by summing binding energies from each of the constituent binary interactions. $\Delta G$ for each interaction ($K_d$) was calculated using the following equation:

$$\Delta G = -k_B T \ln\left(\frac{K_d}{c_{ref}}\right)$$

where $k_B$ is the Boltzmann constant (J·K−1), T is temperature (K), $K_d$ is disassociation constant (M), and $c_{ref}$ is a standard reference concentration of 1 M.

For a low valency $n_c$=2 configuration, very few states are available for occupancy by complex components, and energetic separation between states is relatively small; plotting txn as a function of synTF concentration, a non-cooperative dose response ($n_H$=1.0) was observed. Very little nonlinearity ($n_H$=1.02) is introduced by increasing complex valency (e.g., from $n_c$=2 to 5) despite the greater overall number of states as well as an increase in the free energy differences between them. Here, higher energy binary synTF-promoter states dominate transcriptional output at lower synTF concentrations, while much lower energy, clamp-bound ternary states dominate at higher concentrations. However, when synTF affinities are lowered for DBM (large $K_t$ values) and raised for the clamp (small $K_p$ values) within the $n_c$=5 complex, a sharp jump is seen in dose response cooperativity ($n_H$=3.1), as a result of binary and ternary states becoming energetically separated (data not shown). Thus, this model indicates that it should be readily possible to use different $K_t$, $K_p$, and $n_c$ regimes to program dose-response cooperativity, tuning to either linear or highly switch-like activation profiles.

In order to determine the extent to which the parts collection enables dose response tuning, the parameterized model was used to map the relationship between accessible complex configuration space and behavior space for an inducible single input circuit (see e.g., FIG. 2B). Steady-state GFP output was modeled in response to ncTET-driven transcription of synTF1, which assembles with constitutively expressed (pADH1) clamp (see e.g., MATLAB function MeanTxn_OneTF.m in Table 5). With wishing to be bound by theory, it was reasoned that, because the induction profile for ncTET—the first node in the circuit—is non-cooperative with respect to ATc input (nH=1.53; see e.g., FIG. 8A, FIG. 8B), it should be possible to manipulate the overall cooperativity of circuit input-output by programming complex assembly in the second node. Complex configuration space was obtained from the combinatorial enumeration of the parts set: $K_t$ (13 affinities)+$K_p$ (15 affinities)+(2-5)+(with and without clamp)=855 total configurations (see e.g., FIG. 13A). Using the parameterized thermodynamic model, ATc dose response titrations were simulated for the entire configuration space (ATc range=100-104 ng/µL) and resulting dose responses were fit to the following Hill function (code description in Table 4):

$$txn_{norm} = \left(\frac{a \cdot [ATc]^{nH}}{EC_{50} + [ATc]^{nH}}\right) + c$$

where txnnorm is the normalized transcriptional output for a circuit with a given configuration, EC50 is the ATc concentration at which transcriptional activation is half-maximal, nH is the Hill coefficient, a is the max activation level, and c is basal expression for each circuit. Both non-activating configurations (a/c<2) and configurations with high basal expression (c>0.2) were omitted. EC50 and nH values were extracted from the remaining configurations (603) and plotted as a two-dimensional behavior space (see e.g., FIG. 2B).

As demonstrated by the scatter in FIG. 2B, the nH distribution of low nc (1-3) configurations are narrow and mostly non-cooperative, while higher order configurations ($n_c$=4 and 5) show broader distributions, granting access to regions of more switch-like circuit behavior. For both low and high valency complexes, $EC_{50}$ is tunable over approximately 1.5 logs (~5 ng/mL-150 ng/ml), a range which is constrained by the dose response profile of the ncTET system ($EC_{50}$=60.7 ng/ml). Plotting parameter profiles for configurations in different sectors of the behavior space (see e.g., FIG. 13B) revealed that non-cooperative dose responses were enriched for weak clamp interactions (large $K_p$ values), while the most cooperative configurations were highly enriched for both weak DNA (large $K_t$) and strong clamp (small $K_p$) interactions in a manner consistent with earlier thermodynamic analysis. A number of configurations evenly distributed across the scatter were selected to test experimentally (see e.g., FIG. 2B, FIG. 13A). ATc dose response profiles (ATc=2182, 1190, 649, 354, 193, 105, 57.5, 31.3, 17.1, 9.32, 5.09, 2.77, 1.51. 0.83 ng/mL) were determined using the same method as in FIG. 8A-FIG. 8B and data were fit to the above Hill equation to extract $EC_{50}$ and $n_H$ values. Within this experimental set, configurations were included without clamp and with higher affinity synTF binding sites (e.g., strains #2-5, see e.g., FIG. 13A) to test for potential indirect sources of cooperativity that are not dependent on clamp. With increasing numbers of higher affinity binding sites ($n_c$=2, 3, 4, 5), increases in cooperativity ($n_H$=1.42, 1.58, 1.36, 1.45, respectively) were not observed, and all Hill coefficient values were close to that of the ncTET induction system ($n_H$=1.53). Thus, the clamp plays an essential role in mediating cooperative dose responses in this system.

Finally, comparing model-predicted and experimentally-obtained values of $n_H$ and $EC_{50}$ for each configuration revealed good general correspondence for $n_H$ (MAE=0.3) and to a slightly lesser extent for $EC_{50}$ (MAE=26.7 ng/mL) (see e.g., FIG. 13B). Thus, the model is broadly predictive of complex configurations capable of quantitatively modulating aspects of the dose response curve with some limitations, particularly for the $EC_{50}$, which is likely constrained by the dynamic range and $EC_{50}$ of the ncTET induction system controlling synTF expression.

Mapping Circuit Behavior Space for Two-Input Circuits

Cellular networks sense and integrate concurrent environmental signals in a variety of ways. Signals can be integrated linearly, by summing inputs, or non-linearly, by computing inputs in near-digital fashion. The ability to use programmed cooperative complex assembly was tested to tune between these regimes for a two-input circuit, where regulation is mediated by two differentially inducible synTF species that assemble together into a clamped complex (see e.g., FIG. 2C). Dose response behavior for two-input circuits depends not only on the cooperativity associated with binding of each individual synTF, but also on binding interdependence conferred by the clamp.

This model was used to investigate the relationship between complex configuration and two-input regulatory function (see e.g., FIG. 2C). The configuration space that was tested included 6 Kt affinities for each synTF, 5 Kp affinities, and nc ranging from 2-6 (1-3 for each of the two synTFs), for a total of 8,424 configurations (data not shown). For all circuits that were simulated, synTF1 was expressed from a ncTET promoter, and synTF2 from a ncZEV promoter.

For each configuration, two-input dose response surfaces were simulated by titrating ATc from $10^{-1}$-$40^4$ ng/mL, and EST from 0.05-12.5 nM to generate surfaces containing 96×96 data points (see e.g., MATLAB function MeanTxn_TwoTF.m in Table 5). To identify configurations that exhibit desired target behaviors, Kullback-Leibler divergence ($D_{KL}$) was used, an information theory quantity that measures informational entropy, to assess similarity between simulated and target dose-response surfaces (data not shown). $D_{KL}$ is given by the following equation:

$$D_{KL}(P\|Q) = \sum_i P(i)\ln\frac{P(i)}{Q(i)},$$

which provides a measure of "information lost" when distribution Q is used to approximate distribution P (and thus equals 0 when P and Q are the same). $D_{KL}$ was calculated between surface data for simulated surfaces (Q) and target distributions (P) designed to mimic ideal Boolean logic gate behavior. Target distributions consisted of 12×12 square regions located in the corners of each surface; regions were either uniformly fully transcriptionally active or inactive based on their particular logic (data not shown).

A circuit behavior space was generated (see e.g., FIG. 2C) by plotting $D_{KL}$ for an idealized OR-gate behavior against that of an idealized AND-gate (data not shown). In qualitative terms, the position of a configuration within this space represents the degree to which binding of the synTF species during complex formation is either independent (OR-like) or interdependent (AND-like). Configurations that confer the most AND-like and OR-like circuit behavior cluster at two opposing vertices (see e.g., FIG. 2C), both of which are enriched for higher order ($n_c$=4-6) complexes. Thus, circuits that exhibit more Boolean-like behavior, with sharper decision boundaries, contain more highly-cooperative assemblies. Circuits conferring more non-cooperative, graded surfaces are found in the fronts between vertices, or near the center of the scatter, amongst complexes with lower $n_c$. Configurations conferring sharp AND and OR-like logic are enriched for low $K_t$ affinities and high $K_p$ affinities (data not shown), while those with graded responses show a broader range of parameter values, particularly for Kp.

In addition to AND and OR logic, the behavior space was probed for other Boolean logic behaviors to assess the behavioral capabilities and limitations of the two-input system. NOR, NAND, and XOR gates were queried, but configurations were not found that were capable of accessing these behaviors. It should be noted the types of logic behaviors that can be accessed by this system are likely limited by the exclusive use of activators to engineer transcriptional regulation. Therefore, only logic functions that feature monotonically increasing transcriptional activity with respect to inducer concentration are likely possible. Indeed, there is little evidence of any non-monotonic behavior in our system, including negative cooperativity between binary and ternary complexes, which might be formally possible through competition between transcription factors for binding to free clamp. Here, the model indicates that clamp is expressed at sufficient quantities to prevent such a scenario.

In order to validate model predictions, various circuits were selected within the behavior space distribution to construct and experimentally test (see e.g., FIG. 14A). A simple "4-corners" test was performed, where saturating amounts of ATc (2000 ng/mL) and EST (15 nM) inducer were added either individually, or as a pair (see e.g., FIG. 14B). To quantify the predictive power of the model, model and experimental data in correlation plots of the divergence ($D_{KL}$) were compared with ideal AND and ideal OR logic (see e.g., FIG. 14C). For the majority of the tested configurations, model and data showed close agreement; however, behaviors predicted to be AND-like for several of the circuits was not observed, indicating that AND-like assemblies may be extremely sensitive to assembly parameters. When the performance of configurations predicted to give the best AND-gate logic was further analyzed, these tended to show a greater overall deviation from model predictions than all other configurations (see e.g., FIG. 14C). Data was collected on full surfaces (ATc=500, 298.5, 178.2, 106.4, 63.5, 37.9, 22.6, 13.5, 8.1, 4.8, 2.9, 1.7 ng/mL; EST=12.5, 7.58, 4.59, 2.78, 1.69, 1.02, 0.62, 0.38, 0.23, 0.14, 0.08, 0.05 nM) for a number of these circuits to compare with model predictions, selecting AND- and OR-gate configurations predicted to yield Boolean-like dose response surfaces, as well as configurations predicted to exhibit intermediate behavior (see e.g., FIG. 2C). Using an MAE assessment, good overall agreement was found between the model and measured $D_{KL}$ values (see e.g., FIG. 14C). Interestingly, AND-logic was less well-predicted by the model than other behaviors. This may be due to assemblies underlying AND-logic being extremely sensitive to both component affinity and intracellular concentration. In the case of the AND-gate, this manifests as difficulty with balancing higher order binding energies for each of the ternary states within the complex.

TABLE 5

Simulation Functions

| Name of Custom Function | Function Output | Input Parameters | Associated Figures | Function Description |
|---|---|---|---|---|
| MeanTxn_OneTF.m | one-input dose response | [TF], [Clamp], n, binding affinities | See e.g., FIG. 2A, FIG. 13A-FIG. 13D | uses protein concentrations and thermos. parameters to calculate mean transcriptional rate for a 1 TF, 1 Clamp assembly |
| MeanTxn_TwoTF.m | two-input decision surface | [TF1], [TF2], [Clamp], n, binding affinities | See e.g., FIG. 2B, FIG. 14A-FIG. 14C | uses protein concentrations and thermo. parameters to calculate mean transcriptional rate for a 2 TF, 1 Clamp assembly |
| OneNode.m | one-node cascade dynamics | [GFP] @t = 0, binding affinities, kinetic rates, Dox input | Data not shown | predicts dynamics of a one node circuit for a defined Dox input over time |
| TwoNode.m | two-node cascade dynamics | [TF1], [GFP] @t = 0 binding affinities, kinetic rates, Dox input | See e.g., FIG. 3A, FIG. 3B, FIG. 4A, FIG. 15A-FIG. 15D | predicts dynamics of a two node circuit for a defined Dox input over time |
| ThreeNode.m | three-node cascade dynamics | [TF1], [TF2], [GFP] @t = 0, binding affinities, kinetic rates, Dox input | See e.g., FIG. 3B, FIG. 4A, 15A-FIG. 15D | predicts dynamics of a three node circuit for a defined Dox input over time |
| ThreeNodeFB.m | three-node cascade + FB dynamics | [TF1], [TF2], [GFP] @t = 0, binding affinities, kinetic rates, Dox input | See e.g., FIG. 3B | predicts dynamics of a three node + FB circuit for a defined Dox input over time |
| CFFL.m | CFFL dynamics | [TF1], [TF2], [GFP] @t = 0, binding affinities, kinetic rates, Dox input | See e.g., FIG. 16A-FIG. 16C | predicts dynamics of a CFFL circuit for a defined Dox input over time |
| CFFLFB.m | CFFL + FB dynamics | [TF1], [TF2], [GFP] @t = 0, binding affinities, kinetic rates, Dox input | See e.g., FIG. 16A-FIG. 16C | predicts dynamics of a CFFL + FB circuit for a defined Dox input over time |

Dynamic Model for Circuits Composed of Interacting synTF Assemblies

In order to examine the extent to which programmable complex assembly can be used to program synthetic gene circuit dynamics, a microfluidic workflow was developed to measure single cell response to circuit induction (data not shown). Accumulation and decay of GFP fluorescence was established in response to a single, saturating square pulse of doxycycline (Dox) as a generic assay for dynamic behavior (see e.g., FIG. 3A-FIG. 3B). Prior to testing cooperative assemblies, experimental precision for the 12S2T microfluidic device was assessed using square pulse induction of the ncTET-GFP reporter strain. Population-to-population variation in mean fluorescence measured across different chambers (chamber-to-chamber) and different devices (device-to-device) was found to be minor. Dox was used in place of ATc for time-lapse fluorescence imaging because of its increased photostability relative to ATc. It was verified that the Dox concentration (10 μg/mL) used for microfluidic experiments was administered at saturating levels.

In order to predict the dynamic behavior of circuits measured in microfluidic pulse experiments, a model was developed that incorporates the thermodynamic treatment of cooperative assembly while using a system of first-order differential equations to account for synTF transcriptional dynamics (data not shown). Each equation describes species production from a single circuit "node" (e.g. regulated promoter driving expression of synTF or GFP), and consists of: (i) a basal promoter activity (kbasal), (ii) regulated promoter activity (kact), and (iii) degradation of the protein species (kdeg). For (DBM)miniCyc1-derived promoters regulated by synTF assemblies (see e.g., FIG. 5A), transcriptional regulation is described using thermodynamic polynomials described in FIG. 10 and FIG. 11, which are multiplied by activation rate constants, kact, to obtain locus-specific rates of species production.

Activation/deactivation dynamics were measured for a set of five test circuits to obtain training data for parametric model fitting (data not shown): (1) The ncTET-GFP expression system (one-node), (2) a two-node network where ncTET drives expression of synTF1 ($K_t$=13.6 nM), which activates GFP reporter driven by an nc=2 promoter, (3) a two-node network where synTF1 drives cooperative assembly ($K_t$=224 nM, $K_p$=1.97, $n_c$=4) at the reporter, and (4) a three-node cascade in which synTF1 activates production of synTF2 ($K_t$=15 nM), which subsequently activates GFP with and (5) without clamp (code description in Table 5). Model rate parameters ($k_{basal}$, $k_{act}$, and $k_{deg}$) were extracted by performing a pattern search least squares global fit on data traces (data not shown). During the fit, complex-mediated transcription was calculated using fixed values obtained from previous thermodynamic model fitting ($K_t$, $K_p$, $c_n$, and pADH1-driven $[C]_{tot}$) (see e.g., FIG. 12A-FIG. 12B). Initial guesses for dilution/degradation rate ($k_{deg}$) of protein species were approximated to be 0.003 min-1 (based on the doubling time of yeast cells in YPGal). Fitting multiple circuits allowed us to extract locus-specific promoter activation rates for both synTF and GFP transcription ($k_{act}$). The fit solution revealed close correspondence between model and data across the entire fitting set.

Finally, a general relationship was developed that can be used to scale the extracted promoter activation rates ($k_{act}$) for promoters having different synTF operator numbers ($n_c$) by constructing two-node cascades with promoter (pSynTF1) variants having $n_c$=2-5. The induced maximum circuit output for these variants was measured, and fit this data with a simple logistic function to produce a relationship between $n_c$ and the promoter activation rate (see e.g., code description in Table 4).

Mapping Behavior Space for Circuit Activation/Deactivation Dynamics

In order to assess the extent to which cooperative complex assembly can be used to predictively tune temporal circuit behavior, this integrated model was used to map activation/deactivation behavior space for circuits comprising three different network motifs: a two-node cascade, three-node cascade, and three-node cascade with positive feedback loop at the second node (see e.g., FIG. 3A, FIG. 3B, Table 5). Activation/deactivation dynamics were calculated in response to a 16 h Dox pulse for the full set of assembly configurations available to each motif (total of 64,080). Circuit configurations with low maximum outputs (max GFP<1000 AFU) or weak inducibility (max/basal <1.5) were filtered out, resulting in a "filtered space" of 12,774 circuit configurations (data not shown). Values for activation ($\tau_a$) and decay ($\tau_d$) half-time were respectively defined as the time it takes to reach the half-maximal response following Dox pulse initiation, and time to return to half-maximal response following the end of the pulse (see e.g., FIG. 3A). Circuits that did not decay to less than their half-maximal response within the time frame of the simulation (4000 min) were designated as "no decay". Plotting $\tau_a$ against $\tau_d$ for all circuits yielded the behavior space scatter in FIG. 3B. Circuits designated as no decay were plotted separately in a box above the $\tau_d$ axis. Grey shaded region denotes circuit decay times that exceed the duration of time-lapse imaging in microfluidic devices.

Furthermore, it was demonstrated that behavior space distribution expansion for two- and three-node circuits in FIG. 3B is the result of cooperative complex assembly. Comparing no-feedback configurations with clamp to those without, a dramatic expansion along both $\tau_a$ and $\tau_d$ axes was observed. Various peripheral regions of FIG. 3B behavior space were highlighted, along with parameter distributions for circuit configurations that fall within each region (data not shown). Highlighted categories include 'fast ON/slow OFF', 'slow ON/fast OFF', 'slow ON/slow OFF', 'fast ON/fast OFF', and 'Memory'. Parameter profiles for a number of these regions show enrichment in higher-order configurations (nc>3), once again highlighting the importance of complex assembly in granting access to non-linear behaviors (data not shown). Comparing opposing vertices of the behavior space, it was observed that configurations conferring fast ON/slow OFF behavior are enriched for high synTF2 affinities (small $K_{t2}$ values) at the reporter C-node, while those at the opposing vertex demonstrate a shift to lower affinity values. This was observed for circuits with or without feedback. This affinity difference in the C-node configuration is consistent with a shift from slower to faster complex deactivation times (e.g., see FIG. 3B). Moreover, configurational differences at the B-node are likely important in determining circuit activation time-scales. For example, in the no feedback case, B-node configurations exhibiting fast ON/slow OFF dynamics utilize high affinity clamp interactions (small Kp1), in contrast to those in slow ON/fast OFF, which would enable lower activation thresholds and thus faster responses.

Though complex assembly enables expansion of the behavior space for two- and three-node cascades (data not shown), there is still a strong (inverse) dependency between $\tau_a$ and $\tau_d$, with scatter points lying along the axis connecting the fast ON/slow OFF and slow ON/fast OFF vertices. This analysis reveals that accessing behavior spaces that break this dependency requires feedback; the only configurations emerging that exhibit slow ON/slow OFF were circuits with feedback (data not shown). Similarly, feedback was a required feature of circuit configurations that show either very slow decay rates (high $\tau_d$) or memory. The lower left corner of the behavior space is not accessible due to a combination of synTF affinities and the inherent limitations imposed by transcription/protein synthesis and decay. Not surprisingly, areas of faster ($\tau_a$) and ($\tau_d$) behavior space can be accessed by two-node circuits (data not shown), but the behavior distribution shows the same shape—a curved front with a 'knee'—as that of three-node. This shape likely arises from assembly thermodynamics: fast on times that result from low energy complexes assembling at lower synTF concentrations necessarily take longer to disassemble when input is removed and intracellular synTF begins to decay.

A number of interesting features emerge from analysis of feedback-containing three-node circuits. While both type 1 (homo-assembly; both TFs clamped) and type 2 (hetero-assembly; only one TF clamped) B-node architectures were observed for circuits with slow ON/memory space behavior, only type 2 configurations featuring both synTFs complexed together at the B-node can attain slow ON/slow OFF dynamics (data not shown). In this latter case, weak synTF1 interactions form the basis for the slow ON phase, while stable complex formation resulting from accumulation of higher affinity synTF2 (small Kt2 values) enforces positive feedback, resulting in prolonged decay times and a slow OFF.

To test the ability of this kinetic model to predict experimental circuit behavior, a number of circuits were constructed that are representative of different regions of behavior space, and their behavior was analyzed using microfluidics (see e.g., FIG. 15A-FIG. 15D). Circuits were subjected to a 16 h pulse of Dox (10 µg/mL) on the device after which the inducer was removed and GFP measurements were collected for another 26 h (see e.g., FIG. 15B). From these data, $\tau_a$ and $\tau_d$ were extracted for each circuit, as done with model-predicted traces, and they were then compared to model-predicted $\tau_a$ and $\tau_d$ (see e.g., FIG. 15C). Correspondence was found between model and experiment for ON dynamics (MAE=150.6 min) and, to a slightly lesser extent, OFF dynamics (MAE=273 min), indicating that the model can predict aspects of circuit response dynamics. For a few circuits, GFP profiles showed prolonged decay times, preventing the obtaining of a $\tau_d$ within the experimental measurement window (e.g. strain #9 in FIG. 15B). As a second method for evaluating model performance, model and data for all circuits at specified time points throughout the experiment were directly compared (see e.g., FIG. 15D). For most circuits, the model and data corresponded well through 22 h of measurement (6 h post DOX removal), after which predictive power was diminished for a fraction of circuits. Interestingly, the model tended to under predict decay dynamics for a number of three-node+FB configurations. More specifically, configurations that were predicted to decay slowly instead showed no measurable decay within the measurement window (e.g. strains #15, 19, 20 in FIG. 15A-FIG. 15D). For these configurations, the dynamic model may have underestimated feedback strength conferred by B-node assembly. Consistent with the idea that fine adjustments in assembly thermodynamics can readily tune feedback circuits between mono- and bistable steady-state regimes, it is possible that minute inaccuracies in our complex assembly model may render the behavior of feedback-containing circuits more difficult to predict.

Because GFP is a stable protein and highly resistant to proteasomal degradation in yeast, its clearance closely tracks the rate of cell division. Therefore, maintenance of cellular growth in the microfluidic device can be another potential factor that can affect the predictive power of the model. To investigate this further, cell size was quantified for all measurements. Mean cell size and variation across the population stayed relatively constant throughout the experiments (see e.g., FIG. 16A). Furthermore, analysis of cell number showed that the mean growth rate across the strains (0.0029 $min^{-1}$) is very close to the dilution rate of GFP in the model (0.003 $min^{-1}$), providing a cross-validation for the kinetic model fit. These observations are also consistent with work showing that synTFs (constructed using affinity mutants ZFs 42-10 and 43-8) confer little to no fitness defects in yeast (see e.g., FIG. 16B; Khalil et al., Cell. 150, 647-658 (2012)). Lastly, mean growth rates were compared with the measured activation and decay times of each circuit, and no significant correlation was found (see e.g., FIG. 16C), indicating that variation in growth rate does not strongly impact or drive circuit dynamics.

Engineering Circuits that Interpret and Decode Dynamic Environmental Information In nature, cells are exposed to dynamically-changing environments. Regulatory circuits must interpret fluctuating signals in the environment and precisely translate them into the appropriate cellular response. Because this type of behavior is, by nature, highly non-linear, it was predicted that creating synthetic circuits that respond to temporal features of the environment, or execute time-based signal processing, can be enabled by our ability to program complex assembly. Implementing time-based control can be used to design and tune filtering functions, e.g. that allow cells to distinguish transient environmental fluctuations from prolonged signals, or become activated under particular temporal input regimes.

Persistence Detection: Circuits that can Discriminate Input Pulse Length

As a first step toward engineering dynamically-gated behavior, the inventors attempted to design circuits that can discriminate between input pulses of different duration. Persistence detection behavior was mapped for a configuration space including two- and three-node cascades, and coherent feedforward loops (CFFL) (data not shown) —a motif that is not only accessible within the design space, but one that has been postulated to confer persistence detection behavior in natural systems.

Using the instant model to simulate behavior, each circuit configuration was subjected to a set of 40 input pulses, with durations ranging from 30 min to 12 h of Dox, and calculated maximum GFP output as a function of time for a 12 h time course. Circuit output for each input pulse was normalized to maximum circuit output (following a 9000 min Dox pulse) and then plotted as a function of pulse length to produce a characteristic "temporal dose response" (TDR) for each circuit (data not shown). The inventors filtered out circuit configurations with low maximum outputs (max GFP<1000 AFU) and weak inducibility (max/basal <1.5). Using a linear fit at points closest to the half-maximal response, two metrics were approximated from each TDR that define persistence filtering behavior: (1) input duration threshold (input duration at half-maximal response) and (2) filter sharpness (s, slope of TDR at half-maximal response). Just as Hill coefficient represents sensitivity to concentration changes in a biochemical dose response, temporal filter sharpness serves as an index for the sensitivity of circuit output to changes in pulse length duration.

Temporal filter sharpness (s) was plotted versus input duration threshold for all circuits. Analysis of the resulting behavior space revealed three-node cascades provide the broadest range of persistence filtering behaviors, and comprise nearly all circuits that exhibit the sharpest filtering. Analysis of these filters revealed an enrichment in highly-cooperative assemblies (high n, large $K_t$, small $K_p$ values) (data not shown). CFFL circuit configurations demonstrated many instances of sharper filtering behavior compared with those in the two-node distribution. However, despite previous description of this motif as an effective persistence filter, none of the CFFL configurations were as sharp as the top 4.5% of three-node cascades. Taken together, this analysis demonstrates strong correspondence between circuit node nonlinearity and filter sharpness, indicating that complex assembly can be effectively used to tune temporal dose response.

In order to validate model predictions, a circuit predicted to be a sharp filter was constructed: a three-node cascade with high nc complexes. This 'nonlinear' circuit was compared to the simple 'linear' circuit from FIG. 3A, which is a non-cooperative two-node cascade that falls into the region of behavior space with diminished sharpness (data not shown). Microfluidics was used to measure each circuit's maximum output in response to six pulse lengths (durations ranging from 30 min to 16 h) and observed close agreement between measured and model-predicted behaviors (see e.g., FIG. 4A).

Mapping Frequency Response Behaviors

Dynamic information can be encoded in other aspects of a signal besides the duration of a single pulse. The archetypal example in biology is neural coding, in which a stimulus is coded in the temporal pattern of a neural spike train. Dynamic information coding and decoding appears to be pervasive in cellular regulatory systems as well. For example, a variety of regulatory molecules (e.g. p53, Msn2, etc.) have been shown to display pulsing behavior in cells, and these dynamic patterns of activity can encode information about the nature of an upstream stimulus in temporal features, such as the pulsing frequency. Moreover, experiments subjecting cells to time-varying (oscillatory) stresses have shown that cellular networks may have the ability to decode frequency information from environmental signals.

At the cellular level, systems analysis has identified specific network motifs for their ability to generate characteristic and useful responses to time-dependent inputs. To see whether the available circuit design space can support temporal signal processing, the instant computational methods were extended to assess frequency response behavior. Five circuit motifs accessible to the part space were examined: two-node cascade, three-node cascade, cascade+FB, CFFL, and CFFL+FB (total collection of 169,552 configurations) (data not shown).

Frequency response for each circuit was obtained by simulating circuit output in response to a series of 20 periodic (square wave) Dox inputs, with periods ranging from 90 min (high frequency) to 9000 min (low frequency). All input regimes have the same 33% duty cycle and thus experience an identical duration of total input. A frequency response curve was generated for each circuit by plotting maximum GFP output (normalized to maximum output for constitutive Dox) for each input frequency (data not shown). Examining the resulting response curve database, two patterns of circuit behavior were identified that demonstrate dramatically different output minima and maxima: one which filters high frequency input, only responding to low frequency regimes, and another which responds poorly to low frequency regimes, but is activated at high frequency. These circuit types effectively function as low-pass and band-stop filters, respectively. Since are discretely activated at different points along the frequency input axis.

Within the response curve database, the inventors systematically identified circuits of each filter type based on the following criteria: low-pass filters were defined by a ratio of low to high frequency amplitude >5, while band-stop filters were defined as having ratio of high frequency to minimum amplitude >2 (data not shown). This screen yielded 4,726 low-pass and 327 band-stop candidates. In configurations supporting both behavior types, cooperative, high nc complexes were observed, further validating the prediction that filtering behavior is enabled by cooperative assembly. Circuits with low-pass behavior were comprised primarily of three-node cascades and CFFLs, with B-node enrichment of highly-cooperative assemblies (large $n_c$, large $K_t$, small $K_p$ values) (data not shown). Within CFFLs, an enrichment in configurations is found that exhibits AND-like logic at the C-node (both synTFs in complex), consistent with previous work implicating this type of regulatory logic for sharp filtering. Band-stop circuit configurations all contained B-node feedback, indicating that retaining memory of prior events plays a role in this type of filtering. Indeed, enrichment of B-node configurations is observed that is similar to those conferring slow ON/slow OFF dynamics for single pulses (data not shown). The dynamics of these circuits (weak activation triggers and strongly reinforced type-1 B-node assembly and slow decay) would appear to underpin their ability to filter out mid-range frequencies, while responding to high frequency environments by integrating successive short pulses over time.

Temporal Decoding: Engineering Circuits that can Distinguish Between Different Input Frequencies Since the frequency response profiles for low-pass and band-stop filters have non-overlapping regimes of frequency space, it was surmised that, if tuned properly, these two filter classes can be used to create a 'mixed' cellular population able to readily distinguish between unique frequency environments (temporal decoding). To experimentally demonstrate this, the inventors selected from their analysis top hit low-pass and band-stop configurations for construction (data not shown). mKate2 was placed under expression control of the low-pass (CFFL) circuit and GFP under control of the band-stop (CFFL+FB) circuit (FIG. 4B). Equal concentrations of the two engineered yeast strains were mixed, co-cultured in the 2S6T microfluidic device, and their behavior when exposed to varying Dox input frequencies (with periods ranging between 3 h to 60 h, all with 33% duty cycle) was analyzed. The resulting frequency response curves for each circuit show agreement with model predictions and, critically, reveal distinct regimes of frequency space (low' and 'high') in which the circuits have opposite outputs (data not shown). Representative fluorescence images of the co-cultures exposed to these two regimes confirm the discriminatory ability of the population based on mKate2 and GFP reporter output (data not shown).

Example 4

TF-DBM binding constants were measured in vitro by fluorescence anisotropy (FA). Recombinant proteins were purified and DBM oligos prepared as described herein. MBP-ZF fusion proteins (see e.g., FIG. 5A, FIG. 5B for sequence details) bind to oligonucleotide probes harboring a single DBM repeat. Affinities for the interaction were measured as a function of the increase in fluorescence anisotropy resulting from binding of the fusion to a fluorescently labeled (FITC) oligo probe (data not shown). Oligo probe binding to ZF affinity variants was measured. MBP-ZF was titrated against 10 nM oligo probe. Change in anisotropy was converted to the fraction of bound probe and binding curves were obtained for high and low affinity variants for both 43-8 (TF1) and 42-10 (TF2) species. $K_d$ values were extracted by fitting data to a quadratic binding equation (data not shown). Competition binding experiments were performed to measure binding constants for DBM affinity variants. At concentrations of MBP-ZF and probe at which half-maximal binding was observed in above experiment, unlabeled oligo competitors containing DBM affinity variants were titrated, and anisotropy increases were measured accompanying displacement of the probe by the competitor. Competitor oligo $K_d$ values were extracted by fitting data (converted to fraction probe bound) to a cubic equation describing competitive binding (see e.g., FIG. 6). Sequences for both sets of DBM affinity variants are listed on the right of FIG. 6. Residues mutated from the WT sequence are indicated by bold type.

PDZ-ligand binding constants were measured in vitro by fluorescence anisotropy. Recombinant proteins were purified as described herein. MBP-PDZ fusion proteins (see e.g., FIG. 5A, FIG. 5B for sequence details) bind to peptide ligand probe. Affinities for the interaction were measured as a function of the increase in fluorescence anisotropy resulting from binding of the fusion to a fluorescently-labeled (FITC) oligopeptide probe (data not shown). Peptide probe binding to PDZ domain was measured. MBP-PDZ was titrated against 10 nM peptide ligand probe, and anisotropy data were converted to fraction of bound probe. Binding curves were obtained for high and low affinity variants for the syntrophin PDZ domain. $K_d$ values were extracted by fitting data to a quadratic binding equation (data not shown). Competition binding experiments were conducted to measure binding constants for ligand affinity variants. At concentrations of MBP-PDZ and probe at which half-maximal binding was observed in above experiment, 43-8 synTFs were titrated with appended ligands of various affinities. Anisotropy increases accompanying displacement of the probe by the competitor was measured, and competitor ligand $K_d$ values were extracted by fitting data (converted to fraction probe bound) to a cubic equation describing competitive binding (see e.g., FIG. 7A). FIG. 7B shows a table of competitor ligand $K_d$ values collected for both syntrophin and erbin PDZ domains.

Inducible and constitutive expression systems were next characterized. Experiments were conducted to obtain model input parameters for circuit component expression systems, using GFP as a surrogate to quantitate promoter expression. For inducible expression systems, dose response curves were generated to characterize transfer functions between inducer concentration and transcriptional output. For the ncTET system, ATc was titrated, while EST was titrated for the ncZEV system. Measurements were made for induced cultures at mid-log growth by flow cytometry. Curves were fit according to a Hill model. Minimum and maximum expression levels were determined by fit. Constitutive expression from pADH1 (see e.g., FIG. 5A, FIG. 5B) was measured for both LEU2 and HIS3 loci (data not shown). Parameterization experiments for (DBM)miniCYC1 promoters were also performed (data not shown). GFP expression system was validated by western blotting. In three separate blots, panels were probed with anti-FLAG antibody, or panels were probed with anti-Hex loading controls. Band intensity was measured using ImageJ, and mean normalized intensity data (error bars=std. dev.) were plotted and fitted with a Hill equation (data not shown). FIG. 8C shows the amino acid sequence of the ZEV transcription factor involved in the ncZEV activation system. A 97-4 zinc finger was appended with the estrogen receptor harboring a C-terminal VP16 activation domain. Expression of the resulting coding sequence was driven by the pTEF1 promoter (−417 to 0). FIG. 8D shows that ncZEV does not affect transcription of the reporter in the absence of its target synTF1. Strains were constructed with different combinations of: reporter ((p(43-8)4miniCyc1-GFP), ZEV expression cassette, ZEV-inducible clamp, and ZEV-inducible synTF1. All four strains were grown with and without 25 nM EST. Mean GFP fluorescence values were measured by flow cytometry. Error bars represent standard deviation.

Component anisotropy signal contribution was determined. A control experiment was run to verify minimal contribution of PDZ domain/clamp binding to overall change in anisotropy signal upon complex formation. Molecular weights for components and complexes are indicated to the left of each complex component (see e.g., FIG. 5A, FIG. 5B for sequence information). Binary complex was assembled by titrating MBP-TF against 10 nM fluorescent probe. Saturated binary complex was titrated with a syntrophin PDZ domain. Lines represent Hill fits for both titrations (data not shown).

Experimentally measured values were transformed into in vivo parameter space. For parameter values associated with configurations used in the model fitting (see e.g., FIG. 1E), linear regression was used to model the relationship between experimentally measured values and corresponding fit-derived in vivo parameters (see FIG. 12A-FIG. 12B). Using fitted linear functions, interpolation was used to transform the remaining measured values (see e.g., FIG. 6, FIG. 7A, FIG. 7B, FIG. 8A, FIG. 8B). Experimental expression data for pADH1 was transformed into in vivo pADH1-clamp expression. A linear function was fit to thermodynamic model fit-derived values for ncZEV clamp expression ($[C]_{tot}$, see e.g., FIG. 24) at corresponding experimentally measured GFP expression levels (data not shown). From this, in vivo concentration for pADH1-expressed clamp was interpolated based on pADH1-GFP expression measured from the LEU2 locus (data not shown). Measured affinity values ($K_t$ and $K_p$) were transformed into model parameter space. A log-log function was used to model thermodynamic model fit-derived values for $K_t$ and $K_p$ affinity at corresponding experimentally measured affinities (see e.g., FIG. 6, FIG. 7A, FIG. 7B, FIG. 12). Measured affinity values that were not associated with the thermodynamic model fit in FIG. 1E were used to interpolate in vivo affinities (data not shown). Model-fitted clamp cooperativity constants were extrapolated to infer constants for complexes with $n_c>4$. The extrapolation followed a log-linear relationship (data not shown).

Thermodynamics of complex assembly in the generation of nonlinear dose response was analyzed. The thermodynamic model (see e.g., FIG. 10-FIG. 12) was used to simulate three different synTF/clamp configurations ($n_c$, $K_t$, and $K_p$) predicted to have input/output responses progressing from non-cooperative to nonlinear. Relative free energies were determined for the promoter states (e.g., DNA-only states, binary synTF-DNA states, ternary synTF/clamp-DNA states). A $txn_n$ (see e.g., FIG. 11) dose response of the assembly's transcriptional response when synTF species is titrated were also stipulated, as well as the corresponding $EC_{50}$ ([TF] at half-maximal response) and $n_H$ (Hill coefficient) for the dose response. Nonlinearity is increased by raising the complex valency (from $n_c=2$ to 5), lowering synTF affinity for DNA ($K_t$), and raising affinity for clamp ($K_p$). These configuration changes are accompanied by an increased free energy separation between binary and ternary states (data not shown).

The relationship between cooperative complex configuration and two-input logic was computationally probed. The thermodynamic model was used to map dose response behavior onto configuration space for a two-input circuit, where output is regulated by assembly of two synTFs and a clamp (see e.g., FIG. 2B). For the two-input circuit, ATc and EST induce expression of two different synTFs (from the ncTET and ncZEV promoters), while clamp expression is driven by pADH1. Enumerated configuration search space for the circuit included configurations with and without clamp (data not shown). A method for scoring circuit behavior based on an information theory-based comparison with an ideal (target) behavior was developed. Kullback-Liebler divergence$_{(DKL)}$ uses informational entropy to measure the difference between two distributions: e.g., a reference distribution (P) representing a target behavior and a distribution (Q) representing query data. Lower $D_{KL}$ values signify distributions that are more "similar" to the target. A computational workflow for analyzing two-input logic behavior space was developed. For each configuration in the search space, normalized model transcriptional output ($txn_n$) is simulated across ranges of [ATc] (96 data points, $10^{-1}$-$10^4$ ng/mL) and [EST] (96 data points, 0.5-12.5 nM). Each member of the resulting decision surface database ($Q_1(i)$, $Q_2(i)$, $Q_3(i)$, etc.) is then compared to two ideal (target) distributions: a two-input AND gate (P AND(i)) and an OR gate (P OR(i)). Specifically, DKL(P AND||Qn) and DKL(P OR||Qn) are evaluated by comparing the four corner regions (12×12 data points) of each model surface to those of the target AND OR distributions, respectively. The full set of DKL(P AND||Qn) and DKL(P OR||Qn) was plotted to generate a behavior space representing the degree to which each circuit configuration is AND-like or OR-like (data not shown; see e.g., FIG. 2B).

Logic behavior was mapped onto two-input behavior space. A set of ideal logic (target) distributions was determined. Target distributions were defined by assigning normalized transcriptional activation values (1, 0.5, 0.25, 0) to the four corners of the distribution, where each corner is composed of 12×12 points. The search areas of model-predicted decision surfaces were then compared against these target logic distributions using DKL as described above (data not shown). Areas of behavior space enriched for desired two-input logic functions were identified. For a given logic function (AND, OR, etc.), DKL was evaluated for all configurations in the behavior space. Highlighted within each behavior space are the top 1% of configurations (lowest DKL) corresponding to the target logic function (data not shown). Configurations complex size was determined (data not shown). Parameter frequency was analyzed (Kp, Kt, nc) for highlighted configurations, and example decision surfaces were produced (data not shown).

Microfluidic devices were used for time-lapse experiments. A workflow was developed for microfluidic experiments. Yeast cells were loaded into a device, on-chip valves are used to select media and specify an induction time series, cells are imaged using time-lapse microscopy, and image analysis is performed to extract single-cell fluorescence trajectories. Multi-layer microfluidic devices were used, comprising flow layers and control layers. Cells loaded from inlets are trapped in cell chambers that have been fabricated to the height of a single monolayer of S. cerevisiae cells. Bright field and GFP images of the ncTET-GFP strain were be taken before and after Dox induction (data not shown). The variation in single-cell fluorescence trajectories was measured in cells across different devices (inter-device) and different cell chambers (intra-device) (data not shown). Fluorescence trajectories shown herein represent the mean and standard deviation of many cells aggregated from multiple cell chambers. Dox was used at 10 pg/mL. Dose response curves for the ncTET expression system were determined using the inducers ATc and Dox (data not shown). Because of ATc photodegradation, Dox was used in all microfluidic time-lapse experiments.

Experimental parameterization was performed on the dynamic model for circuits composed of synTF assemblies. As a non-limiting example, the dynamic model was applied to a three-node circuit (cascade). Dox-induced ncTET expression of TF1 from the first node assembles with constitutively expressed clamp (pADH1) at the second node, inducing expression TF2, which subsequently assembles with clamp to drive expression of GFP at the third node (data not shown). Corresponding rate equations were used to describe the change in species concentrations over time. ncTET expression of synTF1 was modeled with a Hill equation ("inducer DR" grey box). For downstream (DBM) miniCyc1 promoters that are regulated by synTF assemblies, such as pSynTF1 and pSynTF2, the thermodynamic model was used to compute the species production rate ("thermo model"). kact=maximum transcriptional activation rate for each promoter; kbasal=basal promoter activity; $k_{deg}$=degradation/dilution rate of each protein (data not shown). The dynamic model was fit to time course data. Rate parameters were obtained from a global fit of the model to microfluidic time course data of strains harboring one-node, two-node, and three-node test circuits (subjected to a Dox pulse of 14.5 or 16 h). Specific circuit configurations were selected, and fits to the experimental data and the extracted rate constants were determined (data not shown). A relationship for scaling promoter activation rates, $_{kact}$, was determined as a function of synTF complex size, $n_c$. Maximum fluorescence outputs were measured for two-node cascades having identical assembly configuration (data not shown), but with $n_c$=2-5 (fold change is relative to maximum output for $n_c$=2 configuration). The data were fit to a logistic function, and used to extrapolate $k_{act}$ values for assemblies of arbitrary size.

The circuit activation/deactivation behavior space was constructed based on a model. The model was used to map behavior space for activation/deactivation kinetics from assembly configuration space for two-node, three-node, and three-node with feedback (+FB) circuits (see e.g., FIG. 3B). For all circuits, ATc (or Dox) was the input, inducing ncTET expression of a synTF, which assembles with constitutively expressed clamp (pADH1) to drive expression of either GFP (two-node) or a second synTF (three-node and three-node+ FB). The second synTF assembles with clamp to drive GFP expression and its own production (for three-node+FB). The configuration search space for these circuits was enumerated (data not shown). This space includes configurations with and without clamp. Output traces were simulated and curated for the circuit configuration space. The model was used to simulate GFP output traces for the full space of circuit configurations in response to a 16 h Dox pulse (10 µg/mL). Traces with weak basal or low fold activation were filtered out, and the remaining traces normalized between 0 and 1 (data not shown).

Temporal behavior was mapped onto activation/deactivation behavior space. The subspace of two-node and three-node cascade configurations was analyzed, highlighting configurations with clamp and without clamp. Clamp configurations expand activation/deactivation space. Circuit configurations were analyzed from six regions of the behavior space representing different activation/deactivation behaviors: fast ON/slow OFF, slow ON/fast OFF, slow ON/slow OFF, fast ON/fast OFF, fast ON/memory, slow ON/memory. For each region, the configurations were selected based on $\tau_a$ and $\tau_d$ cutoff criteria, and were highlighted on the behavior space corresponding to the circuit type: two-node, three-node, three-node+FB. Parameter frequency analyses of ($K_p$, $K_t$, $n_c$) for these selected configurations were determined (data not shown).

A model-based search and analysis of persistence filtering was performed. The configuration search space used for persistence filtering was first enumerated. The space includes two-node and three-node cascades and coherent feed-forward loop (CFFL) circuits (data not shown). Computational search was performed for circuits that perform persistence filtering. For each configuration, the model was used to simulate output traces in response to a Dox pulse of varying lengths (e.g., $T_{ON}$=30-3000 min). A "temporal dose response" curve was generated for each circuit configuration by plotting maximum output amplitude for each pulse length, and used to obtain two filtering metrics: the pulse length threshold (input duration at half-maximal response) and filtering sharpness (slope at threshold) (data not shown). Analysis of behavior space of persistence filtering behavior was performed, comparing input duration threshold vs. filter sharpness (s) for each circuit configuration in the search. Behavior space was examined as a function of circuit type and synTF/clamp complex size (data not shown). Configurations comprising the "linear filter" and "sharp filter" circuits are shown in FIG. 4A. Parameter frequency analyses of ($K_p$, $K_t$, $n_c$) for selected nonlinear and linear filters were determined, along with threshold and sharpness selection criteria (data not shown).

A model-based search and analysis of frequency filtering behaviors was performed. The configuration search space used for frequency filtering was first determined. The space includes two-node and three-node cascades (+/− feedback) and coherent feed-forward loop (CFFL) circuits (+/− feedback). The configuration space was searched for frequency filtering target behaviors: low-pass and band-stop filters. For each circuit configuration, the model was used to simulate output traces in response to periodic Dox pulses of varying frequency (periods ranging from T=90 to 9000 min). Maximum amplitudes of the resulting traces were used to construct frequency response curves for each circuit (data not shown). Low-pass and band-stop filters were then screened based on two different metrics extracted from this curve: the ratio of low to high frequency amplitudes (low/high freq. gain, low-pass) and the ratio of minimum to high frequency amplitudes (min/high freq. gain, band-stop) (data not shown). Computational screen and analysis was performed on low-pass and band-stop filtering circuit configurations. A configuration space was searched corresponding to five circuit motifs. Frequency response curves were generated for the full configuration space, and binned into low-pass (e.g., low/high freq. gain>5) or band-stop (e.g., min/high freq. gain>2). Circuit configurations not meeting either criteria were discarded. Parameter frequency analyses of ($K_p$, $K_t$, $n_c$) for the selected configurations were performed. The predicted response of circuit configs in FIG. 4B was predicted (data not shown).

Frequency response behavior of low-pass and band-stop filter circuits was experimentally verified. Circuit configurations computationally predicted to display low-pass and band-stop filtering were constructed, and their frequency responses were experimentally obtained using microfluidic experiments (data not shown). Strains harboring the low-pass and band-stop circuits, driving expression of mKate and GFP respectively, were co-cultured in the 12S6T device (data not shown), and subjected to periodic square wave pulses of Dox (10 μg/mL, 33% duty cycle) for different frequencies. mKate and GFP traces (mean and standard deviation) were determined for each circuit (data not shown). Two frequency regimes are highlighted in FIG. 4B.

Data (e.g., related to the synTFs described herein) are also described in the following post-filing publication: Bashor et al. Complex signal processing in synthetic gene circuits using cooperative regulatory assemblies. Science. 2019 May 10; 364(6440):593-597. The publication, including all supplemental materials, are incorporated by reference herein in its entirety.

Example 5: Cooperative synTF Assemblies

Cooperative synTF assemblies (composed of low affinity synTFs+clamp) enable specific regulation genome-wide, with little impact on the endogenous transcriptome and no adverse effects on cellular fitness.

RNA-sequencing (RNA-seq) was used to map the impact of synTF expression on genome-wide transcription. The following transcriptomes were probed: *Saccharomyces cerevisiae* strains expressing a low affinity synTF, a high affinity synTF, a low affinity synTF with clamp and a reporter-only strain (no synTF) as a control, all for ZF 13-6 (see e.g., Khalil et al., Cell 2012). Cultures for each strain were induced with 10 ug/mL doxycycline in yeast extract with peptone (YEP) media with 2% galactose for eight hours, lysed with 425-600A acid-washed glass beads (Sigma NC9808208) in a MagNA Lyser bead beater (Roche), and prepared for RNA-seq with the RNeasy kit (Qiagen 74106), then submitted for library preparation (Illumina TruSeq Stranded mRNA) and single-end sequencing of 50 basepairs (Illumina HiSeq 2500). Analysis was completed using the Tuxedo analysis pipeline (see e.g., Trapnell et al., Nature Protocols 2012). These results reveal regulation profiles that are highly specific, with low misregulation of the endogenous transcriptome, for low affinity synTF with or without addition of clamp (see e.g., FIG. 17). Expression of the high affinity synTF in the same conditions imparts increased misregulation.

Next, to functionally determine the effects of gene misregulation, a fitness experiment was performed (see e.g., Wang et al., PLoS Biology, 2015) with *Saccharomyces cerevisiae* strains expressing the synTFs. In simultaneous experiments, strains expressing the low affinity, high affinity and low affinity+clamp synTF versions of each of the 22 zinc finger synTF library members, as well as reporter-only strains for each cognate TFBS, were separately cocultured with a reference strain over 5 days. The reference strain is an mTurquoise reporter integrated in the HO locus under the expression of a constitutive TDH3 promoter. The synTFs of the query strains were integrated in the HO locus and include a fused mRuby fluorescent protein and are induced by a Zif268 transcription factor with a fused ß-estradiol receptor domain and VP16 activation domain (ZEV) that translocates to the nucleus in the presence of ß-estradiol (see e.g., McIsaac et al., Nucleic Acids Research 2013). The synTFs induce expression from a minimal Cyc1 promoter of a Venus fluorescent protein in the uracil locus. Clamp is expressed constitutively from a pTEF1 promoter in the leucine locus. Each of the 88 query strains (22 synTFs x 4 versions), as well as additional controls, were grown in auxotrophy media (synthetic media without uracil or leucine) with 2% glucose and the reference strain was grown in antibiotic media, YEP with 2% glucose and 200 ug/mL Hygromycin B; all were grown for 12 hours.

All cultures were then spiked in synthetic complete media with 2% glucose and grown overnight. The cocultures were then spiked in synthetic complete media with 2% glucose and induced with 0.5 uM ß-estradiol for 5 days with regular dilutions and sampling for subsequent flow cytometry analysis. An initial sample was collected immediately after the cultures were combined as a reference of the ratio of reference:query strain and conserved for downstream fitness measurements. The coculture samples were analyzed on a flow cytometer over the course of the experiment to compare the relative expression of Venus to Turquoise and thereby determine functional query to reference cell populations. Similarly, mRuby to Venus is a synTF to reporter proxy, so synTF concentration and its functionality at the promoter can be monitored. As each of the query strains competes against the same reference strain, relative fitness of the query strains can be computed and compared (see e.g., Kryashimskiy et al., Science 2014).

Poor cellular fitness was observed in strains expressing the high affinity synTF, while strains expressing the low affinity and low affinity+clamp synTFs remained competitive with the reference strain (see e.g., FIG. 18). While some synTFs impose higher fitness costs than others, this pattern was conserved across the library of 22 synTFs. Reporter expression was also monitored throughout the experiment. Venus expression in strains with the high affinity synTF was reduced over time, indicating that circuit loss occurred in uninsulated circuits.

Example 6: Clamp Assembly-Mediated Transcriptional Activation in Mammalian Cells In the work in yeast, clamp-dependent assembly was initially based on the ability of a zinc finger-based synthetic transcription factor (synTF) and clamp to induce higher reporter activation when co-expressed. To test the possibility that assembly-mediated gene expression also works in mammalian cells, a similar approach was taken. Expression plasmids were generated for synTF (sequence descriptions in Example 7) and a 2-unit (nc=2) clamp (sequence description in Example 7), both driven by a strong UBC promoter (pUBC, Ubiquitin C promoter). A corresponding HEK293FT reporter cell line was generated by lentiviral transduction of a synTF-responsive reporter construct, composed of 4 tandem 20-bp DNA-binding motifs (DBMs) upstream of a minimal CMV promoter (pMinCMV) driving expression of an mCherry fluorescent protein.

Figure 19:
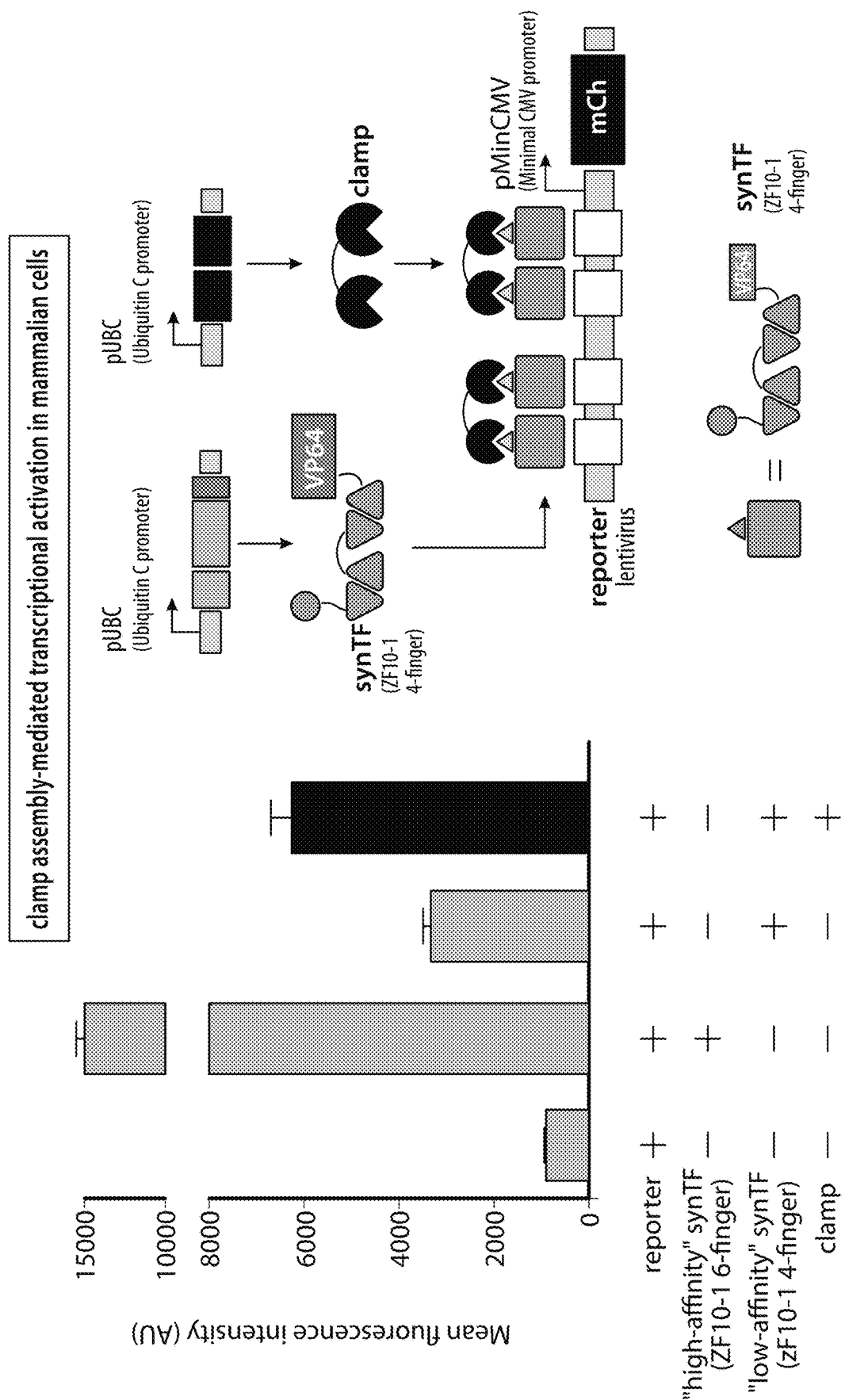
FIG. 19 is a series of schematics and graphs showing clamp-mediated assembly and transcriptional activation in mammalian (HEK293FT) cells.

Different combinations of the synTF and clamp expression plasmids were transfected into the HEK293FT reporter line, and mCherry reporter expression was assayed using flow cytometry (see e.g., FIG. 19). These results show that the "low-affinity" synTF (based on ZF10-1 4-finger) drives lower reporter expression relative to the "high-affinity" synTF (based on ZF10-1 6-finger). Critically, co-expression of the clamp leads to enhancement of reporter activation, providing evidence for clamp-mediated transcriptional activation in mammalian cells.

Example 7: Sequences

SEQ ID NO: 121 below shows an exemplary amino acid sequence for a yeast synTF (see e.g., FIG. 5A). Bold text indicates 3× FLAG. Italics indicates NLS. Bold italicized text indicates VP16. Plain text corresponds to a 43-8 low affinity synTF. In some embodiments the 43-8 low affinity binder shown here can be replaced, e.g., with the 43-8 high affinity binder, 42-10 low affinity binder, or 42-10 high affinity binder shown below. Zigzagunderlinedtext indicates GS linker. Doubleunderlinedtext indicates ligand.

DYKDHDGDYKDHDIDYKDDDDKMAPKKKRKVGIHGVPGGLEAPPTDVSLGDELHLDGEDVA

MAHADALDDFDLDMLGDGDSPGPGFTPHDSAPYGALDMADFEFEQMFTDALGIDEYGGGSRP

GEAPFQCRICMANFSRQDRLDRHTRTHTGEKPFQCRICMANFSQKEHLAGHLRTHTGEKPFQCRI

CMANFSRRDNLNRHLKTHLRGSGSGVKESLV

SEQ ID NO: 122 below shows an exemplary amino acid sequence for an *E. coli* synTF (see e.g., FIG. 5A). Plain text corresponds to a 43-8 low affinity synTF. In some embodiments the 43-8 low affinity binder shown here can be replaced, e.g., with the 43-8 high affinity binder, 42-10 low affinity binder, or 42-10 high affinity binder shown below. Zigzagunderlinedtext indicates GS linker. Doubleunderlinedtext indicates ligand.

GEAPFQCRICMANFSRQDRLDRHTRTHTGEKPFQCRICMANFSQKEHLAGHLRTHTGEKPFQCRI

CMANFSRRDNLNRHLKTHLRGSGSGVKESLV

SEQ ID NO: 123 43-8 low affinity (bolded letter shows mutated residue) (see e.g., FIG. 5A):

GEAPFQCRICMANFSRQDRLDRHTRTHTGEKPFQCRICMANFSQKEHLAG

HLRTHTGEKPFQCRICMANFSRRDNLNRHLKTHLR

SEQ ID NO: 124 43-8 high affinity (bolded letter shows mutated residue) (see e.g., FIG. 5A):

GERPFQCRICMANFSRQDRLDRHTRTHTGEKPFQCRICMANFSQKEHLAG

HLRTHTGEKPFQCRICMANFSRRDNLNRHLKTHLR

SEQ ID NO: 125 42-10 low affinity (bolded letter shows mutated residue) (see e.g., FIG. 5A):

GEAPFQCRICMANFSTGQILDRHTRTHTGEKPFQCRICMANFSVAHSLKR

HLRTHTGEKPFQCRICMANFSDPSNLRRHLKTHLR

SEQ ID NO: 126 42-10 high affinity (bolded letter shows mutated residue) (see e.g., FIG. 5A):

GERPFQCRICMANFSTGQILDRHTRTHTGEKPFQCRICMANFSVAHSLKR

HLRTHTGEKPFQCRICMANFSDPSNLRRHLKTHLR

SEQ ID NO: 127 below shows an exemplary amino acid sequence for a yeast clamp (see e.g., FIG. 5A). Bold text indicates NLS. Italicized text indicates syn PDZ 1. Bold italicized text indicates linker. Plain text indicates PDZ2. An $n_c=2$ clamp sequence is depicted. In some embodiments, the linker and PDZ2 units can be repeated.

PKKKRKVVE*LQRRRVTVRKADAGGLGISIKGGRENKMPILISKIFKGLAA*

*DQTEALFVGDAILSVNGEDLSSATHDEAVQALKKTGKEVVLEVKYMKEVS*

*PYFK**RSGSGSGSGSGSGSGSGSGSGSGSPGL*QRRRVTVRKADAGGLGISIK

GGRENKMPILISKIFKGLAADQTEALFVGDAILSVNGEDLSSATHDEAVQ

ALKKTGKEVVLEVKYMKEVSPYFK

SEQ ID NO: 128 below shows an exemplary amino acid sequence for an *E. coli* clamp (see e.g., FIG. 5A). Italicized text indicates syn PDZ1.

*LQRRRVTVRKADAGGLGISIKGGRENKMPILISKIFKGLAADQTEALFVG*

*DAILSVNGEDLSSATHDEAVQALKKTGKEVVLEVKYMKEVSPYFK*

SEQ ID NO: 129 shows the amino acid sequence for erbin (see e.g., FIG. 5A).

GSHMGHELAKQEIRVRVEKDPELGFSISGGRGGRGNPFRPDDDGIFVTRV

QPEGPASKLLQPGDKIIQANGYSFINIEHGQAVSLLKT

SEQ ID NO: 146 shows the nucleic acid sequence for pADH1, an exemplary constitutive promoter (see e.g., FIG. 5B). Bold text indicates the yeast pADH1 promoter −1500 to 0. Italicized text indicates the associated translational start codon.

aaacaagaagagggttgactacatcacgatgaggggatcgaagaaatga tggtaaatgaaataggaaatcaaggagcatgaaggcaaaagacaaatata agggtcgaacgaaaaataaagtgaaaagtgttgatatgatgtatttggct ttgcggcgccgaaaaaacgagtttacgcaattgcacaatcatgctgactc tgtggcggaccgcgctcttgccggcccggcgataacgctgggcgtgagg ctgtgcccggcggagttttttgcgcctgcattttccaaggtttaccctgc gctaaggggcgagattggagaagcaataagaatgccggttggggttgca tgatgacgaccacgacaactggtgtcattatttaagttgccgaaagaacc -continued ttgctgtcttgctatcaagtataaatagacctgcaaaaaaaaaattatta atcttttgtttcctcgtcattgttctcgttcccttctcttgttttatt ttctgcacaatatttcaagctataccaagcatacaatcaactatctcaTC

TAGAATG

SEQ ID NO: 130 shows an exemplary nucleic acid sequence for a (DBM)miniCyc1 promoter (see e.g., FIG. 5B). Bold text indicates synTF binding (DBM) domains. In some embodiments, the double-underlined unit can be repeated in the 5' direction to create higher order assemblies. Italicized text indicates (DBM)miniCyc1. Bold italicized text indicates Kozak sequence. Zigzagunderlinedtext indicates translational start.

GAATTCaGAGTGAGGAcTCGaGAGTGAGGAc*GGATCCCAGATCCGCCAGGCGTGTATATATAG*

*CGTGGATGGCCAGGCAACTTTAGTGCTGACACATACAGGCATATATATATGTGTGCGACGACACAT*

*GATCATATGGCATGCATGTGCTCTGTATGTATATAAAACTCTTGTTTTCTTCTTTTCTCTAAATATTCT*

*TTCCTTATACATTAGGACCTTTGCAGCATAAATTACTATACTTCTATAGACACACAAACACAAATACA*

*CACACTAATCTAGATATTAAAA*TG

-continued
tgagtgcatttgcaacatgagtatactagaagaatgagccaagacttgcg agacgcgagtttgccggtggtgcgaacaatagagcgaccatgaccttgaa ggtgagacgcgcataaccgctagagtactttgaagaggaaacagcaatag ggttgctaccagtatataaatagacaggtacatacaacactggaaatggttg tctgtttgagtacgctttcaattcatttgggtgtgcactttattatgtta caatatggaagggaactttacacttctcctatgcacatatattaattaaa gtccaatgctagtagagaaggggggtaacaccctccgcgctcttttccg atttttttctaaacgtggaatatttcggatatcttttgttgtttccgg gtgtacaatatggacttcctcttttctggcaaccaaacccatacatcggg attcctataataccttcgttggtctccctaacatgtaggtggcggaggg agatatacaatagaacagataccagacaagacataatgggctaaacaaga ctacaccaattacactgcctcattgatggtggtacataacgaactaatac tgtagccctagacttgatagccatcatcatatcgaagtttcactaccatt ttccatttgccatctattgaagtaataataggcgcatgcaacttcttttc ttttttttctttctctctccccgttgttgtctcaccatatccgcaat gacaaaaaatgatggaagacactaaaggaaaaaattaacgacaaagaca gcaccaacagatgtcgttgttccagagctgatgaggggtatctcgaagca cacgaaacttttcctccttcattcacgcacactactctctaatgagca acggtatacggccttccttccagttacttgaatttgaaataaaaaaagt SEQ ID NO: 99-SEQ ID NO: 101 are exemplary DBM affinity variant nucleic acid sequences for 43-8 (see e.g., FIG. 6). Bold text indicates residues mutated from the WT sequence. SEQ ID NO: 99 is 43-8 DBM1—aGAGT-GAGGAc. SEQ ID NO: 100 is 43-8 DBM2—aCAGT-GAGGAc. SEQ ID NO: 101 is 43-8 DBM3—aTAGT-GAGGAc.

SEQ ID NOS 102, 131, and 104-108 are exemplary DBM affinity variant nucleic acid sequences for 42-10 (see e.g., FIG. 6). Bold text indicates residues mutated from the WT sequence. SEQ ID NO: 102 is 42-10 DBM1—aGACGCTGCTc. SEQ ID NO: 131 is 42-10 DBM2—tGACGCTGCTt. SEQ ID NO: 104 is 42-10 DBM3—aGACGGTGCTc. SEQ ID NO: 105 is 42-10 DBM4—aCACGCTGCTc. SEQ ID NO: 106 is 42-10 DBM5—aGACGCTACTc. SEQ ID NO: 107 is 42-10 DBM6—aGACGCTGCTa. SEQ ID NO: 108 is 42-10 DBM7—aGACTCTGCTc.

SEQ ID NOS 3-8, 132-134, 22, and 23 are exemplary syntropin-specific competitor ligands (see e.g., FIG. 7A). SEQ ID NO: 3 is S1: IRETII; SEQ ID NO: 4 is S2: IRETIL; SEQ ID NO: 5 is S3: IRWTIV; SEQ ID NO: 7 is S4: IRETIV; SEQ ID NO: 6 is S5: VKESLV; SEQ ID NO: 8 is S6: VKEALV; SEQ ID NO: 132 is S7: HLETFF; SEQ ID NO: 133 does not bind to syntropin: VKEAAA.

SEQ ID NOS 134, 22, and 23 are exemplary Erbin-specific competitor ligands (see e.g., FIG. 7A). SEQ ID NO: 134 is E1: WLVTWV; SEQ ID NO: 22 is E2: WLKTWV; SEQ ID NO: 23 is E3: PVDSWV.

SEQ ID NO: 135 shows an exemplary amino acid sequence for the 97-4 ZEV ORF (see e.g., FIG. 8A). Bold text indicates 97-4. Italicized text indicates the EST reporter. Bold italicized text indicates VP16.

MPGERPFQCRICMRNFSRQSNLSRHTRTHTGEKPFQCRICMRNFSRNEHL

VLHLRTHTGEKPFQCRICMRNFSQKTGLRVHLKTHLRGTPAAASTLEDP*S*

*AGDMRAANLWPSPLMIKRSKKNSLALSLTADQMVSALLDAEPPILYSEYD*

*PTRPFSEASMMGLLTNLADRELVHMINWAKRVPGFVDLTLHDQVHLLECA*

*WLEILMIGLVWRSMEHPVKLLFAPNLLLDRNQGKCVEGMVEIFDMLLATS*

*SRFRMMNLQGEEFVCLKSIILLNSGVYTFLSSTLKSLEEKDHIHRVLDKI*

*TDTLIHLMAKAGLTLQQQHQRLAQLLLILSHIRHMSNKGMEHLYSMKCKN*

*VVPLYDLLLEMLDAHRLHAPTSRGGASVEETDQSHLATAGSTSS*ELH

*LDGEDVAMAHADALDDFDLDMLGDGDSPGPGFTPHDSAPYGALDMADFEFEQMFTDALGIDE*

*YGG*

SEQ ID NO: 136 shows an exemplary amino acid sequence for a "high-affinity" synTF comprising a zinc finger array, e.g., ZF10-1 6-finger (see e.g., U.S. patent application Ser. No. 15/686,419, which is incorporated herein by reference in its entirety). Bold text indicates a restriction site. Italicized text indicates a nuclear localization signal. Bold italicized text indicates a zinc finger array. Zigzagunderlinedtext indicates a VP64 activation domain. Dotted underlined text indicates a linker. Doubleunderlinedtext indicates a PDZ ligand. Plain text "XXXXXXX" indicates six helices, e.g., from N terminus to C terminus: helix 1, helix 2, helix 3, helix 4, helix 5, and helix 6.

MFEPKKKRKVFEGTASSR*PGERPFQCRICMRNFS*XXXXXXX*HTRTHTGEKPFQCRICMRNFS*XXXXXXX

*HLRTHTGSQKPFQCRICMRNFS*XXXXXXX*HLRTHTGEKPFQCRICMRNFS*XXXXXXX*HLKTHTGSQKPF*

*QCRICMRNFS*XXXXXXX*HLRTHTGEKPFQCRICMRNFS*XXXXXXX*HLRTHLRGSTC*RGRADALDDFDL

DMLGSDALDDFDLDMLGSDALDDFDLDMLGSDALDDFDLDMLGSETELIRETIV

SEQ ID NO: 137 shows an exemplary amino acid sequence for a "low-affinity" synTF comprising a zinc finger array, e.g., ZF10-1 4-finger (see e.g., U.S. patent application Ser. No. 15/686,419, which is incorporated herein by reference in its entirety). Bold text indicates a restriction site. Italicized text indicates a nuclear localization signal. Bold italicized text indicates a zinc finger array. Zigzagunderlinedtext indicates a VP64 activation domain. Dotted underlined text indicates a linker. Doubleunderlinedtext indicates a PDZ ligand. Plain text "XXXXXXX" indicates four helices, e.g., from N terminus to C terminus: helix 1, helix 2, helix 3, and helix 4.

MFEPKKKRKVFEGTASSR*PGERPFQCRICMRNFS*XXXXXXX*HTRTHTGEKPFQCRICMRNFS*XXXXXXX

*HLRTHTGSQKPFQCRICMRNFS*XXXXXXX*HLRTHTGEKPFQCRICMRNFS*XXXXXXX*HLRTHLRGSTC*

RGRADALDDFDLDMLGSDALDDFDLDMLGSDALDDFDLDMLGSDALDDFDLDMLGSETELIRETIV

SEQ ID NO: 138-SEQ ID NO: 143 are exemplary helices for ZF10-1 6-finger arrays (e.g., SEQ ID NO: 136) or ZF10-1 4-finger arrays (e.g., SEQ ID NO: 137). SEQ ID NO: 138 is helix 1: RRHGLDR; SEQ ID NO: 139 is helix 2: DHSSLKR; SEQ ID NO: 140 is helix 3: VRHNLTR; SEQ ID NO: 141 is helix 4: DHSNLSR; SEQ ID NO: 142 is helix 5: QRSSLVR; SEQ ID NO: 143 is helix 6: ESGHLKR.

SEQ ID NO: 144 shows an exemplary amino acid sequence for a 2-unit clamp. Italicized text indicates a 3× FLAG Tag+Nuclear Localization Sequence. Bold text indicates a linker. Dotted underlined text indicates an α-syntrophin PDZ Domain. Doubleunderlinedtext indicates a restriction site.

*MDYKDHDGDYKDHDIDYKDDDDKMAPKKKRKV*VELQRRRVTVRKADAGGLGISIKGGRENKMPILISKIFK

GLAADQTEALFVGDAILSVNGEDLSSATHDEAVQALKKTGKEVVLEVKYMKEVSPYFKGSGGSSGSGPG

SSGGSGPGSGSSGGSGSGPGSGGSSGPGSETELVELQRRRVTVRKADAGGLGISIKGGRENKMPILISKIFK

GLAADQTEALFVGDAILSVNGEDLSSATHDEAVQALKKTGKEVVLEVKYMKEVSPYFKG

SEQ ID NO: 145 shows an exemplary nucleic acid sequence for a reporter. Bold text indicates DBMs (e.g., ZF10-1). Dotted underlined text indicates a minCMV promoter. Doubleunderlinedtext indicates mCherry.

cgggtttcgtaacaatcgcatgaggattcgcaacgcttcGGCGTAGCCGATGTCGCGctcccgtctcagtaaaggtcGGCGTAGCCGA

TGTCGCGcaatcggactgccttcgtacGGCGTAGCCGATGTCGCGcgtatcagtcgcctcggaacGGCGTAGCCGATGTC

GCGcattcgtaagaggctcactctcccttacacggagtggataACTAGTtaggcgtgtacggtgggaggcctatataagcagagctcgtttagtgaaccgtcaga tcgcctggaACGCGTaccggtgtcGCCACCatggtgagcaagggcgaggaggataacatggccatcatcaaggagttcatgcgcttcaaggtgcacatgga gggctccgtgaacggccacgagttcgagatcgagggcgagggcgagggccgcccctacgagggcacccagaccgccaagctgaaggtgaccaagggtggcccc ctgcccttcgcctgggacatcctgtcccctcagttcatgtacggctccaaggcctacgtgaagcaccccgccgacatccccgactacttgaagctgtccttccc
cgaggg cttcaagtgggagcgcgtgatgaacttcgaggacggcggcgtggtgaccgtgacccaggactcctccctgcaggacggcgagttcatctacaaggtgaagctg
cgcg gcaccaacttcccctccgacggccccgtaatgcagaagaagaccatgggctggcaggcctcctccgagcggatgtacccgaggacggcgccctgaagggcgagat caagcagaggctgaagctgaaggacggcggccactacgacgctgaggtcaagaccacctacaaggccaagaagcccgtgcagctgcccggcgcctacaacgtcaa catcaagttggacatcacctcccacaacgaggactacaccatcgtggaacagtacgaacgcgccgagggccgccactccaccggcggcatggacgagctgtacaag Example 8: Affinities Table 6 below shows exemplary affinity values (Kt) for specific sTFs. As a non-limiting example, a high-affinity sTF can have a Kt of approximately 0.94 nM. As a non-limiting example, a low-affinity sTF can have a Kt of approximately 415 nM. "ZF" indicates zinc finger, and "DBM" indicates DNA binding motif. The 'Type' column in Table 6 refers to the Arginine backbone mutants of the sTFs. In some embodiments, high affinity sTFs have 3 Arginine-to-Alanine (R2A) mutations. In some embodiments, low affinity sTFs have 4 R2A mutations (see e.g., Khalil et al., Cell. 150, 647-658 2012; see e.g., FIG. 6).

TABLE 6 sTF Affinities (Kt)

| ZF | Type | DBM | Sequence | SEQ ID NO: | Affinity (nM) |
|---|---|---|---|---|---|
| ZF1 | High | 1 | aGAGTGAGGAc | 99 | 6.5 |
| ZF1 | High | 2 | aCAGTGAGGAc | 100 | 30 |
| ZF1 | High | 3 | aTAGTGAGGAc | 101 | 42 |
| ZF1 | Low | 1 | aGAGTGAGGAc | 99 | 13.6 |
| ZF1 | Low | 2 | aCAGTGAGGAc | 100 | 143 |
| ZF1 | Low | 3 | aTAGTGAGGAc | 101 | 224 |
| ZF2 | High | 2 | tGACGCTGCTt | 131 | 0.94 |
| ZF2 | Low | 2 | tGACGCTGCTt | 131 | 5.2 |
| ZF2 | Low | 3 | aGACGGTGCTc | 104 | 32 |
| ZF2 | Low | 5 | aGACGCTACTc | 106 | 95 |
| ZF2 | High | 1 | aGACGCTGCTc | 102 | 2.4 |
| ZF2 | Low | 1 | aGACGCTGCTc | 102 | 15 |
| ZF2 | Low | 4 | aCACGCTGCTc | 105 | 67 |
| ZF2 | Low | 6 | aGACGCTGCTa | 107 | 218 |
| ZF2 | Low | 7 | aGACTCTGCTc | 108 | 415 |

Table 7 below shows exemplary PDZ affinity values (Kp) for specific PDZ ligands. As a non-limiting example, a high-affinity PDZ ligand can have a Kp of approximately 0.062 µM. As a non-limiting example, a low-affinity PDZ ligand can have a Kp of approximately 43.2 µM. "Syn" indicates syntrophin, "Erb" indicates Erbin, and "nb indicates no binding (see e.g., FIG. 7B).

TABLE 7

PDZ Affinities (Kp)

| PDZ Ligand | SEQ ID NO: | Syn Kd (µM) | Erb Kd (µM) |
|---|---|---|---|
| IRETII | 3 | 0.062 | nb |
| IRETIL | 4 | 0.18 | nb |
| IRWTIV | 5 | 0.49 | 1.73 |
| IRETIV | 7 | 0.88 | 3.46 |
| VKESLV | 6 | 1.97 | 5.71 |
| VKEALV | 8 | 27.3 | nb |
| HLETFF | 132 | 43.2 | nb |
| VKEAAA | 133 | nb | nb |
| WLVTWV | 134 | nb | 0.1 |
| WLKTWV | 22 | nb | 0.33 |
| PVDSWV | 23 | 1.57 | 0.42 |

---

The invention claimed is:

1. A three-level system for fine-tuning gene expression comprising:
   (a) at least two synthetic transcription factors (sTF), each sTF comprising:
      a. at least one ligand,
      b. a DNA binding domain (DBD) and
      c. a transcription activator (TA) domain or transcriptional repressor (TR) domain, wherein the DBD can bind to at least one target DNA binding motif (DBM) located upstream of a promoter operatively linked to a gene, and
   (b) a molecular clamp comprising n ligand binding domains (LBD), wherein each ligand binding domain comprises a PDZ domain and is connected to at least one other LBD by a linker, wherein each LBD of the molecular clamp binds to at least one ligand of the each sTF; wherein n is an integer between 2 and 50;
   wherein when the molecular clamp and at least two sTF are both present in a cell, each ligand binding domain of the molecular clamp binds to at least one ligand of each sTF,
   wherein when a TA domain is present, the TA domain recruits the RNA pol II machinery to the promoter, thereby turning on gene expression, and wherein when a TR domain is present, the TR domain prevents RNA pol II machinery from binding to the promoter, thereby inhibiting gene expression, and
wherein expression is fine-tuned by the following:
  i. number of LBDs and number of TFs;
  ii. binding affinity of the LBD of the molecular clamp for the ligand on each of the sTFs; and
  iii. binding affinity of the DBD of each of the sTFs for the DBM located upstream of the promoter.

2. The system of claim 1, wherein the linker is a flexible linker or comprises a flexible glycine-serine (GS) linker repeat sequence.

3. The system of claim 2, wherein the GS linker repeat sequence of SEQ ID NO: 56 is repeated 2-25 times.

4. The system of claim 1, wherein the ligand is a peptide ligand and the ligand binding domain (LBD) is a protein binding domain.

5. The system of claim 1, wherein the PDZ domain is a syntrophin PDZ domain, and the ligand is selected from the group consisting of: SEQ ID NO: 3, SEQ ID NO: 4, SEQ ID NO: 5, SEQ ID NO: 6, SEQ ID NO: 7, SEQ ID NO: 132, SEQ ID NO: 23, and SEQ ID NO: 8.

6. The system of claim 1, wherein the PDZ domain is an erbin PDZ domain, and the ligand is selected from the group consisting of: SEQ ID NO: 22, SEQ ID NO: 23, SEQ ID NO: 8, SEQ ID NO: 5, SEQ ID NO: 6, SEQ ID NO: 7, and SEQ ID NO: 134.

7. The system of claim 1, wherein n=2, 3, 4, 5, 6 or between 6-10.

8. The system of claim 1, wherein the DNA binding domain (DBD) is an engineered zinc finger binding domain.

9. The system of claim 8, wherein the DBD is selected from one or more of any of: SEQ ID NOs: 123-124, 125-126, 135, and 136-143, or wherein the DBD binds to DNA binding motifs (DBM) comprising any of: SEQ ID NOs: 99-108 or SEQ ID NO: 131 or any combination thereof.

10. The system of claim 1, wherein the TA domain is VP16 minimal activation domain.

11. The system of claim 1, wherein molecular clamp has the general formula of: $[(X)_n(Y)]_m$, where each X is the same or a different ligand binding domain (LBD), wherein the molecular clamp comprises n ligand binding domains (LBD), wherein n is selected from any of: 3, 4, 5, 6, 7, 8, 9, and 10, where Y is a linker peptide, and where m is an integer from 2 to about 50.

12. The system of claim 1, wherein molecular clamp comprises: NLS-[LBD-linker]n-LBD, where n is 3, 4, 5, 6, 7, 8, 9, or 10.

13. The system of claim 1, wherein the sTF comprises:
  a. a ligand,
  b. at least one DNA binding domain (DBD), and
  c. a transcriptional activator (TA) domain or a transcriptional repressor (TR) domain, and
wherein the DBD can bind to a target DNA binding motif (DBM) located upstream of a promoter operatively linked to a gene, and wherein the ligand is configured to specifically bind to the ligand binding domain (LBD) of the molecular clamp of the system of claim 1.

14. The system of claim 13, wherein the at least one DNA binding domain (DBD) is selected from:
  (i) an engineered zinc finger binding domain,
  (ii) a zinc finger binding domain which comprises at least one mutation compared to a wild-type zinc finger domain, or
  (iii) triple repeat zinc finger array.

15. The system of claim 14, wherein the DBD is selected from one or more of any of: SEQ ID NOs: 123-124, 125-126, 135, and 136-143, or wherein the DBD binds to DNA binding motifs (DBM) comprising any of: SEQ ID NOs: 99-108 or SEQ ID NO: 131 or any combination thereof.

16. The system of claim 13, wherein the TA domain is selected from any of: VP16, VP64 and p65.

17. The system of claim 13, wherein the ligand is
  a. located at the C-terminal end of the sTF, and
  b. selected from the group consisting of: SEQ ID NO: 3, SEQ ID NO: 4, SEQ ID NO: 5, SEQ ID NO: 6, SEQ ID NO: 7, SEQ ID NO: 132, SEQ ID NO: 8, SEQ ID NO: 22, SEQ ID NO: 23, and SEQ ID NO: 134.

18. The system of claim 1, wherein the binding affinity of the LBD of the molecular clamp for the ligand on each of the sTFs is selected from the group consisting of:
  (a) a high affinity between 0.01 µM to 1 µM; and
  (b) a low affinity between 1 µM to 100 µM.

* * * * *

SEQUENCE LISTING

<160> NUMBER OF SEQ IDS NOS: 150

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Lys Lys Lys Arg Lys Val Gly Ile His Gly Val Pro Gly Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Lys Lys Lys Arg Lys Val Val Glu
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 3

Ile Arg Glu Thr Ile Ile
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Arg Glu Thr Ile Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Arg Trp Thr Ile Val
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Lys Glu Ser Leu Val
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Arg Glu Thr Ile Val
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Lys Glu Ala Leu Val
1               5

<210> SEQ ID NO 9
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 9

Ile Glu Ser Asp Val
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Lys Glu Ser Leu Val
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Val Lys Glu Ser Leu Val
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Val Lys Gln Ser Leu Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Val Lys Glu Ser Gly Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Val Lys Glu Ser Leu Val
1               5
```

```
<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Glu Thr Asp Val
1               5

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Val Gly Ala Leu Met His Val Met Gln Lys Arg Ser Arg Ala Ile
1               5                   10                  15

His Ser Ser Asp Glu Gly Glu Asp Gln Ala Gly Asp Glu Asp Glu Asp
            20                  25                  30

<210> SEQ ID NO 17
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu Gly Gly Gly Lys
        35                  40                  45

<210> SEQ ID NO 18
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
            20                  25                  30

Val Ser Gln Tyr Glu Thr Arg Tyr Gly Pro Leu Gly Gly Gly Lys
        35                  40                  45

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 19

Arg Pro Leu Pro Val Ala Pro
1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Pro Pro Ala Leu Pro Pro Lys Arg Arg Arg Pro Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Pro Pro Ala Leu Pro Pro Lys Lys Arg
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Leu Lys Thr Trp Val
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Val Asp Ser Trp Val
1               5

<210> SEQ ID NO 24
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Gly Tyr Gln Tyr Arg Ala Leu Tyr Asp Tyr Lys Lys Glu Arg Glu
1               5                   10                  15

Glu Asp Ile Asp Leu His Leu Gly Asp Ile Leu Thr Val Asn Lys Gly
            20                  25                  30

Ser Leu Val Ala Leu Gly Phe Ser Asp Gly Gln Glu Ala Arg Pro Glu
            35                  40                  45

Glu Ile Gly Trp Leu Asn Gly Tyr Asn Glu Thr Thr Gly Glu Arg Gly
        50                  55                  60

Asp Phe Pro Gly Thr Tyr Val Glu Tyr Ile
65                  70

<210> SEQ ID NO 25
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Tyr Val Arg Ala Leu Phe Asp Phe Asn Gly Asn Asp Glu Glu Asp Leu
1               5                   10                  15

Pro Phe Lys Lys Gly Asp Ile Leu Arg Ile Arg Asp Lys Pro Glu Glu
            20                  25                  30

Gln Trp Trp Asn Ala Glu Asp Ser Glu Gly Lys Arg Gly Met Ile Pro
        35                  40                  45

Val Pro Tyr Val Glu Lys
    50

<210> SEQ ID NO 26
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Glu Tyr Val Arg Ala Leu Phe Asp Phe Asn Gly Asn Asp Glu
1               5                   10                  15

Glu Asp Leu Pro Phe Lys Lys Gly Asp Ile Leu Arg Ile Arg Asp Lys
            20                  25                  30

Pro Glu Glu Gln Trp Trp Asn Ala Glu Asp Ser Glu Gly Lys Arg Gly
        35                  40                  45

Met Ile Pro Val Pro Tyr Val Glu Lys Tyr
    50                  55

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Glu Arg Pro Glu Ile Ser Leu Pro Ser Asp Phe Glu His Thr Ile
1               5                   10                  15

His Val Gly Phe Asp Ala Val Thr Gly Glu Phe Thr Gly Met Pro Glu
            20                  25                  30

Gln Trp Ala Arg
        35

<210> SEQ ID NO 28
<211> LENGTH: 80

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Thr Lys Ala Asp Ile Gly Thr Pro Ser Asn Phe Gln His Ile Gly
1               5                   10                  15

His Val Gly Trp Asp Pro Asn Thr Gly Phe Asp Leu Asn Asn Leu Asp
            20                  25                  30

Pro Glu Leu Lys Asn Leu Phe Asp Met Cys Gly Ile Ser Glu Ala Gln
        35                  40                  45

Leu Lys Asp Arg Glu Thr Ser Lys Val Ile Tyr Asp Phe Ile Glu Lys
    50                  55                  60

Thr Gly Val Glu Ala Val Lys Asn Glu Leu Arg Arg Gln Ala Pro
65                  70                  75                  80

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ala Gly Gly Met
1               5

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Ala Gly Gly Met Pro Pro Ala Ala Ala Gly Gly Met
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Pro Ala Ala Ala Gly Gly Met Met
1               5

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 gccrccatgg                                                          10
```

```
<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 attaaa                                                                       6

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 attaaa                                                                       6

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 agtaaa                                                                       6

<210> SEQ ID NO 36
<211> LENGTH: 7
<212> TYPE: PRT
<213> ORGANISM: Simian virus 40

<400> SEQUENCE: 36

Pro Lys Lys Lys Arg Lys Val
1               5

<210> SEQ ID NO 37
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 37

Lys Arg Pro Ala Ala Thr Lys Lys Ala Gly Gln Ala Lys Lys Lys Lys
1               5                   10                  15

<210> SEQ ID NO 38
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 38

Pro Ala Ala Lys Arg Val Lys Leu Asp
1               5

<210> SEQ ID NO 39
```

```
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 39

Arg Gln Arg Arg Asn Glu Leu Lys Arg Ser Pro
1               5                   10

<210> SEQ ID NO 40
<211> LENGTH: 38
<212> TYPE: PRT
<213> ORGANISM: Homo sapiens

<400> SEQUENCE: 40

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 41
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 41

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 42
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 42

Val Ser Arg Lys Arg Pro Arg Pro
1               5

<210> SEQ ID NO 43
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 43

Pro Pro Lys Lys Ala Arg Glu Asp
1               5

<210> SEQ ID NO 44
```

```
<211> LENGTH: 8
<212> TYPE: PRT
<213> ORGANISM: Homo sapiens

<400> SEQUENCE: 44

Pro Gln Pro Lys Lys Lys Pro Leu
1               5

<210> SEQ ID NO 45
<211> LENGTH: 12
<212> TYPE: PRT
<213> ORGANISM: Mus sp.

<400> SEQUENCE: 45

Ser Ala Leu Ile Lys Lys Lys Lys Lys Met Ala Pro
1               5                   10

<210> SEQ ID NO 46
<211> LENGTH: 5
<212> TYPE: PRT
<213> ORGANISM: Influenza virus

<400> SEQUENCE: 46

Asp Arg Leu Arg Arg
1               5

<210> SEQ ID NO 47
<211> LENGTH: 7
<212> TYPE: PRT
<213> ORGANISM: Influenza virus

<400> SEQUENCE: 47

Pro Lys Gln Lys Lys Arg Lys
1               5

<210> SEQ ID NO 48
<211> LENGTH: 10
<212> TYPE: PRT
<213> ORGANISM: Hepatitis delta virus

<400> SEQUENCE: 48

Arg Lys Leu Lys Lys Lys Ile Lys Lys Leu
1               5                   10

<210> SEQ ID NO 49
<211> LENGTH: 10
<212> TYPE: PRT
<213> ORGANISM: Mus sp.

<400> SEQUENCE: 49

Arg Glu Lys Lys Lys Phe Leu Lys Arg Arg
1               5                   10

<210> SEQ ID NO 50
<211> LENGTH: 20
<212> TYPE: PRT
<213> ORGANISM: Homo sapiens

<400> SEQUENCE: 50

Lys Arg Lys Gly Asp Glu Val Asp Gly Val Asp Glu Val Ala Lys Lys
1               5                   10                  15

Lys Ser Lys Lys
            20
```

<210> SEQ ID NO 51
<211> LENGTH: 17
<212> TYPE: PRT
<213> ORGANISM: Homo sapiens

<400> SEQUENCE: 51

Arg Lys Cys Leu Gln Ala Gly Met Asn Leu Glu Ala Arg Lys Thr Lys
1               5                   10                  15

Lys

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
gaattcgtcc tcactctgga tcc                                          23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
gaattcagac gctgctcgga tcc                                          23

<210> SEQ ID NO 54
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gaattcgtcc tcactcttcg gtcctcactc tggatcc                           37

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
gaattcgtcc tcactcttcg gtcctcactc ttcggtcctc actctggatc c           51

<210> SEQ ID NO 56
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 2-25 'Gly Ser'
      repeating units

<400> SEQUENCE: 56

```
Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
                20                  25                  30

Gly Ser Gly Ser Gly Ser Gly Ser Gly Ser Gly Ser Gly Ser Gly Ser
        35                  40                  45

Gly Ser
    50

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ser Gly Ser Gly Ser Gly Ser Gly Ser
1               5                   10

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser Gly Ser Gly Ser Gly Ser Gly Ser Gly Ser Gly Ser Gly Ser
1               5                   10                  15

Gly Ser Gly Ser
        20

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
                20                  25                  30

Gly Ser Gly Ser Gly Ser Gly Ser
        35                  40

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ser Gly Ser Gly
1               5
```

```
<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MISC_FEATURE
<222> LOCATION: (2)..(5)
<223> OTHER INFORMATION: This region may encompass 2-4 residues
<220> FEATURE:
<221> NAME/KEY: MOD_RES
<222> LOCATION: (7)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MISC_FEATURE
<222> LOCATION: (20)..(24)
<223> OTHER INFORMATION: This region may encompass 3-5 residues

<400> SEQUENCE: 61

Cys Xaa Xaa Xaa Xaa Cys Xaa Xaa Xaa Xaa Xaa Xaa Xaa Xaa Xaa
1               5                  10                  15

Xaa Xaa His Xaa Xaa Xaa Xaa His
            20                  25

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 1-5 'Gly Ser'
      repeating units

<400> SEQUENCE: 62

Gly Ser Gly Ser Gly Ser Gly Ser Gly Ser
1               5                  10

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 6-10 'Gly Ser'
      repeating units

<400> SEQUENCE: 63

Gly Ser Gly Ser Gly Ser Gly Ser Gly Ser Gly Ser Gly Ser Gly Ser
1               5                  10                  15

Gly Ser Gly Ser
            20

<210> SEQ ID NO 64
```

```
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 11-20 'Gly Ser'
      repeating units

<400> SEQUENCE: 64

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser
        35                  40

<210> SEQ ID NO 65
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 21-30 'Gly Ser'
      repeating units

<400> SEQUENCE: 65

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser Gly Ser
        35                  40                  45

Gly Ser Gly Ser Gly Ser Gly Ser Gly Ser Gly Ser
    50                  55                  60

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MISC_FEATURE
<222> LOCATION: (1)..(3)
<223> OTHER INFORMATION: This region may encompass 0-3 residues
<220> FEATURE:
<221> NAME/KEY: MOD_RES
<222> LOCATION: (5)..(9)
<223> OTHER INFORMATION: Any amino acid
<220> FEATURE:
<221> NAME/KEY: MISC_FEATURE
<222> LOCATION: (5)..(9)
<223> OTHER INFORMATION: This region may encompass 1-5 residues
<220> FEATURE:
<221> NAME/KEY: MOD_RES
<222> LOCATION: (11)..(17)
<223> OTHER INFORMATION: Any amino acid
```

-continued

```
<220> FEATURE:
<221> NAME/KEY: MISC_FEATURE
<222> LOCATION: (11)..(17)
<223> OTHER INFORMATION: This region may encompass 2-7 residues
<220> FEATURE:
<221> NAME/KEY: MOD_RES
<222> LOCATION: (18)..(23)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MISC_FEATURE
<222> LOCATION: (25)..(30)
<223> OTHER INFORMATION: This region may encompass 3-6 residues

<400> SEQUENCE: 66

Xaa Xaa Xaa Cys Xaa Xaa Xaa Xaa Xaa Cys Xaa Xaa Xaa Xaa Xaa Xaa
1               5                   10                  15

Xaa Xaa Xaa Xaa Xaa Xaa Xaa His Xaa Xaa Xaa Xaa Xaa Xaa His
            20                  25                  30

<210> SEQ ID NO 67
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid

<400> SEQUENCE: 67

Xaa Xaa Xaa Cys Xaa Xaa Cys Xaa Xaa Xaa Xaa Xaa Xaa Xaa Xaa Xaa
1               5                   10                  15

Xaa Xaa His Xaa Xaa Xaa His
            20

<210> SEQ ID NO 68
<211> LENGTH: 4
<212> TYPE: PRT
<213> ORGANISM: Unknown
<220> FEATURE:
<223> OTHER INFORMATION: Description of Unknown: Synthetic
      "WRPW" repression domain sequence

<400> SEQUENCE: 68

Trp Arg Pro Trp
1

<210> SEQ ID NO 69
<211> LENGTH: 53
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 69

Gly Arg Ala Asp Ala Leu Asp Asp Phe Asp Leu Asp Met Leu Gly Ser
1               5                   10                  15

Asp Ala Leu Asp Asp Phe Asp Leu Asp Met Leu Gly Ser Asp Ala Leu
            20                  25                  30

Asp Asp Phe Asp Leu Asp Met Leu Gly Ser Asp Ala Leu Asp Asp Phe
        35                  40                  45

Asp Leu Asp Met Leu
    50

<210> SEQ ID NO 70
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
        35                  40                  45

Pro Met Asp Leu Ser Thr Ile Lys Arg Lys Leu Asp Thr Gly Gln Tyr
    50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val

```
                275                 280                 285
Lys Pro Gly Met Lys Ala Arg Phe Val Asp Ser Gly Glu Met Ala Glu
            290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
                355                 360                 365

Glu Ile Leu Ile Gly Tyr Leu Glu Tyr Val Lys Lys Leu Gly Tyr Thr
            370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
                435                 440                 445

Thr Ser Ala Lys Glu Leu Pro Tyr Phe Glu Gly Asp Phe Trp Pro Asn
            450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Asn Lys Lys Thr Ser Lys Asn
            500                 505                 510

Lys Ser Ser Leu Ser Arg Gly Asn Lys Lys Pro Gly Met Pro Asn
515                 520                 525

Val Ser Asn Asp Leu Ser Gln Lys Leu Tyr Ala Thr Met Glu Lys His
            530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
                595                 600                 605

Val Glu Leu His Thr Gln Ser Gln Asp
            610                 615

<210> SEQ ID NO 71
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Asp Ala Lys Ser Leu Thr Ala Trp Ser Arg Thr Leu Val Thr Phe
1               5                   10                  15
```

-continued

```
Lys Asp Val Phe Val Asp Phe Thr Arg Glu Glu Trp Lys Leu Leu Asp
             20                  25                  30

Thr Ala Gln Gln Ile Leu Tyr Arg Asn Val Met Leu Glu Asn Tyr Lys
         35                  40                  45

Asn Leu Val Ser Leu Gly Tyr Gln Leu Thr Lys Pro Asp Val Ile Leu
 50                  55                  60

Arg Leu Glu Lys Gly Glu Pro Trp Leu Val Arg Glu Ile His
65                  70                  75                  80

Gln Glu Thr His Pro Asp Ser Glu Thr Ala Phe Glu Ile Lys Ser Ser
             85                  90                  95

Val

<210> SEQ ID NO 72
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Lys Lys Arg Glu Gln Ser Asn Asp Ile Ala Arg Gly Phe Glu Arg
1               5                   10                  15

Gly Leu Glu Pro Glu Lys Ile Ile Gly Ala Thr Asp Ser Cys Gly Asp
             20                  25                  30

Leu Met Phe Leu Met Lys Trp Lys Asp Thr Asp Glu Ala Asp Leu Val
         35                  40                  45

Leu Ala Lys Glu Ala Asn Val Lys Cys Pro Gln Ile Val Ile Ala Phe
 50                  55                  60

Tyr Glu Glu Arg Leu Thr Trp His Ala Tyr Pro Glu Asp Ala Glu Asn
65                  70                  75                  80

Lys Glu Lys

<210> SEQ ID NO 73
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
             20                  25                  30

Asp Ser Pro Pro Ile Leu Glu Ala Ile Arg Thr Pro Glu Ile Arg Gly
         35                  40                  45

Arg Arg Ser Ser Arg Leu Ser Lys Arg Glu Val Ser Ser Leu Leu
 50                  55                  60

Ser Tyr Thr Gln Asp Leu Thr Gly Asp Gly Asp Glu Asp Gly Asp
65                  70                  75                  80

Gly Ser Asp Thr Pro Val Met Pro Lys Leu Phe Arg Glu Thr Arg Thr
             85                  90                  95

Arg Ser Glu Ser Pro Ala Val Arg Thr Arg Asn Asn Asn Ser Val Ser
            100                 105                 110

Ser Arg Glu Arg His Arg Pro Ser Pro Arg Ser Thr Arg Gly Arg Gln
            115                 120                 125
```

```
Gly Arg Asn His Val Asp Glu Ser Pro Val Glu Phe Pro Ala Thr Arg
            130                 135                 140

Ser Leu Arg Arg Arg Ala Thr Ala Ser Ala Gly Thr Pro Trp Pro Ser
145                 150                 155                 160

Pro Pro Ser Ser Tyr Leu Thr Ile Asp Leu Thr Asp Asp Thr Glu Asp
                165                 170                 175

Thr His Gly Thr Pro Gln Ser Ser Thr Pro Tyr Ala Arg Leu Ala
            180                 185                 190

Gln Asp Ser Gln Gln Gly Gly Met Glu Ser Pro Gln Val Glu Ala Asp
                195                 200                 205

Ser Gly Asp Gly Asp Ser Ser Glu Tyr Gln Asp Gly Lys Glu Phe Gly
            210                 215                 220

Ile Gly Asp Leu Val Trp Gly Lys Ile Lys Gly Phe Ser Trp Trp Pro
225                 230                 235                 240

Ala Met Val Val Ser Trp Lys Ala Thr Ser Lys Arg Gln Ala Met Ser
                245                 250                 255

Gly Met Arg Trp Val Gln Trp Phe Gly Asp Gly Lys Phe Ser Glu Val
            260                 265                 270

Ser Ala Asp Lys Leu Val Ala Leu Gly Leu Phe Ser Gln His Phe Asn
            275                 280                 285

Leu Ala Thr Phe Asn Lys Leu Val Ser Tyr Arg Lys Ala Met Tyr His
            290                 295                 300

Ala Leu Glu Lys Ala Arg Val Arg Ala Gly Lys Thr Phe Pro Ser Ser
305                 310                 315                 320

Pro Gly Asp Ser Leu Glu Asp Gln Leu Lys Pro Met Leu Glu Trp Ala
                325                 330                 335

His Gly Gly Phe Lys Pro Thr Gly Ile Glu Gly Leu Lys Pro Asn Asn
            340                 345                 350

Thr Gln Pro Glu Asn Lys Thr Arg Arg Thr Ala Asp Asp Ser Ala
            355                 360                 365

Thr Ser Asp Tyr Cys Pro Ala Pro Lys Arg Leu Lys Thr Asn Cys Tyr
            370                 375                 380

Asn Asn Gly Lys Asp Arg Gly Asp Glu Asp Gln Ser Arg Glu Gln Met
385                 390                 395                 400

Ala Ser Asp Val Ala Asn Asn Lys Ser Ser Leu Glu Asp Gly Cys Leu
                405                 410                 415

Ser Cys Gly Arg Lys Asn Pro Val Ser Phe His Pro Leu Phe Glu Gly
            420                 425                 430

Gly Leu Cys Gln Thr Cys Arg Asp Arg Phe Leu Glu Leu Phe Tyr Met
            435                 440                 445

Tyr Asp Asp Asp Gly Tyr Gln Ser Tyr Cys Thr Val Cys Cys Glu Gly
            450                 455                 460

Arg Glu Leu Leu Leu Cys Ser Asn Thr Ser Cys Cys Arg Cys Phe Cys
465                 470                 475                 480

Val Glu Cys Leu Glu Val Leu Val Gly Thr Gly Thr Ala Ala Glu Ala
                485                 490                 495

Lys Leu Gln Glu Pro Trp Ser Cys Tyr Met Cys Leu Pro Gln Arg Cys
            500                 505                 510

His Gly Val Leu Arg Arg Arg Lys Asp Trp Asn Val Arg Leu Gln Ala
            515                 520                 525

Phe Phe Thr Ser Asp Thr Gly Leu Glu Tyr Glu Ala Pro Lys Leu Tyr
530                 535                 540
```

-continued

```
Pro Ala Ile Pro Ala Ala Arg Arg Arg Pro Ile Arg Val Leu Ser Leu
545                 550                 555                 560

Phe Asp Gly Ile Ala Thr Gly Tyr Leu Val Leu Lys Glu Leu Gly Ile
                565                 570                 575

Lys Val Gly Lys Tyr Val Ala Ser Glu Val Cys Glu Glu Ser Ile Ala
            580                 585                 590

Val Gly Thr Val Lys His Glu Gly Asn Ile Lys Tyr Val Asn Asp Val
        595                 600                 605

Arg Asn Ile Thr Lys Lys Asn Ile Glu Glu Trp Gly Pro Phe Asp Leu
    610                 615                 620

Val Ile Gly Gly Ser Pro Cys Asn Asp Leu Ser Asn Val Asn Pro Ala
625                 630                 635                 640

Arg Lys Gly Leu Tyr Glu Gly Thr Gly Arg Leu Phe Phe Glu Phe Tyr
                645                 650                 655

His Leu Leu Asn Tyr Ser Arg Pro Lys Glu Gly Asp Asp Arg Pro Phe
            660                 665                 670

Phe Trp Met Phe Glu Asn Val Val Ala Met Lys Val Gly Asp Lys Arg
        675                 680                 685

Asp Ile Ser Arg Phe Leu Glu Cys Asn Pro Val Met Ile Asp Ala Ile
    690                 695                 700

Lys Val Ser Ala Ala His Arg Ala Arg Tyr Phe Trp Gly Asn Leu Pro
705                 710                 715                 720

Gly Met Asn Arg Pro Val Ile Ala Ser Lys Asn Asp Lys Leu Glu Leu
                725                 730                 735

Gln Asp Cys Leu Glu Tyr Asn Arg Ile Ala Lys Asp Leu Trp Leu Ser
            740                 745                 750

Cys Ala Leu His Arg Arg Val Gln His Gly Pro Trp Cys Pro Pro Glu
        755                 760                 765

Ala Ala Gly Lys Val Leu Glu Arg Ala Cys His Pro Thr Pro Leu Arg
    770                 775                 780

Pro Ser Glu Gly Leu Leu Cys Met
785                 790

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Gly Glu Lys Pro
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Gly Gly Lys Pro
1               5

<210> SEQ ID NO 76
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Gly Ser Lys Pro
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Gly Gln Lys Pro
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gly Glu Lys Pro
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Gly Ser Lys Pro
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Gly Gln Lys Pro
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Gly Gly Lys Pro
```

```
1               5
```

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 82

```
His His His His His His
1               5
```

<210> SEQ ID NO 83
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 2-30 'Gly Ser'
      repeating units

<400> SEQUENCE: 83

```
Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser
        35                  40                  45

Gly Ser Gly Ser Gly Ser Gly Ser Gly Ser Gly Ser
    50                  55                  60
```

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Pro Gly Glu Arg
1
```

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

```
Thr Gly Ser Gln Lys
1               5
```

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 86

Thr His Leu Arg
1

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Gly Gly Gly Glu Lys Pro
1               5

<210> SEQ ID NO 88
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Phe His Tyr Asp Arg Asn Asn Ile Ala Val Gly Ala Asp Glu Ser Val
1               5                   10                  15

Val Lys Glu Ala His Arg Glu Val Ile Asn Ser Ser Thr Glu Gly Leu
            20                  25                  30

Leu Leu Asn Ile Asp Lys Asp Ile Arg Lys Ile Leu Ser Gly Tyr Ile
        35                  40                  45

Val Glu Ile Glu Asp Thr Glu
    50                  55

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Glu Ile Glu Asp Thr Glu
1               5

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Asp Ile Arg Lys Ile Leu Ser Gly Tyr Ile Val Glu Ile Glu Asp
1               5                   10                  15

Thr Glu

<210> SEQ ID NO 91
<211> LENGTH: 28
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 91

Ser Thr Glu Gly Leu Leu Leu Asn Ile Asp Lys Asp Ile Arg Lys Ile
1               5                   10                  15

Leu Ser Gly Tyr Ile Val Glu Ile Glu Asp Thr Glu
            20                  25

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Val Lys Gln Glu Asn Arg Leu Leu Asn Glu Ser Glu Ser
1               5                   10

<210> SEQ ID NO 93
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Val Gly Ala Asp Glu Ser Val Val Lys Glu Ala His Arg Glu Val Ile
1               5                   10                  15

Asn Ser Ser Thr Glu Gly Leu Leu Leu Asn Ile Asp Lys Asp Ile Arg
            20                  25                  30

Lys Ile Leu Ser Gly Tyr Ile Val Glu Ile Glu Asp Thr Glu
        35                  40                  45

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gly Ser Gly Gly Ser
1               5

<210> SEQ ID NO 95
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-8 'Gly Gly Gly
      Gly Ser' repeating units

<400> SEQUENCE: 95

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 96
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Glu Phe Pro Thr Met Val Phe Pro Ser Gly Gln Ile Ser Gln Ala
1               5                   10                  15

Ser Ala Leu Ala Pro Ala Pro Pro Gln Val Leu Pro Gln Ala Pro Ala
            20                  25                  30

Pro Ala Pro Ala Pro Ala Met Val Ser Ala Leu Ala Gln Ala Pro Ala
        35                  40                  45

Pro Val Pro Val Leu Ala Pro Gly Pro Pro Gln Ala Val Ala Pro Pro
    50                  55                  60

Ala Pro Lys Pro Thr Gln Ala Gly Glu Gly Thr Leu Ser Glu Ala Leu
65                  70                  75                  80

Leu Gln Leu Gln Phe Asp Asp Glu Asp Leu Gly Ala Leu Leu Gly Asn
                85                  90                  95

Ser Thr Asp Pro Ala Val Phe Thr Asp Leu Ala Ser Val Asp Asn Ser
            100                 105                 110

Glu Phe Gln Gln Leu Leu Asn Gln Gly Ile Pro Val Ala Pro His Thr
        115                 120                 125

Thr Glu Pro Met Leu Met Glu Tyr Pro Glu Ala Ile Thr Arg Leu Val
    130                 135                 140

Thr Gly Ala Gln Arg Pro Pro Asp Pro Ala Pro Ala Pro Leu Gly Ala
145                 150                 155                 160

Pro Gly Leu Pro Asn Gly Leu Leu Ser Gly Asp Glu Asp Phe Ser Ser
                165                 170                 175

Ile Ala Asp Met Asp Phe Ser Ala Leu Leu Ser Gln Ile Ser Ser
            180                 185                 190

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Ser
1               5

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 1-8 'Gly Ser' repeating units

<400> SEQUENCE: 98

Gly Ser Gly Ser Gly Ser Gly Ser Gly Ser Gly Ser Gly Ser Gly Ser
1               5                   10                  15

<210> SEQ ID NO 99
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
agagtgagga c                                                                11

<210> SEQ ID NO 100
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
acagtgagga c                                                                11

<210> SEQ ID NO 101
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atagtgagga c                                                                11

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
agacgctgct c                                                                11

<210> SEQ ID NO 103
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tgacgctgct c                                                                11

<210> SEQ ID NO 104
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
agacggtgct c                                                          11

<210> SEQ ID NO 105
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
acacgctgct c                                                          11

<210> SEQ ID NO 106
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
agacgctact c                                                          11

<210> SEQ ID NO 107
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agacgctgct a                                                          11

<210> SEQ ID NO 108
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
agactctgct c                                                          11

<210> SEQ ID NO 109
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccata                  286

<210> SEQ ID NO 110
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
acctgtagga tcgtacaggt ttacgcaaga aaatggtttg ttatagtcga ataaa    55

<210> SEQ ID NO 111
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 111
aatttgggga tcgtacaggt ttacgcaaga aaatggtttg ttatagtcga ataaa    55

<210> SEQ ID NO 112
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
ctggcgggga tcgtacaggt ttacgcaaga aaatggtttg ttatagtcga ataaa    55

<210> SEQ ID NO 113
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
tggggtagga tcgtacaggt ttacgcaaga aaatggtttg ttatagtcga ataaa    55

<210> SEQ ID NO 114
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
gcatgctccc tatcagtgat agagattgac atccctatca gtgatagaga tactgagcac    60
atcagcagga cgcactgacc agga    84

<210> SEQ ID NO 115
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
ccatcgaatg gctgaaatga gctgttgaca attaatcatc cggctcgtat aatgtgtgga    60
attgtgagcg gataacaatt tcacacagga                                           90

<210> SEQ ID NO 116
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ataaatgtga gcggataaca ttgacattgt gagcggataa caagatactg agcactcagc         60
aggacgcact gacc                                                           74

<210> SEQ ID NO 117
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aaaatttatc aaaagagtg ttgacttgtg agcggataac aatgatactt agattcaatt          60
gtgagcggat aacaatttca caca                                                84

<210> SEQ ID NO 118
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
catagcattt ttatccataa gattagcgga tcctaagctt tacaattgtg agcgctcaca         60
attatgatag attcaattgt gagcggataa caatttcaca ca                           102

<210> SEQ ID NO 119
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
gcatgcacag ataaccatct gcggtgataa attatctctg gcggtgttga cataaatacc         60
actggcggtt ataatgagca catcagcagg gtatgcaaag ga                           102

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Val Ser Lys Glu Ser Leu Val
1               5

<210> SEQ ID NO 121

```
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Tyr Lys Asp His Asp Gly Asp Tyr Lys Asp His Asp Ile Asp Tyr
1               5                   10                  15

Lys Asp Asp Asp Asp Lys Met Ala Pro Lys Lys Arg Lys Val Gly
            20                  25                  30

Ile His Gly Val Pro Gly Gly Leu Glu Ala Pro Pro Thr Asp Val Ser
        35                  40                  45

Leu Gly Asp Glu Leu His Leu Asp Gly Glu Asp Val Ala Met Ala His
    50                  55                  60

Ala Asp Ala Leu Asp Asp Phe Asp Leu Asp Met Leu Gly Asp Gly Asp
65                  70                  75                  80

Ser Pro Gly Pro Gly Phe Thr Pro His Asp Ser Ala Pro Tyr Gly Ala
                85                  90                  95

Leu Asp Met Ala Asp Phe Glu Phe Glu Gln Met Phe Thr Asp Ala Leu
            100                 105                 110

Gly Ile Asp Glu Tyr Gly Gly Gly Ser Arg Pro Gly Glu Ala Pro Phe
        115                 120                 125

Gln Cys Arg Ile Cys Met Ala Asn Phe Ser Arg Gln Asp Arg Leu Asp
    130                 135                 140

Arg His Thr Arg Thr His Thr Gly Glu Lys Pro Phe Gln Cys Arg Ile
145                 150                 155                 160

Cys Met Ala Asn Phe Ser Gln Lys Glu His Leu Ala Gly His Leu Arg
                165                 170                 175

Thr His Thr Gly Glu Lys Pro Phe Gln Cys Arg Ile Cys Met Ala Asn
            180                 185                 190

Phe Ser Arg Arg Asp Asn Leu Asn Arg His Leu Lys Thr His Leu Arg
        195                 200                 205

Gly Ser Gly Ser Gly Val Lys Glu Ser Leu Val
    210                 215

<210> SEQ ID NO 122
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gly Glu Ala Pro Phe Gln Cys Arg Ile Cys Met Ala Asn Phe Ser Arg
1               5                   10                  15

Gln Asp Arg Leu Asp Arg His Thr Arg Thr His Thr Gly Glu Lys Pro
            20                  25                  30

Phe Gln Cys Arg Ile Cys Met Ala Asn Phe Ser Gln Lys Glu His Leu
        35                  40                  45

Ala Gly His Leu Arg Thr His Thr Gly Glu Lys Pro Phe Gln Cys Arg
    50                  55                  60

Ile Cys Met Ala Asn Phe Ser Arg Arg Asp Asn Leu Asn Arg His Leu
65                  70                  75                  80

Lys Thr His Leu Arg Gly Ser Gly Ser Gly Val Lys Glu Ser Leu Val
                85                  90                  95
```

<210> SEQ ID NO 123
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Glu Ala Pro Phe Gln Cys Arg Ile Cys Met Ala Asn Phe Ser Arg
1               5                   10                  15

Gln Asp Arg Leu Asp Arg His Thr Arg Thr His Thr Gly Glu Lys Pro
            20                  25                  30

Phe Gln Cys Arg Ile Cys Met Ala Asn Phe Ser Gln Lys Glu His Leu
        35                  40                  45

Ala Gly His Leu Arg Thr His Thr Gly Glu Lys Pro Phe Gln Cys Arg
    50                  55                  60

Ile Cys Met Ala Asn Phe Ser Arg Arg Asp Asn Leu Asn Arg His Leu
65                  70                  75                  80

Lys Thr His Leu Arg
                85

<210> SEQ ID NO 124
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Glu Arg Pro Phe Gln Cys Arg Ile Cys Met Ala Asn Phe Ser Arg
1               5                   10                  15

Gln Asp Arg Leu Asp Arg His Thr Arg Thr His Thr Gly Glu Lys Pro
            20                  25                  30

Phe Gln Cys Arg Ile Cys Met Ala Asn Phe Ser Gln Lys Glu His Leu
        35                  40                  45

Ala Gly His Leu Arg Thr His Thr Gly Glu Lys Pro Phe Gln Cys Arg
    50                  55                  60

Ile Cys Met Ala Asn Phe Ser Arg Arg Asp Asn Leu Asn Arg His Leu
65                  70                  75                  80

Lys Thr His Leu Arg
                85

<210> SEQ ID NO 125
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gly Glu Ala Pro Phe Gln Cys Arg Ile Cys Met Ala Asn Phe Ser Thr
1               5                   10                  15

Gly Gln Ile Leu Asp Arg His Thr Arg Thr His Thr Gly Glu Lys Pro
            20                  25                  30

Phe Gln Cys Arg Ile Cys Met Ala Asn Phe Ser Val Ala His Ser Leu
        35                  40                  45

```
Lys Arg His Leu Arg Thr His Thr Gly Glu Lys Pro Phe Gln Cys Arg
    50                  55                  60

Ile Cys Met Ala Asn Phe Ser Asp Pro Ser Asn Leu Arg Arg His Leu
 65                 70                  75                  80

Lys Thr His Leu Arg
                85

<210> SEQ ID NO 126
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gly Glu Arg Pro Phe Gln Cys Arg Ile Cys Met Ala Asn Phe Ser Thr
 1               5                  10                  15

Gly Gln Ile Leu Asp Arg His Thr Arg Thr His Thr Gly Glu Lys Pro
            20                  25                  30

Phe Gln Cys Arg Ile Cys Met Ala Asn Phe Ser Val Ala His Ser Leu
        35                  40                  45

Lys Arg His Leu Arg Thr His Thr Gly Glu Lys Pro Phe Gln Cys Arg
    50                  55                  60

Ile Cys Met Ala Asn Phe Ser Asp Pro Ser Asn Leu Arg Arg His Leu
 65                 70                  75                  80

Lys Thr His Leu Arg
                85

<210> SEQ ID NO 127
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Pro Lys Lys Lys Arg Lys Val Val Glu Leu Gln Arg Arg Arg Val Thr
 1               5                  10                  15

Val Arg Lys Ala Asp Ala Gly Gly Leu Gly Ile Ser Ile Lys Gly Gly
            20                  25                  30

Arg Glu Asn Lys Met Pro Ile Leu Ile Ser Lys Ile Phe Lys Gly Leu
        35                  40                  45

Ala Ala Asp Gln Thr Glu Ala Leu Phe Val Gly Asp Ala Ile Leu Ser
    50                  55                  60

Val Asn Gly Glu Asp Leu Ser Ser Ala Thr His Asp Glu Ala Val Gln
 65                 70                  75                  80

Ala Leu Lys Lys Thr Gly Lys Glu Val Val Leu Glu Val Lys Tyr Met
                85                  90                  95

Lys Glu Val Ser Pro Tyr Phe Lys Arg Ser Gly Ser Gly Ser Gly Ser
               100                 105                 110

Gly Ser Gly Ser Gly Ser Gly Ser Gly Ser Gly Ser Gly Ser Pro Gly
            115                 120                 125

Leu Gln Arg Arg Arg Val Thr Val Arg Lys Ala Asp Ala Gly Gly Leu
    130                 135                 140

Gly Ile Ser Ile Lys Gly Gly Arg Glu Asn Lys Met Pro Ile Leu Ile
145                 150                 155                 160
```

```
Ser Lys Ile Phe Lys Gly Leu Ala Ala Asp Gln Thr Glu Ala Leu Phe
            165                 170                 175

Val Gly Asp Ala Ile Leu Ser Val Asn Gly Glu Asp Leu Ser Ser Ala
        180                 185                 190

Thr His Asp Glu Ala Val Gln Ala Leu Lys Lys Thr Gly Lys Glu Val
        195                 200                 205

Val Leu Glu Val Lys Tyr Met Lys Glu Val Ser Pro Tyr Phe Lys
    210                 215                 220

<210> SEQ ID NO 128
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Gln Arg Arg Val Thr Val Arg Lys Ala Asp Ala Gly Gly Leu
1               5                   10                  15

Gly Ile Ser Ile Lys Gly Gly Arg Glu Asn Lys Met Pro Ile Leu Ile
            20                  25                  30

Ser Lys Ile Phe Lys Gly Leu Ala Ala Asp Gln Thr Glu Ala Leu Phe
        35                  40                  45

Val Gly Asp Ala Ile Leu Ser Val Asn Gly Glu Asp Leu Ser Ser Ala
    50                  55                  60

Thr His Asp Glu Ala Val Gln Ala Leu Lys Lys Thr Gly Lys Glu Val
65                  70                  75                  80

Val Leu Glu Val Lys Tyr Met Lys Glu Val Ser Pro Tyr Phe Lys
                85                  90                  95

<210> SEQ ID NO 129
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gly Ser His Met Gly His Glu Leu Ala Lys Gln Glu Ile Arg Val Arg
1               5                   10                  15

Val Glu Lys Asp Pro Glu Leu Gly Phe Ser Ile Ser Gly Gly Arg Gly
            20                  25                  30

Gly Arg Gly Asn Pro Phe Arg Pro Asp Asp Asp Gly Ile Phe Val Thr
        35                  40                  45

Arg Val Gln Pro Glu Gly Pro Ala Ser Lys Leu Leu Gln Pro Gly Asp
    50                  55                  60

Lys Ile Ile Gln Ala Asn Gly Tyr Ser Phe Ile Asn Ile Glu His Gly
65                  70                  75                  80

Gln Ala Val Ser Leu Leu Lys Thr
                85

<210> SEQ ID NO 130
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 130
gaattcagag tgaggactcg agagtgagga cggatcccag atccgccagg cgtgtatata    60
tagcgtggat ggccaggcaa ctttagtgct gacacataca ggcatatata tatgtgtgcg   120
acgacacatg atcatatggc atgcatgtgc tctgtatgta tataaaactc ttgttttctt   180
cttttctcta aatattcttt ccttatacat taggaccttt gcagcataaa ttactatact   240
tctatagaca cacaaacaca aatacacaca ctaatctaga tattaaaatg              290

<210> SEQ ID NO 131
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgacgctgct t                                                         11

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

His Leu Glu Thr Phe Phe
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Val Lys Glu Ala Ala Ala
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Leu Val Thr Trp Val
1               5

<210> SEQ ID NO 135
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Pro Gly Glu Arg Pro Phe Gln Cys Arg Ile Cys Met Arg Asn Phe
```

-continued

```
1               5                   10                  15
Ser Arg Gln Ser Asn Leu Ser Arg His Thr Arg Thr His Thr Gly Glu
                20                  25                  30
Lys Pro Phe Gln Cys Arg Ile Cys Met Arg Asn Phe Ser Arg Asn Glu
                35                  40                  45
His Leu Val Leu His Leu Arg Thr His Thr Gly Glu Lys Pro Phe Gln
    50                  55                  60
Cys Arg Ile Cys Met Arg Asn Phe Ser Gln Lys Thr Gly Leu Arg Val
65                  70                  75                  80
His Leu Lys Thr His Leu Arg Gly Thr Pro Ala Ala Ser Thr Leu
                85                  90                  95
Glu Asp Pro Ser Ala Gly Asp Met Arg Ala Ala Asn Leu Trp Pro Ser
                100                 105                 110
Pro Leu Met Ile Lys Arg Ser Lys Lys Asn Ser Leu Ala Leu Ser Leu
                115                 120                 125
Thr Ala Asp Gln Met Val Ser Ala Leu Leu Asp Ala Glu Pro Pro Ile
        130                 135                 140
Leu Tyr Ser Glu Tyr Asp Pro Thr Arg Pro Phe Ser Glu Ala Ser Met
145                 150                 155                 160
Met Gly Leu Leu Thr Asn Leu Ala Asp Arg Glu Leu Val His Met Ile
                165                 170                 175
Asn Trp Ala Lys Arg Val Pro Gly Phe Val Asp Leu Thr Leu His Asp
                180                 185                 190
Gln Val His Leu Leu Glu Cys Ala Trp Leu Glu Ile Leu Met Ile Gly
            195                 200                 205
Leu Val Trp Arg Ser Met Glu His Pro Val Lys Leu Leu Phe Ala Pro
    210                 215                 220
Asn Leu Leu Leu Asp Arg Asn Gln Gly Lys Cys Val Glu Gly Met Val
225                 230                 235                 240
Glu Ile Phe Asp Met Leu Leu Ala Thr Ser Ser Arg Phe Arg Met Met
                245                 250                 255
Asn Leu Gln Gly Glu Glu Phe Val Cys Leu Lys Ser Ile Ile Leu Leu
                260                 265                 270
Asn Ser Gly Val Tyr Thr Phe Leu Ser Ser Thr Leu Lys Ser Leu Glu
            275                 280                 285
Glu Lys Asp His Ile His Arg Val Leu Asp Lys Ile Thr Asp Thr Leu
    290                 295                 300
Ile His Leu Met Ala Lys Ala Gly Leu Thr Leu Gln Gln Gln His Gln
305                 310                 315                 320
Arg Leu Ala Gln Leu Leu Leu Ile Leu Ser His Ile Arg His Met Ser
                325                 330                 335
Asn Lys Gly Met Glu His Leu Tyr Ser Met Lys Cys Lys Asn Val Val
            340                 345                 350
Pro Leu Tyr Asp Leu Leu Leu Glu Met Leu Asp Ala His Arg Leu His
    355                 360                 365
Ala Pro Thr Ser Arg Gly Gly Ala Ser Val Glu Glu Thr Asp Gln Ser
370                 375                 380
His Leu Ala Thr Ala Gly Ser Thr Ser Ser Glu Leu His Leu Asp Gly
385                 390                 395                 400
Glu Asp Val Ala Met Ala His Ala Asp Ala Leu Asp Asp Phe Asp Leu
                405                 410                 415
Asp Met Leu Gly Asp Gly Asp Ser Pro Gly Pro Gly Phe Thr Pro His
            420                 425                 430
```

```
Asp Ser Ala Pro Tyr Gly Ala Leu Asp Met Ala Asp Phe Glu Phe Glu
        435                 440                 445

Gln Met Phe Thr Asp Ala Leu Gly Ile Asp Glu Tyr Gly Gly
    450                 455                 460
```

<210> SEQ ID NO 136
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(41)
<223> OTHER INFORMATION: Any amino acid
<220> FEATURE:
<221> NAME/KEY: MOD_RES
<222> LOCATION: (63)..(69)
<223> OTHER INFORMATION: Any amino acid
<220> FEATURE:
<221> NAME/KEY: MOD_RES
<222> LOCATION: (92)..(98)
<223> OTHER INFORMATION: Any amino acid
<220> FEATURE:
<221> NAME/KEY: MOD_RES
<222> LOCATION: (120)..(126)
<223> OTHER INFORMATION: Any amino acid
<220> FEATURE:
<221> NAME/KEY: MOD_RES
<222> LOCATION: (149)..(155)
<223> OTHER INFORMATION: Any amino acid
<220> FEATURE:
<221> NAME/KEY: MOD_RES
<222> LOCATION: (177)..(183)
<223> OTHER INFORMATION: Any amino acid

<400> SEQUENCE: 136

```
Met Phe Glu Pro Lys Lys Arg Lys Val Phe Gly Thr Ala Ser
1               5                   10                  15

Ser Arg Pro Gly Glu Arg Pro Phe Gln Cys Arg Ile Cys Met Arg Asn
            20                  25                  30

Phe Ser Xaa Xaa Xaa Xaa Xaa Xaa Xaa His Thr Arg Thr His Thr Gly
        35                  40                  45

Glu Lys Pro Phe Gln Cys Arg Ile Cys Met Arg Asn Phe Ser Xaa Xaa
    50                  55                  60

Xaa Xaa Xaa Xaa Xaa His Leu Arg Thr His Thr Gly Ser Gln Lys Pro
65                  70                  75                  80

Phe Gln Cys Arg Ile Cys Met Arg Asn Phe Ser Xaa Xaa Xaa Xaa Xaa
                85                  90                  95

Xaa Xaa His Leu Arg Thr His Thr Gly Glu Lys Pro Phe Gln Cys Arg
            100                 105                 110

Ile Cys Met Arg Asn Phe Ser Xaa Xaa Xaa Xaa Xaa Xaa Xaa His Leu
        115                 120                 125

Lys Thr His Thr Gly Ser Gln Lys Pro Phe Gln Cys Arg Ile Cys Met
    130                 135                 140

Arg Asn Phe Ser Xaa Xaa Xaa Xaa Xaa Xaa Xaa His Leu Arg Thr His
145                 150                 155                 160

Thr Gly Glu Lys Pro Phe Gln Cys Arg Ile Cys Met Arg Asn Phe Ser
                165                 170                 175

Xaa Xaa Xaa Xaa Xaa Xaa Xaa His Leu Arg Thr His Leu Arg Gly Ser
            180                 185                 190

Thr Cys Arg Gly Arg Ala Asp Ala Leu Asp Asp Phe Asp Leu Asp Met
```

```
            195                 200                 205

Leu Gly Ser Asp Ala Leu Asp Asp Phe Asp Leu Asp Met Leu Gly Ser
        210                 215                 220

Asp Ala Leu Asp Asp Phe Asp Leu Asp Met Leu Gly Ser Asp Ala Leu
225                 230                 235                 240

Asp Asp Phe Asp Leu Asp Met Leu Gly Ser Glu Thr Glu Leu Ile Arg
                245                 250                 255

Glu Thr Ile Val
            260

<210> SEQ ID NO 137
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(41)
<223> OTHER INFORMATION: Any amino acid
<220> FEATURE:
<221> NAME/KEY: MOD_RES
<222> LOCATION: (63)..(69)
<223> OTHER INFORMATION: Any amino acid
<220> FEATURE:
<221> NAME/KEY: MOD_RES
<222> LOCATION: (92)..(98)
<223> OTHER INFORMATION: Any amino acid
<220> FEATURE:
<221> NAME/KEY: MOD_RES
<222> LOCATION: (120)..(126)
<223> OTHER INFORMATION: Any amino acid

<400> SEQUENCE: 137

Met Phe Glu Pro Lys Lys Lys Arg Lys Val Phe Glu Gly Thr Ala Ser
1               5                   10                  15

Ser Arg Pro Gly Glu Arg Pro Phe Gln Cys Arg Ile Cys Met Arg Asn
            20                  25                  30

Phe Ser Xaa Xaa Xaa Xaa Xaa Xaa Xaa His Thr Arg Thr His Thr Gly
        35                  40                  45

Glu Lys Pro Phe Gln Cys Arg Ile Cys Met Arg Asn Phe Ser Xaa Xaa
    50                  55                  60

Xaa Xaa Xaa Xaa Xaa His Leu Arg Thr His Thr Gly Ser Gln Lys Pro
65                  70                  75                  80

Phe Gln Cys Arg Ile Cys Met Arg Asn Phe Ser Xaa Xaa Xaa Xaa Xaa
                85                  90                  95

Xaa Xaa His Leu Arg Thr His Thr Gly Glu Lys Pro Phe Gln Cys Arg
            100                 105                 110

Ile Cys Met Arg Asn Phe Ser Xaa Xaa Xaa Xaa Xaa Xaa Xaa His Leu
        115                 120                 125

Arg Thr His Leu Arg Gly Ser Thr Cys Arg Gly Arg Ala Asp Ala Leu
    130                 135                 140

Asp Asp Phe Asp Leu Asp Met Leu Gly Ser Asp Ala Leu Asp Asp Phe
145                 150                 155                 160

Asp Leu Asp Met Leu Gly Ser Asp Ala Leu Asp Asp Phe Asp Leu Asp
                165                 170                 175

Met Leu Gly Ser Asp Ala Leu Asp Asp Phe Asp Leu Asp Met Leu Gly
            180                 185                 190

Ser Glu Thr Glu Leu Ile Arg Glu Thr Ile Val
        195                 200
```

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Arg His Gly Leu Asp Arg
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp His Ser Ser Leu Lys Arg
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Val Arg His Asn Leu Thr Arg
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp His Ser Asn Leu Ser Arg
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Arg Ser Ser Leu Val Arg
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Ser Gly His Leu Lys Arg
1               5

<210> SEQ ID NO 144
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Val Glu Leu Gln Arg Arg Val Thr Val Arg Lys Ala Asp Ala Gly
            35                  40                  45

Gly Leu Gly Ile Ser Ile Lys Gly Gly Arg Glu Asn Lys Met Pro Ile
    50                  55                  60

Leu Ile Ser Lys Ile Phe Lys Gly Leu Ala Ala Asp Gln Thr Glu Ala
65                  70                  75                  80

Leu Phe Val Gly Asp Ala Ile Leu Ser Val Asn Gly Glu Asp Leu Ser
                85                  90                  95

Ser Ala Thr His Asp Glu Ala Val Gln Ala Leu Lys Lys Thr Gly Lys
            100                 105                 110

Glu Val Val Leu Glu Val Lys Tyr Met Lys Glu Val Ser Pro Tyr Phe
        115                 120                 125

Lys Gly Ser Gly Gly Ser Gly Ser Gly Pro Gly Ser Ser Gly Gly
    130                 135                 140

Ser Gly Pro Gly Ser Gly Ser Ser Gly Gly Ser Gly Pro Gly
145                 150                 155                 160

Ser Gly Gly Ser Ser Gly Pro Gly Ser Glu Thr Glu Leu Val Glu Leu
                165                 170                 175

Gln Arg Arg Val Thr Val Arg Lys Ala Asp Ala Gly Gly Leu Gly
        180                 185                 190

Ile Ser Ile Lys Gly Gly Arg Glu Asn Lys Met Pro Ile Leu Ile Ser
    195                 200                 205

Lys Ile Phe Lys Gly Leu Ala Ala Asp Gln Thr Glu Ala Leu Phe Val
    210                 215                 220

Gly Asp Ala Ile Leu Ser Val Asn Gly Glu Asp Leu Ser Ser Ala Thr
225                 230                 235                 240

His Asp Glu Ala Val Gln Ala Leu Lys Lys Thr Gly Lys Glu Val Val
                245                 250                 255

Leu Glu Val Lys Tyr Met Lys Glu Val Ser Pro Tyr Phe Lys Gly
            260                 265                 270

<210> SEQ ID NO 145
<211> LENGTH: 1012
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

```
cgggtttcgt aacaatcgca tgaggattcg caacgccttc ggcgtagccg atgtcgcgct      60
cccgtctcag taaaggtcgg cgtagccgat gtcgcgcaat cggactgcct tcgtacggcg     120
tagccgatgt cgcgcgtatc agtcgcctcg gaacggcgta gccgatgtcg cgcattcgta     180
agaggctcac tctcccttac acggagtgga taactagtta ggcgtgtacg gtgggaggcc     240
tatataagca gagctcgttt agtgaaccgt cagatcgcct ggaacgcgta ccggtgtcgc     300
caccatggtg agcaagggcg aggaggataa catggccatc atcaaggagt tcatgcgctt     360
caaggtgcac atggagggct ccgtgaacgg ccacgagttc gagatcgagg gcgagggcga     420
gggccgcccc tacgagggca cccagaccgc caagctgaag gtgaccaagg gtggccccct     480
gcccttcgcc tgggacatcc tgtcccctca gttcatgtac ggctccaagg cctacgtgaa     540
gcaccccgcc gacatccccg actacttgaa gctgtccttc cccgagggct caagtggga     600 gcgcgtgatg aacttcgagg acggcggcgt ggtgaccgtg acccaggact cctccctgca     660
ggacggcgag ttcatctaca aggtgaagct gcgcggcacc aacttcccct ccgacggccc     720
cgtaatgcag aagaagacca tgggctggca ggcctcctcc gagcggatgt accccgagga     780
cggcgccctg aagggcgaga tcaagcagag gctgaagctg aaggacggcg gccactacga     840
cgctgaggtc aagaccacct acaaggccaa gaagcccgtg cagctgcccg cgcctacaa     900 cgtcaacatc aagttggaca tcacctccca caacgaggac tacaccatcg tggaacagta     960
cgaacgcgcc gagggccgcc actccaccgg cggcatggac gagctgtaca ag           1012

<210> SEQ ID NO 146
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
aaacaagaag agggttgact acatcacgat gaggggatc gaagaaatga tggtaaatga      60
aataggaaat caaggagcat gaaggcaaaa gacaaatata agggtcgaac gaaaaataaa     120
gtgaaaagtg ttgatatgat gtatttggct ttgcggcgcc gaaaaaacga gtttacgcaa     180
ttgcacaatc atgctgactc tgtggcggac ccgcgctctt gccggcccgg cgataacgct     240
gggcgtgagg ctgtgcccgg cggagttttt tgcgcctgca ttttccaagg tttaccctgc     300
gctaaggggc gagattggag aagcaataag aatgccggtt ggggttgcga tgatgacgac     360
cacgacaact ggtgtcatta tttaagttgc cgaaagaacc tgagtgcatt tgcaacatga     420
gtatactaga agaatgagcc aagacttgcg agacgcgagt ttgccggtgg tgcgaacaat     480
agagcgacca tgaccttgaa ggtgagacgc gcataaccgc tagagtactt tgaagaggaa     540
acagcaatag ggttgctacc agtataaata gacaggtaca taacactg gaaatggttg      600 tctgtttgag tacgctttca attcatttgg gtgtgcactt tattatgtta caatatggaa     660 gggaaccttta cacttctcct atgcacatat attaattaaa gtccaatgct agtagagaag     720 ggggtaaca cccctccgcg ctcttttccg atttttttct aaaccgtgga atatttcgga     780 tatcctttg ttgtttccgg gtgtacaata tggacttcct cttttctggc aaccaaaccc     840
atacatcggg attcctataa taccttcgtt ggtctcccta acatgtaggt ggcggagggg     900
agatatacaa tagaacagat accagacaag acataatggg ctaaacaaga ctacaccaat     960
tacactgcct cattgatggt ggtacataac gaactaatac tgtagcccta gacttgatag    1020
```

```
ccatcatcat atcgaagttt cactaccctt tttccatttg ccatctattg aagtaataat    1080
aggcgcatgc aacttctttt ctttttttt cttttctctc tcccccgttg ttgtctcacc    1140
atatccgcaa tgacaaaaaa atgatggaag acactaaagg aaaaaattaa cgacaaagac    1200
agcaccaaca gatgtcgttg ttccagagct gatgaggggt atctcgaagc acacgaaact    1260
ttttccttcc ttcattcacg cacactactc tctaatgagc aacggtatac ggccttcctt    1320
ccagttactt gaatttgaaa taaaaaaaag tttgctgtct tgctatcaag tataaataga    1380
cctgcaaaaa aaaaattatt aatctttttgt ttcctcgtca ttgttctcgt tcccttctct    1440
ccttgtttct ttttctgcac aatatttcaa gctataccaa gcatacaatc aactatctca    1500
tctagaatg                                                           1509
```

```
<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Thr Gly Ser Gln Lys Pro
1               5

<210> SEQ ID NO 148
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 1-8 'Gly Gly Ser'
      repeating units

<400> SEQUENCE: 148

Gly Gly Ser Gly Gly Ser Gly Gly Ser Gly Gly Ser Gly Gly Ser Gly
1               5                   10                  15

Gly Ser Gly Gly Ser Gly Gly Ser
            20

<210> SEQ ID NO 149
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(22)
<223> OTHER INFORMATION: Any amino acid
<220> FEATURE:
<221> NAME/KEY: MOD_RES
<222> LOCATION: (44)..(49)
<223> OTHER INFORMATION: Any amino acid
<220> FEATURE:
<221> NAME/KEY: MOD_RES
<222> LOCATION: (72)..(77)
<223> OTHER INFORMATION: Any amino acid
<220> FEATURE:
<221> NAME/KEY: MOD_RES
<222> LOCATION: (99)..(104)
<223> OTHER INFORMATION: Any amino acid
<220> FEATURE:
```

```
<221> NAME/KEY: MOD_RES
<222> LOCATION: (127)..(132)
<223> OTHER INFORMATION: Any amino acid
<220> FEATURE:
<221> NAME/KEY: MOD_RES
<222> LOCATION: (154)..(159)
<223> OTHER INFORMATION: Any amino acid

<400> SEQUENCE: 149

Pro Gly Glu Arg Pro Phe Gln Cys Arg Ile Cys Met Arg Asn Phe Ser
1               5                   10                  15

Xaa Xaa Xaa Xaa Xaa Xaa His Thr Arg Thr His Thr Gly Glu Lys Pro
                20                  25                  30

Phe Gln Cys Arg Ile Cys Met Arg Asn Phe Ser Xaa Xaa Xaa Xaa Xaa
            35                  40                  45

Xaa His Leu Arg Thr His Thr Gly Ser Gln Lys Pro Phe Gln Cys Arg
    50                  55                  60

Ile Cys Met Arg Asn Phe Ser Xaa Xaa Xaa Xaa Xaa Xaa His Thr Arg
65                  70                  75                  80

Thr His Thr Gly Glu Lys Pro Phe Gln Cys Arg Ile Cys Met Arg Asn
                85                  90                  95

Phe Ser Xaa Xaa Xaa Xaa Xaa Xaa His Leu Arg Thr His Thr Gly Ser
            100                 105                 110

Gln Lys Pro Phe Gln Cys Arg Ile Cys Met Arg Asn Phe Ser Xaa Xaa
            115                 120                 125

Xaa Xaa Xaa Xaa His Thr Arg Thr His Thr Gly Glu Lys Pro Phe Gln
        130                 135                 140

Cys Arg Ile Cys Met Arg Asn Phe Ser Xaa Xaa Xaa Xaa Xaa Xaa His
145                 150                 155                 160

Leu Arg Thr His Leu Arg
                165

<210> SEQ ID NO 150
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ala Asp Ile Gly Thr Pro Ser Asn Phe Gln His Ile Gly His Val Gly
1               5                   10                  15

Trp Asp Pro Asn Thr Gly Phe Asp Leu Asn Asn Leu Asp Pro Glu Leu
                20                  25                  30

Lys Asn Leu Phe Asp Met Cys Gly Ile Ser Glu
            35                  40
```